(12) United States Patent
Choi et al.

(10) Patent No.: US 11,872,193 B2
(45) Date of Patent: *Jan. 16, 2024

(54) COMPOSITIONS CONTAINING PROTEIN LOADED EXOSOME AND METHODS FOR PREPARING AND DELIVERING THE SAME

(71) Applicant: ILIAS BIOLOGICS INC., Daejeon (KR)

(72) Inventors: Chulhee Choi, Daejeon (KR); Nambin Yim, Daejeon (KR); Won Do Heo, Daejeon (KR); Seung-Wook Ryu, Daejeon (KR); Hojun Choi, Daejeon (KR); Kyungsun Choi, Daejeon (KR)

(73) Assignee: ILIAS BIOLOGICS INC., Daejeon (KR)

( * ) Notice: Subject to any disclaimer, the term of this patent is extended or adjusted under 35 U.S.C. 154(b) by 696 days.

This patent is subject to a terminal disclaimer.

(21) Appl. No.: 16/887,029

(22) Filed: May 29, 2020

(65) Prior Publication Data

US 2020/0289614 A1 Sep. 17, 2020

Related U.S. Application Data

(63) Continuation of application No. 15/803,338, filed on Nov. 3, 2017, now Pat. No. 10,702,581, which is a continuation-in-part of application No. PCT/KR2017/011070, filed on Sep. 30, 2017, and a continuation-in-part of application No. PCT/KR2016/004750, filed on May 4, 2016.

(30) Foreign Application Priority Data

| May 4, 2015 | (KR) | 10-2015-0062604 |
| Aug. 27, 2015 | (KR) | 10-2015-0120934 |
| Sep. 30, 2016 | (KR) | 10-2016-0126335 |
| Sep. 30, 2016 | (KR) | 10-2016-0126921 |
| Sep. 30, 2016 | (KR) | 10-2016-0126961 |
| Oct. 4, 2016 | (KR) | 10-2016-0127486 |
| Oct. 13, 2016 | (KR) | 10-2016-0132616 |
| Feb. 10, 2017 | (KR) | 10-2017-0018637 |

(51) Int. Cl.
| C12N 15/62 | (2006.01) |
| C12N 15/85 | (2006.01) |
| A61K 47/69 | (2017.01) |
| A61K 38/17 | (2006.01) |
| C07K 16/28 | (2006.01) |
| C12P 21/02 | (2006.01) |
| C07K 16/18 | (2006.01) |
| C07K 14/705 | (2006.01) |
| A61K 38/00 | (2006.01) |

(52) U.S. Cl.
CPC ........ *A61K 38/177* (2013.01); *A61K 47/6917* (2017.08); *C07K 14/705* (2013.01); *C07K 14/70596* (2013.01); *C07K 16/18* (2013.01); *C07K 16/28* (2013.01); *C12N 15/62* (2013.01); *C12N 15/85* (2013.01); *C12P 21/02* (2013.01); *A61K 38/00* (2013.01); *C07K 2317/80* (2013.01); *C07K 2319/03* (2013.01); *C07K 2319/70* (2013.01)

(58) Field of Classification Search
None
See application file for complete search history.

(56) References Cited

U.S. PATENT DOCUMENTS

| 2004/0197314 A1 | 10/2004 | Delcayre et al. |
| 2013/0078658 A1 | 3/2013 | Park et al. |
| 2014/0348904 A1 | 11/2014 | Wood et al. |
| 2015/0203837 A1 | 7/2015 | Heo et al. |
| 2015/0284439 A1 | 10/2015 | Heo et al. |
| 2016/0137716 A1 | 5/2016 | El Andaloussi |
| 2016/0186208 A1 | 6/2016 | Jaenisch et al. |

FOREIGN PATENT DOCUMENTS

| EP | 1434852 B1 | 4/2007 |
| JP | 2012-529293 A | 11/2012 |
| JP | 2013-505713 A | 2/2013 |
| JP | 2014-507140 A | 3/2014 |
| KR | 20130032646 A | 4/2013 |
| WO | 03/018777 A1 | 3/2003 |
| WO | 2014168548 A2 | 10/2014 |
| WO | 2015/002956 A1 | 1/2015 |
| WO | 2015002956 A1 | 1/2015 |

(Continued)

OTHER PUBLICATIONS

Daniel Schmidt et al: "Natural photoreceptors and their application to synthetic biology", Trends in Biotechnology., Feb. 1, 2015 (Feb. 1, 2015), vol. 33, No. 2, pp. 80-91, XP055498703, GB ISSN: 0167-7799, DOI: 10.1016/j.tibtech.2014.10.007.

(Continued)

*Primary Examiner* — Daniel C Gamett
(74) *Attorney, Agent, or Firm* — Morgan, Lewis & Bockius LLP

(57) ABSTRACT

The present invention relates to a method for the mass-production of exosome comprising a cargo protein, a vector for preparing the exosome, exosome including a cargo protein prepared by the method, and a method for loading the cargo protein to cytosol by using the exosome prepared thereby. According to the method for preparing an exosome comprising a cargo protein provided by the present invention, the exosome loaded with a cargo protein can be produced with a high yield, so that it can be used broadly in the treatment of disease using the exosome.

20 Claims, 27 Drawing Sheets

Specification includes a Sequence Listing.

(56) References Cited

FOREIGN PATENT DOCUMENTS

| WO | 2015/179227 A1 | 11/2015 |
| WO | 2016/044947 A1 | 3/2016 |
| WO | 2016/073864 A1 | 5/2016 |

OTHER PUBLICATIONS

Camilla A. Thompson et al: "Heparanase Regulates Secretion, Composition, and Function of Tumor Cell-derived Exosomes", Journal of Biological Chemistry, Feb. 21, 2013 (Feb. 21, 2013), vol. 288, No. 14, pp. 10093-10099, XP055726237, us ISSN: 0021-9258, DOI: 10.1074/jbc.C112.444562.

International Search Report for International Application No. PCT/KR2016/004750 (2 Pages) (dated Aug. 8, 2016).

Kooijmans et al., "Exosome mimetics: a novel class of drug delivery systems", International Journal of Nanomedicine, 2012, vol. 7, pp. 1525-1542.

Yazawa et al., "Induction of protein-protein interactions in live cells using light", nature biotechnology, vol. 27, No. 10, pp. 941-945.

Rapid blue light induction of protein interactions in living cells, Matthew J. Kennedy et al., Nat Methods. Dec. 2010, 7(12): 973-975.

Roles of peroxiredoxins in cancer, neurodegenerative diseases and inflammatory diseases, Mi Hee Park et al. Pharmacology & Therapeutics 163 (2016) p. 1-23.

Extended European search report, Application No. 16789638.0, dated Aug. 30, 2018.

Exosome engineering for efficient intracellular delivery of soluble proteins using optically reversible protein-protein interaction module, Nambin Yim et al., Nature Communications, 7:12277, DOI: 10.1038/ncomms12277, www.nature.com/naturecommunications, Jul. 22, 2016, XP-002779472.

Exosome-mediated transfer of miR-10b promotes cell invasion in breast cancer, Ramesh Singh et al., Molecular Cancer 2014, 13:256, http://www.molecular-cancer.com/content/13/1/256.

Kennedy et al., "Rapid blue-light-mediated induction of protein interactions in living cells," Nature Methods, 7 (12): 973-975 (2010).

Liu et al., "Direct activation of Bax protein for cancer therapy," Medicinal Research Reviews, 36 (2): 313-341 (2016).

Office Action issued in related Indian Patent Application No. 201817015311 dated Jun. 15, 2023.

Yim et al., "Exosome engineering for efficient intracellular delivery of soluble proteins using optically reversible protein-protein interaction module," Nature Communications, 7: 12277, Supplementary Information (2016).

(a)

(b)

(c)

(a)

(b)

(a)

(b)

Stable cells producing PTEN-loaded exosome

SEQUENCE LISTING

<160> NUMBER OF SEQ ID NOS: 84

<210> SEQ ID NO 1
<211> LENGTH: 317
<212> TYPE: PRT
<213> ORGANISM: Homo sapiens

<400> SEQUENCE: 1

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser

```
            20                  25                  30
Gly Leu Asp Ser Met Lys Asp Glu Tyr Glu Gln Met Val Lys Glu
            35                  40                  45

Leu Gln Glu Ile Arg Leu Glu Pro Gln Glu Val Pro Arg Gly Ser Glu
 50                  55                  60

Pro Trp Lys Gln Gln Leu Thr Glu Asp Gly Asp Ser Phe Leu His Leu
 65                  70                  75                  80

Ala Ile Ile His Glu Glu Lys Ala Leu Thr Met Glu Val Ile Arg Gln
                     85                  90                  95

Val Lys Gly Asp Leu Ala Phe Leu Asn Phe Gln Asn Asn Leu Gln Gln
                100                 105                 110

Thr Pro Leu His Leu Ala Val Ile Thr Asn Gln Pro Glu Ile Ala Glu
                115                 120                 125

Ala Leu Leu Gly Ala Gly Cys Asp Pro Glu Leu Arg Asp Phe Arg Gly
                130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
                180                 185                 190

His Gly Tyr Leu Gly Ile Val Glu Leu Leu Val Ser Leu Gly Ala Asp
                195                 200                 205

Val Asn Ala Gln Glu Pro Cys Asn Gly Arg Thr Ala Leu His Leu Ala
                210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
                260                 265                 270

Thr Leu Glu Asn Leu Gln Met Leu Pro Glu Ser Glu Asp Glu Glu Ser
                275                 280                 285

Tyr Asp Thr Glu Ser Glu Phe Thr Glu Phe Thr Glu Asp Glu Leu Pro
                290                 295                 300

Tyr Asp Asp Cys Val Phe Gly Gly Gln Arg Leu Thr Leu
305                 310                 315

<210> SEQ ID NO 2
<211> LENGTH: 356
<212> TYPE: PRT
<213> ORGANISM: Homo sapiens

<400> SEQUENCE: 2

Met Ala Gly Val Ala Cys Leu Gly Lys Ala Ala Asp Ala Asp Glu Trp
  1               5                  10                  15

Cys Asp Ser Gly Leu Gly Ser Leu Gly Pro Asp Ala Ala Pro Gly
                 20                  25                  30

Gly Pro Gly Leu Gly Ala Glu Leu Gly Pro Gly Leu Ser Trp Ala Pro
                 35                  40                  45

Leu Val Phe Gly Tyr Val Thr Glu Asp Gly Asp Thr Ala Leu His Leu
 50                  55                  60

Ala Val Ile His Gln His Glu Pro Phe Leu Asp Phe Leu Leu Gly Phe
 65                  70                  75                  80
```

```
Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
    130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
    210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255

Leu Glu Leu Leu Leu Arg Ala Gly Ala Asn Pro Ala Ala Arg Met Tyr
            260                 265                 270

Gly Gly Arg Thr Pro Leu Gly Ser Ala Met Leu Arg Pro Asn Pro Ile
        275                 280                 285

Leu Ala Arg Leu Leu Arg Ala His Gly Ala Pro Glu Pro Glu Gly Glu
    290                 295                 300

Asp Glu Lys Ser Gly Pro Cys Ser Ser Ser Asp Ser Asp Ser Gly
305                 310                 315                 320

Asp Glu Gly Asp Glu Tyr Asp Asp Ile Val Val His Ser Ser Arg Ser
                325                 330                 335

Gln Thr Arg Leu Pro Pro Thr Pro Ala Ser Lys Pro Leu Pro Asp Asp
            340                 345                 350

Pro Arg Pro Val
        355

<210> SEQ ID NO 3
<211> LENGTH: 500
<212> TYPE: PRT
<213> ORGANISM: Homo sapiens

<400> SEQUENCE: 3

Met Asn Gln Arg Arg Ser Glu Ser Arg Pro Gly Asn His Arg Leu Gln
1               5                   10                  15

Ala Tyr Ala Glu Pro Gly Lys Gly Asp Ser Gly Gly Ala Gly Pro Leu
            20                  25                  30

Ser Gly Ser Ala Arg Arg Gly Arg Gly Gly Gly Ala Ile Arg Val
        35                  40                  45

Arg Arg Pro Cys Trp Ser Gly Ala Gly Arg Gly Gly Gly Pro Ala
    50                  55                  60

Trp Ala Val Arg Leu Pro Thr Val Thr Ala Gly Trp Thr Trp Pro Ala
65                  70                  75                  80

Leu Arg Thr Leu Ser Ser Leu Arg Ala Gly Pro Ser Glu Pro His Ser
                85                  90                  95
```

```
Pro Gly Arg Arg Pro Arg Ala Gly Arg Pro Leu Cys Gln Ala Asp
            100                 105                 110
Pro Gln Pro Gly Lys Ala Ala Arg Arg Ser Leu Glu Pro Asp Pro Ala
            115                 120                 125
Gln Thr Gly Pro Arg Pro Ala Arg Ala Ala Gly Met Ser Glu Ala Arg
        130                 135                 140
Lys Gly Pro Asp Glu Ala Glu Glu Ser Gln Tyr Asp Ser Gly Ile Glu
145                 150                 155                 160
Ser Leu Arg Ser Leu Arg Ser Leu Pro Glu Ser Thr Ser Ala Pro Ala
                165                 170                 175
Ser Gly Pro Ser Asp Gly Ser Pro Gln Pro Cys Thr His Pro Pro Gly
            180                 185                 190
Pro Val Lys Glu Pro Gln Glu Lys Glu Asp Ala Asp Gly Glu Arg Ala
        195                 200                 205
Asp Ser Thr Tyr Gly Ser Ser Leu Thr Tyr Thr Leu Ser Leu Leu
    210                 215                 220
Gly Gly Pro Glu Ala Glu Asp Pro Ala Pro Arg Leu Pro Leu Pro His
225                 230                 235                 240
Val Gly Ala Leu Ser Pro Gln Gln Leu Glu Ala Leu Thr Tyr Ile Ser
                245                 250                 255
Glu Asp Gly Asp Thr Leu Val His Leu Ala Val Ile His Glu Ala Pro
            260                 265                 270
Ala Val Leu Leu Cys Cys Leu Ala Leu Leu Pro Gln Glu Val Leu Asp
        275                 280                 285
Ile Gln Asn Asn Leu Tyr Gln Thr Ala Leu His Leu Ala Val His Leu
    290                 295                 300
Asp Gln Pro Gly Ala Val Arg Ala Leu Val Leu Lys Gly Ala Ser Arg
305                 310                 315                 320
Ala Leu Gln Asp Arg His Gly Asp Thr Ala Leu His Val Ala Cys Gln
                325                 330                 335
Arg Gln His Leu Ala Cys Ala Arg Cys Leu Leu Glu Gly Arg Pro Glu
            340                 345                 350
Pro Gly Arg Gly Thr Ser His Ser Leu Asp Leu Gln Leu Gln Asn Trp
        355                 360                 365
Gln Gly Leu Ala Cys Leu His Ile Ala Thr Leu Gln Lys Asn Gln Pro
    370                 375                 380
Leu Met Glu Leu Leu Leu Arg Asn Gly Ala Asp Ile Asp Val Gln Glu
385                 390                 395                 400
Gly Thr Ser Gly Lys Thr Ala Leu His Leu Ala Val Glu Thr Gln Glu
                405                 410                 415
Arg Gly Leu Val Gln Phe Leu Leu Gln Ala Gly Ala Gln Val Asp Ala
            420                 425                 430
Arg Met Leu Asn Gly Cys Thr Pro Leu His Leu Ala Ala Gly Arg Gly
        435                 440                 445
Leu Met Gly Ile Ser Ser Thr Leu Cys Lys Ala Gly Ala Asp Ser Leu
    450                 455                 460
Leu Arg Asn Val Glu Asp Glu Thr Pro Gln Asp Leu Thr Glu Glu Ser
465                 470                 475                 480
Leu Val Leu Leu Pro Phe Asp Asp Leu Lys Ile Ser Gly Lys Leu Leu
                485                 490                 495
Leu Cys Thr Asp
            500
```

```
<210> SEQ ID NO 4
<211> LENGTH: 454
<212> TYPE: PRT
<213> ORGANISM: Homo sapiens

<400> SEQUENCE: 4

Met Pro Arg Cys Pro Ala Gly Ala Met Asp Glu Gly Pro Val Asp Leu
1               5                   10                  15

Arg Thr Arg Pro Lys Ala Ala Gly Leu Pro Gly Ala Ala Leu Pro Leu
            20                  25                  30

Arg Lys Arg Pro Leu Arg Ala Pro Ser Pro Glu Pro Ala Ala Pro Arg
        35                  40                  45

Gly Ala Ala Gly Leu Val Val Pro Leu Asp Pro Leu Arg Gly Gly Cys
    50                  55                  60

Asp Leu Pro Ala Val Pro Gly Pro Pro His Gly Leu Ala Arg Pro Glu
65                  70                  75                  80

Ala Leu Tyr Tyr Pro Gly Ala Leu Leu Pro Leu Tyr Pro Thr Arg Ala
                85                  90                  95

Met Gly Ser Pro Phe Pro Leu Val Asn Leu Pro Thr Pro Leu Tyr Pro
            100                 105                 110

Met Met Cys Pro Met Glu His Pro Leu Ser Ala Asp Ile Ala Met Ala
        115                 120                 125

Thr Arg Ala Asp Glu Asp Gly Asp Thr Pro Leu His Ile Ala Val Val
    130                 135                 140

Gln Gly Asn Leu Pro Ala Val His Arg Leu Val Asn Leu Phe Gln Gln
145                 150                 155                 160

Gly Gly Arg Glu Leu Asp Ile Tyr Asn Asn Leu Arg Gln Thr Pro Leu
                165                 170                 175

His Leu Ala Val Ile Thr Thr Leu Pro Ser Val Val Arg Leu Leu Val
            180                 185                 190

Thr Ala Gly Ala Ser Pro Met Ala Leu Asp Arg His Gly Gln Thr Ala
        195                 200                 205

Ala His Leu Ala Cys Glu His Arg Ser Pro Thr Cys Leu Arg Ala Leu
    210                 215                 220

Leu Asp Ser Ala Ala Pro Gly Thr Leu Asp Leu Glu Ala Arg Asn Tyr
225                 230                 235                 240

Asp Gly Leu Thr Ala Leu His Val Ala Val Asn Thr Glu Cys Gln Glu
                245                 250                 255

Thr Val Gln Leu Leu Leu Glu Arg Gly Ala Asp Ile Asp Ala Val Asp
            260                 265                 270

Ile Lys Ser Gly Arg Ser Pro Leu Ile His Ala Val Glu Asn Asn Ser
        275                 280                 285

Leu Ser Met Val Gln Leu Leu Leu Gln His Gly Ala Asn Val Asn Ala
    290                 295                 300

Gln Met Tyr Ser Gly Ser Ser Ala Leu His Ser Ala Ser Gly Arg Gly
305                 310                 315                 320

Leu Leu Pro Leu Val Arg Thr Leu Val Arg Ser Gly Ala Asp Ser Ser
                325                 330                 335

Leu Lys Asn Cys His Asn Asp Thr Pro Leu Met Val Ala Arg Ser Arg
            340                 345                 350

Arg Val Ile Asp Ile Leu Arg Gly Lys Ala Thr Arg Pro Ala Ser Thr
        355                 360                 365

Ser Gln Pro Asp Pro Ser Pro Asp Arg Ser Ala Asn Thr Ser Pro Glu
    370                 375                 380
```

Ser Ser Ser Arg Leu Ser Ser Asn Gly Leu Leu Ser Ala Ser Pro Ser
385                 390                 395                 400

Ser Ser Pro Ser Gln Ser Pro Pro Arg Asp Pro Pro Gly Phe Pro Met
            405                 410                 415

Ala Pro Pro Asn Phe Phe Leu Pro Ser Pro Ser Pro Pro Ala Phe Leu
        420                 425                 430

Pro Phe Ala Gly Val Leu Arg Gly Pro Gly Arg Pro Val Pro Pro Ser
    435                 440                 445

Pro Ala Pro Gly Gly Ser
    450

<210> SEQ ID NO 5
<211> LENGTH: 317
<212> TYPE: PRT
<213> ORGANISM: Homo sapiens

<400> SEQUENCE: 5

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ala
            20                  25                  30

Gly Leu Asp Ala Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro

```
              290                 295                 300
Tyr Asp Asp Cys Val Phe Gly Gly Gln Arg Leu Thr Leu
305                 310                 315

<210> SEQ ID NO 6
<211> LENGTH: 192
<212> TYPE: PRT
<213> ORGANISM: Homo sapiens

<400> SEQUENCE: 6

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
        50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 7
<211> LENGTH: 199
<212> TYPE: PRT
<213> ORGANISM: Homo sapiens

<400> SEQUENCE: 7

Met Ser Ser Gly Asn Ala Lys Ile Gly His Pro Ala Pro Asn Phe Lys
1               5                   10                  15

Ala Thr Ala Val Met Pro Asp Gly Gln Phe Lys Asp Ile Ser Leu Ser
                20                  25                  30

Asp Tyr Lys Gly Lys Tyr Val Val Phe Phe Tyr Pro Leu Asp Phe
            35                  40                  45

Thr Phe Val Cys Pro Thr Glu Ile Ile Ala Phe Ser Asp Arg Ala Glu
        50                  55                  60

Glu Phe Lys Lys Leu Asn Cys Gln Val Ile Gly Ala Ser Val Asp Ser
65                  70                  75                  80

His Phe Cys His Leu Ala Trp Val Asn Thr Pro Lys Lys Gln Gly Gly
                85                  90                  95

Leu Gly Pro Met Asn Ile Pro Leu Val Ser Asp Pro Lys Arg Thr Ile
            100                 105                 110

Ala Gln Asp Tyr Gly Val Leu Lys Ala Asp Glu Gly Ile Ser Phe Arg
```

```
            115                 120                 125
Gly Leu Phe Ile Ile Asp Asp Lys Gly Ile Leu Arg Gln Ile Thr Val
        130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                    165                 170                 175

Trp Lys Pro Gly Ser Asp Thr Ile Lys Pro Asp Val Lys Ser Lys
                180                 185                 190

Glu Tyr Phe Ser Lys Gln Lys
            195
```

<210> SEQ ID NO 8
<211> LENGTH: 198
<212> TYPE: PRT
<213> ORGANISM: Homo sapiens

<400> SEQUENCE: 8

```
Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
            20                  25                  30

Tyr Lys Gly Lys Tyr Val Val Leu Phe Phe Tyr Pro Leu Asp Phe Thr
        35                  40                  45

Phe Val Cys Pro Thr Glu Ile Ile Ala Phe Ser Asn Arg Ala Glu Asp
    50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Thr Asp Glu Gly Ile Ala Tyr Arg Gly
        115                 120                 125

Leu Phe Ile Ile Asp Gly Lys Gly Val Leu Arg Gln Ile Thr Val Asn
    130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195
```

<210> SEQ ID NO 9
<211> LENGTH: 343
<212> TYPE: PRT
<213> ORGANISM: Bacteriophage P1

<400> SEQUENCE: 9

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
```

```
            35                  40                  45
Cys Arg Ser Trp Ala Ala Trp Cys Lys Leu Asn Asn Arg Lys Trp Phe
 50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
                 85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
            115                 120                 125

Glu Arg Ala Lys Gln Ala Leu Ala Phe Glu Arg Thr Asp Phe Asp Gln
        130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
        290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 10
<211> LENGTH: 469
<212> TYPE: PRT
<213> ORGANISM: Streptococcus pyogenes

<400> SEQUENCE: 10

Met His Ser Phe Pro Pro Leu Leu Leu Leu Phe Trp Gly Val Val
 1               5                  10                  15

Ser His Ser Phe Pro Ala Thr Leu Glu Thr Gln Glu Gln Asp Val Asp
                 20                  25                  30

Leu Val Gln Lys Tyr Leu Glu Lys Tyr Tyr Asn Leu Lys Asn Asp Gly
             35                  40                  45

Arg Gln Val Glu Lys Arg Arg Asn Ser Gly Pro Val Val Glu Lys Leu
 50                  55                  60
```

-continued

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
            85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
            115                 120                 125

Asp Val Asp His Ala Ile Glu Lys Ala Phe Gln Leu Trp Ser Asn Val
            130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
            165                 170                 175

Pro Gly Gly Asn Leu Ala His Ala Phe Gln Pro Gly Pro Gly Ile Gly
            180                 185                 190

Gly Asp Ala His Phe Asp Glu Asp Glu Arg Trp Thr Asn Asn Phe Arg
            195                 200                 205

Glu Tyr Asn Leu His Arg Val Ala Ala His Glu Leu Gly His Ser Leu
            210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
            245                 250                 255

Gln Ala Ile Tyr Gly Arg Ser Gln Asn Pro Val Gln Pro Ile Gly Pro
            260                 265                 270

Gln Thr Pro Lys Ala Cys Asp Ser Lys Leu Thr Phe Asp Ala Ile Thr
            275                 280                 285

Thr Ile Arg Gly Glu Val Met Phe Phe Lys Asp Arg Phe Tyr Met Arg
            290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
            325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
            355                 360                 365

Gly Phe Pro Arg Thr Val Lys His Ile Asp Ala Ala Leu Ser Glu Glu
            370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
            405                 410                 415

His Asp Phe Pro Gly Ile Gly His Lys Val Asp Ala Val Phe Met Lys
            420                 425                 430

Asp Gly Phe Phe Tyr Phe Phe His Gly Thr Arg Gln Tyr Lys Phe Asp
            435                 440                 445

Pro Lys Thr Lys Arg Ile Leu Thr Leu Gln Lys Ala Asn Ser Trp Phe
            450                 455                 460

Asn Cys Arg Lys Asn
465

<210> SEQ ID NO 11
<211> LENGTH: 1300
<212> TYPE: PRT
<213> ORGANISM: Francisella tularensis

<400> SEQUENCE: 11

```
Met Ser Ile Tyr Gln Glu Phe Val Asn Lys Tyr Ser Leu Ser Lys Thr
1               5                   10                  15
Leu Arg Phe Glu Leu Ile Pro Gln Gly Lys Thr Leu Glu Asn Ile Lys
            20                  25                  30
Ala Arg Gly Leu Ile Leu Asp Asp Glu Lys Arg Ala Lys Asp Tyr Lys
        35                  40                  45
Lys Ala Lys Gln Ile Ile Asp Lys Tyr His Gln Phe Phe Ile Glu Glu
    50                  55                  60
Ile Leu Ser Ser Val Cys Ile Ser Glu Asp Leu Leu Gln Asn Tyr Ser
65                  70                  75                  80
Asp Val Tyr Phe Lys Leu Lys Lys Ser Asp Asp Asn Leu Gln Lys
                85                  90                  95
Asp Phe Lys Ser Ala Lys Asp Thr Ile Lys Lys Gln Ile Ser Glu Tyr
            100                 105                 110
Ile Lys Asp Ser Glu Lys Phe Lys Asn Leu Phe Asn Gln Asn Leu Ile
        115                 120                 125
Asp Ala Lys Lys Gly Gln Glu Ser Asp Leu Ile Leu Trp Leu Lys Gln
    130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
            180                 185                 190
Asn Asp Ile Pro Thr Ser Ile Ile Tyr Arg Ile Val Asp Asp Asn Leu
        195                 200                 205
Pro Lys Phe Leu Glu Asn Lys Ala Lys Tyr Glu Ser Leu Lys Asp Lys
    210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
        275                 280                 285
Phe Val Asn Gly Glu Asn Thr Lys Arg Lys Gly Ile Asn Glu Tyr Ile
    290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
    370                 375                 380
```

```
Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
        420                 425                 430

Pro Ser Lys Lys Glu Gln Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
```

```
                    805                 810                 815
Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
        850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
        980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val Tyr
    1010                1015                1020

Gln Lys Leu Glu Lys Met Leu Ile Glu Lys Leu Asn Tyr Leu Val Phe
1025                1030                1035                1040

Lys Asp Asn Glu Phe Asp Lys Thr Gly Gly Val Leu Arg Ala Tyr Gln
            1045                1050                1055

Leu Thr Ala Pro Phe Glu Thr Phe Lys Lys Met Gly Lys Gln Thr Gly
        1060                1065                1070

Ile Ile Tyr Tyr Val Pro Ala Gly Phe Thr Ser Lys Ile Cys Pro Val
    1075                1080                1085

Thr Gly Phe Val Asn Gln Leu Tyr Pro Lys Tyr Glu Ser Val Ser Lys
    1090                1095                1100

Ser Gln Glu Phe Phe Ser Lys Phe Asp Lys Ile Cys Tyr Asn Leu Asp
1105                1110                1115                1120

Lys Gly Tyr Phe Glu Phe Ser Phe Asp Tyr Lys Asn Phe Gly Asp Lys
            1125                1130                1135

Ala Ala Lys Gly Lys Trp Thr Ile Ala Ser Phe Gly Ser Arg Leu Ile
        1140                1145                1150

Asn Phe Arg Asn Ser Asp Lys Asn His Asn Trp Asp Thr Arg Glu Val
    1155                1160                1165

Tyr Pro Thr Lys Glu Leu Glu Lys Leu Leu Lys Asp Tyr Ser Ile Glu
    1170                1175                1180

Tyr Gly His Gly Glu Cys Ile Lys Ala Ala Ile Cys Gly Glu Ser Asp
1185                1190                1195                1200

Lys Lys Phe Phe Ala Lys Leu Thr Ser Val Leu Asn Thr Ile Leu Gln
            1205                1210                1215

Met Arg Asn Ser Lys Thr Gly Thr Glu Leu Asp Tyr Leu Ile Ser Pro
        1220                1225                1230
```

Val Ala Asp Val Asn Gly Asn Phe Phe Asp Ser Arg Gln Ala Pro Lys
                1235                1240                1245

Asn Met Pro Gln Asp Ala Asp Ala Asn Gly Ala Tyr His Ile Gly Leu
    1250                1255                1260

Lys Gly Leu Met Leu Leu Gly Arg Ile Lys Asn Asn Gln Glu Gly Lys
1265                1270                1275                1280

Lys Leu Asn Leu Val Ile Lys Asn Glu Glu Tyr Phe Glu Phe Val Gln
                1285                1290                1295

Asn Arg Asn Asn
            1300

<210> SEQ ID NO 12
<211> LENGTH: 536
<212> TYPE: PRT
<213> ORGANISM: Homo sapiens

<400> SEQUENCE: 12

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly

```
            290                 295                 300
Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
                420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
        450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
    530                 535

<210> SEQ ID NO 13
<211> LENGTH: 469
<212> TYPE: PRT
<213> ORGANISM: Homo sapiens

<400> SEQUENCE: 13

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
            35                  40                  45

Arg Gln Val Glu Lys Arg Arg Asn Ser Gly Pro Val Val Glu Lys Leu
        50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
                100                 105                 110

His Leu Thr Tyr Arg Ile Glu Asn Tyr Thr Pro Asp Leu Pro Arg Ala
            115                 120                 125
```

Asp Val Asp His Ala Ile Glu Lys Ala Phe Gln Leu Trp Ser Asn Val
130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
                180                 185                 190

Gly Asp Ala His Phe Asp Glu Asp Glu Arg Trp Thr Asn Asn Phe Arg
                195                 200                 205

Glu Tyr Asn Leu His Arg Val Ala Ala His Glu Leu Gly His Ser Leu
210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
                260                 265                 270

Gln Thr Pro Lys Ala Cys Asp Ser Lys Leu Thr Phe Asp Ala Ile Thr
                275                 280                 285

Thr Ile Arg Gly Glu Val Met Phe Phe Lys Asp Arg Phe Tyr Met Arg
290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
                340                 345                 350

Gly Gln Asn Val Leu His Gly Tyr Pro Lys Asp Ile Tyr Ser Ser Phe
                355                 360                 365

Gly Phe Pro Arg Thr Val Lys His Ile Asp Ala Ala Leu Ser Glu Glu
                370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
                420                 425                 430

Asp Gly Phe Phe Tyr Phe Phe His Gly Thr Arg Gln Tyr Lys Phe Asp
                435                 440                 445

Pro Lys Thr Lys Arg Ile Leu Thr Leu Gln Lys Ala Asn Ser Trp Phe
450                 455                 460

Asn Cys Arg Lys Asn
465

<210> SEQ ID NO 14
<211> LENGTH: 207
<212> TYPE: PRT
<213> ORGANISM: Homo sapiens

<400> SEQUENCE: 14

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
                20                  25                  30

-continued

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
 50                  55                  60

Met Thr Lys Met Tyr Lys Gly Phe Gln Ala Leu Gly Asp Ala Ala Asp
 65                  70                  75                  80

Ile Arg Phe Val Tyr Thr Pro Ala Met Glu Ser Val Cys Gly Tyr Phe
                 85                  90                  95

His Arg Ser His Asn Arg Ser Glu Glu Phe Leu Ile Ala Gly Lys Leu
                100                 105                 110

Gln Asp Gly Leu Leu His Ile Thr Thr Cys Ser Phe Val Ala Pro Trp
            115                 120                 125

Asn Ser Leu Ser Leu Ala Gln Arg Arg Gly Phe Thr Lys Thr Tyr Thr
130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
            195                 200                 205

<210> SEQ ID NO 15
<211> LENGTH: 220
<212> TYPE: PRT
<213> ORGANISM: Homo sapiens

<400> SEQUENCE: 15

Met Gly Ala Ala Ala Arg Thr Leu Arg Leu Ala Leu Gly Leu Leu Leu
 1                   5                  10                  15

Leu Ala Thr Leu Leu Arg Pro Ala Asp Ala Cys Ser Cys Ser Pro Val
                 20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
 50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
                100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala

-continued

```
            195                 200                 205
Pro Pro Lys Gln Glu Phe Leu Asp Ile Glu Asp Pro
    210                 215                 220

<210> SEQ ID NO 16
<211> LENGTH: 211
<212> TYPE: PRT
<213> ORGANISM: Homo sapiens

<400> SEQUENCE: 16

Met Thr Pro Trp Leu Gly Leu Ile Val Leu Gly Ser Trp Ser Leu
1               5                   10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 17
<211> LENGTH: 224
<212> TYPE: PRT
<213> ORGANISM: Homo sapiens

<400> SEQUENCE: 17

Met Pro Gly Ser Pro Arg Pro Ala Pro Ser Trp Val Leu Leu Leu Arg
1               5                   10                  15

Leu Leu Ala Leu Leu Arg Pro Pro Gly Leu Gly Glu Ala Cys Ser Cys
            20                  25                  30

Ala Pro Ala His Pro Gln Gln His Ile Cys His Ser Ala Leu Val Ile
        35                  40                  45

Arg Ala Lys Ile Ser Ser Glu Lys Val Val Pro Ala Ser Ala Asp Pro
    50                  55                  60

Ala Asp Thr Glu Lys Met Leu Arg Tyr Glu Ile Lys Gln Ile Lys Met
65                  70                  75                  80

Phe Lys Gly Phe Glu Lys Val Lys Asp Val Gln Tyr Ile Tyr Thr Pro
```

```
              85                  90                  95
Phe Asp Ser Ser Leu Cys Gly Val Lys Leu Glu Ala Asn Ser Gln Lys
            100                 105                 110

Gln Tyr Leu Leu Thr Gly Gln Val Leu Ser Asp Gly Lys Val Phe Ile
            115                 120                 125

His Leu Cys Asn Tyr Ile Glu Pro Trp Glu Asp Leu Ser Leu Val Gln
            130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
                180                 185                 190

Gln His Tyr Val Cys Met Lys His Val Asp Gly Thr Cys Ser Trp Tyr
                195                 200                 205

Arg Gly His Leu Pro Leu Arg Lys Glu Phe Val Asp Ile Val Gln Pro
210                 215                 220

<210> SEQ ID NO 18
<211> LENGTH: 404
<212> TYPE: PRT
<213> ORGANISM: Homo sapiens

<400> SEQUENCE: 18

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
            115                 120                 125

Ser Glu Gly Asn Val Lys Leu Cys Ser Leu Glu Glu Ala Gln Arg Ile
            130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
                180                 185                 190

Leu Gln Asn Leu Gly Tyr Ser Val Asp Val Lys Lys Asn Leu Thr Ala
                195                 200                 205

Ser Asp Met Thr Thr Glu Leu Glu Ala Phe Ala His Arg Pro Glu His
            210                 215                 220

Lys Thr Ser Asp Ser Thr Phe Leu Val Phe Met Ser His Gly Ile Arg
225                 230                 235                 240
```

```
Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Gln Ala Cys Arg Gly Asp
        275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 19
<211> LENGTH: 452
<212> TYPE: PRT
<213> ORGANISM: Homo sapiens

<400> SEQUENCE: 19

Met Ala Ala Pro Ser Ala Gly Ser Trp Ser Thr Phe Gln His Lys Glu
1               5                   10                  15

Leu Met Ala Ala Asp Arg Gly Arg Arg Ile Leu Gly Val Cys Gly Met
                20                  25                  30

His Pro His His Gln Glu Thr Leu Lys Lys Asn Arg Val Val Leu Ala
            35                  40                  45

Lys Gln Leu Leu Leu Ser Glu Leu Leu Glu His Leu Leu Glu Lys Asp
        50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205
```

```
His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
                245                 250                 255

Asn Phe Ala Gln Leu Pro Ala His Arg Val Thr Asp Ser Cys Ile Val
            260                 265                 270

Ala Leu Leu Ser His Gly Val Glu Gly Ala Ile Tyr Gly Val Asp Gly
        275                 280                 285

Lys Leu Leu Gln Leu Gln Glu Val Phe Gln Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Ala Gly Ser Pro Gly Cys Glu Glu Ser Asp Ala Gly Lys Glu Lys
            340                 345                 350

Leu Pro Lys Met Arg Leu Pro Thr Arg Ser Asp Met Ile Cys Gly Tyr
        355                 360                 365

Ala Cys Leu Lys Gly Thr Ala Ala Met Arg Asn Thr Lys Arg Gly Ser
    370                 375                 380

Trp Tyr Ile Glu Ala Leu Ala Gln Val Phe Ser Glu Arg Ala Cys Asp
385                 390                 395                 400

Met His Val Ala Asp Met Leu Val Lys Val Asn Ala Leu Ile Lys Asp
                405                 410                 415

Arg Glu Gly Tyr Ala Pro Gly Thr Glu Phe His Arg Cys Lys Glu Met
            420                 425                 430

Ser Glu Tyr Cys Ser Thr Leu Cys Arg His Leu Tyr Leu Phe Pro Gly
        435                 440                 445

His Pro Pro Thr
    450

<210> SEQ ID NO 20
<211> LENGTH: 277
<212> TYPE: PRT
<213> ORGANISM: Homo sapiens

<400> SEQUENCE: 20

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125
```

```
Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
                180                 185                 190

Phe Leu Tyr Ala Tyr Ser Thr Ala Pro Gly Tyr Tyr Ser Trp Arg Asn
            195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
                260                 265                 270

Leu Tyr Phe Tyr His
        275

<210> SEQ ID NO 21
<211> LENGTH: 377
<212> TYPE: PRT
<213> ORGANISM: Homo sapiens

<400> SEQUENCE: 21

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Tyr Tyr Asp Ala
            35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65              70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
```

```
            210                 215                 220
Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
            275                 280                 285

Asp Ala Val Tyr Lys Thr His Val Glu Lys Asp Phe Ile Ala Phe Cys
            290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
                340                 345                 350

Pro Arg Ala Lys Ala Gln Met Pro Thr Ile Glu Arg Leu Ser Met Thr
            355                 360                 365

Arg Tyr Phe Tyr Leu Phe Pro Gly Asn
            370                 375

<210> SEQ ID NO 22
<211> LENGTH: 434
<212> TYPE: PRT
<213> ORGANISM: Homo sapiens

<400> SEQUENCE: 22

Met Ala Glu Asp Ser Gly Lys Lys Arg Arg Lys Asn Phe Glu Ala
1                 5                  10                  15

Met Phe Lys Gly Ile Leu Gln Ser Gly Leu Asp Asn Phe Val Ile Asn
                20                  25                  30

His Met Leu Lys Asn Asn Val Ala Gly Gln Thr Ser Ile Gln Thr Leu
            35                  40                  45

Val Pro Asn Thr Asp Gln Lys Ser Thr Ser Val Lys Lys Asp Asn His
        50                  55                  60

Lys Lys Lys Thr Val Lys Met Leu Glu Tyr Leu Gly Lys Asp Val Leu
65                  70                  75                  80

His Gly Val Phe Asn Tyr Leu Ala Lys His Asp Val Leu Thr Leu Lys
                85                  90                  95

Glu Glu Glu Lys Lys Tyr Tyr Asp Thr Lys Ile Glu Asp Lys Ala
            100                 105                 110

Leu Ile Leu Val Asp Ser Leu Arg Lys Asn Arg Val Ala His Gln Met
        115                 120                 125

Phe Thr Gln Thr Leu Leu Asn Met Asp Gln Lys Ile Thr Ser Val Lys
130                 135                 140

Pro Leu Leu Gln Ile Glu Ala Gly Pro Pro Glu Ser Ala Glu Ser Thr
145                 150                 155                 160

Asn Ile Leu Lys Leu Cys Pro Arg Glu Glu Phe Leu Arg Leu Cys Lys
                165                 170                 175

Lys Asn His Asp Glu Ile Tyr Pro Ile Lys Lys Arg Glu Asp Arg Arg
            180                 185                 190

Arg Leu Ala Leu Ile Ile Cys Asn Thr Lys Phe Asp His Leu Pro Ala
        195                 200                 205
```

```
Arg Asn Gly Ala His Tyr Asp Ile Val Gly Met Lys Arg Leu Leu Gln
    210                 215                 220

Gly Leu Gly Tyr Thr Val Val Asp Glu Lys Asn Leu Thr Ala Arg Asp
225                 230                 235                 240

Met Glu Ser Val Leu Arg Ala Phe Ala Arg Pro Glu His Lys Ser
                245                 250                 255

Ser Asp Ser Thr Phe Leu Val Leu Met Ser His Gly Ile Leu Glu Gly
                260                 265                 270

Ile Cys Gly Thr Ala His Lys Lys Lys Pro Asp Val Leu Leu Tyr
            275                 280                 285

Asp Thr Ile Phe Gln Ile Phe Asn Asn Arg Asn Cys Leu Ser Leu Lys
290                 295                 300

Asp Lys Pro Lys Val Ile Val Gln Ala Cys Arg Gly Glu Lys His
305                 310                 315                 320

Gly Glu Leu Trp Val Arg Asp Ser Pro Ala Ser Leu Ala Leu Ile Ser
                325                 330                 335

Ser Gln Ser Ser Glu Asn Leu Glu Ala Asp Ser Val Cys Lys Ile His
            340                 345                 350

Glu Glu Lys Asp Phe Ile Ala Phe Cys Ser Ser Thr Pro His Asn Val
            355                 360                 365

Ser Trp Arg Asp Arg Thr Arg Gly Ser Ile Phe Ile Thr Glu Leu Ile
370                 375                 380

Thr Cys Phe Gln Lys Tyr Ser Cys Cys Cys His Leu Met Glu Ile Phe
385                 390                 395                 400

Arg Lys Val Gln Lys Ser Phe Glu Val Pro Gln Ala Lys Ala Gln Met
                405                 410                 415

Pro Thr Ile Glu Arg Ala Thr Leu Thr Arg Asp Phe Tyr Leu Phe Pro
                420                 425                 430

Gly Asn

<210> SEQ ID NO 23
<211> LENGTH: 293
<212> TYPE: PRT
<213> ORGANISM: Homo sapiens

<400> SEQUENCE: 23

Met Ser Ser Ala Ser Gly Leu Arg Arg Gly His Pro Ala Gly Gly Glu
1               5                   10                  15

Glu Asn Met Thr Glu Thr Asp Ala Phe Tyr Lys Arg Glu Met Phe Asp
                20                  25                  30

Pro Ala Glu Lys Tyr Lys Met Asp His Arg Arg Arg Gly Ile Ala Leu
            35                  40                  45

Ile Phe Asn His Glu Arg Phe Phe Trp His Leu Thr Leu Pro Glu Arg
        50                  55                  60

Arg Gly Thr Cys Ala Asp Arg Asp Asn Leu Thr Arg Arg Phe Ser Asp
65                  70                  75                  80

Leu Gly Phe Glu Val Lys Cys Phe Asn Asp Leu Lys Ala Glu Glu Leu
                85                  90                  95

Leu Leu Lys Ile His Glu Val Ser Thr Val Ser His Ala Asp Ala Asp
                100                 105                 110

Cys Phe Val Cys Val Phe Leu Ser His Gly Glu Gly Asn His Ile Tyr
            115                 120                 125

Ala Tyr Asp Ala Lys Ile Glu Ile Gln Thr Leu Thr Gly Leu Phe Lys
        130                 135                 140
```

-continued

```
Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290

<210> SEQ ID NO 24
<211> LENGTH: 303
<212> TYPE: PRT
<213> ORGANISM: Homo sapiens

<400> SEQUENCE: 24

Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
                20                  25                  30

Pro Ser Leu Phe Ser Lys Lys Lys Lys Asn Val Thr Met Arg Ser Ile
            35                  40                  45

Lys Thr Thr Arg Asp Arg Val Pro Thr Tyr Gln Tyr Asn Met Asn Phe
50                  55                  60

Glu Lys Leu Gly Lys Cys Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
        115                 120                 125

Glu Asp His Thr Asn Ala Ala Cys Phe Ala Cys Ile Leu Leu Ser His
    130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
    210                 215                 220
```

-continued

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
            245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
            275                 280                 285

Pro Cys Val Val Ser Met Leu Thr Lys Glu Leu Tyr Phe Ser Gln
            290                 295                 300

<210> SEQ ID NO 25
<211> LENGTH: 479
<212> TYPE: PRT
<213> ORGANISM: Homo sapiens

<400> SEQUENCE: 25

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
            115                 120                 125

Ser Lys Cys Lys Leu Asp Asp Asp Met Asn Leu Leu Asp Ile Phe Ile
        130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
            275                 280                 285

Val Glu Gln Ile Tyr Glu Ile Leu Lys Ile Tyr Gln Leu Met Asp His

```
                290                 295                 300
Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
                340                 345                 350

Lys Val Phe Phe Ile Gln Ala Cys Gln Gly Asp Asn Tyr Gln Lys Gly
                355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
                420                 425                 430

Cys Pro Arg Gly Asp Asp Ile Leu Thr Ile Leu Thr Glu Val Asn Tyr
                435                 440                 445

Glu Val Ser Asn Lys Asp Lys Lys Asn Met Gly Lys Gln Met Pro
                450                 455                 460

Gln Pro Thr Phe Thr Leu Arg Lys Lys Leu Val Phe Pro Ser Asp
465                 470                 475

<210> SEQ ID NO 26
<211> LENGTH: 416
<212> TYPE: PRT
<213> ORGANISM: Homo sapiens

<400> SEQUENCE: 26

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
                20                  25                  30

Glu Leu Phe Arg Pro His Met Ile Glu Asp Ile Gln Arg Ala Gly Ser
                35                  40                  45

Gly Ser Arg Arg Asp Gln Ala Arg Gln Leu Ile Asp Leu Glu Thr
50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
                100                 105                 110

Pro Glu Ile Arg Lys Pro Glu Val Leu Arg Pro Glu Thr Pro Arg Pro
                115                 120                 125

Val Asp Ile Gly Ser Gly Gly Phe Gly Asp Val Gly Ala Leu Glu Ser
                130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
                180                 185                 190
```

-continued

```
Arg Phe Ser Ser Leu His Phe Met Val Glu Val Lys Gly Asp Leu Thr
            195                 200                 205

Ala Lys Lys Met Val Leu Ala Leu Leu Glu Leu Ala Gln Gln Asp His
210                 215                 220

Gly Ala Leu Asp Cys Cys Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 27
<211> LENGTH: 521
<212> TYPE: PRT
<213> ORGANISM: Homo sapiens

<400> SEQUENCE: 27

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ala Ser Asp Val Phe Glu His
    50                  55                  60

Leu Leu Ala Glu Asp Leu Leu Ser Glu Glu Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160
```

Lys Ile Asp Glu Asp Asn Leu Thr Cys Leu Glu Asp Leu Cys Lys Thr
            165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
            195                 200                 205

Gln Gly Glu Glu Glu Leu Val Ser Gln Thr Asp Val Lys Thr Phe Leu
        210                 215                 220

Glu Ala Leu Pro Gln Glu Ser Trp Gln Asn Lys His Ala Gly Ser Asn
225                 230                 235                 240

Gly Asn Arg Ala Thr Asn Gly Ala Pro Ser Leu Val Ser Arg Gly Met
            245                 250                 255

Gln Gly Ala Ser Ala Asn Thr Leu Asn Ser Glu Thr Ser Thr Lys Arg
        260                 265                 270

Ala Ala Val Tyr Arg Met Asn Arg Asn His Arg Gly Leu Cys Val Ile
        275                 280                 285

Val Asn Asn His Ser Phe Thr Ser Leu Lys Asp Arg Gln Gly Thr His
        290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
            325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
        355                 360                 365

Glu Ala Leu Ile Pro Ile Arg Glu Ile Met Ser His Phe Thr Ala Leu
    370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
            405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
        435                 440                 445

Phe Arg His Val Glu Glu Gly Ser Trp Tyr Ile Gln Ser Leu Cys Asn
    450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
            485                 490                 495

Ser Ala Thr Ser Leu Pro Thr Ala Ile Ser Ala Gln Thr Pro Arg Pro
        500                 505                 510

Pro Met Arg Arg Trp Ser Ser Val Ser
            515                 520

<210> SEQ ID NO 28
<211> LENGTH: 373
<212> TYPE: PRT
<213> ORGANISM: Homo sapiens

<400> SEQUENCE: 28

Met Ala Glu Asn Lys His Pro Asp Lys Pro Leu Lys Val Leu Glu Gln

```
            1               5              10              15
Leu Gly Lys Glu Val Leu Thr Glu Tyr Leu Glu Lys Leu Val Gln Ser
                20                      25                      30

Asn Val Leu Lys Leu Lys Glu Glu Asp Lys Gln Lys Phe Asn Asn Ala
                35                      40                      45

Glu Arg Ser Asp Lys Arg Trp Val Phe Val Asp Ala Met Lys Lys Lys
        50                      55                      60

His Ser Lys Val Gly Glu Met Leu Leu Gln Thr Phe Phe Ser Val Asp
 65                     70                      75                      80

Pro Gly Ser His His Gly Glu Ala Asn Leu Glu Met Glu Pro Glu
                    85                      90                      95

Glu Ser Leu Asn Thr Leu Lys Leu Cys Ser Pro Glu Phe Thr Arg
                100                     105                     110

Leu Cys Arg Glu Lys Thr Gln Glu Ile Tyr Pro Ile Lys Glu Ala Asn
                115                     120                     125

Gly Arg Thr Arg Lys Ala Leu Ile Ile Cys Asn Thr Glu Phe Lys His
        130                     135                     140

Leu Ser Leu Arg Tyr Gly Ala Asn Phe Asp Ile Ile Gly Met Lys Gly
145                     150                     155                     160

Leu Leu Glu Asp Leu Gly Tyr Asp Val Val Val Lys Glu Glu Leu Thr
                165                     170                     175

Ala Glu Gly Met Glu Ser Glu Met Lys Asp Phe Ala Ala Leu Ser Glu
                180                     185                     190

His Gln Thr Ser Asp Ser Thr Phe Leu Val Leu Met Ser His Gly Thr
                195                     200                     205

Leu His Gly Ile Cys Gly Thr Met His Ser Glu Lys Thr Pro Asp Val
210                     215                     220

Leu Gln Tyr Asp Thr Ile Tyr Gln Ile Phe Asn Asn Cys His Cys Pro
225                     230                     235                     240

Gly Leu Arg Asp Lys Pro Lys Val Ile Val Gln Ala Cys Arg Gly
                245                     250                     255

Gly Asn Ser Gly Glu Met Trp Ile Arg Glu Ser Ser Lys Pro Gln Leu
                260                     265                     270

Cys Arg Gly Val Asp Leu Pro Arg Asn Met Glu Ala Asp Ala Val Lys
                275                     280                     285

Leu Ser His Val Glu Lys Asp Phe Ile Ala Phe Tyr Ser Thr Thr Pro
                290                     295                     300

His His Leu Ser Tyr Arg Asp Lys Thr Gly Gly Ser Tyr Phe Ile Thr
305                     310                     315                     320

Arg Leu Ile Ser Cys Phe Arg Lys His Ala Cys Ser Cys His Leu Phe
                    325                     330                     335

Asp Ile Phe Leu Lys Val Gln Gln Ser Phe Glu Lys Ala Ser Ile His
                340                     345                     350

Ser Gln Met Pro Thr Ile Asp Arg Ala Thr Leu Thr Arg Tyr Phe Tyr
                355                     360                     365

Leu Phe Pro Gly Asn
        370
```

<210> SEQ ID NO 29
<211> LENGTH: 341
<212> TYPE: PRT
<213> ORGANISM: Homo sapiens

<400> SEQUENCE: 29

```
Met Ala Asp Glu Lys Pro Ser Asn Gly Val Leu Val His Met Val Lys
1               5                   10                  15

Leu Leu Ile Lys Thr Phe Leu Asp Gly Ile Phe Asp Asp Leu Met Glu
            20                  25                  30

Asn Asn Val Leu Asn Thr Asp Glu Ile His Leu Ile Gly Lys Cys Leu
            35                  40                  45

Lys Phe Val Val Ser Asn Ala Glu Asn Leu Val Asp Asp Ile Thr Glu
        50                  55                  60

Thr Ala Gln Thr Ala Gly Lys Ile Phe Arg Glu His Leu Trp Asn Ser
65                  70                  75                  80

Lys Lys Gln Leu Ser Ser Asp Ile Ser Ser Asp Gly Glu Arg Glu Ala
                85                  90                  95

Asn Met Pro Gly Leu Asn Ile Arg Asn Lys Glu Phe Asn Tyr Leu His
            100                 105                 110

Asn Arg Asn Gly Ser Glu Leu Asp Leu Leu Gly Met Arg Asp Leu Leu
            115                 120                 125

Glu Asn Leu Gly Tyr Ser Val Val Ile Lys Glu Asn Leu Thr Ala Gln
            130                 135                 140

Glu Met Glu Thr Ala Leu Arg Gln Phe Ala Ala His Pro Glu His Gln
145                 150                 155                 160

Ser Ser Asp Ser Thr Phe Leu Val Phe Met Ser His Ser Ile Leu Asn
                165                 170                 175

Gly Ile Cys Gly Thr Lys His Trp Asp Gln Pro Asp Val Leu His
            180                 185                 190

Asp Asp Thr Ile Phe Glu Ile Phe Asn Asn Arg Asn Cys Gln Ser Leu
            195                 200                 205

Lys Asp Lys Pro Lys Val Ile Ile Met Gln Ala Cys Arg Gly Asn Gly
            210                 215                 220

Ala Gly Ile Val Trp Phe Thr Thr Asp Ser Gly Lys Ala Gly Ala Asp
225                 230                 235                 240

Thr His Gly Arg Leu Leu Gln Gly Asn Ile Cys Asn Asp Ala Val Thr
            245                 250                 255

Lys Ala His Val Glu Lys Asp Phe Ile Ala Phe Lys Ser Ser Thr Pro
            260                 265                 270

His Asn Val Ser Trp Arg His Glu Thr Asn Gly Ser Val Phe Ile Ser
            275                 280                 285

Gln Ile Ile Tyr Tyr Phe Arg Glu Tyr Ser Trp Ser His His Leu Glu
            290                 295                 300

Glu Ile Phe Gln Lys Val Gln His Ser Phe Glu Thr Pro Asn Ile Leu
305                 310                 315                 320

Thr Gln Leu Pro Thr Ile Glu Arg Leu Ser Met Thr Arg Tyr Phe Tyr
            325                 330                 335

Leu Phe Pro Gly Asn
            340

<210> SEQ ID NO 30
<211> LENGTH: 377
<212> TYPE: PRT
<213> ORGANISM: Homo sapiens

<400> SEQUENCE: 30

Met Ala Glu Asp Lys His Asn Lys Asn Pro Leu Lys Met Leu Glu Ser
1               5                   10                  15

Leu Gly Lys Glu Leu Ile Ser Gly Leu Leu Asp Asp Phe Val Glu Lys
            20                  25                  30
```

Asn Val Leu Lys Leu Glu Glu Glu Lys Lys Ile Tyr Asp Ala
    35              40              45

Lys Leu Gln Asp Lys Ala Arg Val Leu Val Asp Ser Ile Arg Gln Lys
50              55                  60

Asn Gln Glu Ala Gly Gln Val Phe Val Gln Thr Phe Leu Asn Ile Asp
65              70              75              80

Lys Asn Ser Thr Ser Ile Lys Ala Pro Glu Thr Val Ala Gly Pro
            85              90              95

Asp Glu Ser Val Gly Ser Ala Ala Thr Leu Lys Leu Cys Pro His Glu
            100             105             110

Glu Phe Leu Lys Leu Cys Lys Arg Ala Gly Glu Ile Tyr Pro Ile
            115             120             125

Lys Glu Arg Lys Asp Arg Thr Arg Leu Ala Leu Ile Ile Cys Asn Thr
130             135             140

Glu Phe Asp His Met Pro Pro Arg Asn Gly Ala Ala Leu Asp Ile Leu
145             150             155             160

Gly Met Lys Gln Leu Leu Glu Gly Leu Gly Tyr Thr Val Glu Val Glu
            165             170             175

Glu Lys Leu Thr Ala Arg Asp Met Glu Ser Val Leu Trp Lys Phe Ala
            180             185             190

Ala Arg Glu Glu His Lys Ser Ser Asp Ser Thr Phe Leu Val Phe Met
            195             200             205

Ser His Gly Ile Leu Asp Gly Ile Cys Gly Thr Met His Ser Glu Glu
            210             215             220

Glu Pro Asp Val Leu Pro Tyr Asp Thr Ile Phe Arg Thr Phe Asn Asn
225             230             235             240

Arg Asn Cys Leu Ser Leu Lys Asp Lys Pro Lys Val Ile Ile Val Gln
            245             250             255

Ala Cys Arg Gly Ala Asn Arg Gly Glu Leu Trp Val Ser Asp Ser Pro
            260             265             270

Pro Ala Leu Ala Asp Ser Phe Ser Gln Ser Ser Glu Asn Leu Glu Glu
            275             280             285

Asp Ala Val Tyr Lys Thr His Val Glu Lys Asp Phe Ile Ala Phe Cys
            290             295             300

Ser Ser Thr Pro His Asn Val Ser Trp Arg Asp Ile Lys Lys Gly Ser
305             310             315             320

Leu Phe Ile Thr Arg Leu Ile Thr Cys Phe Gln Lys Tyr Ala Trp Cys
            325             330             335

Cys His Leu Glu Glu Val Phe Arg Lys Val Gln Gln Ser Phe Glu Lys
            340             345             350

Pro Asn Val Lys Ala Gln Met Pro Thr Val Glu Arg Leu Ser Met Thr
            355             360             365

Arg Tyr Phe Tyr Leu Phe Pro Gly Asn
    370             375

<210> SEQ ID NO 31
<211> LENGTH: 242
<212> TYPE: PRT
<213> ORGANISM: Homo sapiens

<400> SEQUENCE: 31

Met Ser Asn Pro Arg Ser Leu Glu Glu Glu Lys Tyr Asp Met Ser Gly
1               5                   10              15

Ala Arg Leu Ala Leu Ile Leu Cys Val Thr Lys Ala Arg Glu Gly Ser

```
                    20                  25                  30
        Glu Glu Asp Leu Asp Ala Leu Glu His Met Phe Arg Gln Leu Arg Phe
                        35                  40                  45

Glu Ser Thr Met Lys Arg Asp Pro Thr Ala Glu Gln Phe Gln Glu Glu
         50                  55                  60

Leu Glu Lys Phe Gln Gln Ala Ile Asp Ser Arg Glu Asp Pro Val Ser
         65                  70                  75                  80

Cys Ala Phe Val Val Leu Met Ala His Gly Arg Glu Gly Phe Leu Lys
                        85                  90                  95

Gly Glu Asp Gly Glu Met Val Lys Leu Glu Asn Leu Phe Glu Ala Leu
                       100                 105                 110

Asn Asn Lys Asn Cys Gln Ala Leu Arg Ala Lys Pro Lys Val Tyr Ile
                    115                 120                 125

Ile Gln Ala Cys Arg Gly Glu Gln Arg Asp Pro Gly Glu Thr Val Gly
                130                 135                 140

Gly Asp Glu Ile Val Met Val Ile Lys Asp Ser Pro Gln Thr Ile Pro
        145                 150                 155                 160

Thr Tyr Thr Asp Ala Leu His Val Tyr Ser Thr Val Glu Gly Tyr Ile
                        165                 170                 175

Ala Tyr Arg His Asp Gln Lys Gly Ser Cys Phe Ile Gln Thr Leu Val
                        180                 185                 190

Asp Val Phe Thr Lys Arg Lys Gly His Ile Leu Glu Leu Leu Thr Glu
                    195                 200                 205

Val Thr Arg Arg Met Ala Glu Ala Glu Leu Val Gln Glu Gly Lys Ala
        210                 215                 220

Arg Lys Thr Asn Pro Glu Ile Gln Ser Thr Leu Arg Lys Arg Leu Tyr
        225                 230                 235                 240

Leu Gln

<210> SEQ ID NO 32
<211> LENGTH: 480
<212> TYPE: PRT
<213> ORGANISM: Homo sapiens

<400> SEQUENCE: 32

Met Ile Arg Ala Ala Pro Pro Pro Leu Phe Leu Leu Leu Leu Leu Leu
        1               5                   10                  15

Leu Leu Leu Val Ser Trp Ala Ser Arg Gly Glu Ala Ala Pro Asp Gln
                        20                  25                  30

Asp Glu Ile Gln Arg Leu Pro Gly Leu Ala Lys Gln Pro Ser Phe Arg
                        35                  40                  45

Gln Tyr Ser Gly Tyr Leu Lys Gly Ser Gly Ser Lys His Leu His Tyr
         50                  55                  60

Trp Phe Val Glu Ser Gln Lys Asp Pro Glu Asn Ser Pro Val Val Leu
         65                  70                  75                  80

Trp Leu Asn Gly Gly Pro Gly Cys Ser Ser Leu Asp Gly Leu Leu Thr
                        85                  90                  95

Glu His Gly Pro Phe Leu Val Gln Pro Asp Gly Val Thr Leu Glu Tyr
                       100                 105                 110

Asn Pro Tyr Ser Trp Asn Leu Ile Ala Asn Val Leu Tyr Leu Glu Ser
                    115                 120                 125

Pro Ala Gly Val Gly Phe Ser Tyr Ser Asp Asp Lys Phe Tyr Ala Thr
                130                 135                 140

Asn Asp Thr Glu Val Ala Gln Ser Asn Phe Glu Ala Leu Gln Asp Phe
```

```
            145                 150                 155                 160
    Phe Arg Leu Phe Pro Glu Tyr Lys Asn Asn Lys Leu Phe Leu Thr Gly
                    165                 170                 175

Glu Ser Tyr Ala Gly Ile Tyr Ile Pro Thr Leu Ala Val Leu Val Met
                    180                 185                 190

Gln Asp Pro Ser Met Asn Leu Gln Gly Leu Ala Val Gly Asn Gly Leu
                    195                 200                 205

Ser Ser Tyr Glu Gln Asn Asp Asn Ser Leu Val Tyr Phe Ala Tyr Tyr
            210                 215                 220

His Gly Leu Leu Gly Asn Arg Leu Trp Ser Ser Leu Gln Thr His Cys
    225                 230                 235                 240

Cys Ser Gln Asn Lys Cys Asn Phe Tyr Asp Asn Lys Asp Leu Glu Cys
                    245                 250                 255

Val Thr Asn Leu Gln Glu Val Ala Arg Ile Val Gly Asn Ser Gly Leu
                    260                 265                 270

Asn Ile Tyr Asn Leu Tyr Ala Pro Cys Ala Gly Gly Val Pro Ser His
                    275                 280                 285

Phe Arg Tyr Glu Lys Asp Thr Val Val Gln Asp Leu Gly Asn Ile
                    290                 295                 300

Phe Thr Arg Leu Pro Leu Lys Arg Met Trp His Gln Ala Leu Leu Arg
    305                 310                 315                 320

Ser Gly Asp Lys Val Arg Met Asp Pro Pro Cys Thr Asn Thr Thr Ala
                    325                 330                 335

Ala Ser Thr Tyr Leu Asn Asn Pro Tyr Val Arg Lys Ala Leu Asn Ile
                    340                 345                 350

Pro Glu Gln Leu Pro Gln Trp Asp Met Cys Asn Phe Leu Val Asn Leu
                    355                 360                 365

Gln Tyr Arg Arg Leu Tyr Arg Ser Met Asn Ser Gln Tyr Leu Lys Leu
                    370                 375                 380

Leu Ser Ser Gln Lys Tyr Gln Ile Leu Leu Tyr Asn Gly Asp Val Asp
    385                 390                 395                 400

Met Ala Cys Asn Phe Met Gly Asp Glu Trp Phe Val Asp Ser Leu Asn
                    405                 410                 415

Gln Lys Met Glu Val Gln Arg Arg Pro Trp Leu Val Lys Tyr Gly Asp
                    420                 425                 430

Ser Gly Glu Gln Ile Ala Gly Phe Val Lys Glu Phe Ser His Ile Ala
                    435                 440                 445

Phe Leu Thr Ile Lys Gly Ala Gly His Met Val Pro Thr Asp Lys Pro
    450                 455                 460

Leu Ala Ala Phe Thr Met Phe Ser Arg Phe Leu Asn Lys Gln Pro Tyr
    465                 470                 475                 480

<210> SEQ ID NO 33
<211> LENGTH: 339
<212> TYPE: PRT
<213> ORGANISM: Homo sapiens

<400> SEQUENCE: 33

Met Trp Gln Leu Trp Ala Ser Leu Cys Cys Leu Leu Val Leu Ala Asn
    1               5                   10                  15

Ala Arg Ser Arg Pro Ser Phe His Pro Leu Ser Asp Glu Leu Val Asn
                    20                  25                  30

Tyr Val Asn Lys Arg Asn Thr Thr Trp Gln Ala Gly His Asn Phe Tyr
                    35                  40                  45
```

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
            115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
            195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
            275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 34
<211> LENGTH: 463
<212> TYPE: PRT
<213> ORGANISM: Homo sapiens

<400> SEQUENCE: 34

Met Gly Ala Gly Pro Ser Leu Leu Leu Ala Ala Leu Leu Leu Leu Leu
1               5                   10                  15

Ser Gly Asp Gly Ala Val Arg Cys Asp Thr Pro Ala Asn Cys Thr Tyr
            20                  25                  30

Leu Asp Leu Leu Gly Thr Trp Val Phe Gln Val Gly Ser Ser Gly Ser
            35                  40                  45

Gln Arg Asp Val Asn Cys Ser Val Met Gly Pro Gln Glu Lys Lys Val
    50                  55                  60

Val Val Tyr Leu Gln Lys Leu Asp Thr Ala Tyr Asp Asp Leu Gly Asn
65                  70                  75                  80

Ser Gly His Phe Thr Ile Ile Tyr Asn Gln Gly Phe Glu Ile Val Leu
                85                  90                  95

Asn Asp Tyr Lys Trp Phe Ala Phe Phe Lys Tyr Lys Glu Glu Gly Ser
                100                 105                 110

Lys Val Thr Thr Tyr Cys Asn Glu Thr Met Thr Gly Trp Val His Asp
                115                 120                 125

Val Leu Gly Arg Asn Trp Ala Cys Phe Thr Gly Lys Lys Val Gly Thr
                130                 135                 140

Ala Ser Glu Asn Val Tyr Val Asn Ile Ala His Leu Lys Asn Ser Gln
145                 150                 155                 160

Glu Lys Tyr Ser Asn Arg Leu Tyr Lys Tyr Asp His Asn Phe Val Lys
                165                 170                 175

Ala Ile Asn Ala Ile Gln Lys Ser Trp Thr Ala Thr Thr Tyr Met Glu
                180                 185                 190

Tyr Glu Thr Leu Thr Leu Gly Asp Met Ile Arg Arg Ser Gly Gly His
                195                 200                 205

Ser Arg Lys Ile Pro Arg Pro Lys Pro Ala Pro Leu Thr Ala Glu Ile
                210                 215                 220

Gln Gln Lys Ile Leu His Leu Pro Thr Ser Trp Asp Trp Arg Asn Val
225                 230                 235                 240

His Gly Ile Asn Phe Val Ser Pro Val Arg Asn Gln Ala Ser Cys Gly
                245                 250                 255

Ser Cys Tyr Ser Phe Ala Ser Met Gly Met Leu Glu Ala Arg Ile Arg
                260                 265                 270

Ile Leu Thr Asn Asn Ser Gln Thr Pro Ile Leu Ser Pro Gln Glu Val
                275                 280                 285

Val Ser Cys Ser Gln Tyr Ala Gln Gly Cys Glu Gly Gly Phe Pro Tyr
290                 295                 300

Leu Ile Ala Gly Lys Tyr Ala Gln Asp Phe Gly Leu Val Glu Glu Ala
305                 310                 315                 320

Cys Phe Pro Tyr Thr Gly Thr Asp Ser Pro Cys Lys Met Lys Glu Asp
                325                 330                 335

Cys Phe Arg Tyr Tyr Ser Ser Glu Tyr His Tyr Val Gly Gly Phe Tyr
                340                 345                 350

Gly Gly Cys Asn Glu Ala Leu Met Lys Leu Glu Leu Val His His Gly
                355                 360                 365

Pro Met Ala Val Ala Phe Glu Val Tyr Asp Asp Phe Leu His Tyr Lys
                370                 375                 380

Lys Gly Ile Tyr His His Thr Gly Leu Arg Asp Pro Phe Asn Pro Phe
385                 390                 395                 400

Glu Leu Thr Asn His Ala Val Leu Leu Val Gly Tyr Gly Thr Asp Ser
                405                 410                 415

Ala Ser Gly Met Asp Tyr Trp Ile Val Lys Asn Ser Trp Gly Thr Gly
                420                 425                 430

Trp Gly Glu Asn Gly Tyr Phe Arg Ile Arg Arg Gly Thr Asp Glu Cys
                435                 440                 445

Ala Ile Glu Ser Ile Ala Val Ala Ala Thr Pro Ile Pro Lys Leu
450                 455                 460

<210> SEQ ID NO 35
<211> LENGTH: 412
<212> TYPE: PRT
<213> ORGANISM: Homo sapiens

<400> SEQUENCE: 35

```
Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
            20                  25                  30

Arg Arg Thr Met Ser Glu Val Gly Ser Val Glu Asp Leu Ile Ala
            35                  40                  45

Lys Gly Pro Val Ser Lys Tyr Ser Gln Ala Val Pro Ala Val Thr Glu
50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160

Gln Ser Ala Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
        275                 280                 285

Gly Cys Glu Ala Ile Val Asp Thr Gly Thr Ser Leu Met Val Gly Pro
    290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Gly Lys Gly Tyr Lys Leu Ser Pro Glu
            340                 345                 350

Asp Tyr Thr Leu Lys Val Ser Gln Ala Gly Lys Thr Leu Cys Leu Ser
        355                 360                 365

Gly Phe Met Gly Met Asp Ile Pro Pro Pro Ser Gly Pro Leu Trp Ile
    370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
                405                 410
```

<210> SEQ ID NO 36
<211> LENGTH: 401
<212> TYPE: PRT
<213> ORGANISM: Homo sapiens

<400> SEQUENCE: 36

```
Met Lys Thr Leu Leu Leu Leu Leu Val Leu Leu Glu Leu Gly Glu
 1               5                  10                  15

Ala Gln Gly Ser Leu His Arg Val Pro Leu Arg Arg His Pro Ser Leu
            20                  25                  30

Lys Lys Lys Leu Arg Ala Arg Ser Gln Leu Ser Glu Phe Trp Lys Ser
            35                  40                  45

His Asn Leu Asp Met Ile Gln Phe Thr Glu Ser Cys Ser Met Asp Gln
        50                  55                  60

Ser Ala Lys Glu Pro Leu Ile Asn Tyr Leu Asp Met Glu Tyr Phe Gly
 65                  70                  75                  80

Thr Ile Ser Ile Gly Ser Pro Pro Gln Asn Phe Thr Val Ile Phe Asp
                    85                  90                  95

Thr Gly Ser Ser Asn Leu Trp Val Pro Ser Val Tyr Cys Thr Ser Pro
                100                 105                 110

Ala Cys Lys Thr His Ser Arg Phe Gln Pro Ser Gln Ser Ser Thr Tyr
            115                 120                 125

Ser Gln Pro Gly Gln Ser Phe Ser Ile Gln Tyr Gly Thr Gly Ser Leu
        130                 135                 140

Ser Gly Ile Ile Gly Ala Asp Gln Val Ser Ala Phe Ala Thr Gln Val
145                 150                 155                 160

Glu Gly Leu Thr Val Val Gly Gln Gln Phe Gly Glu Ser Val Thr Glu
                165                 170                 175

Pro Gly Gln Thr Phe Val Asp Ala Glu Phe Asp Gly Ile Leu Gly Leu
            180                 185                 190

Gly Tyr Pro Ser Leu Ala Val Gly Gly Val Thr Pro Val Phe Asp Asn
        195                 200                 205

Met Met Ala Gln Asn Leu Val Asp Leu Pro Met Phe Ser Val Tyr Met
210                 215                 220

Ser Ser Asn Pro Glu Gly Gly Ala Gly Ser Glu Leu Ile Phe Gly Gly
225                 230                 235                 240

Tyr Asp His Ser His Phe Ser Gly Ser Leu Asn Trp Val Pro Val Thr
                245                 250                 255

Lys Gln Ala Tyr Trp Gln Ile Ala Leu Asp Asn Ile Gln Val Gly Gly
            260                 265                 270

Thr Val Met Phe Cys Ser Glu Gly Cys Gln Ala Ile Val Asp Thr Gly
        275                 280                 285

Thr Ser Leu Ile Thr Gly Pro Ser Asp Lys Ile Lys Gln Leu Gln Asn
290                 295                 300

Ala Ile Gly Ala Ala Pro Val Asp Gly Glu Tyr Ala Val Glu Cys Ala
305                 310                 315                 320

Asn Leu Asn Val Met Pro Asp Val Thr Phe Thr Ile Asn Gly Val Pro
                325                 330                 335

Tyr Thr Leu Ser Pro Thr Ala Tyr Thr Leu Leu Asp Phe Val Asp Gly
            340                 345                 350

Met Gln Phe Cys Ser Ser Gly Phe Gln Gly Leu Asp Ile His Pro Pro
        355                 360                 365

Ala Gly Pro Leu Trp Ile Leu Gly Asp Val Phe Ile Arg Gln Phe Tyr
        370                 375                 380
```

```
Ser Val Phe Asp Arg Gly Asn Asn Arg Val Gly Leu Ala Pro Ala Val
385                 390                 395                 400

Pro
```

<210> SEQ ID NO 37
<211> LENGTH: 484
<212> TYPE: PRT
<213> ORGANISM: Homo sapiens

<400> SEQUENCE: 37

```
Met Ala Pro Trp Leu Gln Leu Ser Leu Leu Gly Leu Leu Pro Gly
1               5                   10                  15

Ala Val Ala Ala Pro Ala Gln Pro Arg Ala Ala Ser Phe Gln Ala Trp
            20                  25                  30

Gly Pro Pro Ser Pro Glu Leu Leu Ala Pro Thr Arg Phe Ala Leu Glu
        35                  40                  45

Met Phe Asn Arg Gly Arg Ala Ala Gly Thr Arg Ala Val Leu Gly Leu
    50                  55                  60

Val Arg Gly Arg Val Arg Arg Ala Gly Gln Gly Ser Leu Tyr Ser Leu
65                  70                  75                  80

Glu Ala Thr Leu Glu Glu Pro Pro Cys Asn Asp Pro Met Val Cys Arg
                85                  90                  95

Leu Pro Val Ser Lys Lys Thr Leu Leu Cys Ser Phe Gln Val Leu Asp
            100                 105                 110

Glu Leu Gly Arg His Val Leu Leu Arg Lys Asp Cys Gly Pro Val Asp
        115                 120                 125

Thr Lys Val Pro Gly Ala Gly Glu Pro Lys Ser Ala Phe Thr Gln Gly
    130                 135                 140

Ser Ala Met Ile Ser Ser Leu Ser Gln Asn His Pro Asp Asn Arg Asn
145                 150                 155                 160

Glu Thr Phe Ser Ser Val Ile Ser Leu Leu Asn Glu Asp Pro Leu Ser
                165                 170                 175

Gln Asp Leu Pro Val Lys Met Ala Ser Ile Phe Lys Asn Phe Val Ile
            180                 185                 190

Thr Tyr Asn Arg Thr Tyr Glu Ser Lys Glu Glu Ala Arg Trp Arg Leu
        195                 200                 205

Ser Val Phe Val Asn Asn Met Val Arg Ala Gln Lys Ile Gln Ala Leu
    210                 215                 220

Asp Arg Gly Thr Ala Gln Tyr Gly Val Thr Lys Phe Ser Asp Leu Thr
225                 230                 235                 240

Glu Glu Glu Phe Arg Thr Ile Tyr Leu Asn Thr Leu Leu Arg Lys Glu
                245                 250                 255

Pro Gly Asn Lys Met Lys Gln Ala Lys Ser Val Gly Asp Leu Ala Pro
            260                 265                 270

Pro Glu Trp Asp Trp Arg Ser Lys Gly Ala Val Thr Lys Val Lys Asp
        275                 280                 285

Gln Gly Met Cys Gly Ser Cys Trp Ala Phe Ser Val Thr Gly Asn Val
    290                 295                 300

Glu Gly Gln Trp Phe Leu Asn Gln Gly Thr Leu Leu Ser Leu Ser Glu
305                 310                 315                 320

Gln Glu Leu Leu Asp Cys Asp Lys Met Asp Lys Ala Cys Met Gly Gly
                325                 330                 335

Leu Pro Ser Asn Ala Tyr Ser Ala Ile Lys Asn Leu Gly Gly Leu Glu
            340                 345                 350
```

```
Thr Glu Asp Asp Tyr Ser Tyr Gln Gly His Met Gln Ser Cys Asn Phe
            355                 360                 365

Ser Ala Glu Lys Ala Lys Val Tyr Ile Asn Asp Ser Val Glu Leu Ser
    370                 375                 380

Gln Asn Glu Gln Lys Leu Ala Ala Trp Leu Ala Lys Arg Gly Pro Ile
385                 390                 395                 400

Ser Val Ala Ile Asn Ala Phe Gly Met Gln Phe Tyr Arg His Gly Ile
                405                 410                 415

Ser Arg Pro Leu Arg Pro Leu Cys Ser Pro Trp Leu Ile Asp His Ala
            420                 425                 430

Val Leu Leu Val Gly Tyr Gly Asn Arg Ser Asp Val Pro Phe Trp Ala
            435                 440                 445

Ile Lys Asn Ser Trp Gly Thr Asp Trp Gly Glu Lys Gly Tyr Tyr Tyr
    450                 455                 460

Leu His Arg Gly Ser Gly Ala Cys Gly Val Asn Thr Met Ala Ser Ser
465                 470                 475                 480

Ala Val Val Asp

<210> SEQ ID NO 38
<211> LENGTH: 255
<212> TYPE: PRT
<213> ORGANISM: Homo sapiens

<400> SEQUENCE: 38

Met Gln Pro Leu Leu Leu Leu Ala Phe Leu Leu Pro Thr Gly Ala
1               5                   10                  15

Glu Ala Gly Glu Ile Ile Gly Gly Arg Glu Ser Arg Pro His Ser Arg
                20                  25                  30

Pro Tyr Met Ala Tyr Leu Gln Ile Gln Ser Pro Ala Gly Gln Ser Arg
            35                  40                  45

Cys Gly Gly Phe Leu Val Arg Glu Asp Phe Val Leu Thr Ala Ala His
    50                  55                  60

Cys Trp Gly Ser Asn Ile Asn Val Thr Leu Gly Ala His Asn Ile Gln
65                  70                  75                  80

Arg Arg Glu Asn Thr Gln Gln His Ile Thr Ala Arg Ala Ile Arg
                85                  90                  95

His Pro Gln Tyr Asn Gln Arg Thr Ile Gln Asn Asp Ile Met Leu Leu
            100                 105                 110

Gln Leu Ser Arg Arg Val Arg Arg Asn Arg Asn Val Asn Pro Val Ala
            115                 120                 125

Leu Pro Arg Ala Gln Glu Gly Leu Arg Pro Gly Thr Leu Cys Thr Val
130                 135                 140

Ala Gly Trp Gly Arg Val Ser Met Arg Arg Gly Thr Asp Thr Leu Arg
145                 150                 155                 160

Glu Val Gln Leu Arg Val Gln Arg Asp Arg Gln Cys Leu Arg Ile Phe
                165                 170                 175

Gly Ser Tyr Asp Pro Arg Arg Gln Ile Cys Val Gly Asp Arg Arg Glu
            180                 185                 190

Arg Lys Ala Ala Phe Lys Gly Asp Ser Gly Gly Pro Leu Leu Cys Asn
        195                 200                 205

Asn Val Ala His Gly Ile Val Ser Tyr Gly Lys Ser Ser Gly Val Pro
    210                 215                 220

Pro Glu Val Phe Thr Arg Val Ser Ser Phe Leu Pro Trp Ile Arg Thr
225                 230                 235                 240
```

```
Thr Met Arg Ser Phe Lys Leu Leu Asp Gln Met Glu Thr Pro Leu
            245                 250                 255
```

<210> SEQ ID NO 39
<211> LENGTH: 335
<212> TYPE: PRT
<213> ORGANISM: Homo sapiens

<400> SEQUENCE: 39

```
Met Trp Ala Thr Leu Pro Leu Leu Cys Ala Gly Ala Trp Leu Leu Gly
 1               5                  10                  15

Val Pro Val Cys Gly Ala Ala Glu Leu Cys Val Asn Ser Leu Glu Lys
                20                  25                  30

Phe His Phe Lys Ser Trp Met Ser Lys His Arg Lys Thr Tyr Ser Thr
            35                  40                  45

Glu Glu Tyr His His Arg Leu Gln Thr Phe Ala Ser Asn Trp Arg Lys
         50                  55                  60

Ile Asn Ala His Asn Asn Gly Asn His Thr Phe Lys Met Ala Leu Asn
 65                  70                  75                  80

Gln Phe Ser Asp Met Ser Phe Ala Glu Ile Lys His Lys Tyr Leu Trp
                 85                  90                  95

Ser Glu Pro Gln Asn Cys Ser Ala Thr Lys Ser Asn Tyr Leu Arg Gly
            100                 105                 110

Thr Gly Pro Tyr Pro Pro Ser Val Asp Trp Arg Lys Lys Gly Asn Phe
        115                 120                 125

Val Ser Pro Val Lys Asn Gln Gly Ala Cys Gly Ser Cys Trp Thr Phe
130                 135                 140

Ser Thr Thr Gly Ala Leu Glu Ser Ala Ile Ala Ile Ala Thr Gly Lys
145                 150                 155                 160

Met Leu Ser Leu Ala Glu Gln Gln Leu Val Asp Cys Ala Gln Asp Phe
                165                 170                 175

Asn Asn His Gly Cys Gln Gly Gly Leu Pro Ser Gln Ala Phe Glu Tyr
            180                 185                 190

Ile Leu Tyr Asn Lys Gly Ile Met Gly Glu Asp Thr Tyr Pro Tyr Gln
        195                 200                 205

Gly Lys Asp Gly Tyr Cys Lys Phe Gln Pro Gly Lys Ala Ile Gly Phe
    210                 215                 220

Val Lys Asp Val Ala Asn Ile Thr Ile Tyr Asp Glu Glu Ala Met Val
225                 230                 235                 240

Glu Ala Val Ala Leu Tyr Asn Pro Val Ser Phe Ala Phe Glu Val Thr
                245                 250                 255

Gln Asp Phe Met Met Tyr Arg Thr Gly Ile Tyr Ser Ser Thr Ser Cys
            260                 265                 270

His Lys Thr Pro Asp Lys Val Asn His Ala Val Leu Ala Val Gly Tyr
        275                 280                 285

Gly Glu Lys Asn Gly Ile Pro Tyr Trp Ile Val Lys Asn Ser Trp Gly
    290                 295                 300

Pro Gln Trp Gly Met Asn Gly Tyr Phe Leu Ile Glu Arg Gly Lys Asn
305                 310                 315                 320

Met Cys Gly Leu Ala Ala Cys Ala Ser Tyr Pro Ile Pro Leu Val
                325                 330                 335
```

<210> SEQ ID NO 40
<211> LENGTH: 329
<212> TYPE: PRT

<213> ORGANISM: Homo sapiens

<400> SEQUENCE: 40

Met Trp Gly Leu Lys Val Leu Leu Leu Pro Val Val Ser Phe Ala Leu
1               5                   10                  15

Tyr Pro Glu Glu Ile Leu Asp Thr His Trp Glu Leu Trp Lys Lys Thr
            20                  25                  30

His Arg Lys Gln Tyr Asn Asn Lys Val Asp Glu Ile Ser Arg Arg Leu
        35                  40                  45

Ile Trp Glu Lys Asn Leu Lys Tyr Ile Ser Ile His Asn Leu Glu Ala
    50                  55                  60

Ser Leu Gly Val His Thr Tyr Glu Leu Ala Met Asn His Leu Gly Asp
65                  70                  75                  80

Met Thr Ser Glu Glu Val Val Gln Lys Met Thr Gly Leu Lys Val Pro
                85                  90                  95

Leu Ser His Ser Arg Ser Asn Asp Thr Leu Tyr Ile Pro Glu Trp Glu
            100                 105                 110

Gly Arg Ala Pro Asp Ser Val Asp Tyr Arg Lys Lys Gly Tyr Val Thr
        115                 120                 125

Pro Val Lys Asn Gln Gly Gln Cys Gly Ser Cys Trp Ala Phe Ser Ser
    130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
            180                 185                 190

Arg Gly Ile Asp Ser Glu Asp Ala Tyr Pro Tyr Val Gly Gln Glu Glu
        195                 200                 205

Ser Cys Met Tyr Asn Pro Thr Gly Lys Ala Ala Lys Cys Arg Gly Tyr
    210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Ser Cys Asn Ser Asp
            260                 265                 270

Asn Leu Asn His Ala Val Leu Ala Val Gly Tyr Gly Ile Gln Lys Gly
        275                 280                 285

Asn Lys His Trp Ile Ile Lys Asn Ser Trp Gly Glu Asn Trp Gly Asn
    290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325

<210> SEQ ID NO 41
<211> LENGTH: 333
<212> TYPE: PRT
<213> ORGANISM: Homo sapiens

<400> SEQUENCE: 41

Met Asn Pro Thr Leu Ile Leu Ala Ala Phe Cys Leu Gly Ile Ala Ser
1               5                   10                  15

Ala Thr Leu Thr Phe Asp His Ser Leu Glu Ala Gln Trp Thr Lys Trp

```
                20                  25                  30
Lys Ala Met His Asn Arg Leu Tyr Gly Met Asn Glu Glu Gly Trp Arg
                35                  40                  45

Arg Ala Val Trp Glu Lys Asn Met Lys Met Ile Glu Leu His Asn Gln
        50                  55                  60

Glu Tyr Arg Glu Gly Lys His Ser Phe Thr Met Ala Met Asn Ala Phe
65                  70                  75                  80

Gly Asp Met Thr Ser Glu Glu Phe Arg Gln Val Met Asn Gly Phe Gln
                85                  90                  95

Asn Arg Lys Pro Arg Lys Gly Lys Val Phe Gln Glu Pro Leu Phe Tyr
            100                 105                 110

Glu Ala Pro Arg Ser Val Asp Trp Arg Glu Lys Gly Tyr Val Thr Pro
            115                 120                 125

Val Lys Asn Gln Gly Gln Cys Gly Ser Cys Trp Ala Phe Ser Ala Thr
        130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
            195                 200                 205

Glu Ser Cys Lys Tyr Asn Pro Lys Tyr Ser Val Ala Asn Asp Thr Gly
        210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Val Gly Tyr Gly Phe Glu Ser Thr
            275                 280                 285

Glu Ser Asp Asn Asn Lys Tyr Trp Leu Val Lys Asn Ser Trp Gly Glu
        290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330

<210> SEQ ID NO 42
<211> LENGTH: 334
<212> TYPE: PRT
<213> ORGANISM: Homo sapiens

<400> SEQUENCE: 42

Met Asn Leu Ser Leu Val Leu Ala Ala Phe Cys Leu Gly Ile Ala Ser
1               5                   10                  15

Ala Val Pro Lys Phe Asp Gln Asn Leu Asp Thr Lys Trp Tyr Gln Trp
                20                  25                  30

Lys Ala Thr His Arg Arg Leu Tyr Gly Ala Asn Glu Glu Gly Trp Arg
                35                  40                  45

Arg Ala Val Trp Glu Lys Asn Met Lys Met Ile Glu Leu His Asn Gly
        50                  55                  60
```

```
Glu Tyr Ser Gln Gly Lys His Gly Phe Thr Met Ala Met Asn Ala Phe
 65                  70                  75                  80

Gly Asp Met Thr Asn Glu Glu Phe Arg Gln Met Met Gly Cys Phe Arg
                 85                  90                  95

Asn Gln Lys Phe Arg Lys Gly Lys Val Phe Arg Glu Pro Leu Phe Leu
            100                 105                 110

Asp Leu Pro Lys Ser Val Asp Trp Arg Lys Lys Gly Tyr Val Thr Pro
        115                 120                 125

Val Lys Asn Gln Lys Gln Cys Gly Ser Cys Trp Ala Phe Ser Ala Thr
    130                 135                 140

Gly Ala Leu Glu Gly Gln Met Phe Arg Lys Thr Gly Lys Leu Val Ser
145                 150                 155                 160

Leu Ser Glu Gln Asn Leu Val Asp Cys Ser Arg Pro Gln Gly Asn Gln
                165                 170                 175

Gly Cys Asn Gly Gly Phe Met Ala Arg Ala Phe Gln Tyr Val Lys Glu
            180                 185                 190

Asn Gly Gly Leu Asp Ser Glu Glu Ser Tyr Pro Tyr Val Ala Val Asp
        195                 200                 205

Glu Ile Cys Lys Tyr Arg Pro Glu Asn Ser Val Ala Asn Asp Thr Gly
    210                 215                 220

Phe Thr Val Val Ala Pro Gly Lys Glu Lys Ala Leu Met Lys Ala Val
225                 230                 235                 240

Ala Thr Val Gly Pro Ile Ser Val Ala Met Asp Ala Gly His Ser Ser
                245                 250                 255

Phe Gln Phe Tyr Lys Ser Gly Ile Tyr Phe Glu Pro Asp Cys Ser Ser
            260                 265                 270

Lys Asn Leu Asp His Gly Val Leu Val Val Gly Tyr Gly Phe Glu Gly
        275                 280                 285

Ala Asn Ser Asn Asn Ser Lys Tyr Trp Leu Val Lys Asn Ser Trp Gly
    290                 295                 300

Pro Glu Trp Gly Ser Asn Gly Tyr Val Lys Ile Ala Lys Asp Lys Asn
305                 310                 315                 320

Asn His Cys Gly Ile Ala Thr Ala Ala Ser Tyr Pro Asn Val
                325                 330

<210> SEQ ID NO 43
<211> LENGTH: 321
<212> TYPE: PRT
<213> ORGANISM: Homo sapiens

<400> SEQUENCE: 43

Met Asp Val Arg Ala Leu Pro Trp Leu Pro Trp Leu Leu Trp Leu Leu
1               5                   10                  15

Cys Arg Gly Gly Gly Asp Ala Asp Ser Arg Ala Pro Phe Thr Pro Thr
                20                  25                  30

Trp Pro Arg Ser Arg Glu Arg Glu Ala Ala Ala Phe Arg Glu Ser Leu
            35                  40                  45

Asn Arg His Arg Tyr Leu Asn Ser Leu Phe Pro Ser Glu Asn Ser Thr
        50                  55                  60

Ala Phe Tyr Gly Ile Asn Gln Phe Ser Tyr Leu Phe Pro Glu Glu Phe
 65                 70                  75                  80

Lys Ala Ile Tyr Leu Arg Ser Lys Pro Ser Lys Phe Pro Arg Tyr Ser
                85                  90                  95

Ala Glu Val His Met Ser Ile Pro Asn Val Ser Leu Pro Leu Arg Phe
            100                 105                 110
```

```
Asp Trp Arg Asp Lys Gln Val Thr Gln Val Arg Asn Gln Gln Met
            115                 120                 125

Cys Gly Gly Cys Trp Ala Phe Ser Val Val Gly Ala Val Glu Ser Ala
        130                 135                 140

Tyr Ala Ile Lys Gly Lys Pro Leu Glu Asp Leu Ser Val Gln Gln Val
145                 150                 155                 160

Ile Asp Cys Ser Tyr Asn Asn Tyr Gly Cys Asn Gly Gly Ser Thr Leu
                165                 170                 175

Asn Ala Leu Asn Trp Leu Asn Lys Met Gln Val Lys Leu Val Lys Asp
            180                 185                 190

Ser Glu Tyr Pro Phe Lys Ala Gln Asn Gly Leu Cys His Tyr Phe Ser
        195                 200                 205

Gly Ser His Ser Gly Phe Ser Ile Lys Gly Tyr Ser Ala Tyr Asp Phe
    210                 215                 220

Ser Asp Gln Glu Asp Glu Met Ala Lys Ala Leu Leu Thr Phe Gly Pro
225                 230                 235                 240

Leu Val Val Ile Val Asp Ala Val Ser Trp Gln Asp Tyr Leu Gly Gly
                245                 250                 255

Ile Ile Gln His His Cys Ser Ser Gly Glu Ala Asn His Ala Val Leu
            260                 265                 270

Ile Thr Gly Phe Asp Lys Thr Gly Ser Thr Pro Tyr Trp Ile Val Arg
        275                 280                 285

Asn Ser Trp Gly Ser Trp Gly Val Asp Gly Tyr Ala His Val Lys
    290                 295                 300

Met Gly Ser Asn Val Cys Gly Ile Ala Asp Ser Val Ser Ser Ile Phe
305                 310                 315                 320

Val

<210> SEQ ID NO 44
<211> LENGTH: 331
<212> TYPE: PRT
<213> ORGANISM: Homo sapiens

<400> SEQUENCE: 44

Met Lys Arg Leu Val Cys Val Leu Leu Val Cys Ser Ser Ala Val Ala
1               5                   10                  15

Gln Leu His Lys Asp Pro Thr Leu Asp His His Trp His Leu Trp Lys
            20                  25                  30

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Pro Asn
            100                 105                 110

Arg Ile Leu Pro Asp Ser Val Asp Trp Arg Glu Lys Gly Cys Val Thr
        115                 120                 125

Glu Val Lys Tyr Gln Gly Ser Cys Gly Ala Cys Trp Ala Phe Ser Ala
    130                 135                 140

Val Gly Ala Leu Glu Ala Gln Leu Lys Leu Lys Thr Gly Lys Leu Val
145                 150                 155                 160
```

```
Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205

Met Asp Gln Lys Cys Gln Tyr Asp Ser Lys Tyr Arg Ala Ala Thr Cys
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu
        275                 280                 285

Asn Gly Lys Glu Tyr Trp Leu Val Lys Asn Ser Trp Gly His Asn Phe
    290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330

<210> SEQ ID NO 45
<211> LENGTH: 376
<212> TYPE: PRT
<213> ORGANISM: Homo sapiens

<400> SEQUENCE: 45

Met Ala Leu Thr Ala His Pro Ser Cys Leu Leu Ala Leu Leu Val Ala
1               5                   10                  15

Gly Leu Ala Gln Gly Ile Arg Gly Pro Leu Arg Ala Gln Asp Leu Gly
                20                  25                  30

Pro Gln Pro Leu Glu Leu Lys Glu Ala Phe Lys Leu Phe Gln Ile Gln
            35                  40                  45

Phe Asn Arg Ser Tyr Leu Ser Pro Glu Glu His Ala His Arg Leu Asp
    50                  55                  60

Ile Phe Ala His Asn Leu Ala Gln Ala Gln Arg Leu Gln Glu Glu Asp
65                  70                  75                  80

Leu Gly Thr Ala Glu Phe Gly Val Thr Pro Phe Ser Asp Leu Thr Glu
                85                  90                  95

Glu Glu Phe Gly Gln Leu Tyr Gly Tyr Arg Arg Ala Ala Gly Gly Val
            100                 105                 110

Pro Ser Met Gly Arg Glu Ile Arg Ser Glu Pro Glu Glu Ser Val
            115                 120                 125

Pro Phe Ser Cys Asp Trp Arg Lys Val Ala Ser Ala Ile Ser Pro Ile
    130                 135                 140

Lys Asp Gln Lys Asn Cys Asn Cys Cys Trp Ala Met Ala Ala Ala Gly
145                 150                 155                 160

Asn Ile Glu Thr Leu Trp Arg Ile Ser Phe Trp Asp Phe Val Asp Val
                165                 170                 175

Ser Val Gln Glu Leu Leu Asp Cys Gly Arg Cys Gly Asp Gly Cys His
            180                 185                 190

Gly Gly Phe Val Trp Asp Ala Phe Ile Thr Val Leu Asn Asn Ser Gly
```

```
                    195                 200                 205
Leu Ala Ser Glu Lys Asp Tyr Pro Phe Gln Gly Lys Val Arg Ala His
    210                 215                 220
Arg Cys His Pro Lys Lys Tyr Gln Lys Val Ala Trp Ile Gln Asp Phe
225                 230                 235                 240
Ile Met Leu Gln Asn Asn Glu His Arg Ile Ala Gln Tyr Leu Ala Thr
                245                 250                 255
Tyr Gly Pro Ile Thr Val Thr Ile Asn Met Lys Pro Leu Gln Leu Tyr
            260                 265                 270
Arg Lys Gly Val Ile Lys Ala Thr Pro Thr Thr Cys Asp Pro Gln Leu
        275                 280                 285
Val Asp His Ser Val Leu Leu Val Gly Phe Gly Ser Val Lys Ser Glu
    290                 295                 300
Glu Gly Ile Trp Ala Glu Thr Val Ser Ser Gln Ser Gln Pro Gln Pro
305                 310                 315                 320
Pro His Pro Thr Pro Tyr Trp Ile Leu Lys Asn Ser Trp Gly Ala Gln
                325                 330                 335
Trp Gly Glu Lys Gly Tyr Phe Arg Leu His Arg Gly Ser Asn Thr Cys
            340                 345                 350
Gly Ile Thr Lys Phe Pro Leu Thr Ala Arg Val Gln Lys Pro Asp Met
        355                 360                 365
Lys Pro Arg Val Ser Cys Pro Pro
    370                 375

<210> SEQ ID NO 46
<211> LENGTH: 303
<212> TYPE: PRT
<213> ORGANISM: Homo sapiens

<400> SEQUENCE: 46

Met Ala Arg Arg Gly Pro Gly Trp Arg Pro Leu Leu Leu Val Leu
1               5                   10                  15
Leu Ala Gly Ala Ala Gln Gly Gly Leu Tyr Phe Arg Arg Gly Gln Thr
                20                  25                  30
Cys Tyr Arg Pro Leu Arg Gly Asp Gly Leu Ala Pro Leu Gly Arg Ser
            35                  40                  45
Thr Tyr Pro Arg Pro His Glu Tyr Leu Ser Pro Ala Asp Leu Pro Lys
        50                  55                  60
Ser Trp Asp Trp Arg Asn Val Asp Gly Val Asn Tyr Ala Ser Ile Thr
65                  70                  75                  80
Arg Asn Gln His Ile Pro Gln Tyr Cys Gly Ser Cys Trp Ala His Ala
                85                  90                  95
Ser Thr Ser Ala Met Ala Asp Arg Ile Asn Ile Lys Arg Lys Gly Ala
                100                 105                 110
Trp Pro Ser Thr Leu Leu Ser Val Gln Asn Val Ile Asp Cys Gly Asn
            115                 120                 125
Ala Gly Ser Cys Glu Gly Gly Asn Asp Leu Ser Val Trp Asp Tyr Ala
        130                 135                 140
His Gln His Gly Ile Pro Asp Glu Thr Cys Asn Asn Tyr Gln Ala Lys
145                 150                 155                 160
Asp Gln Glu Cys Asp Lys Phe Asn Gln Cys Gly Thr Cys Asn Glu Phe
                165                 170                 175
Lys Glu Cys His Ala Ile Arg Asn Tyr Thr Leu Trp Arg Val Gly Asp
            180                 185                 190
```

```
Tyr Gly Ser Leu Ser Gly Arg Glu Lys Met Met Ala Glu Ile Tyr Ala
            195                 200                 205

Asn Gly Pro Ile Ser Cys Gly Ile Met Ala Thr Glu Arg Leu Ala Asn
        210                 215                 220

Tyr Thr Gly Gly Ile Tyr Ala Glu Tyr Gln Asp Thr Thr Tyr Ile Asn
225                 230                 235                 240

His Val Val Ser Val Ala Gly Trp Gly Ile Ser Asp Gly Thr Glu Tyr
                245                 250                 255

Trp Ile Val Arg Asn Ser Trp Gly Glu Pro Trp Gly Glu Arg Gly Trp
                260                 265                 270

Leu Arg Ile Val Thr Ser Thr Tyr Lys Asp Gly Lys Gly Ala Arg Tyr
                275                 280                 285

Asn Leu Ala Ile Glu Glu His Cys Thr Phe Gly Asp Pro Ile Val
        290                 295                 300

<210> SEQ ID NO 47
<211> LENGTH: 338
<212> TYPE: PRT
<213> ORGANISM: Homo sapiens

<400> SEQUENCE: 47

Met Leu Gln Lys Pro Lys Ser Val Lys Leu Arg Ala Leu Arg Ser Pro
1               5                   10                  15

Arg Lys Phe Gly Val Ala Gly Arg Ser Cys Gln Glu Val Leu Arg Lys
                20                  25                  30

Gly Cys Leu Arg Phe Gln Leu Pro Glu Arg Gly Ser Arg Leu Cys Leu
            35                  40                  45

Tyr Glu Asp Gly Thr Glu Leu Thr Glu Asp Tyr Phe Pro Ser Val Pro
    50                  55                  60

Asp Asn Ala Glu Leu Val Leu Leu Thr Leu Gly Gln Ala Trp Gln Gly
65                  70                  75                  80

Tyr Val Ser Asp Ile Arg Arg Phe Leu Ser Ala Phe His Glu Pro Gln
                85                  90                  95

Val Gly Leu Ile Gln Ala Ala Gln Gln Leu Leu Cys Asp Glu Gln Ala
            100                 105                 110

Pro Gln Arg Gln Arg Leu Leu Ala Asp Leu Leu His Asn Val Ser Gln
        115                 120                 125

Asn Ile Ala Ala Glu Thr Arg Ala Glu Asp Pro Pro Trp Phe Glu Gly
    130                 135                 140

Leu Glu Ser Arg Phe Gln Ser Lys Ser Gly Tyr Leu Arg Tyr Ser Cys
145                 150                 155                 160

Glu Ser Arg Ile Arg Ser Tyr Leu Arg Glu Val Ser Ser Tyr Pro Ser
                165                 170                 175

Thr Val Gly Ala Glu Ala Gln Glu Glu Phe Leu Arg Val Leu Gly Ser
            180                 185                 190

Met Cys Gln Arg Leu Arg Ser Met Gln Tyr Asn Gly Ser Tyr Phe Asp
        195                 200                 205

Arg Gly Ala Lys Gly Gly Ser Arg Leu Cys Thr Pro Glu Gly Trp Phe
    210                 215                 220

Ser Cys Gln Gly Pro Phe Asp Met Asp Ser Cys Leu Ser Arg His Ser
225                 230                 235                 240

Ile Asn Pro Tyr Ser Asn Arg Glu Ser Arg Ile Leu Phe Ser Thr Trp
                245                 250                 255

Asn Leu Asp His Ile Ile Glu Lys Lys Arg Thr Ile Ile Pro Thr Leu
            260                 265                 270
```

```
Val Glu Ala Ile Lys Glu Gln Asp Gly Arg Glu Val Asp Trp Glu Tyr
            275                 280                 285

Phe Tyr Gly Leu Leu Phe Thr Ser Glu Asn Leu Lys Leu Val His Ile
        290                 295                 300

Val Cys His Lys Lys Thr Thr His Lys Leu Asn Cys Asp Pro Ser Arg
305                 310                 315                 320

Ile Tyr Lys Pro Gln Thr Arg Leu Lys Arg Lys Gln Pro Val Arg Lys
                325                 330                 335

Arg Gln

<210> SEQ ID NO 48
<211> LENGTH: 360
<212> TYPE: PRT
<213> ORGANISM: Homo sapiens

<400> SEQUENCE: 48

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300
```

```
His Ala Tyr Phe Ala Gln Tyr His Asp Pro Asp Glu Pro Val Ala
305                 310                 315                 320

Asp Pro Tyr Asp Gln Ser Phe Glu Ser Arg Asp Leu Leu Ile Asp Glu
            325                 330                 335

Trp Lys Ser Leu Thr Tyr Asp Glu Val Ile Ser Phe Val Pro Pro Pro
        340                 345                 350

Leu Asp Gln Glu Glu Met Glu Ser
        355                 360

<210> SEQ ID NO 49
<211> LENGTH: 364
<212> TYPE: PRT
<213> ORGANISM: Homo sapiens

<400> SEQUENCE: 49

Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His
    50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Ile
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
        115                 120                 125

Phe Leu Val Tyr Gln Leu Leu Arg Gly Leu Lys Tyr Ile His Ser Ala
    130                 135                 140

Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                165                 170                 175

Glu Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Gln Gly Lys Ala Leu Phe Pro
    210                 215                 220

Gly Ser Asp Tyr Ile Asp Gln Leu Lys Arg Ile Met Glu Val Val Gly
225                 230                 235                 240

Thr Pro Ser Pro Glu Val Leu Ala Lys Ile Ser Ser Glu His Ala Arg
                245                 250                 255

Thr Tyr Ile Gln Ser Leu Pro Pro Met Pro Gln Lys Asp Leu Ser Ser
            260                 265                 270

Ile Phe Arg Gly Ala Asn Pro Leu Ala Ile Asp Leu Leu Gly Arg Met
        275                 280                 285

Leu Val Leu Asp Ser Asp Gln Arg Val Ser Ala Ala Glu Ala Leu Ala
    290                 295                 300

His Ala Tyr Phe Ser Gln Tyr His Asp Pro Glu Asp Glu Pro Glu Ala
```

```
               305                 310                 315                 320
Glu Pro Tyr Asp Glu Ser Val Glu Ala Lys Glu Arg Thr Leu Glu Glu
                    325                 330                 335

Trp Lys Glu Leu Thr Tyr Gln Glu Val Leu Ser Phe Lys Pro Pro Glu
                340                 345                 350

Pro Pro Lys Pro Pro Gly Ser Leu Glu Ile Glu Gln
            355                 360

<210> SEQ ID NO 50
<211> LENGTH: 367
<212> TYPE: PRT
<213> ORGANISM: Homo sapiens

<400> SEQUENCE: 50

Met Ser Ser Pro Pro Ala Arg Ser Gly Phe Tyr Arg Gln Glu Val
1               5                   10                  15

Thr Lys Thr Ala Trp Glu Val Arg Ala Val Tyr Arg Asp Leu Gln Pro
                20                  25                  30

Val Gly Ser Gly Ala Tyr Gly Ala Val Cys Ser Ala Val Asp Gly Arg
            35                  40                  45

Thr Gly Ala Lys Val Ala Ile Lys Lys Leu Tyr Arg Pro Phe Gln Ser
        50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
            115                 120                 125

Arg Ile Gln Phe Leu Val Tyr Gln Met Leu Lys Gly Leu Arg Tyr Ile
        130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Met Arg Tyr Thr Gln Thr Val Asp
        195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
            260                 265                 270

Phe Ala Ser Ile Leu Thr Asn Ala Ser Pro Leu Ala Val Asn Leu Leu
        275                 280                 285

Glu Lys Met Leu Val Leu Asp Ala Glu Gln Arg Val Thr Ala Gly Glu
    290                 295                 300

Ala Leu Ala His Pro Tyr Phe Glu Ser Leu His Asp Thr Glu Asp Glu
305                 310                 315                 320
```

```
Pro Gln Val Gln Lys Tyr Asp Asp Ser Phe Asp Val Asp Arg Thr
            325                 330                 335

Leu Asp Glu Trp Lys Arg Val Thr Tyr Lys Glu Val Leu Ser Phe Lys
        340                 345                 350

Pro Pro Arg Gln Leu Gly Ala Arg Val Ser Lys Glu Thr Pro Leu
        355                 360                 365
```

<210> SEQ ID NO 51
<211> LENGTH: 365
<212> TYPE: PRT
<213> ORGANISM: Homo sapiens

<400> SEQUENCE: 51

```
Met Ser Leu Ile Arg Lys Lys Gly Phe Tyr Lys Gln Asp Val Asn Lys
1               5                   10                  15

Thr Ala Trp Glu Leu Pro Lys Thr Tyr Val Ser Pro Thr His Val Gly
            20                  25                  30

Ser Gly Ala Tyr Gly Ser Val Cys Ser Ala Ile Asp Lys Arg Ser Gly
        35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
        115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Ala Gln Ala Leu Thr
    290                 295                 300

His Pro Phe Phe Glu Pro Phe Arg Asp Pro Glu Glu Thr Glu Ala
305                 310                 315                 320

Gln Gln Pro Phe Asp Asp Ser Leu Glu His Glu Lys Leu Thr Val Asp
                325                 330                 335
```

Glu Trp Lys Gln His Ile Tyr Lys Glu Ile Val Asn Phe Ser Pro Ile
            340                 345                 350

Ala Arg Lys Asp Ser Arg Arg Ser Gly Met Lys Leu
            355                 360                 365

<210> SEQ ID NO 52
<211> LENGTH: 403
<212> TYPE: PRT
<213> ORGANISM: Homo sapiens

<400> SEQUENCE: 52

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
        50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
        130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
        210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
        290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu

```
                    340                 345                 350
Glu Pro Ser Asn Pro Glu Ala Ser Ser Ser Thr Ser Val Thr Pro Asp
                355                 360                 365
Val Ser Asp Asn Glu Pro Asp His Tyr Arg Tyr Ser Asp Thr Thr Asp
            370                 375                 380
Ser Asp Pro Glu Asn Glu Pro Phe Asp Glu Asp Gln His Thr Gln Ile
385                 390                 395                 400
Thr Lys Val

<210> SEQ ID NO 53
<211> LENGTH: 1154
<212> TYPE: PRT
<213> ORGANISM: Homo sapiens

<400> SEQUENCE: 53

Met Gln Tyr Leu Asn Ile Lys Glu Asp Cys Asn Ala Met Ala Phe Cys
1               5                   10                  15
Ala Lys Met Arg Ser Ser Lys Lys Thr Glu Val Asn Leu Glu Ala Pro
            20                  25                  30
Glu Pro Gly Val Glu Val Ile Phe Tyr Leu Ser Asp Arg Glu Pro Leu
        35                  40                  45
Arg Leu Gly Ser Gly Glu Tyr Thr Ala Glu Glu Leu Cys Ile Arg Ala
    50                  55                  60
Ala Gln Ala Cys Arg Ile Ser Pro Leu Cys His Asn Leu Phe Ala Leu
65                  70                  75                  80
Tyr Asp Glu Asn Thr Lys Leu Trp Tyr Ala Pro Asn Arg Thr Ile Thr
                85                  90                  95
Val Asp Asp Lys Met Ser Leu Arg Leu His Tyr Arg Met Arg Phe Tyr
            100                 105                 110
Phe Thr Asn Trp His Gly Thr Asn Asp Asn Glu Gln Ser Val Trp Arg
        115                 120                 125
His Ser Pro Lys Lys Gln Lys Asn Gly Tyr Glu Lys Lys Lys Ile Pro
    130                 135                 140
Asp Ala Thr Pro Leu Leu Asp Ala Ser Ser Leu Glu Tyr Leu Phe Ala
145                 150                 155                 160
Gln Gly Gln Tyr Asp Leu Val Lys Cys Leu Ala Pro Ile Arg Asp Pro
                165                 170                 175
Lys Thr Glu Gln Asp Gly His Asp Ile Glu Asn Glu Cys Leu Gly Met
            180                 185                 190
Ala Val Leu Ala Ile Ser His Tyr Ala Met Met Lys Lys Met Gln Leu
        195                 200                 205
Pro Glu Leu Pro Lys Asp Ile Ser Tyr Lys Arg Tyr Ile Pro Glu Thr
    210                 215                 220
Leu Asn Lys Ser Ile Arg Gln Arg Asn Leu Leu Thr Arg Met Arg Ile
225                 230                 235                 240
Asn Asn Val Phe Lys Asp Phe Leu Lys Glu Phe Asn Asn Lys Thr Ile
                245                 250                 255
Cys Asp Ser Ser Val Ser Thr His Asp Leu Lys Val Lys Tyr Leu Ala
            260                 265                 270
Thr Leu Glu Thr Leu Thr Lys His Tyr Gly Ala Glu Ile Phe Glu Thr
        275                 280                 285
Ser Met Leu Leu Ile Ser Ser Glu Asn Glu Met Asn Trp Phe His Ser
    290                 295                 300
Asn Asp Gly Gly Asn Val Leu Tyr Tyr Glu Val Met Val Thr Gly Asn
```

```
              305                 310                 315                 320
Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
                340                 345                 350

Asp Glu Glu Lys Asn Lys Ile Arg Glu Glu Trp Asn Asn Phe Ser Tyr
                355                 360                 365

Phe Pro Glu Ile Thr His Ile Val Ile Lys Glu Ser Val Val Ser Ile
370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
                420                 425                 430

Val His Asn Ile Gln Asn Gly Cys His Gly Pro Ile Cys Thr Glu Tyr
                435                 440                 445

Ala Ile Asn Lys Leu Arg Gln Glu Gly Ser Glu Gly Met Tyr Val
450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
                500                 505                 510

Asp Arg Ser Phe Pro Ser Leu Gly Asp Leu Met Ser His Leu Lys Lys
                515                 520                 525

Gln Ile Leu Arg Thr Asp Asn Ile Ser Phe Met Leu Lys Arg Cys Cys
                530                 535                 540

Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
                565                 570                 575

Arg Ile Leu Lys Lys Asp Leu Val Gln Gly Glu His Leu Gly Arg Gly
                580                 585                 590

Thr Arg Thr His Ile Tyr Ser Gly Thr Leu Met Asp Tyr Lys Asp Asp
                595                 600                 605

Glu Gly Thr Ser Glu Glu Lys Lys Ile Lys Val Ile Leu Lys Val Leu
                610                 615                 620

Asp Pro Ser His Arg Asp Ile Ser Leu Ala Phe Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Glu Phe Val Glu Gly
                660                 665                 670

Gly Pro Leu Asp Leu Phe Met His Arg Lys Ser Asp Val Leu Thr Thr
                675                 680                 685

Pro Trp Lys Phe Lys Val Ala Lys Gln Leu Ala Ser Ala Leu Ser Tyr
                690                 695                 700

Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735
```

```
Leu Ser Asp Pro Gly Ile Pro Ile Thr Val Leu Ser Arg Gln Glu Cys
            740                 745                 750

Ile Glu Arg Ile Pro Trp Ile Ala Pro Glu Cys Val Glu Asp Ser Lys
            755                 760                 765

Asn Leu Ser Val Ala Ala Asp Lys Trp Ser Phe Gly Thr Thr Leu Trp
            770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu
            835                 840                 845

Glu Glu Gln Asn Pro Asp Ile Val Ser Glu Lys Lys Pro Ala Thr Glu
            850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
            915                 920                 925

Leu Arg Asn Leu Tyr His Glu Asn Ile Val Lys Tyr Lys Gly Ile Cys
            930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
            980                 985                 990

Tyr Leu Gly Ser Arg Gln Tyr Val His Arg Asp Leu Ala Ala Arg Asn
            995                 1000                1005

Val Leu Val Glu Ser Glu His Gln Val Lys Ile Gly Asp Phe Gly Leu
    1010                1015                1020

Thr Lys Ala Ile Glu Thr Asp Lys Glu Tyr Tyr Thr Val Lys Asp Asp
1025                1030                1035                1040

Arg Asp Ser Pro Val Phe Trp Tyr Ala Pro Glu Cys Leu Met Gln Ser
                1045                1050                1055

Lys Phe Tyr Ile Ala Ser Asp Val Trp Ser Phe Gly Val Thr Leu His
            1060                1065                1070

Glu Leu Leu Thr Tyr Cys Asp Ser Asp Ser Ser Pro Met Ala Leu Phe
            1075                1080                1085

Leu Lys Met Ile Gly Pro Thr His Gly Gln Met Thr Val Thr Arg Leu
            1090                1095                1100

Val Asn Thr Leu Lys Glu Gly Lys Arg Leu Pro Cys Pro Pro Asn Cys
1105                1110                1115                1120

Pro Asp Glu Val Tyr Gln Leu Met Arg Lys Cys Trp Glu Phe Gln Pro
                1125                1130                1135

Ser Asn Arg Thr Ser Phe Gln Asn Leu Ile Glu Gly Phe Glu Ala Leu
            1140                1145                1150
```

Leu Lys

<210> SEQ ID NO 54
<211> LENGTH: 1132
<212> TYPE: PRT
<213> ORGANISM: Homo sapiens

<400> SEQUENCE: 54

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

-continued

```
Ile Asp Gly Tyr Tyr Arg Leu Thr Ala Asp Ala His His Tyr Leu Cys
    370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
                420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
    450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
                500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
                580                 585                 590

Ser Phe Phe Glu Ala Ala Ser Met Met Ser Lys Leu Ser His Lys His
            595                 600                 605

Leu Val Leu Asn Tyr Gly Val Cys Val Cys Gly Asp Glu Asn Ile Leu
    610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670

Asn Val Cys Ala Lys Asn Ile Leu Leu Ile Arg Glu Glu Asp Arg Lys
    675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
            755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
```

```
                785                 790                 795                 800
        Ile Ile Arg Asp Leu Asn Ser Leu Phe Thr Pro Asp Tyr Glu Leu Leu
                        805                 810                 815

Thr Glu Asn Asp Met Leu Pro Asn Met Arg Ile Gly Ala Leu Gly Phe
                    820                 825                 830

Ser Gly Ala Phe Glu Asp Arg Asp Pro Thr Gln Phe Glu Arg His
                835                 840                 845

Leu Lys Phe Leu Gln Gln Leu Gly Lys Gly Asn Phe Gly Ser Val Glu
            850                 855                 860

Met Cys Arg Tyr Asp Pro Leu Gln Asp Asn Thr Gly Glu Val Val Ala
        865                 870                 875                 880

Val Lys Lys Leu Gln His Ser Thr Glu Glu His Leu Arg Asp Phe Glu
                        885                 890                 895

Arg Glu Ile Glu Ile Leu Lys Ser Leu Gln His Asp Asn Ile Val Lys
                    900                 905                 910

Tyr Lys Gly Val Cys Tyr Ser Ala Gly Arg Arg Asn Leu Lys Leu Ile
                915                 920                 925

Met Glu Tyr Leu Pro Tyr Gly Ser Leu Arg Asp Tyr Leu Gln Lys His
            930                 935                 940

Lys Glu Arg Ile Asp His Ile Lys Leu Leu Gln Tyr Thr Ser Gln Ile
        945                 950                 955                 960

Cys Lys Gly Met Glu Tyr Leu Gly Thr Lys Arg Tyr Ile His Arg Asp
                        965                 970                 975

Leu Ala Thr Arg Asn Ile Leu Val Glu Asn Glu Asn Arg Val Lys Ile
                    980                 985                 990

Gly Asp Phe Gly Leu Thr Lys Val Leu Pro Gln Asp Lys Glu Tyr Tyr
                995                 1000                1005

Lys Val Lys Glu Pro Gly Glu Ser Pro Ile Phe Trp Tyr Ala Pro Glu
            1010                1015                1020

Ser Leu Thr Glu Ser Lys Phe Ser Val Ala Ser Asp Val Trp Ser Phe
        1025                1030                1035                1040

Gly Val Val Leu Tyr Glu Leu Phe Thr Tyr Ile Glu Lys Ser Lys Ser
                        1045                1050                1055

Pro Pro Ala Glu Phe Met Arg Met Ile Gly Asn Asp Lys Gln Gly Gln
                    1060                1065                1070

Met Ile Val Phe His Leu Ile Glu Leu Leu Lys Asn Asn Gly Arg Leu
                1075                1080                1085

Pro Arg Pro Asp Gly Cys Pro Asp Glu Ile Tyr Met Ile Met Thr Glu
            1090                1095                1100

Cys Trp Asn Asn Asn Val Asn Gln Arg Pro Ser Phe Arg Asp Leu Ala
        1105                1110                1115                1120

Leu Arg Val Asp Gln Ile Arg Asp Asn Met Ala Gly
                        1125                1130

<210> SEQ ID NO 55
<211> LENGTH: 1124
<212> TYPE: PRT
<213> ORGANISM: Homo sapiens

<400> SEQUENCE: 55

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30
```

-continued

```
Arg Gly Pro Gly Pro Pro Gln Arg Leu Ser Phe Ser Phe Gly Asp His
             35                  40                  45
Leu Ala Glu Asp Leu Cys Val Gln Ala Ala Lys Ala Ser Gly Ile Leu
 50                  55                  60
Pro Val Tyr His Ser Leu Phe Ala Leu Ala Thr Glu Asp Leu Ser Cys
 65                  70                  75                  80
Trp Phe Pro Pro Ser His Ile Phe Ser Val Glu Asp Ala Ser Thr Gln
                 85                  90                  95
Val Leu Leu Tyr Arg Ile Arg Phe Tyr Phe Pro Asn Trp Phe Gly Leu
                100                 105                 110
Glu Lys Cys His Arg Phe Gly Leu Arg Lys Asp Leu Ala Ser Ala Ile
            115                 120                 125
Leu Asp Leu Pro Val Leu Glu His Leu Phe Ala Gln His Arg Ser Asp
130                 135                 140
Leu Val Ser Gly Arg Leu Pro Val Gly Leu Ser Leu Lys Glu Gln Gly
145                 150                 155                 160
Glu Cys Leu Ser Leu Ala Val Leu Asp Leu Ala Arg Met Ala Arg Glu
                165                 170                 175
Gln Ala Gln Arg Pro Gly Glu Leu Leu Lys Thr Val Ser Tyr Lys Ala
            180                 185                 190
Cys Leu Pro Pro Ser Leu Arg Asp Leu Ile Gln Gly Leu Ser Phe Val
            195                 200                 205
Thr Arg Arg Arg Ile Arg Arg Thr Val Arg Arg Ala Leu Arg Arg Val
            210                 215                 220
Ala Ala Cys Gln Ala Asp Arg His Ser Leu Met Ala Lys Tyr Ile Met
225                 230                 235                 240
Asp Leu Glu Arg Leu Asp Pro Ala Gly Ala Ala Glu Thr Phe His Val
                245                 250                 255
Gly Leu Pro Gly Ala Leu Gly Gly His Asp Gly Leu Gly Leu Leu Arg
                260                 265                 270
Val Ala Gly Asp Gly Gly Ile Ala Trp Thr Gln Gly Glu Gln Glu Val
            275                 280                 285
Leu Gln Pro Phe Cys Asp Phe Pro Glu Ile Val Asp Ile Ser Ile Lys
290                 295                 300
Gln Ala Pro Arg Val Gly Pro Ala Gly Glu His Arg Leu Val Thr Val
305                 310                 315                 320
Thr Arg Thr Asp Asn Gln Ile Leu Glu Ala Glu Phe Pro Gly Leu Pro
                325                 330                 335
Glu Ala Leu Ser Phe Val Ala Leu Val Asp Gly Tyr Phe Arg Leu Thr
                340                 345                 350
Thr Asp Ser Gln His Phe Phe Cys Lys Glu Val Ala Pro Pro Arg Leu
            355                 360                 365
Leu Glu Glu Val Ala Glu Gln Cys His Gly Pro Ile Thr Leu Asp Phe
370                 375                 380
Ala Ile Asn Lys Leu Lys Thr Gly Gly Ser Arg Pro Gly Ser Tyr Val
385                 390                 395                 400
Leu Arg Arg Ser Pro Gln Asp Phe Asp Ser Phe Leu Leu Thr Val Cys
                405                 410                 415
Val Gln Asn Pro Leu Gly Pro Asp Tyr Lys Gly Cys Leu Ile Arg Arg
            420                 425                 430
Ser Pro Thr Gly Thr Phe Leu Leu Val Gly Leu Ser Arg Pro His Ser
            435                 440                 445
Ser Leu Arg Glu Leu Leu Ala Thr Cys Trp Asp Gly Gly Leu His Val
```

```
              450                 455                 460
Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
                500                 505                 510

Phe His Lys Ile Pro Ala Asp Ser Leu Glu Trp His Glu Asn Leu Gly
            515                 520                 525

His Gly Ser Phe Thr Lys Ile Tyr Arg Gly Cys Arg His Glu Val Val
        530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
                580                 585                 590

Ala Gly Asp Ser Thr Met Val Gln Glu Phe Val His Leu Gly Ala Ile
            595                 600                 605

Asp Met Tyr Leu Arg Lys Arg Gly His Leu Val Pro Ala Ser Trp Lys
        610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
                660                 665                 670

Gly Val Ser Pro Ala Val Leu Ser Leu Glu Met Leu Thr Asp Arg Ile
            675                 680                 685

Pro Trp Val Ala Pro Glu Cys Leu Arg Glu Ala Gln Thr Leu Ser Leu
        690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
                740                 745                 750

Ala Leu Leu Ile Gln Gln Cys Met Ala Tyr Glu Pro Val Gln Arg Pro
            755                 760                 765

Ser Phe Arg Ala Val Ile Arg Asp Leu Asn Ser Leu Ile Ser Ser Asp
        770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
                820                 825                 830

Phe Gly Ser Val Glu Leu Cys Arg Tyr Asp Pro Leu Gly Asp Asn Thr
            835                 840                 845

Gly Ala Leu Val Ala Val Lys Gln Leu Gln His Ser Gly Pro Asp Gln
        850                 855                 860

Gln Arg Asp Phe Gln Arg Glu Ile Gln Ile Leu Lys Ala Leu His Ser
865                 870                 875                 880
```

```
Asp Phe Ile Val Lys Tyr Arg Gly Val Ser Tyr Gly Pro Gly Arg Gln
            885                 890                 895

Ser Leu Arg Leu Val Met Glu Tyr Leu Pro Ser Gly Cys Leu Arg Asp
        900                 905                 910

Phe Leu Gln Arg His Arg Ala Arg Leu Asp Ala Ser Arg Leu Leu Leu
    915                 920                 925

Tyr Ser Ser Gln Ile Cys Lys Gly Met Glu Tyr Leu Gly Ser Arg Arg
930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
        995                 1000                1005

Asp Val Trp Ser Phe Gly Val Val Leu Tyr Glu Leu Phe Thr Tyr Cys
    1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
                1045                1050                1055

Gly Gln Arg Leu Pro Ala Pro Ala Cys Pro Ala Glu Val His Glu
            1060                1065                1070

Leu Met Lys Leu Cys Trp Ala Pro Ser Pro Gln Asp Arg Pro Ser Phe
        1075                1080                1085

Ser Ala Leu Gly Pro Gln Leu Asp Met Leu Trp Ser Gly Ser Arg Gly
    1090                1095                1100

Cys Glu Thr His Ala Phe Thr Ala His Pro Glu Gly Lys His His Ser
1105                1110                1115                1120

Leu Ser Phe Ser

<210> SEQ ID NO 56
<211> LENGTH: 1187
<212> TYPE: PRT
<213> ORGANISM: Homo sapiens

<400> SEQUENCE: 56

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125
```

```
Gly Thr Glu Ala Ser Ser Asp Gln Thr Ala Gln Gly Met Gln Leu Leu
    130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
                260                 265                 270

Glu Arg Val Pro Val Cys His Leu Arg Leu Leu Ala Gln Ala Glu Gly
            275                 280                 285

Glu Pro Cys Tyr Ile Arg Asp Ser Gly Val Ala Pro Thr Asp Pro Gly
        290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
        355                 360                 365

Pro Arg Glu Pro Leu Trp Ala Tyr Phe Cys Asp Phe Arg Asp Ile Thr
    370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
                405                 410                 415

Val Ser Leu Val Asp Gly Tyr Phe Arg Leu Thr Ala Asp Ser Ser His
                420                 425                 430

Tyr Leu Cys His Glu Val Ala Pro Arg Leu Val Met Ser Ile Arg
            435                 440                 445

Asp Gly Ile His Gly Pro Leu Leu Glu Pro Phe Val Gln Ala Lys Leu
        450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495

Met Gln Ser Leu Arg Leu Arg Lys Phe Pro Ile Glu Gln Gln Asp Gly
            500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
530                 535                 540
```

```
Phe Ser Leu Arg Arg Cys Cys Leu Pro Gln Pro Gly Glu Thr Ser Asn
545                 550                 555                 560

Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
    610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
                660                 665                 670

Val His Gly Val Cys Val Arg Gly Pro Glu Asn Ile Met Val Thr Glu
            675                 680                 685

Tyr Val Glu His Gly Pro Leu Asp Val Trp Leu Arg Arg Glu Arg Gly
        690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
                740                 745                 750

Pro Phe Ile Lys Leu Ser Asp Pro Gly Val Gly Leu Gly Ala Leu Ser
            755                 760                 765

Arg Glu Glu Arg Val Glu Arg Ile Pro Trp Leu Ala Pro Glu Cys Leu
        770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
        835                 840                 845

Leu Thr Tyr Glu Pro Thr Gln Arg Pro Ser Phe Arg Thr Ile Leu Arg
    850                 855                 860

Asp Leu Thr Arg Leu Gln Pro His Asn Leu Ala Asp Val Leu Thr Val
865                 870                 875                 880

Asn Pro Asp Ser Pro Ala Ser Asp Pro Thr Val Phe His Lys Arg Tyr
                885                 890                 895

Leu Lys Lys Ile Arg Asp Leu Gly Glu Gly His Phe Gly Lys Val Ser
                900                 905                 910

Leu Tyr Cys Tyr Asp Pro Thr Asn Asp Gly Thr Gly Glu Met Val Ala
            915                 920                 925

Val Lys Ala Leu Lys Ala Asp Cys Gly Pro Gln His Arg Ser Gly Trp
        930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
```

```
            965                 970                 975
Val Met Glu Tyr Val Pro Leu Gly Ser Leu Arg Asp Tyr Leu Pro Arg
            980                 985                 990

His Ser Ile Gly Leu Ala Gln Leu Leu Phe Ala Gln Gln Ile Cys
            995                1000                1005

Glu Gly Met Ala Tyr Leu His Ala Gln His Tyr Ile His Arg Asp Leu
           1010                1015                1020

Ala Ala Arg Asn Val Leu Leu Asp Asn Asp Arg Leu Val Lys Ile Gly
1025                1030                1035                1040

Asp Phe Gly Leu Ala Lys Ala Val Pro Glu Gly His Glu Tyr Tyr Arg
           1045                1050                1055

Val Arg Glu Asp Gly Asp Ser Pro Val Phe Trp Tyr Ala Pro Glu Cys
           1060                1065                1070

Leu Lys Glu Tyr Lys Phe Tyr Tyr Ala Ser Asp Val Trp Ser Phe Gly
           1075                1080                1085

Val Thr Leu Tyr Glu Leu Leu Thr His Cys Asp Ser Ser Gln Ser Pro
           1090                1095                1100

Pro Thr Lys Phe Leu Glu Leu Ile Gly Ile Ala Gln Gly Gln Met Thr
1105                1110                1115                1120

Val Leu Arg Leu Thr Glu Leu Leu Glu Arg Gly Glu Arg Leu Pro Arg
           1125                1130                1135

Pro Asp Lys Cys Pro Cys Glu Val Tyr His Leu Met Lys Asn Cys Trp
           1140                1145                1150

Glu Thr Glu Ala Ser Phe Arg Pro Thr Phe Glu Asn Leu Ile Pro Ile
           1155                1160                1165

Leu Lys Thr Val His Glu Lys Tyr Gln Gly Gln Ala Pro Ser Val Phe
           1170                1175                1180

Ser Val Cys
1185

<210> SEQ ID NO 57
<211> LENGTH: 906
<212> TYPE: PRT
<213> ORGANISM: Homo sapiens

<400> SEQUENCE: 57

Met Ala Gly Asn Val Lys Lys Ser Ser Gly Ala Gly Gly Ser Gly
1               5                  10                  15

Ser Gly Gly Ser Gly Ser Gly Gly Leu Ile Gly Leu Met Lys Asp Ala
            20                  25                  30

Phe Gln Pro His His His His His His Leu Ser Pro His Pro Pro
            35                  40                  45

Gly Thr Val Asp Lys Lys Met Val Glu Lys Cys Trp Lys Leu Met Asp
        50                  55                  60

Lys Val Val Arg Leu Cys Gln Asn Pro Lys Leu Ala Leu Lys Asn Ser
65                  70                  75                  80

Pro Pro Tyr Ile Leu Asp Leu Leu Pro Asp Thr Tyr Gln His Leu Arg
            85                  90                  95

Thr Ile Leu Ser Arg Tyr Glu Gly Lys Met Glu Thr Leu Gly Glu Asn
            100                 105                 110

Glu Tyr Phe Arg Val Phe Met Glu Asn Leu Met Lys Lys Thr Lys Gln
            115                 120                 125

Thr Ile Ser Leu Phe Lys Glu Gly Lys Glu Arg Met Tyr Glu Glu Asn
        130                 135                 140
```

```
Ser Gln Pro Arg Arg Asn Leu Thr Lys Leu Ser Leu Ile Phe Ser His
145                 150                 155                 160

Met Leu Ala Glu Leu Lys Gly Ile Phe Pro Ser Gly Leu Phe Gln Gly
            165                 170                 175

Asp Thr Phe Arg Ile Thr Lys Ala Asp Ala Ala Glu Phe Trp Arg Lys
            180                 185                 190

Ala Phe Gly Glu Lys Thr Ile Val Pro Trp Lys Ser Phe Arg Gln Ala
            195                 200                 205

Leu His Glu Val His Pro Ile Ser Ser Gly Leu Glu Ala Met Ala Leu
            210                 215                 220

Lys Ser Thr Ile Asp Leu Thr Cys Asn Asp Tyr Ile Ser Val Phe Glu
225                 230                 235                 240

Phe Asp Ile Phe Thr Arg Leu Phe Gln Pro Trp Ser Ser Leu Leu Arg
                245                 250                 255

Asn Trp Asn Ser Leu Ala Val Thr His Pro Gly Tyr Met Ala Phe Leu
                260                 265                 270

Thr Tyr Asp Glu Val Lys Ala Arg Leu Gln Lys Phe Ile His Lys Pro
            275                 280                 285

Gly Ser Tyr Ile Phe Arg Leu Ser Cys Thr Arg Leu Gly Gln Trp Ala
            290                 295                 300

Ile Gly Tyr Val Thr Ala Asp Gly Asn Ile Leu Gln Thr Ile Pro His
305                 310                 315                 320

Asn Lys Pro Leu Phe Gln Ala Leu Ile Asp Gly Phe Arg Glu Gly Phe
                325                 330                 335

Tyr Leu Phe Pro Asp Gly Arg Asn Gln Asn Pro Asp Leu Thr Gly Leu
                340                 345                 350

Cys Glu Pro Thr Pro Gln Asp His Ile Lys Val Thr Gln Glu Gln Tyr
            355                 360                 365

Glu Leu Tyr Cys Glu Met Gly Ser Thr Phe Gln Leu Cys Lys Ile Cys
            370                 375                 380

Ala Glu Asn Asp Lys Asp Val Lys Ile Glu Pro Cys Gly His Leu Met
385                 390                 395                 400

Cys Thr Ser Cys Leu Thr Ser Trp Gln Glu Ser Glu Gly Gln Gly Cys
                405                 410                 415

Pro Phe Cys Arg Cys Glu Ile Lys Gly Thr Glu Pro Ile Val Val Asp
            420                 425                 430

Pro Phe Asp Pro Arg Gly Ser Gly Ser Leu Leu Arg Gln Gly Ala Glu
            435                 440                 445

Gly Ala Pro Ser Pro Asn Tyr Asp Asp Asp Asp Glu Arg Ala Asp
450                 455                 460

Asp Thr Leu Phe Met Met Lys Glu Leu Ala Gly Ala Lys Val Glu Arg
465                 470                 475                 480

Pro Pro Ser Pro Phe Ser Met Ala Pro Gln Ala Ser Leu Pro Pro Val
            485                 490                 495

Pro Pro Arg Leu Asp Leu Leu Pro Gln Arg Val Cys Val Pro Ser Ser
            500                 505                 510

Ala Ser Ala Leu Gly Thr Ala Ser Lys Ala Ala Ser Gly Ser Leu His
            515                 520                 525

Lys Asp Lys Pro Leu Pro Val Pro Pro Thr Leu Arg Asp Leu Pro Pro
            530                 535                 540

Pro Pro Pro Pro Asp Arg Pro Tyr Ser Val Gly Ala Glu Ser Arg Pro
545                 550                 555                 560

Gln Arg Arg Pro Leu Pro Cys Thr Pro Gly Asp Cys Pro Ser Arg Asp
```

```
                 565                 570                 575
Lys Leu Pro Pro Val Pro Ser Ser Arg Leu Gly Asp Ser Trp Leu Pro
            580                 585                 590

Arg Pro Ile Pro Lys Val Pro Ser Ala Pro Ser Ser Ser Asp Pro
        595                 600                 605

Trp Thr Gly Arg Glu Leu Thr Asn Arg His Ser Leu Pro Phe Ser Leu
        610                 615                 620

Pro Ser Gln Met Glu Pro Arg Pro Asp Val Pro Arg Leu Gly Ser Thr
625                 630                 635                 640

Phe Ser Leu Asp Thr Ser Met Ser Met Asn Ser Ser Pro Leu Val Gly
            645                 650                 655

Pro Glu Cys Asp His Pro Lys Ile Lys Pro Ser Ser Ser Ala Asn Ala
        660                 665                 670

Ile Tyr Ser Leu Ala Ala Arg Pro Leu Pro Val Pro Lys Leu Pro Pro
        675                 680                 685

Gly Glu Gln Cys Glu Gly Glu Glu Asp Thr Glu Tyr Met Thr Pro Ser
        690                 695                 700

Ser Arg Pro Leu Arg Pro Leu Asp Thr Ser Gln Ser Ser Arg Ala Cys
705                 710                 715                 720

Asp Cys Asp Gln Gln Ile Asp Ser Cys Thr Tyr Glu Ala Met Tyr Asn
                725                 730                 735

Ile Gln Ser Gln Ala Pro Ser Ile Thr Glu Ser Ser Thr Phe Gly Glu
            740                 745                 750

Gly Asn Leu Ala Ala Ala His Ala Asn Thr Gly Pro Glu Glu Ser Glu
            755                 760                 765

Asn Glu Asp Asp Gly Tyr Asp Val Pro Lys Pro Pro Val Pro Ala Val
        770                 775                 780

Leu Ala Arg Arg Thr Leu Ser Asp Ile Ser Asn Ala Ser Ser Ser Phe
785                 790                 795                 800

Gly Trp Leu Ser Leu Asp Gly Asp Pro Thr Thr Asn Val Thr Glu Gly
                805                 810                 815

Ser Gln Val Pro Glu Arg Pro Pro Lys Pro Phe Pro Arg Arg Ile Asn
            820                 825                 830

Ser Glu Arg Lys Ala Gly Ser Cys Gln Gln Gly Ser Gly Pro Ala Ala
        835                 840                 845

Ser Ala Ala Thr Ala Ser Pro Gln Leu Ser Ser Glu Ile Glu Asn Leu
    850                 855                 860

Met Ser Gln Gly Tyr Ser Tyr Gln Asp Ile Gln Lys Ala Leu Val Ile
865                 870                 875                 880

Ala Gln Asn Asn Ile Glu Met Ala Lys Asn Ile Leu Arg Glu Phe Val
                885                 890                 895

Ser Ile Ser Ser Pro Ala His Val Ala Thr
            900                 905

<210> SEQ ID NO 58
<211> LENGTH: 465
<212> TYPE: PRT
<213> ORGANISM: Homo sapiens

<400> SEQUENCE: 58

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30
```

-continued

Arg Gln Gly Val Pro Ala Asp Gln Leu Arg Val Ile Phe Ala Gly Lys
            35                  40                  45

Glu Leu Arg Asn Asp Trp Thr Val Gln Asn Cys Asp Leu Asp Gln Gln
 50                  55                  60

Ser Ile Val His Ile Val Gln Arg Pro Trp Arg Lys Gly Gln Glu Met
65                  70                  75                  80

Asn Ala Thr Gly Gly Asp Pro Arg Asn Ala Ala Gly Gly Cys Glu
                85                  90                  95

Arg Glu Pro Gln Ser Leu Thr Arg Val Asp Leu Ser Ser Val Leu
                100                 105                 110

Pro Gly Asp Ser Val Gly Leu Ala Val Ile Leu His Thr Asp Ser Arg
            115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Ser Val
    210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285

Cys Val Ala Gly Cys Pro Asn Ser Leu Ile Lys Glu Leu His His Phe
    290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
        355                 360                 365

Lys Glu Ala Tyr His Glu Gly Glu Cys Ser Ala Val Phe Glu Ala Ser
    370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
        435                 440                 445

Cys Gly Cys Glu Trp Asn Arg Val Cys Met Gly Asp His Trp Phe Asp

-continued

```
                450                 455                 460

Val
465

<210> SEQ ID NO 59
<211> LENGTH: 108
<212> TYPE: PRT
<213> ORGANISM: Homo sapiens

<400> SEQUENCE: 59

Met Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
                20                  25                  30

Trp Ala Trp Asp Ile Val Val Asp Asn Cys Ala Ile Cys Arg Asn His
                35                  40                  45

Ile Met Asp Leu Cys Ile Glu Cys Gln Ala Asn Gln Ala Ser Ala Thr
50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
                100                 105

<210> SEQ ID NO 60
<211> LENGTH: 501
<212> TYPE: PRT
<213> ORGANISM: Homo sapiens

<400> SEQUENCE: 60

Met Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
                20                  25                  30

Leu Cys Ser Ala Cys Arg Asn Val Leu Arg Arg Pro Phe Gln Ala Gln
                35                  40                  45

Cys Gly His Arg Tyr Cys Ser Phe Cys Leu Ala Ser Ile Leu Ser Ser
        50                  55                  60

Gly Pro Gln Asn Cys Ala Ala Cys Val His Glu Gly Ile Tyr Glu Glu
65                  70                  75                  80

Gly Ile Ser Ile Leu Glu Ser Ser Ala Phe Pro Asp Asn Ala Ala
                85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
        115                 120                 125

Cys Pro Leu Met Leu Thr Glu Cys Pro Ala Cys Lys Gly Leu Val Arg
        130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
```

```
                    195                 200                 205
        Cys Gly Lys Cys Arg Val Pro Cys Arg Phe His Ala Ile Gly Cys Leu
                    210                 215                 220

Glu Thr Val Glu Gly Glu Lys Gln Gln Glu His Glu Val Gln Trp Leu
        225                 230                 235                 240

Arg Glu His Leu Ala Met Leu Leu Ser Ser Val Leu Glu Ala Lys Pro
                            245                 250                 255

Leu Leu Gly Asp Gln Ser His Ala Gly Ser Glu Leu Leu Gln Arg Cys
                        260                 265                 270

Glu Ser Leu Glu Lys Lys Thr Ala Thr Phe Glu Asn Ile Val Cys Val
                    275                 280                 285

Leu Asn Arg Glu Val Glu Arg Val Ala Met Thr Ala Glu Ala Cys Ser
        290                 295                 300

Arg Gln His Arg Leu Asp Gln Asp Lys Ile Glu Ala Leu Ser Ser Lys
        305                 310                 315                 320

Val Gln Gln Leu Glu Arg Ser Ile Gly Leu Lys Asp Leu Ala Met Ala
                        325                 330                 335

Asp Leu Glu Gln Lys Val Leu Glu Met Glu Ala Ser Thr Tyr Asp Gly
                    340                 345                 350

Val Phe Ile Trp Lys Ile Ser Asp Phe Ala Arg Lys Arg Gln Glu Ala
                355                 360                 365

Val Ala Gly Arg Ile Pro Ala Ile Phe Ser Pro Ala Phe Tyr Thr Ser
        370                 375                 380

Arg Tyr Gly Tyr Lys Met Cys Leu Arg Ile Tyr Leu Asn Gly Asp Gly
        385                 390                 395                 400

Thr Gly Arg Gly Thr His Leu Ser Leu Phe Phe Val Val Met Lys Gly
                        405                 410                 415

Pro Asn Asp Ala Leu Leu Arg Trp Pro Phe Asn Gln Lys Val Thr Leu
                    420                 425                 430

Met Leu Leu Asp Gln Asn Asn Arg Glu His Val Ile Asp Ala Phe Arg
                435                 440                 445

Pro Asp Val Thr Ser Ser Ser Phe Gln Arg Pro Val Asn Asp Met Asn
        450                 455                 460

Ile Ala Ser Gly Cys Pro Leu Phe Cys Pro Val Ser Lys Met Glu Ala
        465                 470                 475                 480

Lys Asn Ser Tyr Val Arg Asp Asp Ala Ile Phe Ile Lys Ala Ile Val
                        485                 490                 495

Asp Leu Thr Gly Leu
                        500

<210> SEQ ID NO 61
<211> LENGTH: 491
<212> TYPE: PRT
<213> ORGANISM: Homo sapiens

<400> SEQUENCE: 61

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
                20                  25                  30

Leu Leu Leu Lys Leu Leu Lys Ser Val Gly Ala Gln Lys Asp Thr Tyr
            35                  40                  45

Thr Met Lys Glu Val Leu Phe Tyr Leu Gly Gln Tyr Ile Met Thr Lys
        50                  55                  60
```

-continued

```
Arg Leu Tyr Asp Glu Lys Gln Gln His Ile Val Tyr Cys Ser Asn Asp
 65                  70                  75                  80

Leu Leu Gly Asp Leu Phe Gly Val Pro Ser Phe Ser Val Lys Glu His
                 85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
            115                 120                 125

Leu Glu Gly Gly Ser Asp Gln Lys Asp Leu Val Gln Glu Leu Gln Glu
            130                 135                 140

Glu Lys Pro Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
            195                 200                 205

Arg Ser Ser Ser Glu Ser Thr Gly Thr Pro Ser Asn Pro Asp Leu
210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
            275                 280                 285

Asp Ser Phe Glu Glu Asp Pro Glu Ile Ser Leu Ala Asp Tyr Trp Lys
            290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
            355                 360                 365

Asp Ser Arg Glu Ser Cys Val Glu Glu Asn Asp Lys Ile Thr Gln
            370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Ser Val Glu Ser Ser Leu Pro Leu
            420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
            450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
```

<210> SEQ ID NO 62
<211> LENGTH: 240
<212> TYPE: PRT
<213> ORGANISM: Renilla reniformis

<400> SEQUENCE: 62

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

<210> SEQ ID NO 63
<211> LENGTH: 320
<212> TYPE: PRT
<213> ORGANISM: Homo sapiens

<400> SEQUENCE: 63

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp

```
                        85                  90                  95
Ala Cys Lys Ala Cys Lys Arg Lys Thr Thr Asn Ala Asp Arg Arg Lys
            100                 105                 110

Ala Ala Thr Met Arg Glu Arg Arg Leu Ser Lys Val Asn Glu Ala
            115                 120                 125

Phe Glu Thr Leu Lys Arg Cys Thr Ser Ser Asn Pro Asn Gln Arg Leu
            130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Ala Phe Tyr Ala Pro Gly Pro Leu Pro Pro Gly Arg Gly Gly Glu His
                180                 185                 190

Tyr Ser Gly Asp Ser Asp Ala Ser Ser Pro Arg Ser Asn Cys Ser Asp
                195                 200                 205

Gly Met Met Asp Tyr Ser Gly Pro Pro Ser Gly Ala Arg Arg Arg Asn
            210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
                245                 250                 255

Glu Arg Ile Ser Thr Glu Ser Pro Ala Ala Pro Ala Leu Leu Leu Ala
                260                 265                 270

Asp Val Pro Ser Glu Ser Pro Pro Arg Arg Gln Glu Ala Ala Ala Pro
            275                 280                 285

Ser Glu Gly Glu Ser Ser Gly Asp Pro Thr Gln Ser Pro Asp Ala Ala
            290                 295                 300

Pro Gln Cys Pro Ala Gly Ala Asn Pro Asn Pro Ile Tyr Gln Val Leu
305                 310                 315                 320

<210> SEQ ID NO 64
<211> LENGTH: 607
<212> TYPE: PRT
<213> ORGANISM: Homo sapiens

<400> SEQUENCE: 64

Met Ala Glu Lys Arg Arg Gly Ser Pro Cys Ser Met Leu Ser Leu Lys
1               5                   10                  15

Ala His Ala Phe Ser Val Glu Ala Leu Ile Gly Ala Glu Lys Gln Gln
                20                  25                  30

Gln Leu Gln Lys Lys Arg Arg Lys Leu Gly Ala Glu Ala Ala Gly
            35                  40                  45

Ala Val Asp Asp Gly Gly Cys Ser Arg Gly Gly Gly Ala Gly Glu Lys
50                  55                  60

Gly Ser Ser Glu Gly Asp Glu Gly Ala Ala Leu Pro Pro Pro Ala Gly
65                  70                  75                  80

Ala Thr Ser Gly Pro Ala Arg Ser Gly Ala Asp Leu Glu Arg Gly Ala
                85                  90                  95

Ala Gly Gly Cys Glu Asp Gly Phe Gln Gln Gly Ala Ser Pro Leu Ala
            100                 105                 110

Ser Pro Gly Gly Ser Pro Lys Gly Ser Pro Ala Arg Ser Leu Ala Arg
            115                 120                 125

Pro Gly Thr Pro Leu Pro Ser Pro Gln Ala Pro Arg Val Asp Leu Gln
            130                 135                 140
```

-continued

```
Gly Ala Glu Leu Trp Lys Arg Phe His Glu Ile Gly Thr Glu Met Ile
145                 150                 155                 160

Ile Thr Lys Ala Gly Arg Arg Met Phe Pro Ala Met Arg Val Lys Ile
                165                 170                 175

Ser Gly Leu Asp Pro His Gln Gln Tyr Tyr Ile Ala Met Asp Ile Val
            180                 185                 190

Pro Val Asp Asn Lys Arg Tyr Arg Tyr Val Tyr His Ser Ser Lys Trp
        195                 200                 205

Met Val Ala Gly Asn Ala Asp Ser Pro Val Pro Arg Val Tyr Ile
    210                 215                 220

His Pro Asp Ser Pro Ala Ser Gly Glu Thr Trp Met Arg Gln Val Ile
225                 230                 235                 240

Ser Phe Asp Lys Leu Lys Leu Thr Asn Asn Glu Leu Asp Asp Gln Gly
                245                 250                 255

His Ile Ile Leu His Ser Met His Lys Tyr Gln Pro Arg Val His Val
            260                 265                 270

Ile Arg Lys Asp Cys Gly Asp Asp Leu Ser Pro Ile Lys Pro Val Pro
        275                 280                 285

Ser Gly Glu Gly Val Lys Ala Phe Ser Phe Pro Glu Thr Val Phe Thr
290                 295                 300

Thr Val Thr Ala Tyr Gln Asn Gln Ile Thr Arg Leu Lys Ile Asp
305                 310                 315                 320

Arg Asn Pro Phe Ala Lys Gly Phe Arg Asp Ser Gly Arg Asn Arg Met
                325                 330                 335

Gly Leu Glu Ala Leu Val Glu Ser Tyr Ala Phe Trp Arg Pro Ser Leu
            340                 345                 350

Arg Thr Leu Thr Phe Glu Asp Ile Pro Gly Ile Pro Lys Gln Gly Asn
        355                 360                 365

Ala Ser Ser Ser Thr Leu Leu Gln Gly Thr Gly Asn Gly Val Pro Ala
370                 375                 380

Thr His Pro His Leu Leu Ser Gly Ser Ser Cys Ser Ser Pro Ala Phe
385                 390                 395                 400

His Leu Gly Pro Asn Thr Ser Gln Leu Cys Ser Leu Ala Pro Ala Asp
                405                 410                 415

Tyr Ser Ala Cys Ala Arg Ser Gly Leu Thr Leu Asn Arg Tyr Ser Thr
            420                 425                 430

Ser Leu Ala Glu Thr Tyr Asn Arg Leu Thr Asn Gln Ala Gly Glu Thr
        435                 440                 445

Phe Ala Pro Pro Arg Thr Pro Ser Tyr Val Gly Val Ser Ser Ser Thr
450                 455                 460

Ser Val Asn Met Ser Met Gly Gly Thr Asp Gly Asp Thr Phe Ser Cys
465                 470                 475                 480

Pro Gln Thr Ser Leu Ser Met Gln Ile Ser Gly Met Ser Pro Gln Leu
                485                 490                 495

Gln Tyr Ile Met Pro Ser Pro Ser Ser Asn Ala Phe Ala Thr Asn Gln
            500                 505                 510

Thr His Gln Gly Ser Tyr Asn Thr Phe Arg Leu His Ser Pro Cys Ala
        515                 520                 525

Leu Tyr Gly Tyr Asn Phe Ser Thr Ser Pro Lys Leu Ala Ala Ser Pro
530                 535                 540

Glu Lys Ile Val Ser Ser Gln Gly Ser Phe Leu Gly Ser Ser Pro Ser
545                 550                 555                 560

Gly Thr Met Thr Asp Arg Gln Met Leu Pro Pro Val Glu Gly Val His
```

```
                        565                 570                 575
Leu Leu Ser Ser Gly Gly Gln Gln Ser Phe Phe Asp Ser Arg Thr Leu
                    580                 585                 590

Gly Ser Leu Thr Leu Ser Ser Ser Gln Val Ser Ala His Met Val
            595                 600                 605

<210> SEQ ID NO 65
<211> LENGTH: 393
<212> TYPE: PRT
<213> ORGANISM: Homo sapiens

<400> SEQUENCE: 65

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335
```

```
Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 66
<211> LENGTH: 215
<212> TYPE: PRT
<213> ORGANISM: Homo sapiens

<400> SEQUENCE: 66

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 67
<211> LENGTH: 356
<212> TYPE: PRT
<213> ORGANISM: Homo sapiens

<400> SEQUENCE: 67

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Leu Glu Thr Met Asn Ala
        35                  40                  45
```

Glu Glu Asp Ser Leu Arg Asn Gly Gly Glu Glu Asp Glu Asp Glu
 50                  55                  60

Asp Leu Glu Glu Glu Glu Glu Glu Glu Asp Asp Asp Gln Lys
 65                  70                  75              80

Pro Lys Arg Arg Gly Pro Lys Lys Lys Met Thr Lys Ala Arg Leu
                 85                  90                  95

Glu Arg Phe Lys Leu Arg Arg Met Lys Ala Asn Ala Arg Glu Arg Asn
                100                 105                 110

Arg Met His Gly Leu Asn Ala Ala Leu Asp Asn Leu Arg Lys Val Val
            115                 120                 125

Pro Cys Tyr Ser Lys Thr Gln Lys Leu Ser Lys Ile Glu Thr Leu Arg
130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
            195                 200                 205

Thr Ala Ser Ala Ser Phe Pro Val His Pro Tyr Ser Tyr Gln Ser Pro
210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
            275                 280                 285

Pro Ser Ala Glu Phe Glu Lys Asn Tyr Ala Phe Thr Met His Tyr Pro
290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355

<210> SEQ ID NO 68
<211> LENGTH: 498
<212> TYPE: PRT
<213> ORGANISM: Homo sapiens

<400> SEQUENCE: 68

Met Asn Gln Ser Ile Pro Val Ala Pro Thr Pro Pro Arg Arg Val Arg
 1               5                  10                  15

Leu Lys Pro Trp Leu Val Ala Gln Val Asn Ser Cys Gly Tyr Pro Gly
                20                  25                  30

Leu Gln Trp Val Asn Gly Glu Lys Lys Leu Phe Cys Ile Pro Trp Arg
            35                  40                  45

His Ala Thr Arg His Gly Pro Ser Gln Asp Gly Asp Asn Thr Ile Phe
 50                  55                  60

```
Lys Ala Trp Ala Lys Glu Thr Gly Lys Tyr Thr Gly Val Asp Glu
 65                  70                  75                  80

Ala Asp Pro Ala Lys Trp Lys Ala Asn Leu Arg Cys Ala Leu Asn Lys
                 85                  90                  95

Ser Arg Asp Phe Arg Leu Ile Tyr Asp Gly Pro Arg Asp Met Pro Pro
            100                 105                 110

Gln Pro Tyr Lys Ile Tyr Glu Val Cys Ser Asn Gly Pro Ala Pro Thr
        115                 120                 125

Asp Ser Gln Pro Pro Glu Asp Tyr Ser Phe Gly Ala Gly Glu Glu Glu
            130                 135                 140

Glu Glu Glu Glu Glu Leu Gln Arg Met Leu Pro Ser Leu Ser Leu Thr
145                 150                 155                 160

Glu Asp Val Lys Trp Pro Pro Thr Leu Gln Pro Pro Thr Leu Arg Pro
                165                 170                 175

Pro Thr Leu Gln Pro Pro Thr Leu Gln Pro Pro Val Val Leu Gly Pro
            180                 185                 190

Pro Ala Pro Asp Pro Ser Pro Leu Ala Pro Pro Gly Asn Pro Ala
        195                 200                 205

Gly Phe Arg Glu Leu Leu Ser Glu Val Leu Glu Pro Gly Pro Leu Pro
210                 215                 220

Ala Ser Leu Pro Pro Ala Gly Glu Gln Leu Leu Pro Asp Leu Leu Ile
225                 230                 235                 240

Ser Pro His Met Leu Pro Leu Thr Asp Leu Glu Ile Lys Phe Gln Tyr
            245                 250                 255

Arg Gly Arg Pro Pro Arg Ala Leu Thr Ile Ser Asn Pro His Gly Cys
            260                 265                 270

Arg Leu Phe Tyr Ser Gln Leu Glu Ala Thr Gln Glu Gln Val Glu Leu
        275                 280                 285

Phe Gly Pro Ile Ser Leu Glu Gln Val Arg Phe Pro Ser Pro Glu Asp
        290                 295                 300

Ile Pro Ser Asp Lys Gln Arg Phe Tyr Thr Asn Gln Leu Leu Asp Val
305                 310                 315                 320

Leu Asp Arg Gly Leu Ile Leu Gln Leu Gln Gly Gln Asp Leu Tyr Ala
                325                 330                 335

Ile Arg Leu Cys Gln Cys Lys Val Phe Trp Ser Gly Pro Cys Ala Ser
            340                 345                 350

Ala His Asp Ser Cys Pro Asn Pro Ile Gln Arg Glu Val Lys Thr Lys
        355                 360                 365

Leu Phe Ser Leu Glu His Phe Leu Asn Glu Leu Ile Leu Phe Gln Lys
370                 375                 380

Gly Gln Thr Asn Thr Pro Pro Phe Glu Ile Phe Phe Cys Phe Gly
385                 390                 395                 400

Glu Glu Trp Pro Asp Arg Lys Pro Arg Glu Lys Lys Leu Ile Thr Val
                405                 410                 415

Gln Val Val Pro Val Ala Ala Arg Leu Leu Glu Met Phe Ser Gly
                420                 425                 430

Glu Leu Ser Trp Ser Ala Asp Ser Ile Arg Leu Gln Ile Ser Asn Pro
        435                 440                 445

Asp Leu Lys Asp Arg Met Val Glu Gln Phe Lys Glu Leu His His Ile
        450                 455                 460

Trp Gln Ser Gln Gln Arg Leu Gln Pro Val Ala Gln Ala Pro Pro Gly
465                 470                 475                 480
```

```
Ala Gly Leu Gly Val Gly Gln Gly Pro Trp Pro Met His Pro Ala Gly
            485                 490                 495

Met Gln

<210> SEQ ID NO 69
<211> LENGTH: 427
<212> TYPE: PRT
<213> ORGANISM: Homo sapiens

<400> SEQUENCE: 69

Met Gly Thr Pro Lys Pro Arg Ile Leu Pro Trp Leu Val Ser Gln Leu
1               5                   10                  15

Asp Leu Gly Gln Leu Glu Gly Val Ala Trp Val Asn Lys Ser Arg Thr
            20                  25                  30

Arg Phe Arg Ile Pro Trp Lys His Gly Leu Arg Gln Asp Ala Gln Gln
        35                  40                  45

Glu Asp Phe Gly Ile Phe Gln Ala Trp Ala Glu Ala Thr Gly Ala Tyr
    50                  55                  60

Val Pro Gly Arg Asp Lys Pro Asp Leu Pro Thr Trp Lys Arg Asn Phe
65                  70                  75                  80

Arg Ser Ala Leu Asn Arg Lys Glu Gly Leu Arg Leu Ala Glu Asp Arg
                85                  90                  95

Ser Lys Asp Pro His Asp Pro His Lys Ile Tyr Glu Phe Val Asn Ser
            100                 105                 110

Gly Val Gly Asp Phe Ser Gln Pro Asp Thr Ser Pro Asp Thr Asn Gly
        115                 120                 125

Gly Gly Ser Thr Ser Asp Thr Gln Glu Asp Ile Leu Asp Glu Leu Leu
    130                 135                 140

Gly Asn Met Val Leu Ala Pro Leu Pro Asp Pro Gly Pro Pro Ser Leu
145                 150                 155                 160

Ala Val Ala Pro Glu Pro Cys Pro Gln Pro Leu Arg Ser Pro Ser Leu
                165                 170                 175

Asp Asn Pro Thr Pro Phe Pro Asn Leu Gly Pro Ser Glu Asn Pro Leu
            180                 185                 190

Lys Arg Leu Leu Val Pro Gly Glu Glu Trp Glu Phe Glu Val Thr Ala
        195                 200                 205

Phe Tyr Arg Gly Arg Gln Val Phe Gln Gln Thr Ile Ser Cys Pro Glu
    210                 215                 220

Gly Leu Arg Leu Val Gly Ser Glu Val Gly Asp Arg Thr Leu Pro Gly
225                 230                 235                 240

Trp Pro Val Thr Leu Pro Asp Pro Gly Met Ser Leu Thr Asp Arg Gly
                245                 250                 255

Val Met Ser Tyr Val Arg His Val Leu Ser Cys Leu Gly Gly Gly Leu
            260                 265                 270

Ala Leu Trp Arg Ala Gly Gln Trp Leu Trp Ala Gln Arg Leu Gly His
        275                 280                 285

Cys His Thr Tyr Trp Ala Val Ser Glu Glu Leu Leu Pro Asn Ser Gly
    290                 295                 300

His Gly Pro Asp Gly Glu Val Pro Lys Asp Lys Glu Gly Gly Val Phe
305                 310                 315                 320

Asp Leu Gly Pro Phe Ile Val Asp Leu Ile Thr Phe Thr Glu Gly Ser
                325                 330                 335

Gly Arg Ser Pro Arg Tyr Ala Leu Trp Phe Cys Val Gly Glu Ser Trp
            340                 345                 350
```

```
Pro Gln Asp Gln Pro Trp Thr Lys Arg Leu Val Met Lys Val Val
            355                 360                 365

Pro Thr Cys Leu Arg Ala Leu Val Glu Met Ala Arg Val Gly Gly Ala
            370                 375                 380

Ser Ser Leu Glu Asn Thr Val Asp Leu His Ile Ser Asn Ser His Pro
385                 390                 395                 400

Leu Ser Leu Thr Ser Asp Gln Tyr Lys Ala Tyr Leu Gln Asp Leu Val
            405                 410                 415

Glu Gly Met Asp Phe Gln Gly Pro Gly Glu Ser
            420                 425

<210> SEQ ID NO 70
<211> LENGTH: 750
<212> TYPE: PRT
<213> ORGANISM: Homo sapiens

<400> SEQUENCE: 70

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300
```

-continued

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Val Lys Leu Gln
            340                 345                 350

Glu Leu Asn Tyr Asn Leu Lys Val Lys Val Leu Phe Asp Lys Asp Val
                355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
            435                 440                 445

Glu Thr Thr Ser Leu Pro Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
                485                 490                 495

Gln Leu Ser Glu Val Leu Ser Trp Gln Phe Ser Ser Val Thr Lys Arg
                500                 505                 510

Gly Leu Asn Val Asp Gln Leu Asn Met Leu Gly Glu Lys Leu Leu Gly
                515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
                610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
                675                 680                 685

Glu Pro Met Glu Leu Asp Gly Pro Lys Gly Thr Gly Tyr Ile Lys Thr
                690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
            740                 745                 750

<210> SEQ ID NO 71
<211> LENGTH: 225
<212> TYPE: PRT
<213> ORGANISM: Homo sapiens

<400> SEQUENCE: 71

Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
        115                 120                 125

Pro Pro Pro Gly Ala Pro Ser Phe Pro Ser Pro Pro Thr Glu Pro Ser
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225

<210> SEQ ID NO 72
<211> LENGTH: 770
<212> TYPE: PRT
<213> ORGANISM: Homo sapiens

<400> SEQUENCE: 72

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

```
Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
                180                 185                 190

Gln Ser Val Thr Arg Gln Lys Met Gln Gln Leu Glu Gln Met Leu Thr
            195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
```

```
            485                 490                 495
Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
        530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770

<210> SEQ ID NO 73
<211> LENGTH: 246
<212> TYPE: PRT
<213> ORGANISM: Homo sapiens

<400> SEQUENCE: 73

Met Glu Leu Val Leu Thr Gln Thr Pro Ser Pro Val Ser Ala Val Val
1               5                   10                  15

Gly Gly Thr Val Thr Ile Asn Cys Gln Ser Ser Gln Ser Val Trp Gly
            20                  25                  30

Asn Asn Arg Leu Ser Trp Tyr Gln Gln Lys Pro Gly Gln Pro Pro Arg
        35                  40                  45

Leu Leu Met Tyr Tyr Ala Ser Asn Leu Ala Ser Gly Val Ser Ser Arg
    50                  55                  60

Phe Lys Gly Ser Gly Ser Gly Thr Gln Phe Thr Leu Thr Ile Ser Asp
65                  70                  75                  80
```

Val Gln Cys Asp Asp Ala Ala Thr Tyr Tyr Cys Gln Gly Gly Phe Glu
            85                  90                  95

Cys Ser Gly Gly Asp Cys Val Gly Phe Gly Gly Gly Thr Glu Leu Glu
            100                 105                 110

Ile Leu Gly Gly Ser Ser Arg Ser Ser Ser Gly Gly Gly Ser
            115                 120                 125

Gly Gly Gly Gly Gln Ser Val Glu Ser Gly Gly Arg Leu Val Ala
            130                 135                 140

Pro Gly Gly Ser Leu Thr Leu Thr Cys Thr Val Ser Gly Ile Asp Leu
145                 150                 155                 160

Ser Ser Asp Ala Met Ser Trp Val Arg Gln Ala Pro Gly Lys Gly Leu
            165                 170                 175

Glu Trp Ile Gly Thr Ile Tyr Gly Ser Ala Gly Thr Tyr Tyr Ala Thr
            180                 185                 190

Trp Ala Lys Gly Arg Phe Thr Ile Ser Lys Thr Ser Thr Thr Val Asp
            195                 200                 205

Leu Lys Met Thr Ser Leu Thr Thr Glu Asp Thr Ala Thr Tyr Phe Cys
            210                 215                 220

Thr Arg Ala Phe Ser Asn Thr Arg Leu Asp Leu Trp Gly Gln Gly Thr
225                 230                 235                 240

Leu Val Thr Ile Ser Ser
            245

<210> SEQ ID NO 74
<211> LENGTH: 233
<212> TYPE: PRT
<213> ORGANISM: Homo sapiens

<400> SEQUENCE: 74

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
        50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
            85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
            130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
            165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
            195                 200                 205

Arg Phe Asn Arg Trp Phe Leu Thr Gly Met Thr Val Ala Gly Val Val
210                 215                 220

Leu Leu Gly Ser Leu Phe Ser Arg Lys
225                 230

<210> SEQ ID NO 75
<211> LENGTH: 312
<212> TYPE: PRT
<213> ORGANISM: Homo sapiens

<400> SEQUENCE: 75

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
                20                  25                  30

Lys Glu Lys Ala Ile Leu Gln Ala Thr Leu Arg Glu Glu Lys Lys Leu
            35                  40                  45

Arg Val Glu Asn Ala Lys Leu Lys Glu Ile Glu Glu Leu Lys Lys Gln
        50                  55                  60

Glu Leu Ile Gln Ala Glu Ile Gln Asn Gly Val Lys Gln Ile Pro Phe
65                  70                  75                  80

Pro Ser Gly Thr Pro Leu His Ala Asn Ser Met Val Ser Glu Asn Val
                85                  90                  95

Ile Gln Ser Thr Ala Val Thr Val Ser Ser Gly Thr Lys Glu Gln
            100                 105                 110

Ile Lys Gly Gly Thr Gly Asp Glu Lys Ala Lys Glu Lys Ile Glu
            115                 120                 125

Lys Lys Gly Glu Lys Lys Glu Lys Lys Gln Gln Ser Ile Ala Gly Ser
130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
            195                 200                 205

Leu Leu Cys Asn Leu Lys Pro Ala Lys Met Arg Gly Val Leu Ser Gln
210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Ile Trp Glu
            260                 265                 270

Gln Ile Gln Pro Asp Leu His Thr Asn Asp Glu Cys Val Ala Thr Tyr
            275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310

<210> SEQ ID NO 76
<211> LENGTH: 320
<212> TYPE: PRT

<213> ORGANISM: Homo sapiens

<400> SEQUENCE: 76

```
Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Glu Glu Ser
        35                  40                  45

Asn Leu Ser Leu Gln Ala Leu Glu Ser Arg Gln Asp Asp Ile Leu Lys
    50                  55                  60

Arg Leu Tyr Glu Leu Lys Ala Ala Val Asp Gly Leu Ser Lys Met Ile
65                  70                  75                  80

Gln Thr Pro Asp Ala Asp Leu Asp Val Thr Asn Ile Ile Gln Ala Asp
                85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
    130                 135                 140

His Phe Arg Val Leu Ser Thr Val His Thr His Ser Ser Val Lys Ser
145                 150                 155                 160

Val Pro Glu Asn Leu Leu Lys Cys Phe Gly Glu Gln Asn Lys Lys Gln
                165                 170                 175

Pro Arg Gln Asp Tyr Gln Leu Gly Phe Thr Leu Ile Trp Lys Asn Val
            180                 185                 190

Pro Lys Thr Gln Met Lys Phe Ser Ile Gln Thr Met Cys Pro Ile Glu
        195                 200                 205

Gly Glu Gly Asn Ile Ala Arg Phe Leu Phe Ser Leu Phe Gly Gln Lys
    210                 215                 220

His Asn Ala Val Asn Ala Thr Leu Ile Asp Ser Trp Val Asp Ile Ala
225                 230                 235                 240

Ile Phe Gln Leu Lys Glu Gly Ser Ser Lys Gln Lys Ala Ala Val Phe
                245                 250                 255

Arg Ser Met Asn Ser Ala Leu Gly Lys Ser Pro Trp Leu Ala Gly Asn
            260                 265                 270

Glu Leu Thr Val Ala Asp Val Val Leu Trp Ser Val Leu Gln Gln Ile
        275                 280                 285

Gly Gly Cys Ser Val Thr Val Pro Ala Asn Val Gln Arg Trp Met Arg
    290                 295                 300

Ser Cys Glu Asn Leu Ala Pro Phe Asn Thr Ala Leu Lys Leu Leu Lys
305                 310                 315                 320
```

<210> SEQ ID NO 77
<211> LENGTH: 233
<212> TYPE: PRT
<213> ORGANISM: Homo sapiens

<400> SEQUENCE: 77

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
```

```
                35                  40                  45
Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
                195                 200                 205

His Asn Glu Asp Tyr Thr Ile Val Glu Gln Tyr Glu Arg Ala Glu Gly
210                 215                 220

Arg His Ser Thr Gly Gly Met Asp Glu
225                 230

<210> SEQ ID NO 78
<211> LENGTH: 267
<212> TYPE: PRT
<213> ORGANISM: Homo sapiens

<400> SEQUENCE: 78

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

```
Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Gly Ser Gly Leu Arg Ser Arg Ala Gln Ala Ser Asn Ser Ala Val
                245                 250                 255

Asp Gly Thr Ala Gly Pro Gly Ser Thr Gly Ser
                260                 265

<210> SEQ ID NO 79
<211> LENGTH: 425
<212> TYPE: PRT
<213> ORGANISM: Homo sapiens

<400> SEQUENCE: 79

Met Ala Asp Lys Glu Ala Ala Phe Asp Asp Ala Val Glu Glu Arg Val
1               5                   10                  15

Ile Asn Glu Glu Tyr Lys Ile Trp Lys Lys Asn Thr Pro Phe Leu Tyr
                20                  25                  30

Asp Leu Val Met Thr His Ala Leu Glu Trp Pro Ser Leu Thr Ala Gln
            35                  40                  45

Trp Leu Pro Asp Val Thr Arg Pro Glu Gly Lys Asp Phe Ser Ile His
    50                  55                  60

Arg Leu Val Leu Gly Thr His Thr Ser Asp Glu Gln Asn His Leu Val
65                  70                  75                  80

Ile Ala Ser Val Gln Leu Pro Asn Asp Asp Ala Gln Phe Asp Ala Ser
                85                  90                  95

His Tyr Asp Ser Glu Lys Gly Glu Phe Gly Gly Phe Gly Ser Val Ser
            100                 105                 110

Gly Lys Ile Glu Ile Glu Ile Lys Ile Asn His Glu Gly Glu Val Asn
        115                 120                 125

Arg Ala Arg Tyr Met Pro Gln Asn Pro Cys Ile Ile Ala Thr Lys Thr
    130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190

Leu Leu Ser Ala Ser Asp Asp His Thr Ile Cys Leu Trp Asp Ile Ser
        195                 200                 205

Ala Val Pro Lys Glu Gly Lys Val Val Asp Ala Lys Thr Ile Phe Thr
    210                 215                 220

Gly His Thr Ala Val Val Glu Asp Val Ser Trp His Leu Leu His Glu
225                 230                 235                 240

Ser Leu Phe Gly Ser Val Ala Asp Asp Gln Lys Leu Met Ile Trp Asp
                245                 250                 255

Thr Arg Ser Asn Asn Thr Ser Lys Pro Ser His Ser Val Asp Ala His
            260                 265                 270

Thr Ala Glu Val Asn Cys Leu Ser Phe Asn Pro Tyr Ser Glu Phe Ile
        275                 280                 285
```

```
Leu Ala Thr Gly Ser Ala Asp Lys Thr Val Ala Leu Trp Asp Leu Arg
        290                 295                 300

Asn Leu Lys Leu Lys Leu His Ser Phe Glu Ser His Lys Asp Glu Ile
305                 310                 315                 320

Phe Gln Val Gln Trp Ser Pro His Asn Glu Thr Ile Leu Ala Ser Ser
                325                 330                 335

Gly Thr Asp Arg Arg Leu Asn Val Trp Asp Leu Ser Lys Ile Gly Glu
                340                 345                 350

Glu Gln Ser Pro Glu Asp Ala Glu Asp Gly Pro Pro Glu Leu Leu Phe
            355                 360                 365

Ile His Gly Gly His Thr Ala Lys Ile Ser Asp Phe Ser Trp Asn Pro
        370                 375                 380

Asn Glu Pro Trp Val Ile Cys Ser Val Ser Glu Asp Asn Ile Met Gln
385                 390                 395                 400

Val Trp Gln Met Ala Glu Asn Ile Tyr Asn Asp Glu Asp Pro Glu Gly
                405                 410                 415

Ser Val Asp Pro Glu Gly Gln Gly Ser
                420                 425

<210> SEQ ID NO 80
<211> LENGTH: 375
<212> TYPE: PRT
<213> ORGANISM: Homo sapiens

<400> SEQUENCE: 80

Met Ala Asp His Ser Phe Ser Asp Gly Val Pro Ser Asp Ser Val Glu
1               5                   10                  15

Ala Ala Lys Asn Ala Ser Asn Thr Glu Lys Leu Thr Asp Gln Val Met
                20                  25                  30

Gln Asn Pro Arg Val Leu Ala Ala Leu Gln Glu Arg Leu Asp Asn Val
            35                  40                  45

Pro His Thr Pro Ser Ser Tyr Ile Glu Thr Leu Pro Lys Ala Val Lys
        50                  55                  60

Arg Arg Ile Asn Ala Leu Lys Gln Leu Gln Val Arg Cys Ala His Ile
65                  70                  75                  80

Glu Ala Lys Phe Tyr Glu Glu Val His Asp Leu Glu Arg Lys Tyr Ala
                85                  90                  95

Ala Leu Tyr Gln Pro Leu Phe Asp Lys Arg Arg Glu Phe Ile Thr Gly
                100                 105                 110

Asp Val Glu Pro Thr Asp Ala Glu Ser Glu Trp His Ser Glu Asn Glu
            115                 120                 125

Glu Glu Glu Lys Leu Ala Gly Asp Met Lys Ser Lys Val Val Val Thr
130                 135                 140

Glu Lys Ala Ala Ala Thr Ala Glu Glu Pro Asp Pro Lys Gly Ile Pro
145                 150                 155                 160

Glu Phe Trp Phe Thr Ile Phe Arg Asn Val Asp Met Leu Ser Glu Leu
                165                 170                 175

Val Gln Glu Tyr Asp Glu Pro Ile Leu Lys His Leu Gln Asp Ile Lys
            180                 185                 190

Val Lys Phe Ser Asp Pro Gly Gln Pro Met Ser Phe Val Leu Glu Phe
        195                 200                 205

His Phe Glu Pro Asn Asp Tyr Phe Thr Asn Ser Val Leu Thr Lys Thr
210                 215                 220

Tyr Lys Met Lys Ser Glu Pro Asp Lys Ala Asp Pro Phe Ser Phe Glu
```

```
                225                 230                 235                 240
Gly Pro Glu Ile Val Asp Cys Asp Gly Cys Thr Ile Asp Trp Lys Lys
                245                 250                 255

Gly Lys Asn Val Thr Val Lys Thr Ile Lys Lys Gln Lys His Lys
                260                 265                 270

Gly Arg Gly Thr Val Arg Thr Ile Thr Lys Gln Val Pro Asn Glu Ser
                275                 280                 285

Phe Phe Asn Phe Phe Asn Pro Leu Lys Ala Ser Gly Asp Gly Glu Ser
                290                 295                 300

Leu Asp Glu Asp Ser Glu Phe Thr Leu Ala Ser Asp Phe Glu Ile Gly
305                 310                 315                 320

His Phe Phe Arg Glu Arg Ile Val Pro Arg Ala Val Leu Tyr Phe Thr
                325                 330                 335

Gly Glu Ala Ile Glu Asp Asp Asn Phe Glu Gly Glu Glu Gly
                340                 345                 350

Glu Glu Glu Glu Leu Glu Gly Asp Glu Glu Gly Glu Asp Glu Asp Asp
                355                 360                 365

Ala Glu Ile Asn Pro Lys Val
                370                 375

<210> SEQ ID NO 81
<211> LENGTH: 1132
<212> TYPE: PRT
<213> ORGANISM: Homo sapiens

<400> SEQUENCE: 81

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
                180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
210                 215                 220
```

```
Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
            245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
        290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
```

```
                645                 650                 655
Arg Val Lys Ala Leu Phe Ser Val Leu Asn Tyr Glu Arg Ala Arg Arg
                660                 665                 670

Pro Gly Leu Leu Gly Ala Ser Val Gly Leu Asp Asp Ile His Arg
            675                 680                 685

Ala Trp Arg Thr Phe Val Leu Arg Val Arg Ala Gln Asp Pro Pro
705                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
        770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070
```

```
Leu Cys His Gln Ala Phe Leu Leu Lys Leu Thr Arg His Arg Val Thr
            1075                1080                1085

Tyr Val Pro Leu Leu Gly Ser Leu Arg Thr Ala Gln Thr Gln Leu Ser
        1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
            1125                1130

<210> SEQ ID NO 82
<211> LENGTH: 462
<212> TYPE: PRT
<213> ORGANISM: Homo sapiens

<400> SEQUENCE: 82

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
        115                 120                 125

Ala Val Glu Cys Leu Asn Tyr Gln His Tyr Lys Gly Ser Asp Phe Asp
    130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
        195                 200                 205

Ile Leu Asp Leu Ile Ser Glu Ser Pro Ile Lys Gly Arg Ala Gln Pro
    210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Gly Arg Pro
            260                 265                 270

Met Pro Pro Ser Arg Arg Asp Tyr Asp Asp Met Ser Pro Arg Arg Gly
        275                 280                 285

Pro Pro Pro Pro Pro Gly Arg Gly Arg Gly Gly Ser Arg Ala
    290                 295                 300

Arg Asn Leu Pro Leu Pro Pro Pro Pro Pro Arg Gly Gly Asp Leu
```

```
            305                 310                 315                 320
Met Ala Tyr Asp Arg Arg Gly Arg Pro Gly Asp Arg Tyr Asp Gly Met
                    325                 330                 335

Val Gly Phe Ser Ala Asp Glu Thr Trp Asp Ser Ala Ile Asp Thr Trp
                340                 345                 350

Ser Pro Ser Glu Trp Gln Met Ala Tyr Glu Pro Gln Gly Gly Ser Gly
            355                 360                 365

Tyr Asp Tyr Ser Tyr Ala Gly Arg Gly Ser Tyr Gly Asp Leu Gly
        370                 375                 380

Gly Pro Ile Ile Thr Thr Gln Val Thr Ile Pro Lys Asp Leu Ala Gly
385                 390                 395                 400

Ser Ile Ile Gly Lys Gly Gln Arg Ile Lys Gln Ile Arg His Glu
                405                 410                 415

Ser Gly Ala Ser Ile Lys Ile Asp Glu Pro Leu Glu Gly Ser Glu Asp
                420                 425                 430

Arg Ile Ile Thr Ile Thr Gly Thr Gln Asp Gln Ile Gln Asn Ala Gln
                435                 440                 445

Tyr Leu Leu Gln Asn Ser Val Lys Gln Tyr Ser Gly Lys Phe
        450                 455                 460
```

<210> SEQ ID NO 83
<211> LENGTH: 745
<212> TYPE: PRT
<213> ORGANISM: Homo sapiens

<400> SEQUENCE: 83

```
Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
                20                  25                  30

Gln His Arg Glu Leu Asp Leu Lys Ile Ala Ile Lys Ser Cys Arg Leu
            35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220
```

```
Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Val Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
```

```
                    645                 650                 655
Ala Cys Thr Gln Ser Ser Ala Arg Ser Leu Val Gly Ser Ser Leu Glu
                660                 665                 670

Gly Ala Val Thr Pro Gln Thr Ser Ala Trp Leu Pro Pro Thr Ser Ala
            675                 680                 685

Glu His Asp His Ser Leu Ser Cys Val Val Thr Pro Gln Asp Gly Glu
        690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Gln Gly Asn Ser Met Met
                725                 730                 735

Asn Leu Asp Trp Ser Trp Leu Thr Glu
                740                 745

<210> SEQ ID NO 84
<211> LENGTH: 968
<212> TYPE: PRT
<213> ORGANISM: Homo sapiens

<400> SEQUENCE: 84

Met Ala Glu Asp Asp Pro Tyr Leu Gly Arg Pro Glu Gln Met Phe His
1               5                   10                  15

Leu Asp Pro Ser Leu Thr His Thr Ile Phe Asn Pro Glu Val Phe Gln
            20                  25                  30

Pro Gln Met Ala Leu Pro Thr Asp Gly Pro Tyr Leu Gln Ile Leu Glu
        35                  40                  45

Gln Pro Lys Gln Arg Gly Phe Arg Phe Arg Tyr Val Cys Glu Gly Pro
    50                  55                  60

Ser His Gly Gly Leu Pro Gly Ala Ser Ser Glu Lys Asn Lys Lys Ser
65                  70                  75                  80

Tyr Pro Gln Val Lys Ile Cys Asn Tyr Val Gly Pro Ala Lys Val Ile
                85                  90                  95

Val Gln Leu Val Thr Asn Gly Lys Asn Ile His Leu His Ala His Ser
            100                 105                 110

Leu Val Gly Lys His Cys Glu Asp Gly Ile Cys Thr Val Thr Ala Gly
        115                 120                 125

Pro Lys Asp Met Val Val Gly Phe Ala Asn Leu Gly Ile Leu His Val
    130                 135                 140

Thr Lys Lys Lys Val Phe Glu Thr Leu Glu Ala Arg Met Thr Glu Ala
145                 150                 155                 160

Cys Ile Arg Gly Tyr Asn Pro Gly Leu Leu Val His Pro Asp Leu Ala
                165                 170                 175

Tyr Leu Gln Ala Glu Gly Gly Gly Asp Arg Gln Leu Gly Asp Arg Glu
            180                 185                 190

Lys Glu Leu Ile Arg Gln Ala Ala Leu Gln Gln Thr Lys Glu Met Asp
        195                 200                 205

Leu Ser Val Val Arg Leu Met Phe Thr Ala Phe Leu Pro Asp Ser Thr
    210                 215                 220

Gly Ser Phe Thr Arg Arg Leu Glu Pro Val Val Ser Asp Ala Ile Tyr
225                 230                 235                 240

Asp Ser Lys Ala Pro Asn Ala Ser Asn Leu Lys Ile Val Arg Met Asp
                245                 250                 255

Arg Thr Ala Gly Cys Val Thr Gly Gly Glu Glu Ile Tyr Leu Leu Cys
            260                 265                 270
```

```
Asp Lys Val Gln Lys Asp Asp Ile Gln Ile Arg Phe Tyr Glu Glu Glu
            275                 280                 285
Glu Asn Gly Gly Val Trp Glu Gly Phe Gly Asp Phe Ser Pro Thr Asp
        290                 295                 300
Val His Arg Gln Phe Ala Ile Val Phe Lys Thr Pro Lys Tyr Lys Asp
305                 310                 315                 320
Ile Asn Ile Thr Lys Pro Ala Ser Val Phe Val Gln Leu Arg Arg Lys
                325                 330                 335
Ser Asp Leu Glu Thr Ser Glu Pro Lys Pro Phe Leu Tyr Tyr Pro Glu
            340                 345                 350
Ile Lys Asp Lys Glu Glu Val Gln Arg Lys Arg Gln Lys Leu Met Pro
        355                 360                 365
Asn Phe Ser Asp Ser Phe Gly Gly Gly Ser Gly Ala Gly Ala Gly Gly
    370                 375                 380
Gly Gly Met Phe Gly Ser Gly Gly Gly Gly Gly Thr Gly Ser Thr
385                 390                 395                 400
Gly Pro Gly Tyr Ser Phe Pro His Tyr Gly Phe Pro Thr Tyr Gly Gly
                405                 410                 415
Ile Thr Phe His Pro Gly Thr Thr Lys Ser Asn Ala Gly Met Lys His
            420                 425                 430
Gly Thr Met Asp Thr Glu Ser Lys Lys Asp Pro Glu Gly Cys Asp Lys
        435                 440                 445
Ser Asp Asp Lys Asn Thr Val Asn Leu Phe Gly Lys Val Ile Glu Thr
    450                 455                 460
Thr Glu Gln Asp Gln Glu Pro Ser Glu Ala Thr Val Gly Asn Gly Glu
465                 470                 475                 480
Val Thr Leu Thr Tyr Ala Thr Gly Thr Lys Glu Glu Ser Ala Gly Val
                485                 490                 495
Gln Asp Asn Leu Phe Leu Glu Lys Ala Met Gln Leu Ala Lys Arg His
            500                 505                 510
Ala Asn Ala Leu Phe Asp Tyr Ala Val Thr Gly Asp Val Lys Met Leu
        515                 520                 525
Leu Ala Val Gln Arg His Leu Thr Ala Val Gln Asp Glu Asn Gly Asp
    530                 535                 540
Ser Val Leu His Leu Ala Ile Ile His Leu His Ser Gln Leu Val Arg
545                 550                 555                 560
Asp Leu Leu Glu Val Thr Ser Gly Leu Ile Ser Asp Asp Ile Ile Asn
                565                 570                 575
Met Arg Asn Asp Leu Tyr Gln Thr Pro Leu His Leu Ala Val Ile Thr
            580                 585                 590
Lys Gln Glu Asp Val Val Glu Asp Leu Leu Arg Ala Gly Ala Asp Leu
        595                 600                 605
Ser Leu Leu Asp Arg Leu Gly Asn Ser Val Leu His Leu Ala Ala Lys
    610                 615                 620
Glu Gly His Asp Lys Val Leu Ser Ile Leu Leu Lys His Lys Lys Ala
625                 630                 635                 640
Ala Leu Leu Leu Asp His Pro Asn Gly Asp Gly Leu Asn Ala Ile His
                645                 650                 655
Leu Ala Met Met Ser Asn Ser Leu Pro Cys Leu Leu Leu Leu Val Ala
            660                 665                 670
Ala Gly Ala Asp Val Asn Ala Gln Glu Gln Lys Ser Gly Arg Thr Ala
        675                 680                 685
Leu His Leu Ala Val Glu His Asp Asn Ile Ser Leu Ala Gly Cys Leu
```

-continued

```
            690                 695                 700
Leu Leu Glu Gly Asp Ala His Val Asp Ser Thr Thr Tyr Asp Gly Thr
705                     710                 715                 720

Thr Pro Leu His Ile Ala Ala Gly Arg Gly Ser Thr Arg Leu Ala Ala
                725                 730                 735

Leu Leu Lys Ala Ala Gly Ala Asp Pro Leu Val Glu Asn Phe Glu Pro
            740                 745                 750

Leu Tyr Asp Leu Asp Asp Ser Trp Glu Asn Ala Gly Glu Asp Glu Gly
        755                 760                 765

Val Val Pro Gly Thr Thr Pro Leu Asp Met Ala Thr Ser Trp Gln Val
    770                 775                 780

Phe Asp Ile Leu Asn Gly Lys Pro Tyr Glu Pro Glu Phe Thr Ser Asp
785                 790                 795                 800

Asp Leu Leu Ala Gln Gly Asp Met Lys Gln Leu Ala Glu Asp Val Lys
                805                 810                 815

Leu Gln Leu Tyr Lys Leu Leu Glu Ile Pro Asp Pro Asp Lys Asn Trp
            820                 825                 830

Ala Thr Leu Ala Gln Lys Leu Gly Leu Gly Ile Leu Asn Asn Ala Phe
            835                 840                 845

Arg Leu Ser Pro Ala Pro Ser Lys Thr Leu Met Asp Asn Tyr Glu Val
        850                 855                 860

Ser Gly Gly Thr Val Arg Glu Leu Val Glu Ala Leu Arg Gln Met Gly
865                 870                 875                 880

Tyr Thr Glu Ala Ile Glu Val Ile Gln Ala Ala Ser Ser Pro Val Lys
                885                 890                 895

Thr Thr Ser Gln Ala His Ser Leu Pro Leu Ser Pro Ala Ser Thr Arg
                900                 905                 910

Gln Gln Ile Asp Glu Leu Arg Asp Ser Asp Ser Val Cys Asp Ser Gly
            915                 920                 925

Val Glu Thr Ser Phe Arg Lys Leu Ser Phe Thr Glu Ser Leu Thr Ser
        930                 935                 940

Gly Ala Ser Leu Leu Thr Leu Asn Lys Met Pro His Asp Tyr Gly Gln
945                 950                 955                 960

Glu Gly Pro Leu Glu Gly Lys Ile
            965
```

COMPOSITIONS CONTAINING PROTEIN LOADED EXOSOME AND METHODS FOR PREPARING AND DELIVERING THE SAME

CROSS-REFERENCE TO RELATED APPLICATIONS

This application is a continuation of U.S. patent application Ser. No. 15/803,338 filed Nov. 3, 2017, which is a continuation-in-part of PCT/KR2016/004750 filed May 4, 2016, and a continuation-in-part of PCT/KR2017/011070, filed Sep. 30, 2017, wherein PCT/KR2016/004750 claims the benefit of priority from Korean Patent Application No. 10-2015-0062604 filed May 4, 2015, Korean Patent Application No. 10-2015-0120934 filed Aug. 27, 2015, and Korean Patent Application No. 10-2016-0055687 filed May 4, 2016, and wherein PCT/KR2017/011070 claims benefit from Korean Patent Application No. 10-2016-0126335 filed Sep. 30, 2016, Korean Patent Application No. 10-2016-0126921 filed Sep. 30, 2016, Korean Patent Application No. 10-2016-0126961 filed Sep. 30, 2016, Korean Patent Application No. 10-2016-0127486 filed Oct. 4, 2016, Korean Patent Application No. 10-2016-0132616 filed Oct. 13, 2016, and Korean Patent Application No. 10-2017-0018637 filed Feb. 10, 2017, the contents of each of which are incorporated herein by reference.

FIELD OF THE INVENTION

The present invention relates to compositions containing protein loaded exosome, methods for preparing exosome loaded with a cargo protein using a photo-specific binding protein, and a method for delivering the cargo protein to cytosol using the exosome prepared thereby.

BACKGROUND OF THE INVENTION

The human body is composed of about 200 kinds of 100 trillion cells, in which the physiological activity is regulated by the action of various proteins to maintain life.

Cells are surrounded by membranes in bilayer structure composed of phospholipids, which block the entry of foreign substances into cells. Most of the protein drugs which have developed so far cannot pass through the cell membrane to enter the cell and can act on the outside of the cell or act on a receptor on the cell membrane to deliver the signal into the cell in order to show physiological effect.

Cytosol has lots of proteins which interact with each other to regulate physiological activity. So, if only a protein drug can be delivered inside the cell, that is, inside the cytosol, the cell activity would be controlled more effectively.

Recently, studies have been actively going on to establish a method for delivering a cargo protein directly into cells via cell membrane. When a recombinant protein of a cargo protein and protein transduction domains (PTDs), the peptide that passes through the cell membrane, is prepared and administered, it can enter the cytosol through the cell membrane (FIG. 1). PTD is exemplified by HIV-1 TAT, HSV VP22, Antp, dfTAT, and Hph-1. A fusion protein prepared by combining the PTDs and a cargo protein is produced as a recombinant protein and at this time a separation process is required. However, this process is problematic in that the protein refolding is not performed properly, the activity is decreased, the protein is nonspecifically transferred, the risk of causing an immune reaction in vivo is large, the cost is high, and the yield is low.

The cargo protein conjugated with various nanoparticles can enter the cytosol through the cell membrane by endocytosis (FIG. 2). At this time, the nanoparticles are exemplified by Gold NP, Liposome NP, Magnetic NP, and Polymeric NP, etc. The separation of the nanoparticles from the cargo protein occurs mostly in lysosome in the cell, so the cargo protein is decomposed inside lysosome to lose its activity. Or the nanoparticles are difficult to be separated from the cargo protein in cytosol and toxicity of the nanoparticles can be another problem.

Exosome is a small vesicle with a membrane structure in the size of 50~200 nm, which is secreted out of the cell with containing protein, DNA, and RNA for intercellular signaling.

Exosome was first found in the process of leaving only hemoglobin in the red blood cells by eliminating intracellular proteins at the last stage of red blood cell maturation. From the observation under electron microscope, it was confirmed that exosome is not separated directly from plasma membrane but discharged extracellular from the intracellular specific zone, called multi-vesicular bodies (MVBs). That is, when MVBs are fused with plasma membrane, such vesicles are discharged outside of the cell, which are called exosome (FIG. 3).

It has not been clearly disclosed the molecular mechanism of the exosome generation. However, it is known that various immune cells including B-lymphocytes, T-lymphocytes, dendritic cells, megakaryocytes, and macrophages, stem cells, and tumor cells produce and secrete exosomes when they are alive.

Exosome contains various intracellular proteins, DNA, and RNA. The substances secreted out of the cells contained in these exosomes can be reintroduced into other cells by fusion or endocytosis and serve as intercellular messengers. By analyzing such substances that are secreted out of the cell as included in exosome, specific disease can be diagnosed.

Exosome also includes various types of microRNAs. A method for diagnosing a disease by detecting the presence or absence and the abundance thereof has been reported (KR 10-2010-0127768A). International Patent Publication No. WO2009-015357A describes a method for predicting and diagnosing a specific disease by detecting exosome in the cancer patient originated samples (blood, saliva, tears, etc.). In particular, the exosome obtained from a patient having a specific disease (lung disease) is analyzed and the relationship between a specific microRNA and lung disease is specifically described. Studies have been still going on to establish a method to diagnose kidney disease, in addition to lung disease, by using a specific protein included in exosome.

Exosome might also include antigens. In antigen presenting cells (APC), antigen peptide is loaded in MHC (major histocompatibility complex) class II molecule in the intracellular compartment having a membrane structure including polycystic bodies. Therefore, the exosome originated therefrom also has the antigen peptide-MHC class II complex. So, exosome acts as an immunogen carrier to present antigen peptide to CD4+ T lymphocytes and thereby can induce immune response such as T lymphocyte proliferation. The molecules that are able to stimulate immune response such as MHC class I and heat-shock proteins (HSPs) are concentrated in exosome, so that exosome can be used to increase or decrease immune response for the treatment of cancer or auto-immune disease.

SUMMARY OF THE INVENTION

The present invention provides compositions containing exosome loaded with a cargo protein.

In another embodiment, the present invention provides a method for preparing the exosome loaded with a cargo protein using a photo-specific binding protein.

In a further embodiment, the present invention provides a method of delivering the cargo protein to cytosol using the exosome.

Control: HEK293T cells treated with nothing;
OVER: HEK293T cells introduced with Luciferase-mCherry-CRY2 alone;
XP: HEK293T cells introduced with XPACK-Luciferase-mCherry by using XPACK (Systems Biosciences), the commercial vector designed for exosome loading technique;
EXPLOR: HEK293T cells introduced with Luciferase-mCherry-CRY2 and CIBN-EGFP-CD9 according to the present invention.

Figure 14:
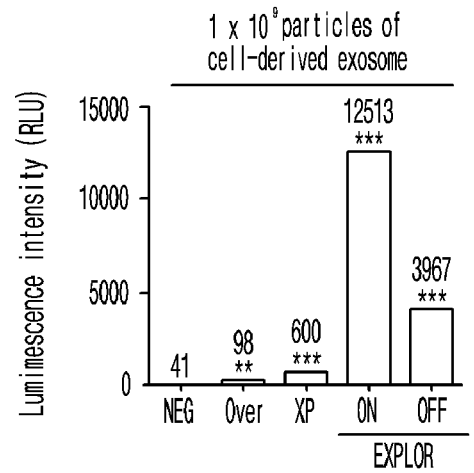
Figure 14:
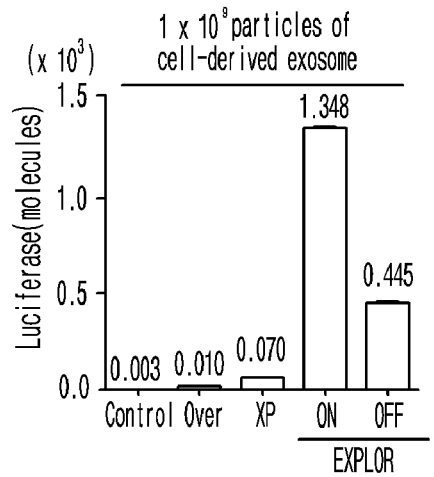

FIG. 14 illustrates the luciferase activity (a) and the number of molecules (b) in the produced exosome:
NEG: exosome produced in the HEK293T cells treated with nothing;
OVER: exosome produced in the HEK293T cells introduced with Luciferase-mCherry-CRY2;
XP: exosome produced in the HEK293T cells introduced with)(PACK-Luciferase-mCherry by using XPACK (Systems Biosciences), the commercial vector designed for exosome loading technique;
EXPLOR: exosome produced in the HEK293T cells introduced with Luciferase-mCherry-CRY2 and CIBN-EGFP-CD9 according to the present invention;
ON: exosome produced by culturing under the irradiation of 200 µW blue light for 72 hours,
OFF: exosome produced by culturing under the light-free condition for 72 hours.

Figure 15:
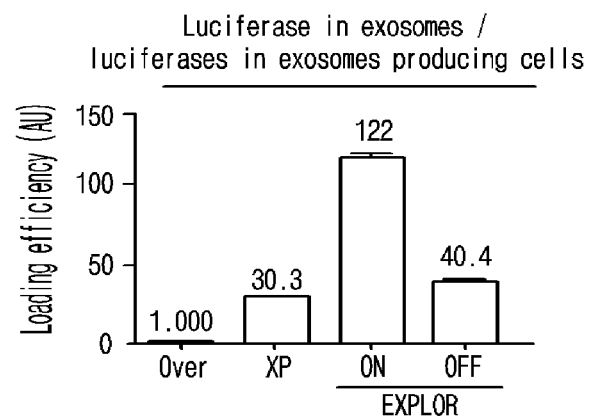

FIG. 15 illustrates the loading efficiency of a cargo protein in the exosome produced above.

Figure 16:
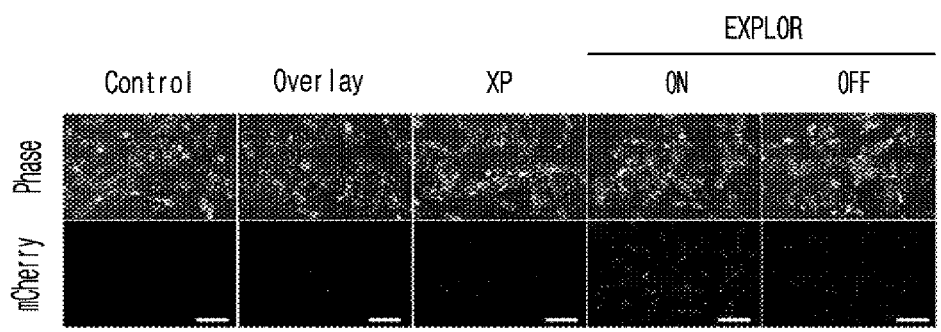
Figure 16:
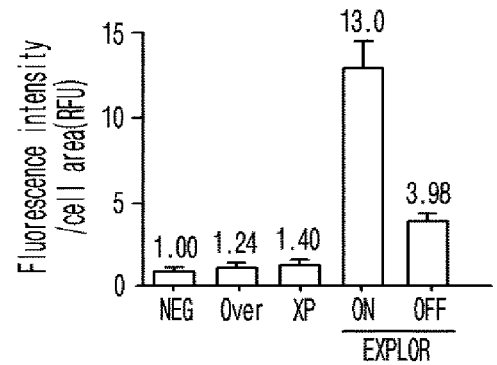

FIG. 16 illustrates the transfer efficiency of a cargo protein into the target cells (HeLa) using exosome:
Control: exosome produced in the HEK293T cells treated with nothing;
OVER: exosome produced in the HEK293T cells introduced with Luciferase-mCherry-CRY2;
XP: exosome produced in the HEK293T cells introduced with XPACK-Luciferase-mCherry by using XPACK (Systems Biosciences), the commercial vector designed for exosome loading technique;
EXPLOR: exosome produced in the HEK293T cells introduced with Luciferase-mCherry-CRY2 and CIBN-EGFP-CD9 according to the present invention;
ON: exosome produced by culturing under the irradiation of 200 µW blue light for 72 hours,
OFF: exosome produced by culturing under the light-free condition for 72 hours.

Figure 17:
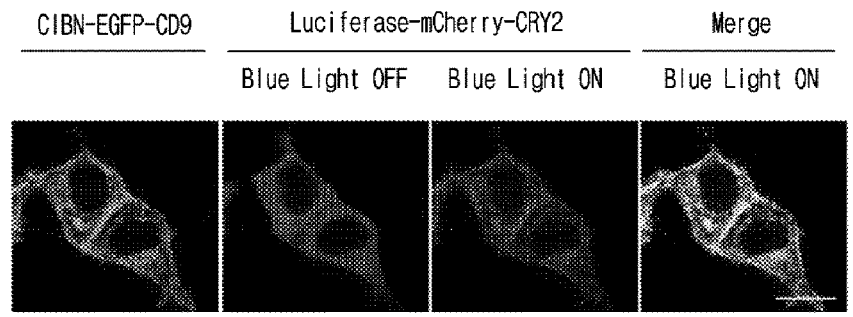

FIG. 17 illustrates the location of the expression of Luciferase-mCherry-CRY2 and CIBN-EGFP-CD9 in HEK293T cells, indicating they share the same position for the expression.

Figure 18:
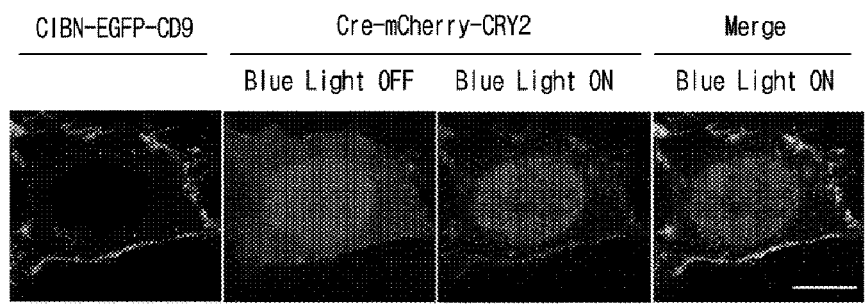

FIG. 18 illustrates the location of the expression of Cre-mCherry-CRY2 and CIBN-EGFP-CD9 in HEK293T cells, indicating they share the same position for the expression.

Figure 19A:
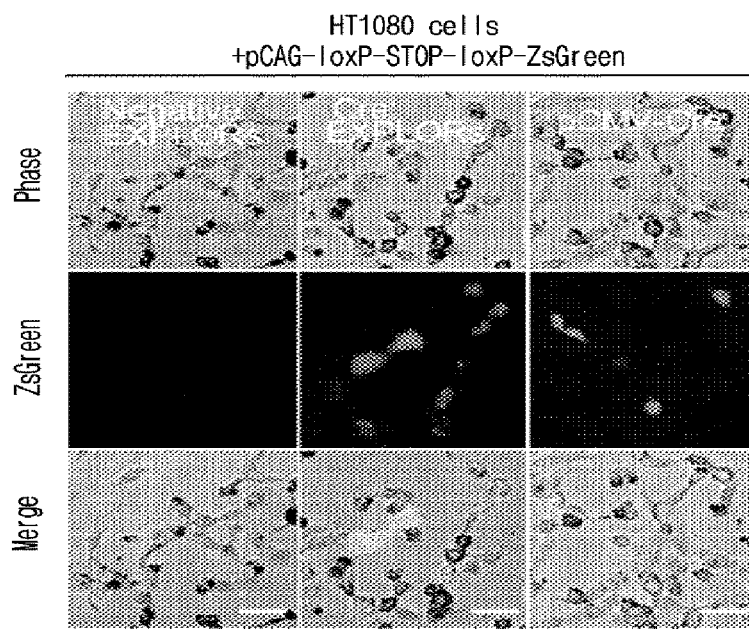

FIG. 19A illustrates that treatment with Cre: EXPLOR induced the expression of ZsGreen in HT1080 cells transiently transfected with pCAG-loxP-STOP-loxP-ZsGreen (Scale bars, 40 µm):
Negative: EXPLOR: no cre-loaded exosome as negative control;
Cre: EXPLOR: Cre-loaded exosome; and
pcMV-Cre: pCMV-Cre vector transfection as positive control.

Figure 19B:
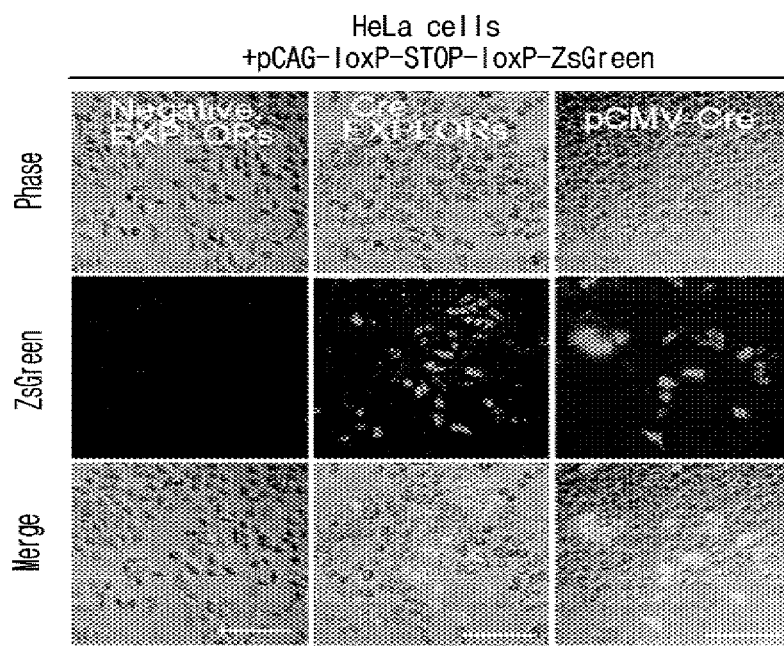

FIG. 19B illustrates that treatment with Cre: EXPLOR induced the expression of ZsGreen in HeLa cells transiently transfected with pCAG-loxP-STOP-loxP-ZsGreen (Scale bars, 40 µm):

Negative: EXPLOR: no Cre-loaded exosome as negative control;
Cre: EXPLOR: Cre-loaded exosome; and
pcMV-Cre: pCMV-Cre vector transfection as positive control.

Figure 20:
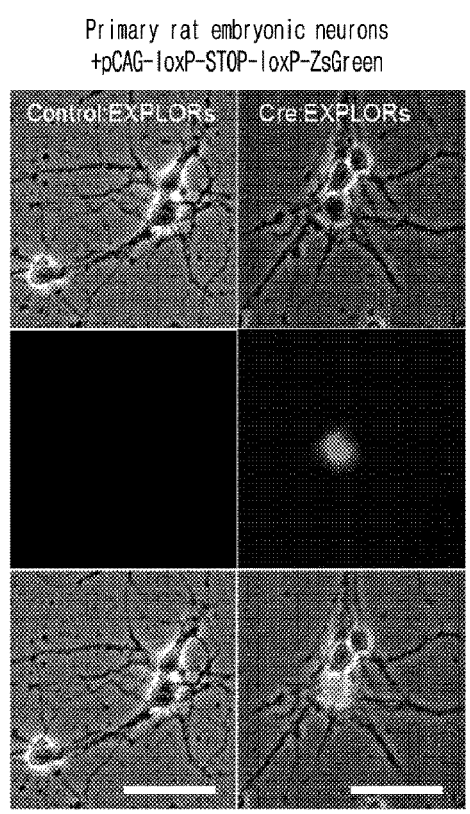

FIG. 20 illustrates that treatment with Cre: EXPLOR induced the expression of ZsGreen in primary rat embryonic neuron transiently transfected with pCAG-loxP-STOP-loxP-ZsGreen (Scale bars, 100 μm):
Control: EXPLOR: no Cre-loaded exosome as negative control; and
Cre: EXPLOR: Cre-loaded exosome.

Figure 21:
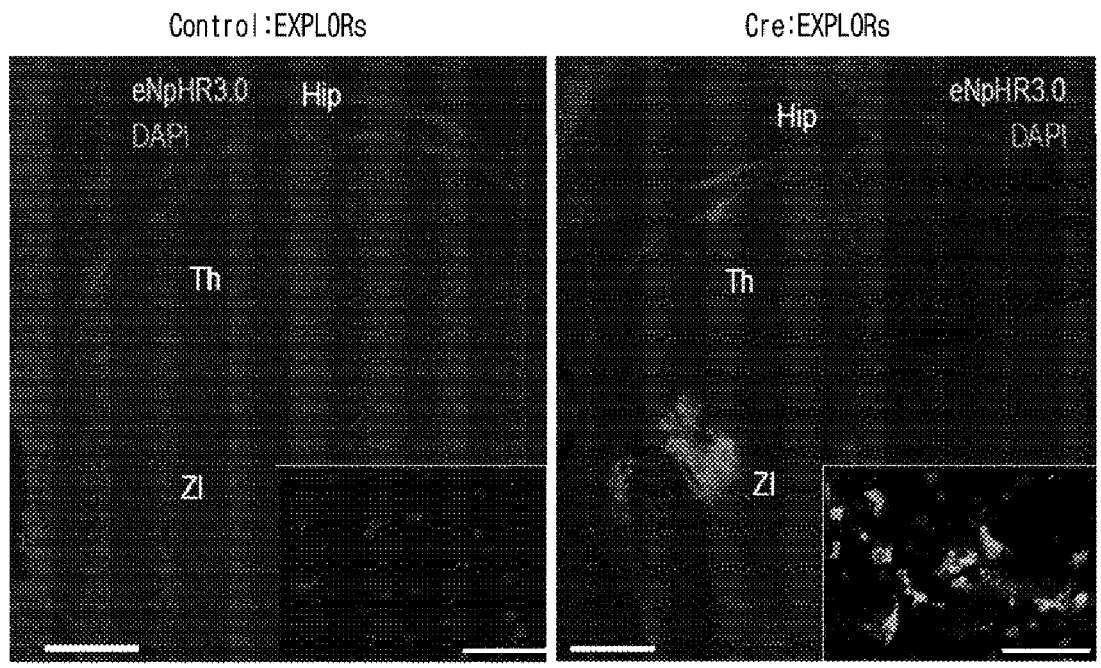

FIG. 21 illustrates that treatment with Cre:EXPLOR induced the expression of ZsGreen in transgenic mice having pCAG-loxP-STOP-loxP-eNpHR3.0-EYFP gene (Scale bars, 500 μm):
Control: EXPLOR: no Cre-loaded exosome as negative control;
Cre: EXPLOR: Cre-loaded exosome;
Hip: hippocampus; and
Th: thalamus.

Figure 22:
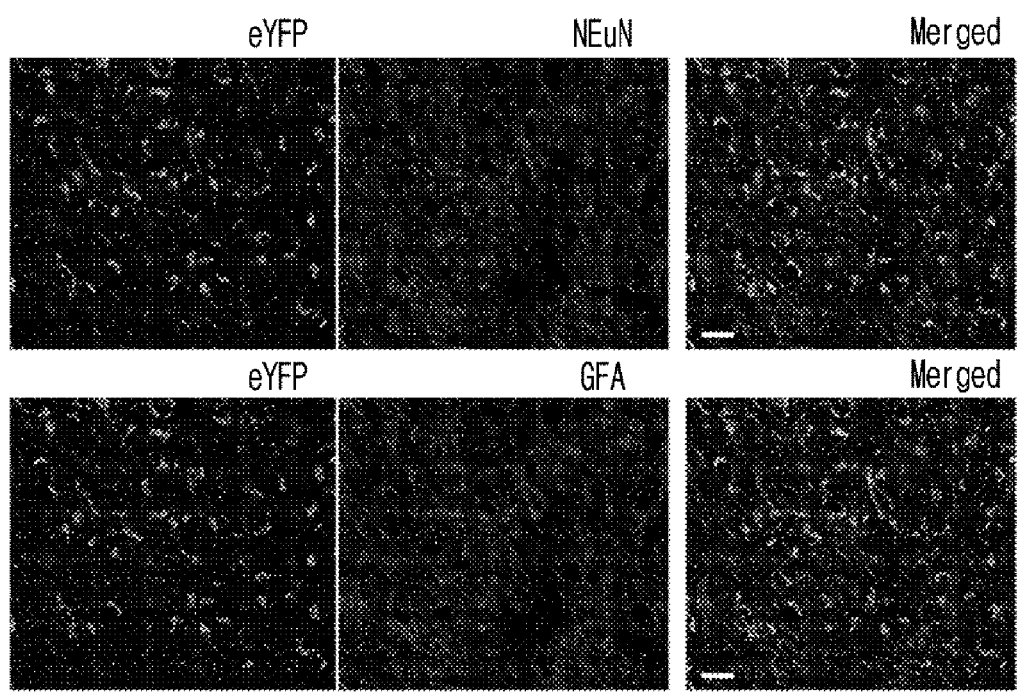

FIG. 22 illustrates the results of immunohistochemistry for NEuN/GFAP in transgenic mice having pCAG-loxP-STOP-loxP-eNpHR3.0-EYFP gene
Pink: neuronal-specific nuclear protein; NEuN, positive neurons; and
Red: glial fibrillary acidic protein; GFAP, positive astrocyte cells.
Objective lens, 40×. Scale bar, 20 μm.

Figure 23:
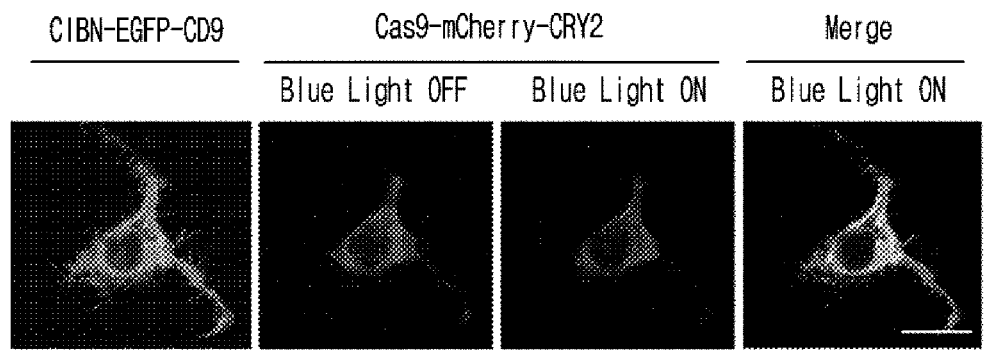

FIG. 23 illustrates the location of the expression of Cas9-mCherry-CRY2 and CIBN-EGFP-CD9 in HEK293T cells, indicating they share the same position for the expression.

Figure 24:
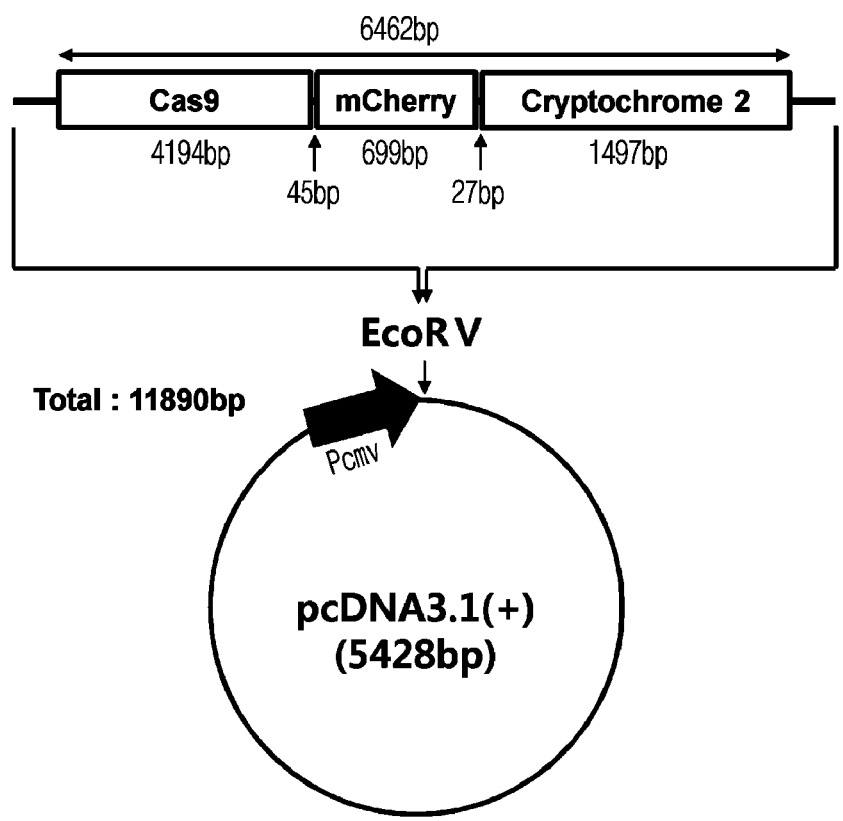

FIG. 24 illustrates the generation of DNA constructs used for the production of Cas9-loaded exosome.

Figure 25:
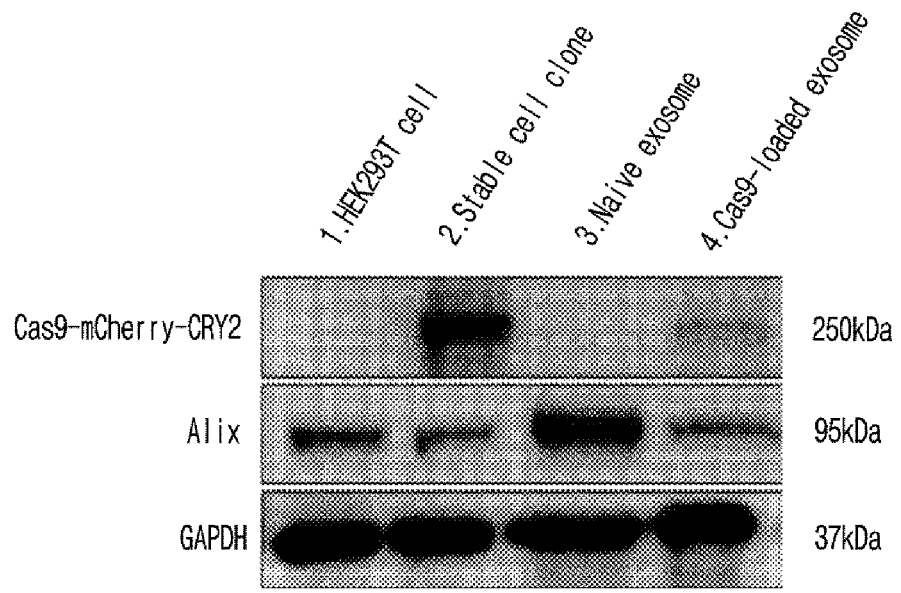

FIG. 25 illustrates the results of measuring the content of a cargo protein (CRISPR-Cas9 protein) captured in exosome.

Figure 26:
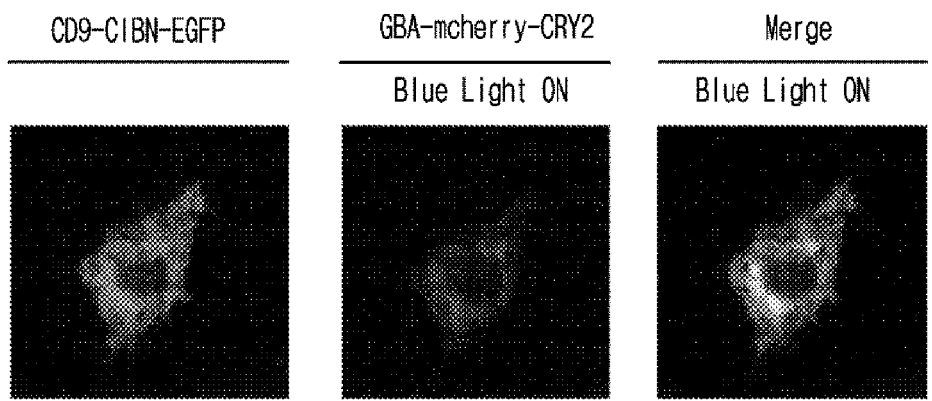

FIG. 26 illustrates the location of the expression of GBA-mCherry-CRY2 and CIBN-EGFP-CD9 in HEK293T cells, indicating they share the same position for the expression.

Figure 27:
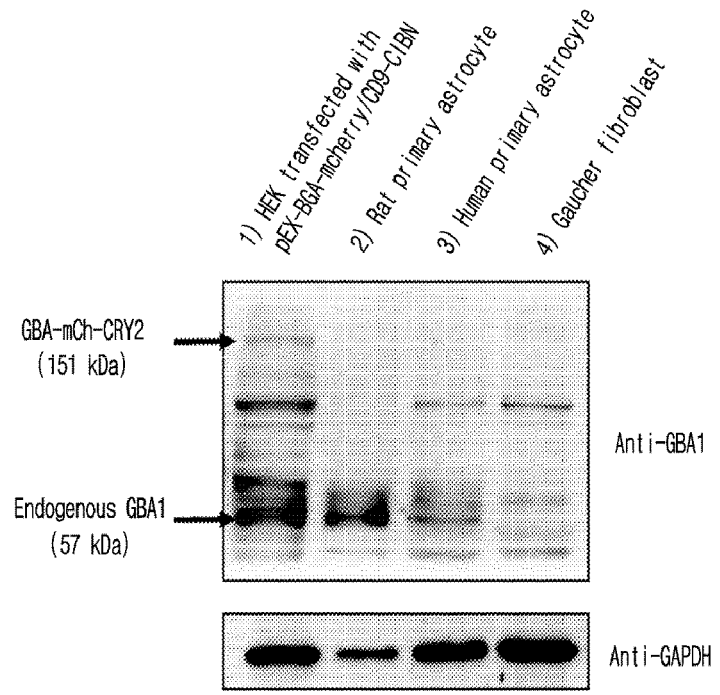

FIG. 27 illustrates the expression of endogenous GBA and GBA-mcherry-CRY2 fusion protein in HEK293T cell transiently transfected with GBA-mCh-CRY2 and CIBN-EGFP-CD9, rat primary astrocyte, human primary astrocyte and Gaucher fibroblast.

Figure 28:
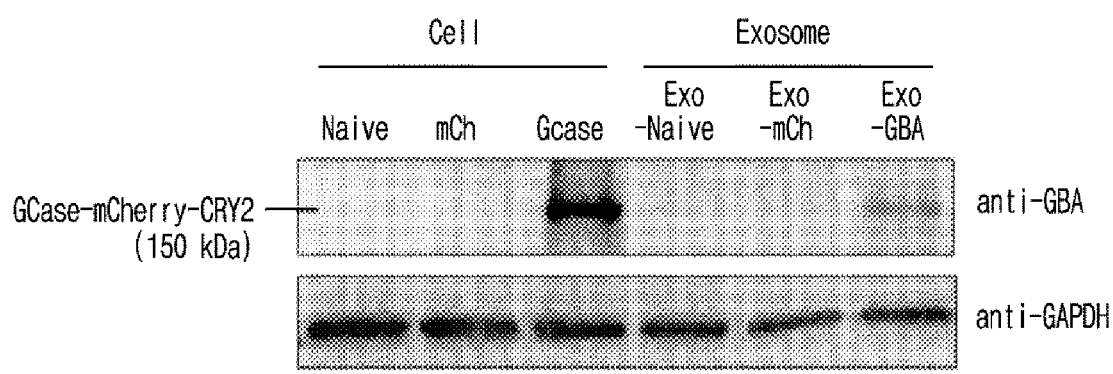

FIG. 28 illustrates the results of measuring the content of a cargo protein (GBA protein) captured in exosome.

Figure 29:
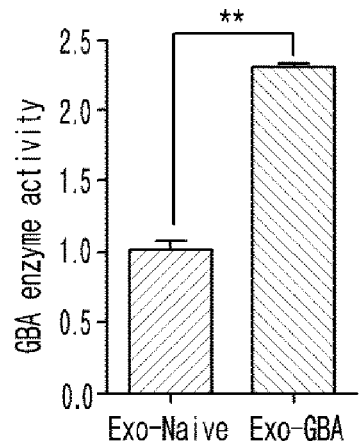
Figure 30:
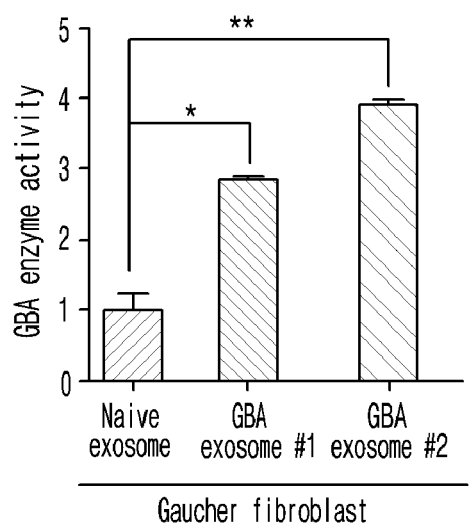

FIG. 29 illustrates the results of measuring the enzymatic activity of β-glucocerebrosidase, a cargo protein (GBA protein) captured in exosome.
Exo-Naive: HEK293T-derived exosome
Exo-GBA: exosome including β-glucocerebrosidase FIG. 30 illustrates the results of treatment of GBA-exosomes to Gaucher disease patient-derived fibroblasts, indicating treatment with GBA-exosomes significantly induced the enzymatic activity in β-glucocerebrosidase-deficient cells.

Figure 31:
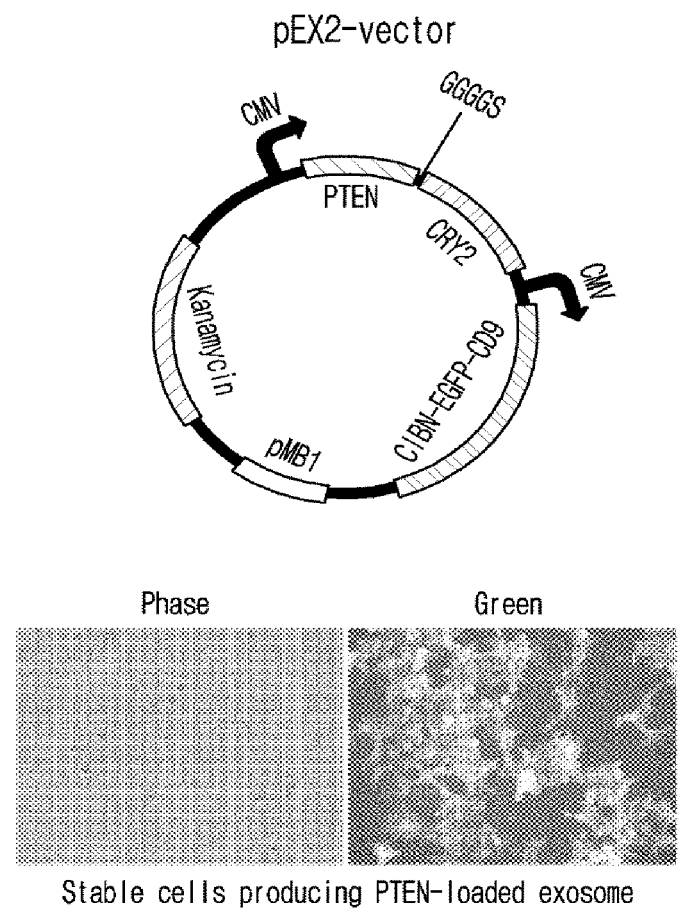

FIG. 31 illustrates the generation of DNA constructs used for the production of PTEN-loaded exosome and cells stably expressing PTEN-loaded exosome.

Figure 32:
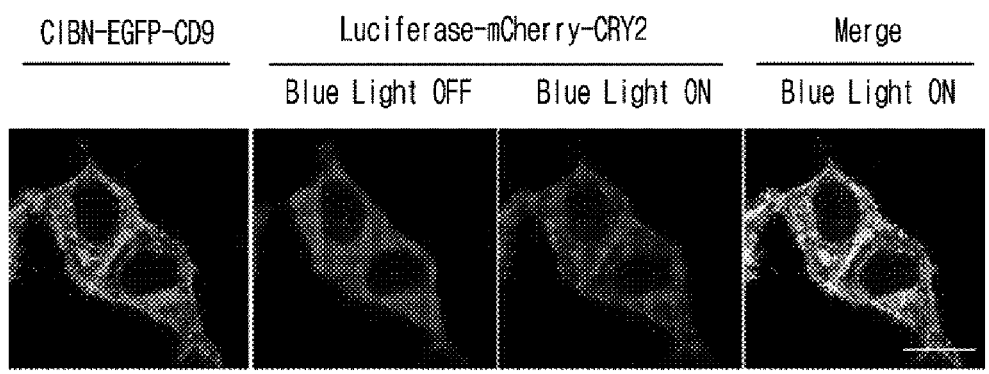

FIG. 32 illustrates the location of the expression of luciferase-mCherry-CRY2 and CIBN-EGFP-CD9 in HEK293T cells, indicating they share the same position for the expression.

Figure 33:
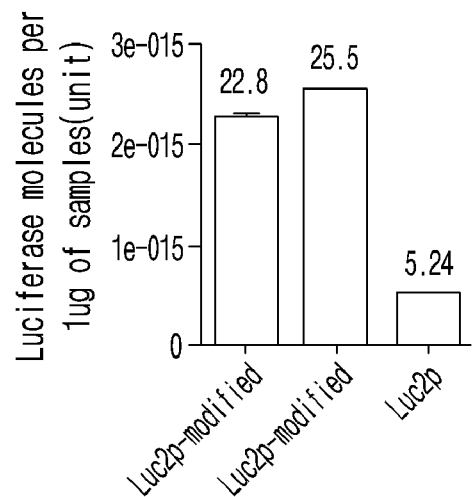

FIG. 33 illustrates the results of measurement of quantitative luciferase activity based on the number of luciferase molecules.

Figure 34:
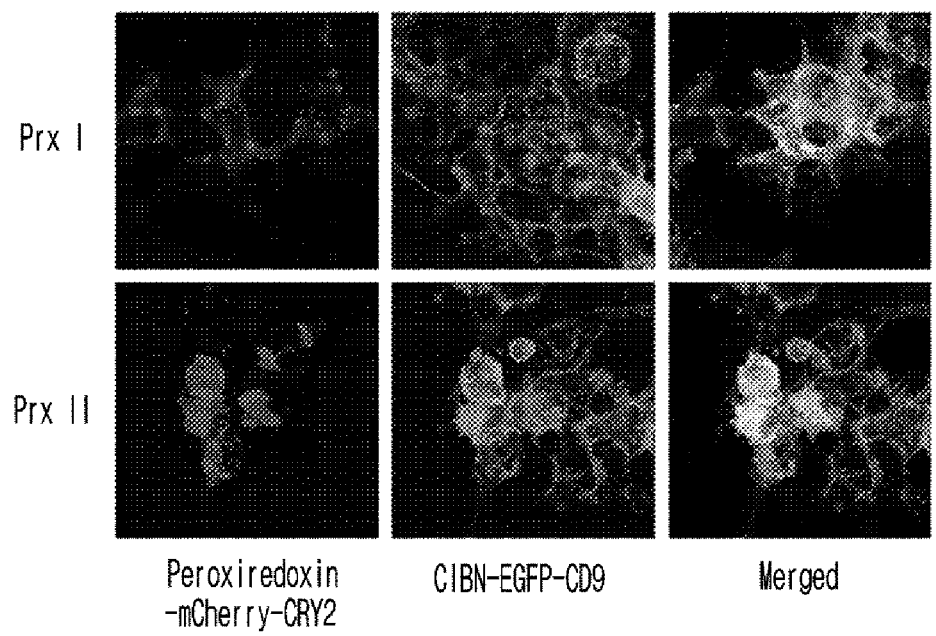
Figure 35:
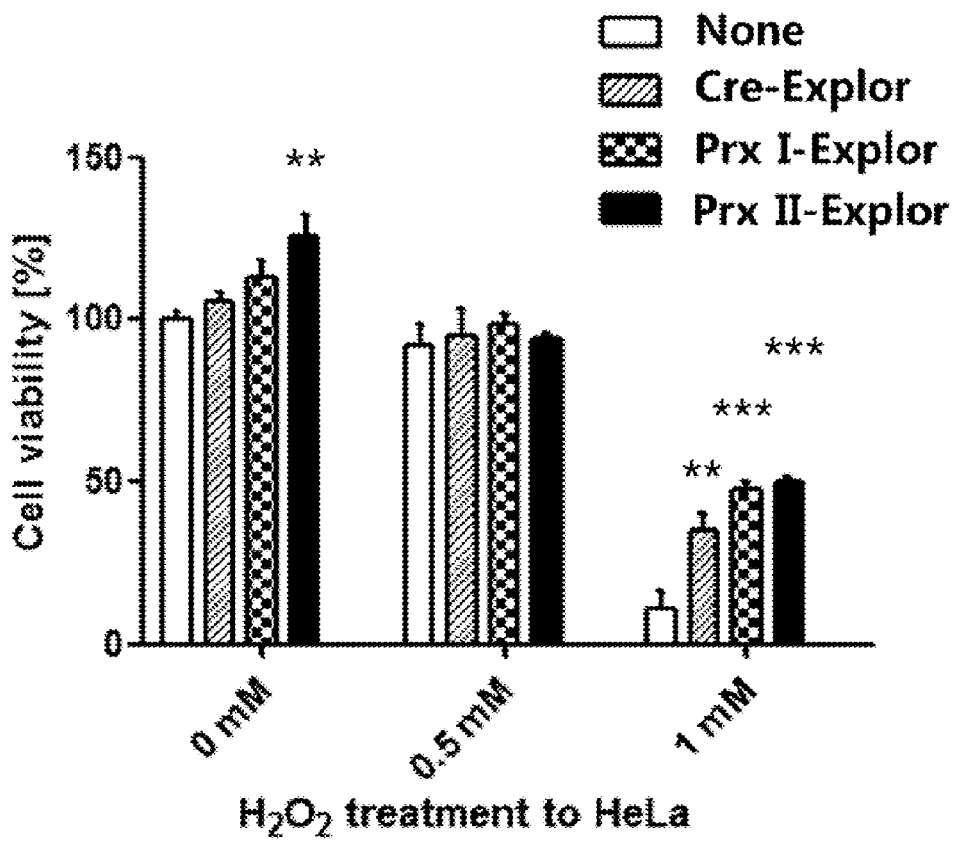

FIG. 34 illustrates the location of the expression of PrxI/II-mCherry-CRY2 and CIBN-EGFP-CD9 in HEK293T cells, indicating they share the same position for the expression.
Prx I: peroxiredoxin I
Prx II: peroxiredoxin II FIG. 35 illustrates the protective effect of PrxI/II-loaded exosomes in $H_2O_2$-induced oxidative stress and cytotoxicity.
None: $H_2O_2$-treated group;
Cre: EXPLOR: Cre-loaded exosome
Prx I: EXPLOR: PrxI-loaded exosomes; and
Prx II: EXPLOR: PrxII-loaded exosomes.

Figure 36:
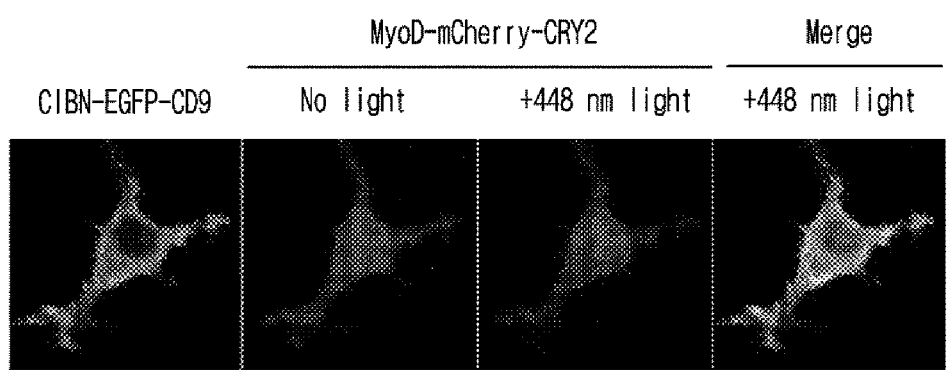

FIG. 36 illustrates the location of the expression of MyoD-mCherry-CRY2 and CIBN-EGFP-CD9 in HEK293T cells, indicating they share the same position for the expression.

Figure 37:
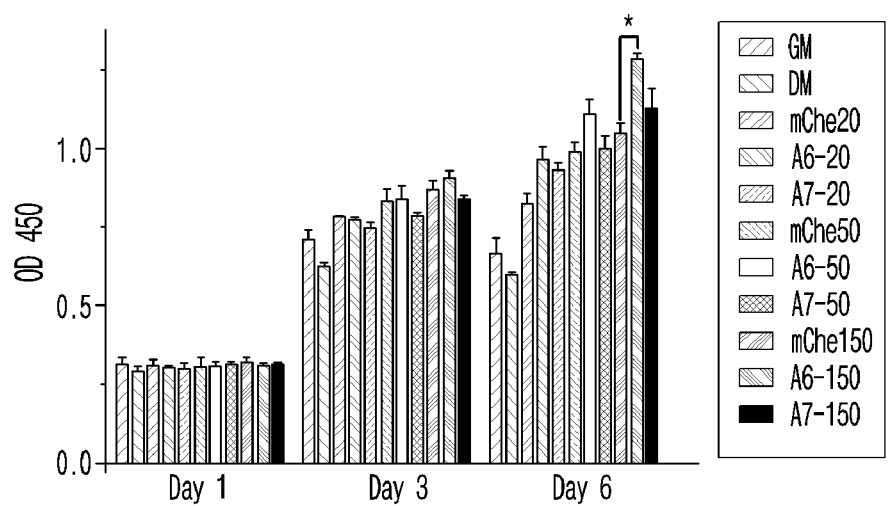

FIG. 37 illustrates the results of treatment of MyoD-loaded exosomes to adipose-derived stem cells and, indicating treatment with MyoD-exosomes (clone #A6) induced the proliferation of cells after 6 days.

Figure 38:
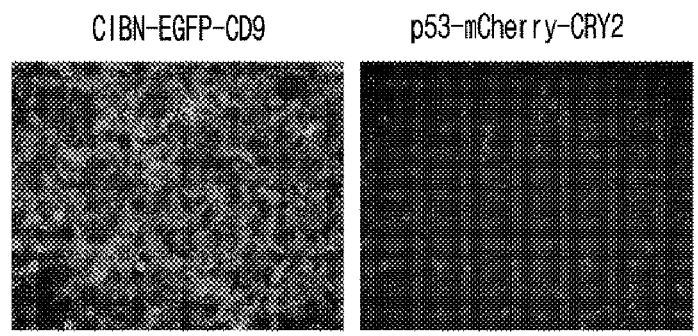

FIG. 38 illustrates the generation of cells stably expressing p53-loaded exosome.

Figure 39:
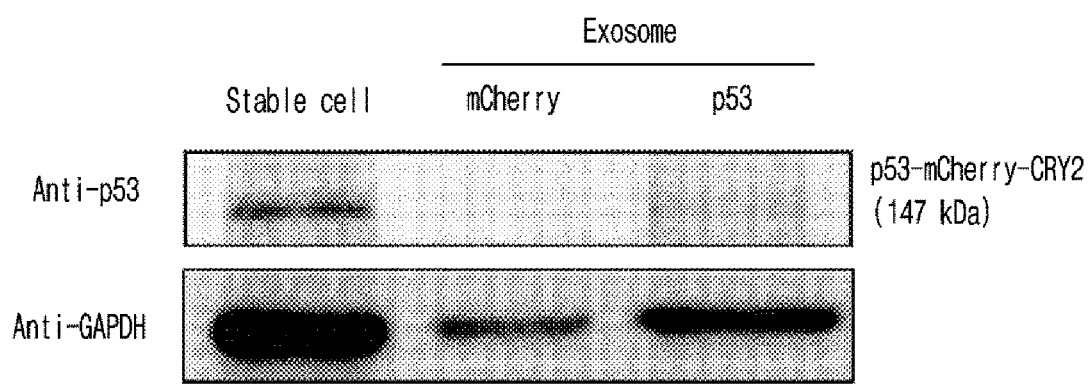
Figure 40:
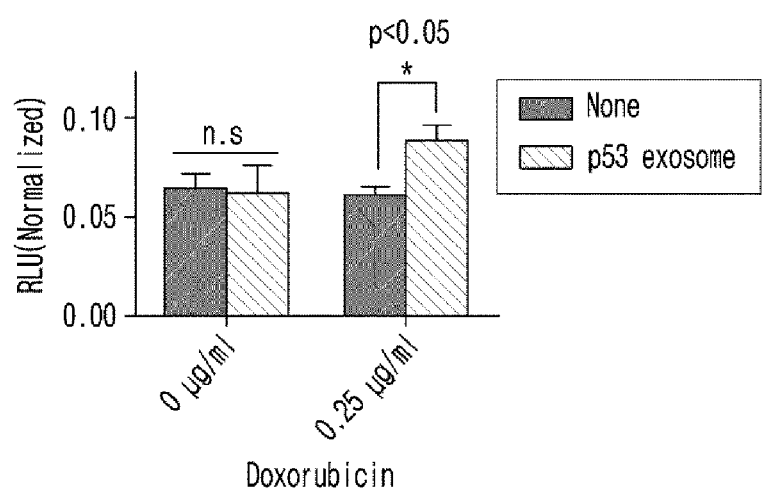

FIG. 39 illustrates the results of measuring the content of a cargo protein (p53 protein) captured in exosome.
Stable cell: cells stably expressing p53-loaded exosome.
mCherry: mCherry-loaded exosome
p53: p53-loaded exosome FIG. 40 illustrates the results of measurement of transcriptional activity of p53 using luciferase reporter gene, indicating treatment with p53-loaded exosomes induced transcriptional activity of p53 in doxorubicin-treated HeLa cells.

Figure 41:
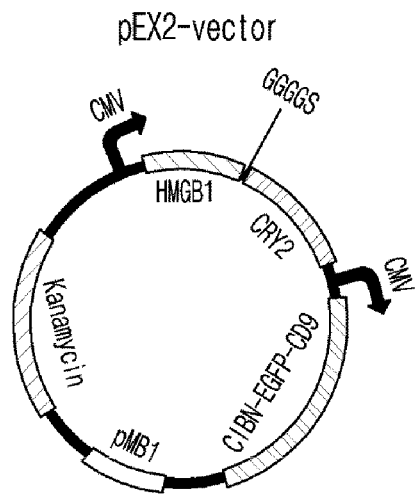
Figure 41:
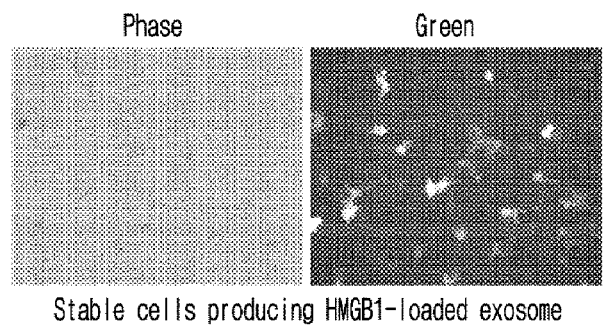

FIG. 41 illustrates the generation of DNA constructs used for the production of HMGB1-loaded exosome and cells stably expressing HMGB1-loaded exosome.

Figure 42:
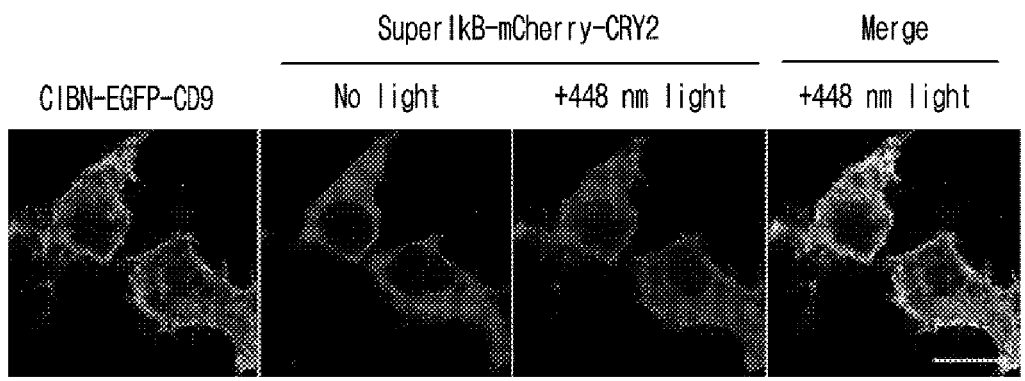

FIG. 42 illustrates the location of the expression of srIκB-mCherry-CRY2 and CIBN-EGFP-CD9 in HEK293T cells, indicating they share the same position for the expression.

Figure 43:
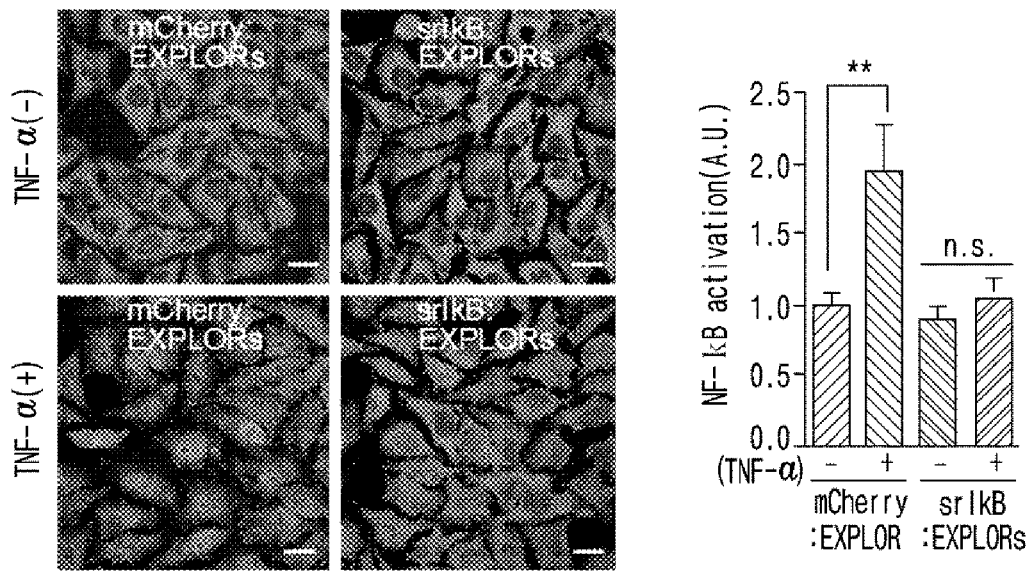

FIG. 43 illustrates that treatment with srIκB-mCherry: EXPLORs significantly reduced tumor necrosis factor-α-induced translocation and DNA binding of the p65 subunit of NF-κB in HeLa cells.

Figure 44:
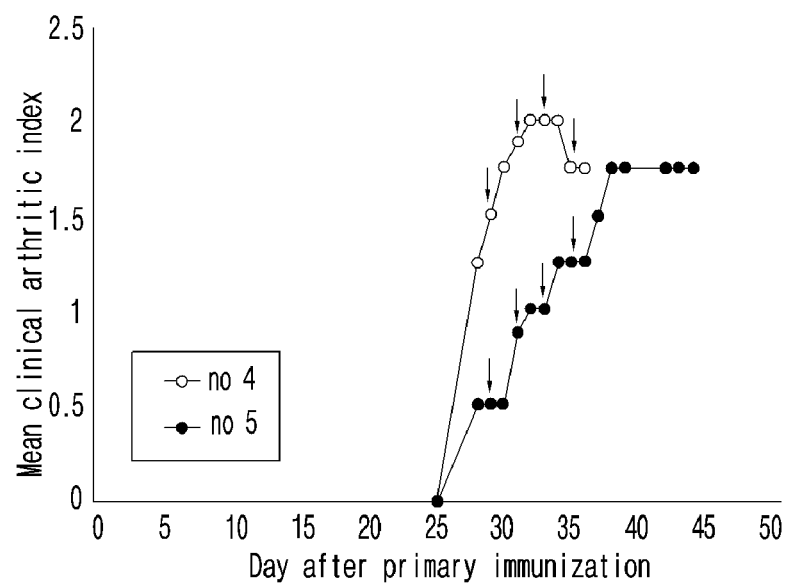

FIG. 44 illustrates the analysis of disease progression after administration of srIkB-loaded exosomes to rheumatoid arthritis animal model.

Figure 45:
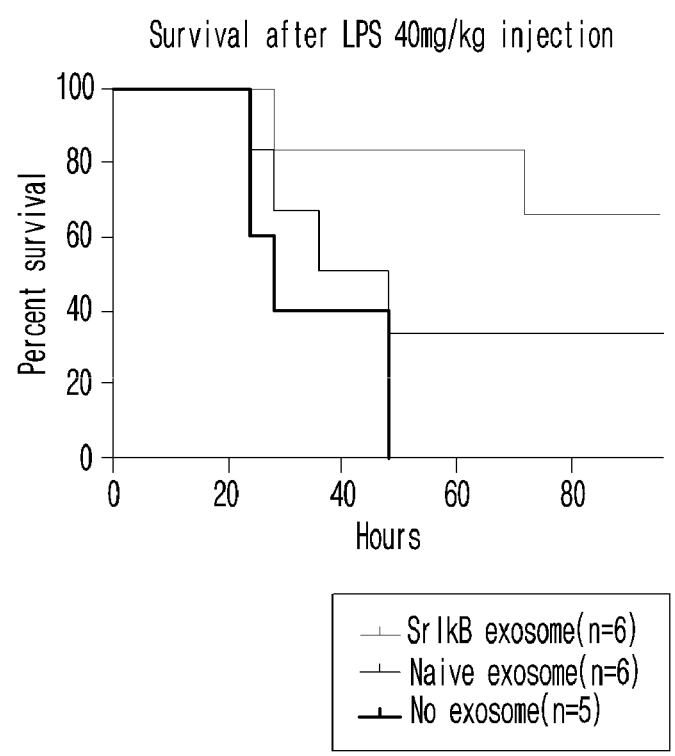
Figure 46:
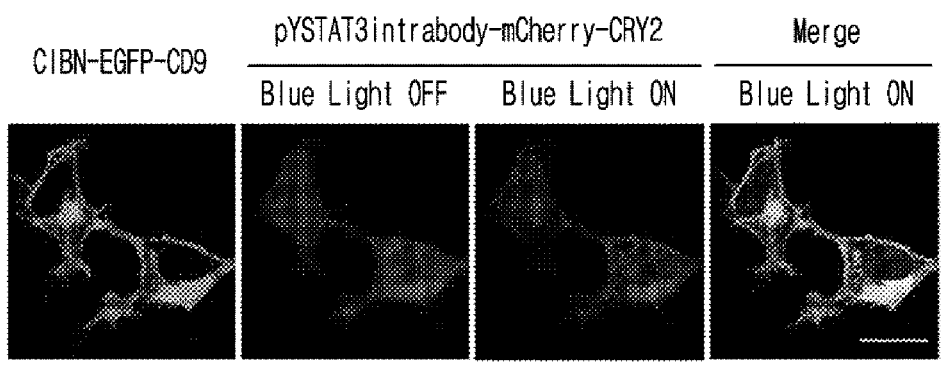

FIG. 45 illustrates the survival curve of groups treated with srIkB-loaded exosomes in LPS-induced sepsis model.
No exosome: only LPS treated group
Naive exosome: group treated with HEK293T-derived exosome
srIkB exosome: group treated with srIkB-loaded exosomes FIG. 46 illustrates the location of the expression of pYSTAT3 intrabody-mCherry-CRY2 and CIBN-EGFP-CD9 in HEK293T cells, indicating they share the same position for the expression.

Figure 47:
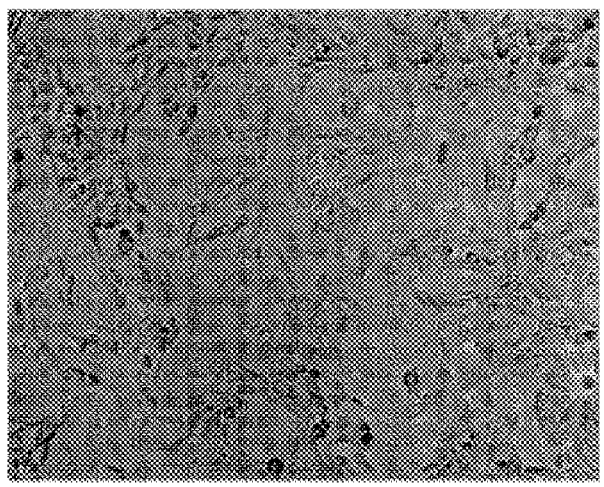

FIG. 47 illustrates the intracellular delivery of pYSTAT3 intrabody to target cells using pYSTAT3 intrabody-loaded exosomes.

Figure 48:
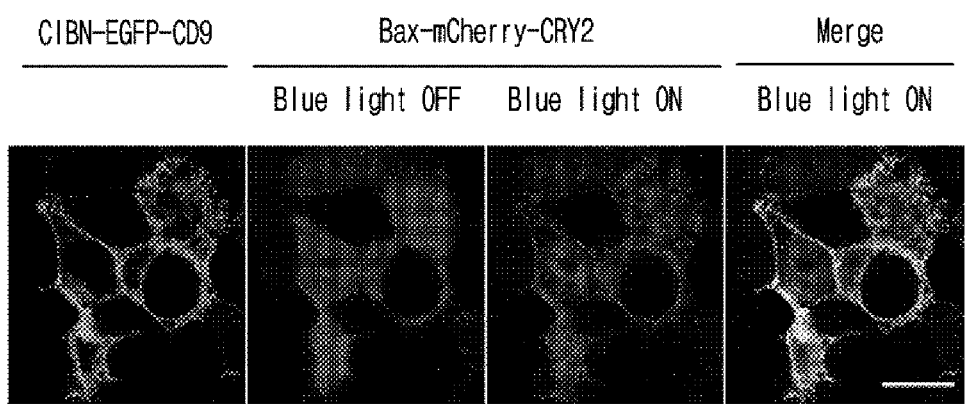

FIG. 48 illustrates location of the expression of Bax-mCherry-CRY2 and CIBN-EGFP-CD9 in HEK293T cells, indicating they share the same position for the expression.

Figure 49:
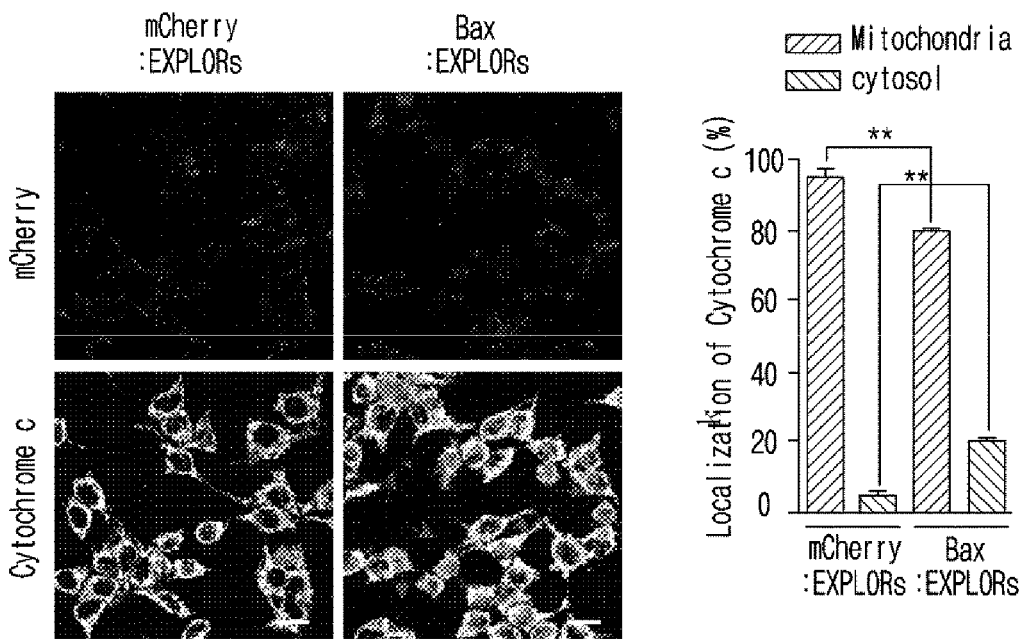
Figure 50:
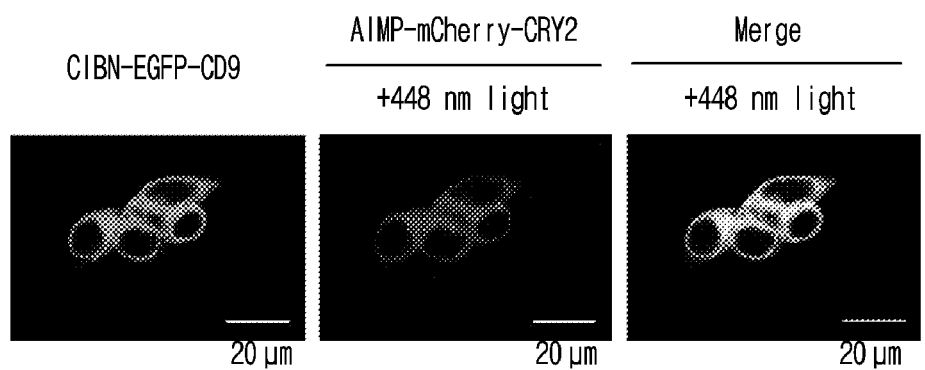

FIG. 49 illustrates that treatment with Bax-loaded exosome induced a rapid release of cytochrome c from the mitochondria in HeLa cells FIG. 50 illustrates location of the expression of AIMP-mCherry-CRY2 and CIBN-EGFP-CD9 in HEK293T cells, indicating they share the same position for the expression.

Figure 51:
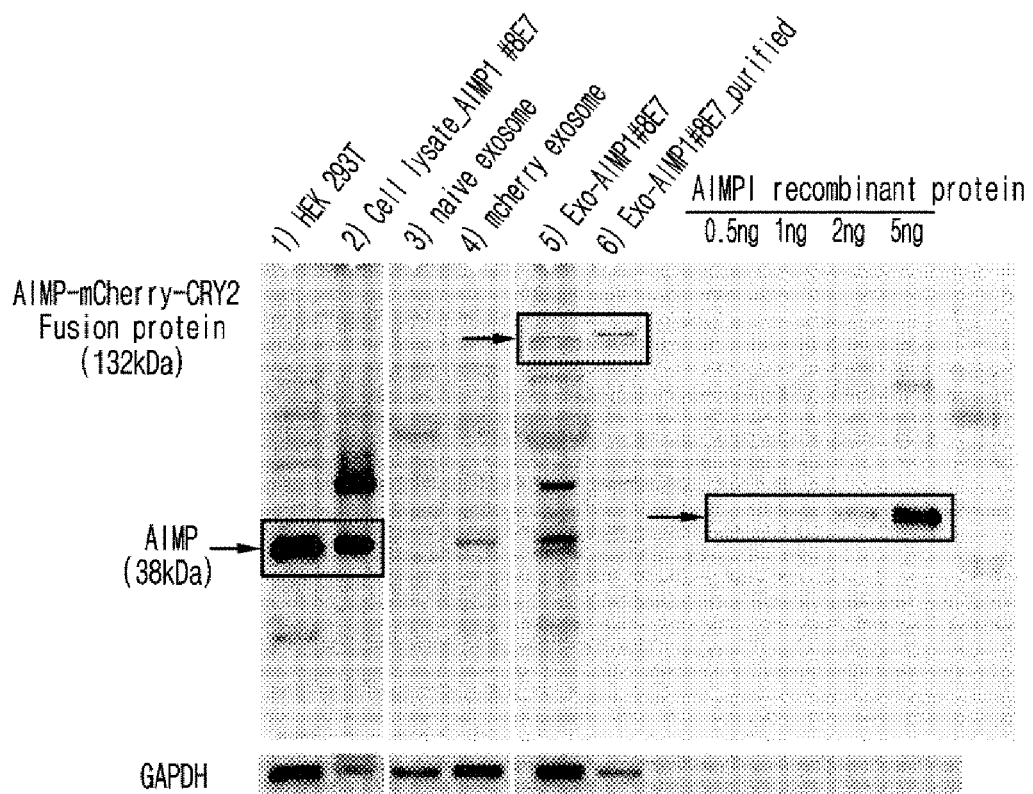

FIG. 51 illustrates the results of measuring the content of a cargo protein (AIMP protein) captured in exosome.

Figure 52:
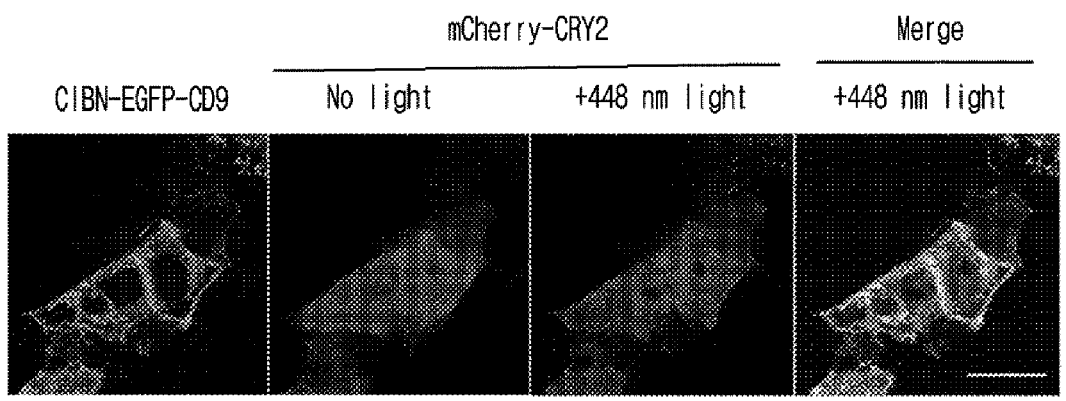

FIG. 52 illustrates location of the expression of mCherry-CRY2 and CIBN-EGFP-CD9 in HEK293T cells, indicating they share the same position for the expression.

Figure 53:
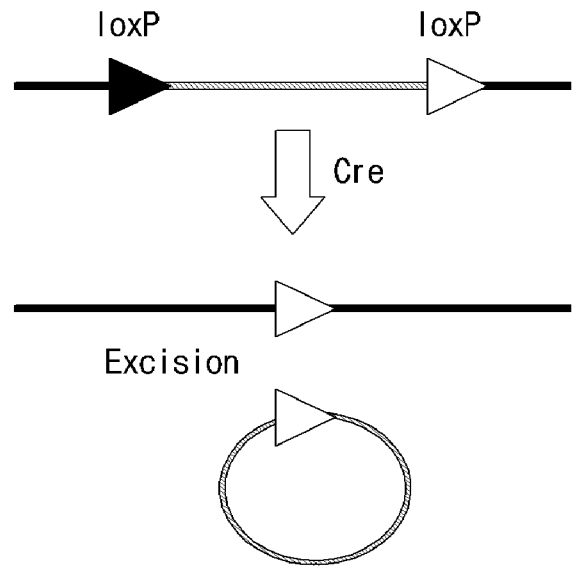

FIG. 53 illustrates DNA deletion by Cre recombinase.

Figure 54:
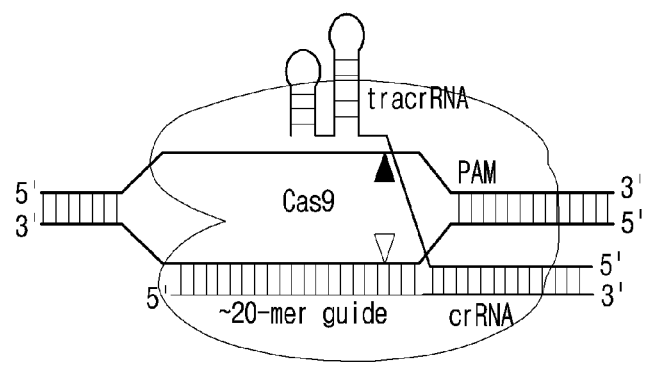
Figure 54:
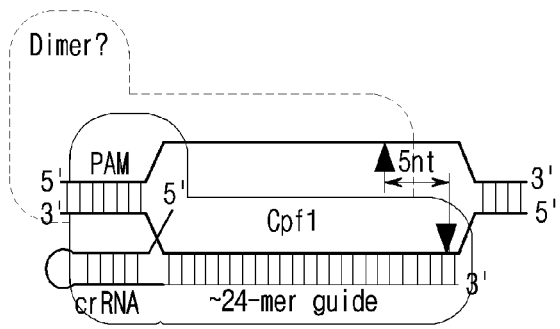

FIG. 54 illustrates difference between Cas9 and Cpf1 protein.

DETAILED DESCRIPTION OF THE INVENTION

The present invention provides compositions containing exosome loaded with a cargo protein.

In another embodiment, the present invention provides a method for preparing the exosome loaded with a cargo protein using a photo-specific binding protein.

In a further embodiment, the present invention provides a method of delivering the cargo protein to cytosol using the exosome.

In another embodiment, the present invention provides a method for the mass-production of exosome containing a fusion protein composed of an exosome specific marker and a cargo protein.

The present invention provides a method for the mass-production of exosome containing a cargo protein separated from the membrane of exosome by using a photo-specific binding protein pair.

The present invention also provides a vector for preparing exosome which is usable for the preparation of the exosome.

The present invention further provides a method to introduce a cargo protein in cytosol by using the exosome above.

In one embodiment, the present invention provides pharmaceutical compostions containing exosomes loaded with a cargo proteins and a method for preparing the same.

In a preferred embodiment, the cargo protein is super-repressor-IκB protein inhibiting NF-κB, Bax(Bcl-2-associated X protein), Peroxiredoxin I, Peroxiredoxin II, Cre recombinase, Cas9 (CRISPR associated protein 9), Cpf1 (CRISPR from Prevotella and Francisella 1) or GBA(β-glucocerebrosidase).

Figure 1:
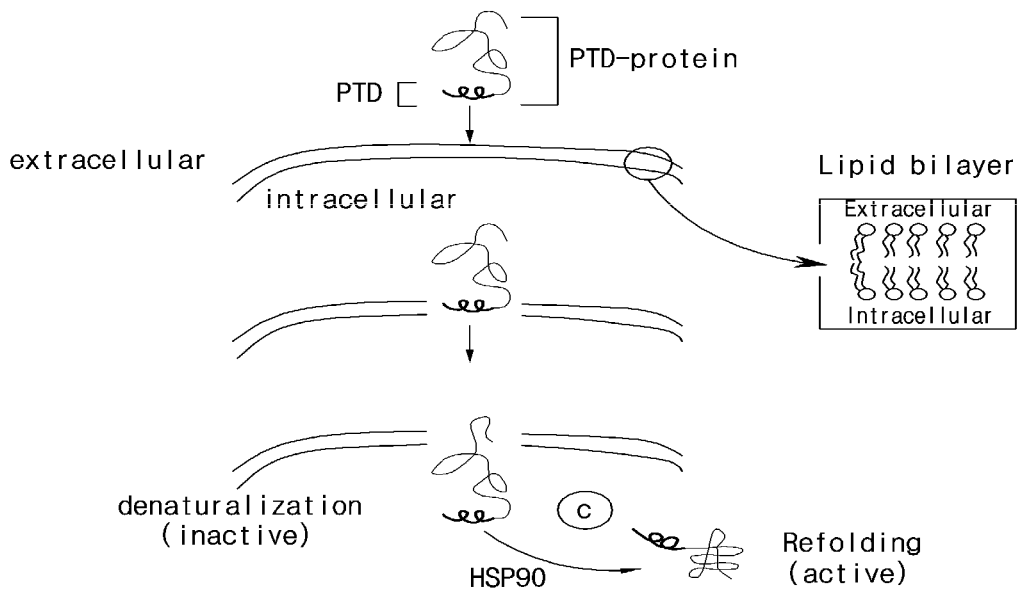
FIG. 1 illustrates the method for delivering a cargo protein through a recombinant protein of a cargo protein and protein transduction domains (PTDs) (Steven R. et al. Protein transduction: unrestricted delivery into all cells Trends in Cell Biology, 2000).
Figure 2:
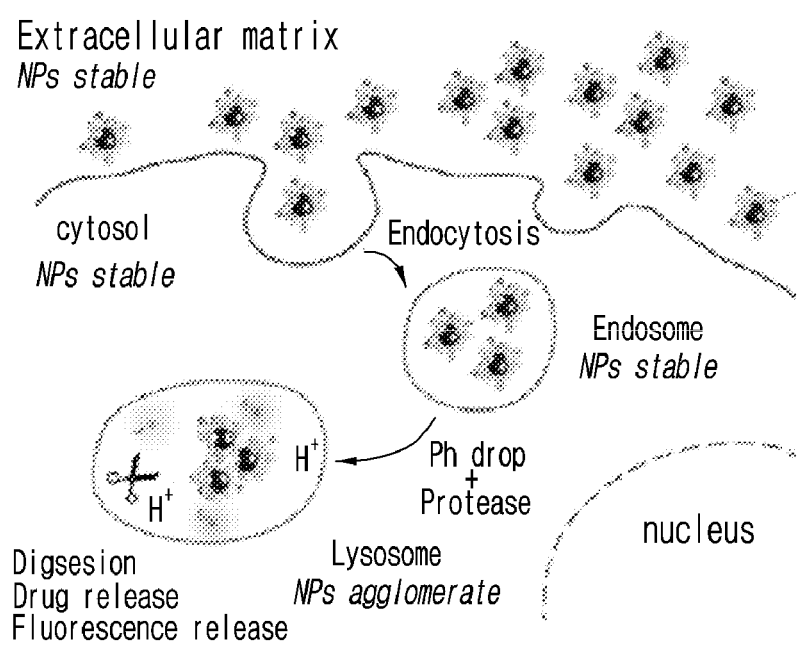
FIG. 2 illustrates the method for delivering a cargo protein to cytosol using a complex of nanoparticles and a cargo protein via endocytosis (Munish Chanana et al. Physicochemical properties of protein-coated gold nanoparticles in biological fluids and cells before and after proteolytic digestion. Angew. Chem. Int. Ed. 2013).
Figure 3:
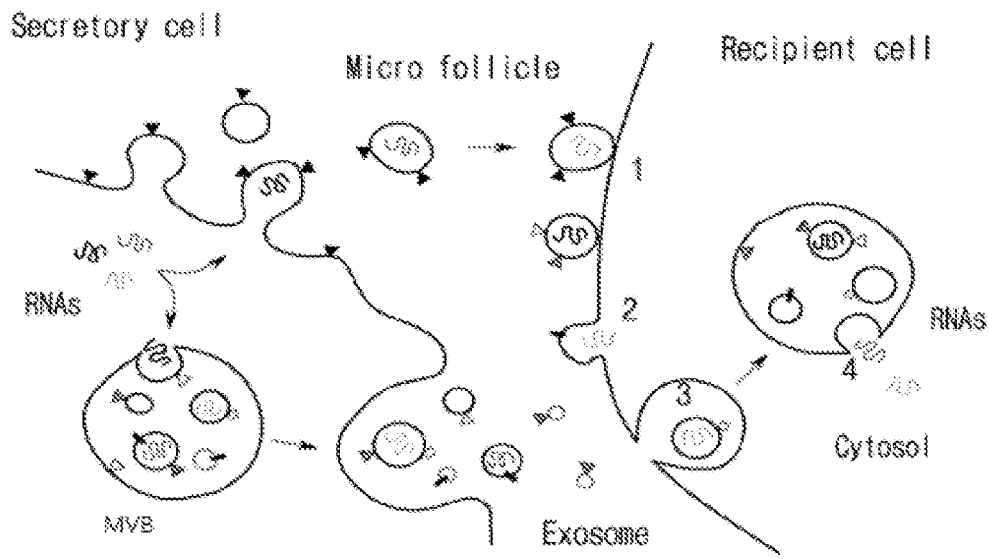
FIG. 3 illustrates the process in which exosome is separated and released from multi-vesicular bodies (MVBs) (Graca Raposo and Willem Stoorvogel. Extracellular vesicles: Exosomes, microvesicles, and friends. Cell Biology 200(4), 373-383, 2013).
Figure 4:
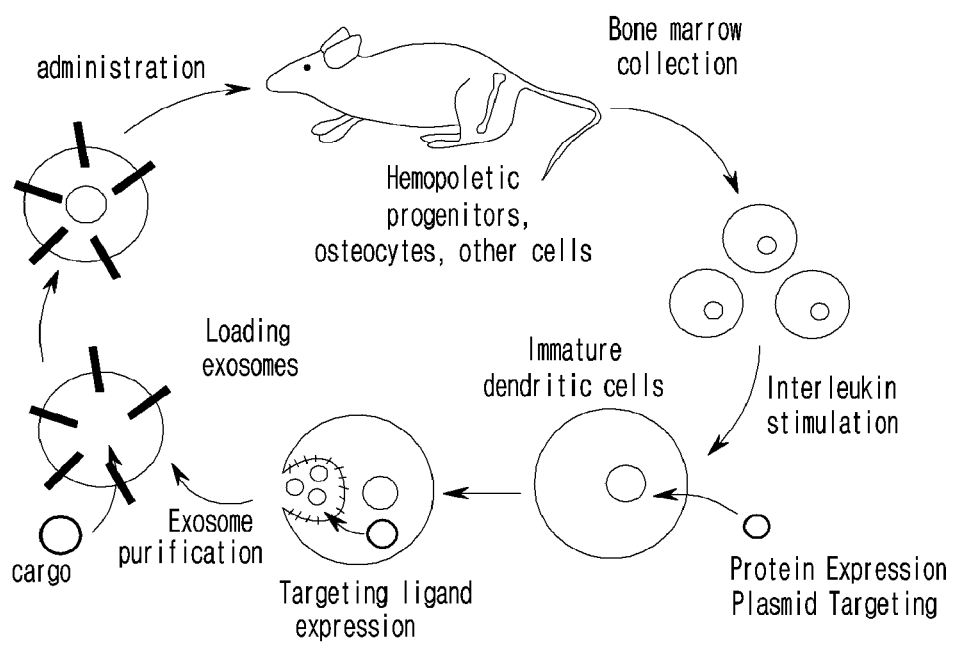
FIG. 4 illustrates the process of treating cancer by delivering siRNA in vivo through the targeted exosome (Alvarez-Erviti, L. et al. Delivery of siRNA to the mouse brain by systemic injection of targeted exosomes. Nature Biotechnology 29, 341-345, 2011).

The present invention provides exosome comprising a cargo protein which can be used for the treatment of various diseases in vivo by delivering the cargo protein. For example, exosome can be prepared to include a protein or siRNA having an anticancer activity and then treated to cancer cells for cancer treatment (FIG. 4).

For the exosomes containing a cargo protein used for the treatment of disease, the exosomes needs to be prepared efficiently to have proper load of the cargo protein. Korean Patent Publication No. 2004-0015508 describes a method for preparing exosome comprising a specific antigen. Precisely, it describes a method of discharging a cargo protein by using exosome, wherein a gene encoding a specific antigen is inserted in a host cell line and a protein of the introduced gene is stably expressed in the cell line which is discharged extracellularly through exosome, and a method using the exosome as a vaccine.

However exosome is formed naturally within the cells. So, even though a gene encoding a cargo protein is inserted in the cell producing exosome endogenously, it is very difficult to prepare exosome comprising the expressed protein in it thereby.

Figure 5:
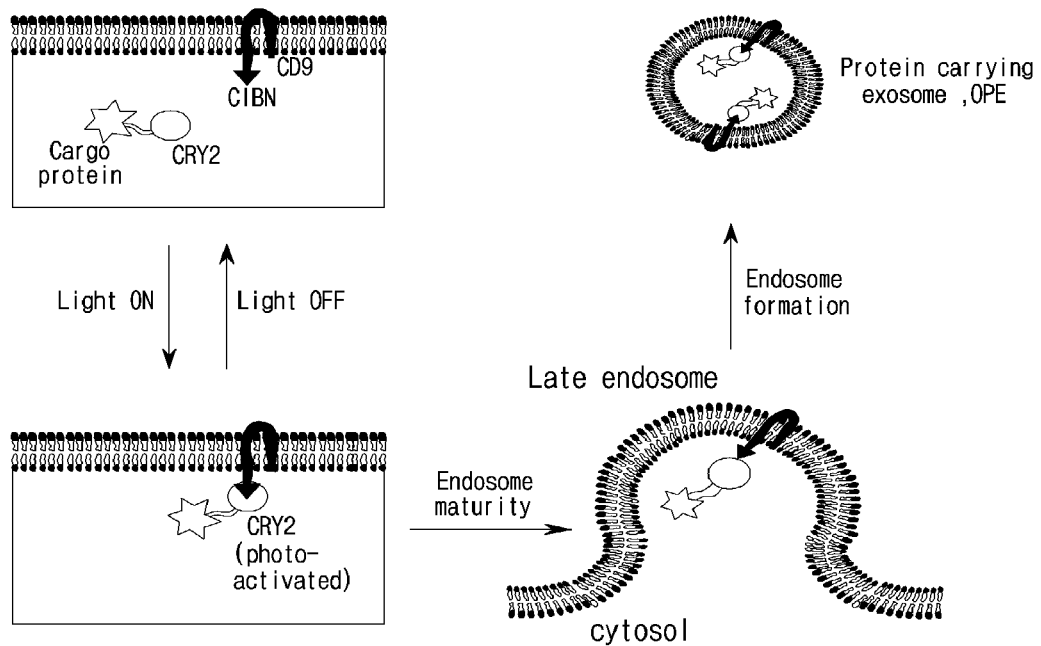
FIG. 5 illustrates the preparation process of optogenetically-designed protein-carrying exosomes (EXPLORs) according to the present invention.

The present invention provides methods for preparing exosome comprising a cargo protein more efficiently. As a result, the inventors succeeded in preparing exosome comprising a cargo protein efficiently by expressing a fusion protein composed of an exosome specific marker and a cargo protein massively in the cell producing exosome endogenously at a high concentration (FIG. 5).

Figure 6:
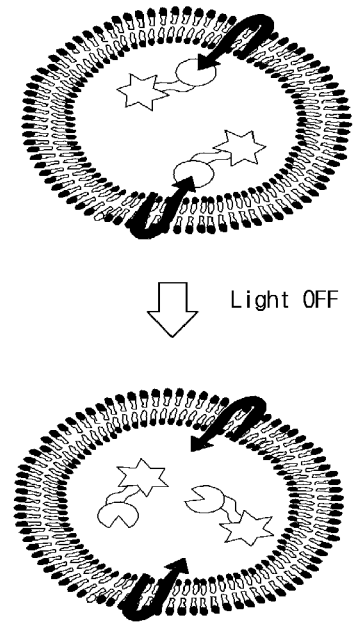
FIG. 6 illustrates the process of separating the fusion protein of a cargo protein and a photo-specific binding protein in the inside of exosome when the light irradiation on EXPLORs is stopped.

The cargo protein is attached on the membrane of exosome, according to the method above. So, the fusion protein composed of a pair of an exosome specific marker and a cargo protein is expressed in the cell producing exosome at a high concentration, followed by irradiation to induce the linkage of the fusion protein. Then, the fusion protein is introduced inside the exosome by the action of the exosome specific marker. When the irradiation is terminated after the introduction, the fusion protein is separated into a cargo protein and a photo-specific binding protein inside the exosome. As a result, the exosome containing a free cargo protein separated from the fusion protein can be prepared efficiently (FIG. 6).

The cargo proteins loaded in the exosome in the present invention includes, but not limited to, natural or non-natural proteins, truncated form or mutated form. Examples of the cargo proteins are listed, but not limited to, in the following table.

TABLE 1

| Classification | Sub-Class | Example |
| --- | --- | --- |
| Enzymes | Proteases (extracellular & intracellular) and their inhibitors | MMPs and TIMP (tissue inhibitor metalloproteases) Caspases and their inhibitors Cathepsins and their inhibitors |
| | Nucleases | Cre recombinase CRISPR/cas9 Caspase-activated DNase |
| | hydrolytic enzymes | Lysosomal enzymes including Beta-glucocerebrosidase |
| | Kinases and phosphatase | Mitogen activated kinases: p38 MAP kinase Inhibitor kappa B kinase (IKK) PTEN phosphatase Janus kinase |
| | others | Ubiquitin ligase luciferase peroxiredoxins |
| Transcription factors | Transcription factors and their inhibitors | NF-kB/super repressor IkB MyoD Tbx18 (T-box transcription factor 18) p53 HMGB1 (High mobility group box 1 protein) |
| Antibodies | Antibodies and associated peptides | pYSTAT3 intrabody |
| others | unclassified | Pro-apoptotic proteins: Bax Anti-apoptotic proteins: BcL-xL Multifunctional signal molecules: AIMP (Aminoacyl-tRNA synthetase-interacting multifunctional proteins) Fluorescent proteins (mCherry, GFP) Nucleic acid-binding proteins (ex. RNPs) |

<Enzymes>

Enzymes are biological catalytic molecules accelerating chemical reactions in living organisms. Enzymes bind to their substrates and facilitate the reaction rate by lowering its activation energy. Enzymes can be classified as follows; proteases, nucleases, hydrolytic enzymes, kinases, phosphatase and other types of enzymes.

The target proteins loaded in the exosomes in the present invention include enzymes and their regulators. Examples of the target proteins are listed, but not limited to, in the following description.

—Proteases and their Inhibitors

MMPs and TIMP

Matrix metalloproteinases (MMPs), also known as matrixins, are calcium-dependent zinc-containing endopeptidases. MMPs are capable of degrading all kinds of extracellular matrix proteins and known to be involved in the cleavage of cell surface receptors, the release of apoptotic ligands (such as the FAS ligand), and chemokine/cytokine inactivation. MMPs are also thought to play a major role in cell behaviors such as cell proliferation, migration (adhesion/dispersion), differentiation, angiogenesis, apoptosis, and host defense.

The matrix metalloproteinases are inhibited by specific endogenous tissue inhibitors of metalloproteinases (TIMPs), which comprise a family of four protease inhibitors: TIMP1, TIMP2, TIMP3 and TIMP4.

The balance of MMPs and TIMPs plays an important role in tissue remodeling associated with various physiological or pathological processes such as morphogenesis, angiogenesis, tissue repair, cirrhosis, arthritis, and metastasis. MMP-2 and MMP-9 are thought to be important in metastasis. MMP-1 is thought to be important in rheumatoid arthritis and osteoarthritis. Dysregulation of the balance between MMPs and TIMPs is also a characteristic of acute and chronic cardiovascular diseases.

The exosomes comprising MMPs and TIMPs are prepared by expressing a fusion protein composed of an exosome specific marker and a target protein massively in the cell producing the exosomes at a high concentration. The exosomes loaded with MMPs or TIMPs can be used to treat MMP-associated diseases including rheumatoid arthritis.

Caspases and their Inhibitors

Caspases (cysteine-aspartic proteases, cysteine aspartases or cysteine-dependent aspartate-directed proteases) are a family of protease enzymes playing essential roles in programmed cell death including apoptosis, pyroptosis and necroptosis. These forms of cell death are important for protecting an organism from stress signals and pathogenic attack. Caspases also have a role in inflammation, whereby it directly processes pro-inflammatory cytokines such as pro-IL1β. These are signaling molecules that allow recruitment of immune cells to an infected cell or tissue. There are other identified roles of caspases such as cell proliferation, tumor suppression, cell differentiation, neural development and axon guidance and ageing.

Caspase deficiency has been identified as a cause of tumor development. Tumor growth can occur by a combination of factors, including a mutation in a cell cycle gene which removes the restraints on cell growth, combined with mutations in apoptotic proteins such as Caspases that would respond by inducing cell death in abnormally growing cells.

Conversely, over-activation of some caspases such as caspase-3 can lead to excessive programmed cell death. This is seen in several neurodegenerative diseases where neural cells are lost, such as Alzheimer's disease. Caspases involved with processing inflammatory signals are also implicated in disease. Insufficient activation of these caspases can increase an organism's susceptibility to infection, as an appropriate immune response may not be activated. The integral role caspases play in cell death and disease has led to research on using caspases as a drug target. For example, inflammatory caspase-1 has been implicated in causing autoimmune diseases.

The exosomes comprising caspases and their inhibitors are prepared by expressing a fusion protein composed of an exosome specific marker and a target protein massively in the cell producing the exosomes at a high concentration. The exosomes loaded with caspases or their inhibitors can be used to treat caspase-associated diseases including neurodegenerative diseases or autoimmune diseases.

Cathepsins and their Inhibitors

Cathepsins are proteases found in all animals as well as other organisms. There are approximately a dozen members of this family, which are distinguished by their structure, catalytic mechanism, and which proteins they cleave. Most of the members become activated at the low pH found in lysosomes. Thus, the activity of this family lies almost entirely within those organelles.

Cathepsins have been implicated in cancer, stroke, Alzheimer's disease, arthritis, Ebola, COPD, chronic periodontitis, pancreatitis and several ocular disorders including keratoconus. Especially for cancer, cathepsin D is a mitogen and it attenuates the anti-tumor immune response of decaying chemokines to inhibit the function of dendritic cells. Cathepsin B and L are involved in matrix degradation and cell invasion.

The exosomes comprising cathepsins and their inhibitors are prepared by expressing a fusion protein composed of an exosome specific marker and a target protein massively in the cell producing the exosomes at a high concentration. The exosomes loaded with cathepsins or their inhibitors can be used to treat varying cathepsin-associated diseases including cancer and Alzheimer's disease.

—Nucleases

Cre Recombinase

Cre recombinase is the protein isolated from P1 bacteriophage, and induces recombination by detecting two different loxP region. The loxP is DNA fragment with 34 bp and is composed of two 13 bp palindromic sequence on both extremes and 8 bp asymmetrical core spacer on middle. The Cre recombinase binds to palindromic sequence, change the spacer region of DNA after cutting, and then recombine DNA (FIG. 53). Excision or inversion of DNA sequence between two different lowP regions based on the directionality of spacer. The excision or inversion is occurred if direction of lowP region is same or reverse, respectively.

One of the representative examples of Cre recombinase utilization is the conditional knockout mouse which can inhibit mutated period and expressed tissues of specific gene. This technology is that eliminating specific target gene in some isolated cells by producing loxP inserted mouse between front and end of specific target gene, mating with Cre-expressing transgenic mouse, or directly treating Cre recombinase to specific cell. The conditional knockout mouse is efficient to confirm the function of specific gene by expressing such gene, which is lethal in early phase of embryo development, in late phase of embryo development or adult.

The present invention provides exosomes loaded with Cre recombinase protein and confirmed that Cre recombinase protein was delivered to the cytosol of the target cells. The results indicate that the exosome of the present invention loaded with Cre recombinase protein can be used for conditional gene manipulation.

CRISPR/Cas9

CRISPR-Cas9 is an RNA-based artificial restriction enzyme that makes DNA correction be possible by restricting specific region of genes. Recently, it is remarkably spotlighted as the key element of genetic engineering.

CRISPR, which is kind of palindromic sequence, is the abbreviated form of Clustered regularly-interspaced short palindromic repeats and first observed acquired immunity system of bacterium. Firstly, Cas9 protein recognizes and restricts invaded virus. Then the restricted virus sequence is inserted into CRISPR sequence, and combined virus and CRISPR sequence is transcribed as RNA. This RNA is used in formation of Cas9 complex. After this process, transcribed 'CRISPR+ virus sequence' is combined with Cas9 and eliminates same invaded virus faster than Cas9 alone. This mechanism can be applied in genetic engineering by combining target sequence with Cas9 complex to restrict target sequence.

Cpf1 is protein with similar function with Cas9 protein from aforementioned engineered endonuclease CRISPR-Cas9 system. As shown in FIG. 54, Cpf1 recognizes protospace adjacent motif (PAM) sequence unlike Cas9. It can be used on the region unrecognized by Cas9, and especially it is more practical because short crispr RNA (crRNA) alone can be worked. In case of Cas9, tracrRNA is additionally needed.

The present invention provides exosomes loaded with Cas9 or Cpf1 protein and confirmed that Cas9 or Cpf1 protein was delivered to the cytosol of the target cells. The results indicate that the exosome of the present invention loaded with Cas9 or Cpf1 protein can be used for removing, adding or altering sections of the DNA sequence.

Caspase-Activated DNase

Caspase-Activated DNase (CAD) or DNA fragmentation factor subunit beta (DFFB) is a protein that is encoded by the DFFB gene in humans. It breaks up the DNA during apoptosis and promotes cell differentiation. It is usually an inactive monomer inhibited by ICAD. This is cleaved before dimerization.

Apoptosis is a cell death process that removes toxic and/or useless cells during mammalian development. The apoptotic process is accompanied by shrinkage and fragmentation of the cells and nuclei and degradation of the chromosomal DNA into nucleosomal units. DNA fragmentation factor (DFF) is a heterodimeric protein of 40-kD (DFFB) and 45-kD (DFFA) subunits. DFFA is the substrate for caspase-3 and triggers DNA fragmentation during apoptosis. DFF becomes activated when DFFA is cleaved by caspase-3. The cleaved fragments of DFFA dissociate from DFFB, the active component of DFF. DFFB has been found to trigger both DNA fragmentation and chromatin condensation during apoptosis.

The exosomes comprising Caspase-activated DNase are prepared by expressing a fusion protein composed of an exosome specific marker and a target protein massively in the cell producing the exosomes at a high concentration. The exosomes loaded with Caspase-activated DNase can be used to regulate apoptosis in diverse systems.

—Hydrolytic Enzymes

Lysosomal Enzyme Including Beta-Glucocerebrosidase

Lysosomal storage disorder is the disease because of storage of materials degraded by lysosome according to the innate deficiency of lysosome. One of the common lysosomal storage disorder is Gaucher disease which is induced by genetic deficiency of β-glucocerebrosidase (GBA), lysosomal enzyme.

Lack of GBA induces malfunction on liver, spleen, and bone marrow, and so on by storing glucocerebrosidase/glucosylsphingosine on lysosome of macrophage. Also it induces hematologic abnormality such as anemia, thrombocytopenia, and leukopenia, gepatolientalny, osteoclasia, and central nerve injury, etc.

Present treatment of Gaucher disease is the enzyme replacement therapy injecting GBA analogue, cerezyme, by intravenous injection. However, these kinds of protein drugs have various disadvantage such as short half-life in blood, low efficiency because of antibody production, difficulty of delivery to lysosome, and the impossibility on applying neurogenic Gaucher disease, etc.

The present invention provides exosomes loaded with GBA (β-glucocerebrosidase) protein and confirmed that GBA (β-glucocerebrosidase) protein was delivered to the cytosol of the target cells. The results indicate that the exosome of the present invention loaded with GBA (β-glucocerebrosidase) protein can be used for treatment of Gaucher disease.

—Kinases and Phosphatase

Mitogen Activated Kinases: p38 MAP Kinase

P38 mitogen-activated protein kinases are a class of mitogen-activated protein kinases (MAPKs) that are responsive to stress stimuli, such as cytokines, ultraviolet irradiation, heat shock, and osmotic shock. P38 MAP kinase are involved in cell differentiation, apoptosis and autophagy.

P38 MAP Kinase (MAPK) participates in a signaling cascade controlling cellular responses to cytokines and stress. P38 inhibitors are being sought for possible therapeutic effect on autoimmune diseases and inflammatory processes.

The exosomes comprising p38 MAPK and its inhibitor are prepared by expressing a fusion protein composed of an exosome specific marker and a target protein massively in the cell producing the exosomes at a high concentration. The exosomes loaded with p38 MAPK or its inhibitors can be used to treat p38 MAPK-associated diseases including autoimmune diseases.

Inhibitor Kappa B Kinase (IKK)

The IκB kinase (IKK) is an enzyme complex that is involved in propagating the cellular response to inflammation. The IκB kinase enzyme complex is part of the upstream NF-κB signal transduction cascade. The IκBα (inhibitor of kappa B) protein inactivates the NF-κB transcription factor by masking the nuclear localization signals (NLS) of NF-κB proteins and keeping them sequestered in an inactive state in the cytoplasm. IKK phosphorylates the inhibitory IκBα protein. This phosphorylation results in the dissociation of IκBα from NF-κB. NF-κB, which is now free, migrates into the nucleus and activates the expression of at least 150 genes; some of which are anti-apoptotic.

IκB kinase activity is essential for activation of members of the nuclear factor-kB (NF-κB) family of transcription factors, which play a fundamental role in lymphocyte immune-regulation. Activation of the canonical NF-κB pathway begins in response to stimulation by various pro-inflammatory stimuli, including lipopolysaccharide (LPS) expressed on the surface of pathogens, or the release of pro-inflammatory cytokines such as tumor necrosis factor (TNF) or interleukin-1 (IL-1). Following immune cell stimulation, a signal transduction cascade leads to the activation of the IKK complex, an event characterized by the binding of NEMO to the homologous kinase subunits IKK-α and IKK-ƒ3.

Though functionally adaptive in response to inflammatory stimuli, deregulation of NF-κB signaling has been exploited in various disease states. Increased NF-κB activity as a result of constitutive IKK-mediated phosphorylation of IκBα has been observed in the development of atherosclerosis, asthma, rheumatoid arthritis, inflammatory bowel diseases, and multiple sclerosis. Specifically, constitutive NF-κB activity promotes continuous inflammatory signaling at the molecular level that translates to chronic inflammation phenotypically. Furthermore, the ability of NF-κB to simultaneously suppress apoptosis and promote continuous lymphocyte growth and proliferation explains its intimate connection with many types of cancer.

The exosomes comprising IKK are prepared by expressing a fusion protein composed of an exosome specific marker and a target protein massively in the cell producing the exosomes at a high concentration. The exosomes loaded with IKK can be used to treat NF-κB-associated diseases including cancers.

PTEN Phosphatase

Phosphatase and tensin homolog (PTEN) is identified as a tumor suppressor protein. Mutations of this gene are a step in the development of many cancers. The protein contains a tensin-like domain as well as a catalytic domain similar to that of the dual specificity protein tyrosine phosphatases. Unlike most of the protein tyrosine phosphatases, this protein preferentially dephosphorylates phosphoinositide substrates. It negatively regulates intracellular levels of phosphatidylinositol-3, 4, 5-trisphosphate in cells and functions as a tumor suppressor by negatively regulating Akt/PKB signaling pathway.

PTEN loss or mutation is closely related with cancer, non-cancerous neoplasia and autism. Especially during tumor development, mutations and deletions of PTEN occur that inactivate its enzymatic activity leading to increased cell proliferation and reduced cell death. Frequent genetic inactivation of PTEN occurs in glioblastoma, endometrial cancer, and prostate cancer; and reduced expression is found in many other tumor types such as lung and breast cancer. Furthermore, PTEN mutation also causes a variety of inherited predispositions to cancer.

Mutations in the PTEN gene cause several other disorders that, like Cowden syndrome, are characterized by the development of non-cancerous tumors called hamartomas. These disorders include Bannayan-Riley-Ruvalcaba syndrome and Proteus-like syndrome. Together, the disorders caused by PTEN mutations are called PTEN hamartoma tumor syndromes, or PHTS. Mutations responsible for these syndromes cause the resulting protein to be non-functional or absent. The defective protein allows the cell to divide in an uncontrolled way and prevents damaged cells from dying, which can lead to the growth of tumors.

The exosomes comprising PTEN are prepared by expressing a fusion protein composed of an exosome specific marker and a target protein massively in the cell producing the exosomes at a high concentration. The exosomes loaded with PTEN can be used to treat varying types of cancers.

Janus Kinase

Janus kinase (JAK) is a family of intracellular, nonreceptor tyrosine kinases that transduce cytokine-mediated signals via the JAK-STAT pathway. Since members of the type I and type II cytokine receptor families possess no catalytic kinase activity, they rely on the JAK family of tyrosine kinases to phosphorylate and activate downstream proteins involved in their signal transduction pathways. After the receptor associates with its respective cytokine/ligand, it goes through a conformational change, bringing the two JAKs close enough to phosphorylate each other. The JAK auto-phosphorylation induces a conformational change within itself, enabling it to transduce the intracellular signal by further phosphorylating and activating transcription factors called STATs (Signal Transducer and Activator of Transcription). The activated STATs dissociate from the receptor and form dimers before translocating to the cell nucleus, where they regulate transcription of selected genes.

Some examples of the molecules that use the JAK/STAT signaling pathway are colony-stimulating factor, prolactin, growth hormone, and many cytokines. JAK inhibitors are under development for the treatment of psoriasis, rheumatoid arthritis, polycythemia vera, alopecia, essential thrombocythemia, ulcerative colitis, myeloid metaplasia with myelofibrosis and vitiligo.

The exosomes comprising JAK and its inhibitors are prepared by expressing a fusion protein composed of an exosome specific marker and a target protein massively in the cell producing the exosomes at a high concentration. The exosomes loaded with JAK or its inhibitors can be used to treat JAK-associated diseases including cancers.

—Others

Ubiquitin Ligase

A ubiquitin ligase (also called an E3 ubiquitin ligase) is a protein that recruits an E2 ubiquitin-conjugating enzyme that has been loaded with ubiquitin, recognizes a protein substrate, and assists or directly catalyzes the transfer of ubiquitin from the E2 to the protein substrate. The ubiquitin is attached to a lysine on the target protein by an isopeptide bond. E3 ligases interact with both the target protein and the E2 enzyme, and so impart substrate specificity to the E2.

Ubiquitination by E3 ligases regulates diverse areas such as cell trafficking, DNA repair, and signaling and is of profound importance in cell biology. E3 ligases are also key players in cell cycle control, mediating the degradation of cyclins, as well as cyclin dependent kinase inhibitor proteins.

E3 ubiquitin ligases regulate homeostasis, cell cycle, and DNA repair pathways, and as a result, a number of these proteins are involved in a variety of cancers, including famously MDM2, BRCA1, and Von Hippel-Lindau tumor suppressor. For example, a mutation of MDM2 has been found in stomach cancer, renal cell carcinoma, and liver cancer (amongst others) to deregulate MDM2 concentrations by increasing its promoter's affinity for the Sp1 transcription factor, causing increased transcription of MDM2 mRNA.

The exosomes comprising Ubiquitin ligase are prepared by expressing a fusion protein composed of an exosome specific marker and a target protein massively in the cell producing the exosomes at a high concentration. The exosomes loaded with Ubiquitin ligase can be used to treat ubiquitination-associated diseases including cancers.

Luciferase

Luciferase is a generic term for the class of oxidative enzymes that produce bioluminescence, and is usually distinguished from a photoprotein. Luciferases are widely used in biotechnology, for microscopy and as reporter genes, for many of the same applications as fluorescent proteins. However, unlike fluorescent proteins, luciferases do not require an external light source, but do require addition of luciferin, the consumable substrate.

All luciferases are classified as oxidoreductases (EC 1.13.12.-), meaning they act on single donors with incorporation of molecular oxygen. Because luciferases are from many diverse protein families that are unrelated, there is no unifying mechanism, as any mechanism depends on the luciferase and luciferin combination. However, all characterized luciferase-luciferin reactions to date have been shown to require molecular oxygen at some stage.

In biological research, luciferase is commonly used as a reporter to assess the transcriptional activity in cells that are transfected with a genetic construct containing the luciferase gene under the control of a promoter of interest. Additionally, pro-luminescent molecules that are converted to luciferin upon activity of a particular enzyme can be used to detect enzyme activity in coupled or two-step luciferase assays. Such substrates have been used to detect caspase activity and cytochrome P450 activity, among others. Luciferase can also be used to detect the level of cellular ATP in cell viability assays or for kinase activity assays. Luciferase can act as an ATP sensor protein through biotinylation. Biotinylation will immobilize luciferase on the cell-surface by binding to a streptavidin-biotin complex. This allows luciferase to detect the efflux of ATP from the cell and will effectively display the real-time release of ATP through bioluminescence. Luciferase can additionally be made more sensitive for ATP detection by increasing the luminescence intensity by changing certain amino acid residues in the sequence of the protein.

Whole animal imaging (referred to as in vivo or, occasionally, ex vivo imaging) can be performed using luciferase-expressing cell line injection. Different types of cells (e.g. bone marrow stem cells, T-cells) can be engineered to express a luciferase allowing their non-invasive visualization inside a live animal using a sensitive charge-couple device camera (CCD camera). This technique has been used to follow tumorigenesis and response of tumors to treatment in animal models.

The present invention prepared exosomes loaded with luciferase protein and confirmed that luciferase protein was delivered to the cytosol of the target cells. The results indicate that the exosome of the present invention loaded with luciferase protein can be used for cell viability assay, kinase activity assay and whole animal imaging.

Peroxiredoxins

Peroxiredoxin (Prx) is representative antioxidant enzyme in cytoplasm and obtain 0.1~0.8% of water-soluble protein in mammalian cells. Prx has the role to reduce hydroperoxide to $H_2O$ and ROH– by receiving 2e– in cells. Prx also involves in cell proliferation, differentiation, death, and cell signal transduction by participating the formation and elimination of $H_2O_2$ (nmol concentration). Prx is classified more specifically into 1-Cys Prx, or 2-Cys Prx based on the number of cysteine amino acid. Furthermore, 2-Cys prx is subdivided into 'typical' or 'atypical' based on structural, and mechanistic difference. All three Prx have difference in oxidation-reduction from second process of formation of Cys-SOH. Prx I-Prx IV are typical 2-Cys Prx, and Prx V is atypical 2-Cys Prc, and Prx VI is 1-Cys Prx. Some cases of 2-Cys Prx form oligomer.

Prx I, and II involve in activation of receptor-signaling pathway by regulating the concentration of $H_2O_2$ in cell generated by growth factor and TNF-α. Specifically, Prx II has the role in protecting cells from stimulus of cell-death inducing factor such as serum starvation, ceramide, and etoposide.

In normal cells, Prx I have the role to maintain activity of PTEN phosphatase by inhibiting its oxidation. However, in case of increased oxidative stress, the activity of PTEN is inhibited by $H_2O_2$ through separation of Prx from PTEN by irreversible oxidation. Consequently, it induces tumor through continuous activation of cell proliferating signal such as Akt.

It has a significant relation with disease that quantitative change of Prx in cell. During the process of cancer development, arteriosclerosis, respiratory inflammation, osteoporosis, obesity, and degenerative dementia, quantitative change of reactive oxygen species has a close connection.

The present invention provides exosomes loaded with Peroxiredoxin I or Peroxiredoxin II protein and confirmed that Peroxiredoxin I or Peroxiredoxin II protein was delivered to the cytosol of the target cells. The results indicates that the exosome of the present invention loaded with Peroxiredoxin I or Peroxiredoxin II protein can be used for treatment of reactive oxygen-related diseases.

Transcription factors are proteins regulating mRNA transcription from DNA in eukaryotes. Transcription factors are associated with the basal transcription regulation, organism development, response to intercellular signals or environment, cell cycle control and pathogenesis.

The target proteins loaded in the exosomes in the present invention include transcription factors and their regulators (enhancers or inhibitors). Examples of the target proteins are listed, but not limited to, in the following description.

—Transcription Factors and their Regulators

NF-kB regulator, super-repressor IkB

NF-κB is the major transcription factor inducing the inflammatory response, and regulates the expression of inflammatory-related genes in various types of cells especially immune cells. Therefore, it can be effective therapeutic strategy for incurable chronic inflammatory disease such as rheumatoid arthritis, sepsis, and psoriasis that selectively inhibits the overactive NF-κB signaling pathway in immune cells. In addition, activation of NF-κB has the role that inhibits apoptosis by increasing the expression of anti-apoptotic factors. From this role, continuous activation of NF-κB signaling pathway in cancer is the cause for anticancer drug resistance and then decreases the therapeutic effects of anticancer drugs.

Most NF-κB is on inactive phase by binding with IκB, which is the inhibitory protein of NF-κB, in normal cells. IκB Kinase (IKK) complex activated by various stimuli such as TNF-α and LPS phosphorylates IκB. The phosphorylated IκB is then ubiquitinated and finally degraded by proteasome. Through degradation of IκB, NF-κB (p50/p65) bound on IκB passes through nuclear membrane. After passing, it activates mRNA transcription by binding on the promotor region of target genes in nucleus. This is the important element of immune response that induces transcription of cytokine and inflammatory mediator such as iNOS, COX-2, NO, PGE2, TNF-α, and IL-1 (Lappas et al., Biol. Reprod. 67:668673, 2002).

Super-repressor IκB which is S32A and S36A mutant form of IκB can continuously inhibit NF-κB because it is not phosphorylated by IκB Kinase and degraded by proteasome. Therefore, it has the great potential as treatment for various inflammatory diseases. The present invention provides exosomes loaded with Super-repressor IκB protein and confirmed that Super-repressor IκB protein was delivered to the cytosol of the target cells. The results indicate that the exosome of the present invention loaded with Super-repressor IκB protein can be used for treatment of inflammatory diseases.

MyoD

MyoD is a protein that plays critical role in regulating muscle differentiation. MyoD belongs to a family of proteins known as myogenic regulatory factors (MRFs). MyoD is known to have binding interactions with hundreds of muscular gene promoters and to permit myoblast proliferation.

Also, one of the main functions of MyoD is to remove cells from the cell cycle by enhancing the transcription of p21 and myogenin.

The exosomes comprising MyoD protein are prepared by expressing a fusion protein composed of an exosome specific marker and a target protein massively in the cell producing the exosomes at a high concentration. The exosomes loaded with MyoD can be used to treat myoblast-associated diseases.

Tbx18 (T-Box Transcription Factor 18)

Tbx18 codes for a member of an evolutionarily conserved family of transcription factors that plays a crucial role in embryonic development. Tbx18 is characterized by the presence of the DNA-binding T-box domain and it belongs to the vertebrate specific Tbx1 sub-family. Tbx18 acts as a transcriptional repressor by antagonizing transcriptional activators in the T-box family. Tbx18 is required in various developmental process in tissues and organs, including the heart and coronary vessels, the ureter and the vertebral column. It is also required for sinoatrial node (SAN) head area.

Tbx18 transduction is a method of turning on genes in heart muscle cells as a treatment for certain cardiac arrhythmias. In a healthy heart, sinoatrial nodal cells act as the heart's pacemaker and cause the heart to beat in a regular rhythm. The problem in sick sinus syndrome is that SA node is not functioning properly and is causing an irregular heartbeat. Expression of Tbx18 using adenovirus into atrial myocytes converts atrial muscle cells into SA node cells that initiate the heartbeat. Tbx18 can be a one of many forms of gene therapy that can cure cardiac arrhythmias.

The exosomes comprising Tbx18 protein are prepared by expressing a fusion protein composed of an exosome specific marker and a target protein massively in the cell producing the exosomes at a high concentration. The exosomes loaded with Tbx18 protein can be used for the treatment of sick sinus syndrome.

p53

Tumor protein p53 is known as the guardian of the genome because it conserves the stability of genome by preventing genome mutation. p53 can activate DNA repair proteins when DNA has sustained damage. In addition, p53 can arrest growth by holding the cell cycle at the G1/S regulation point on DNA damage recognition. Upon DNA damage and it is irreparable, p53 can induce apoptosis. Lastly, p53 is essential for the senescence response to short telomeres. p53 becomes activated in response to myriad stressors, including DNA damage, oxidative stress, osmotic shock, ribonucleotide depletion and deregulated oncogene expression.

If the p53 is damaged, tumor suppression is severely compromised. People who inherit only one functional copy of p53 gene will most likely develop tumors in early adulthood. Increasing the amount of p53 may seem a solution for treatment of tumors or prevention of their spreading.

The exosomes comprising p53 protein are prepared by expressing a fusion protein composed of an exosome specific marker and a target protein massively in the cell producing the exosomes at a high concentration. The exosomes loaded with p53 protein can be used for the treatment of varying types of cancers.

HMGB1 (High Mobility Group Box 1 Protein)

HMGB1 is among the most important chromatin proteins like histones. In the nucleus, HMGB1 interacts with nucleosomes, transcription factors and histones. This nuclear protein organizes the DNA and regulates transcriptions. After binding, HMGB1 bends DNA, which facilitates the binding of other proteins. It also interacts with nucleosomes to loosen packed DNA and remodel the chromatin.

HMGB1 is secreted by immune cells through leaderless secretory pathway. Activated macrophages and monocytes secrete HMGB1 as a cytokine mediator of inflammation. Antibodies that neutralize HMGB1 confer protection against damage and tissue injury during arthritis, colitis, ischemia, sepsis, etc.

The exosomes comprising HMGB1 protein are prepared by expressing a fusion protein composed of an exosome specific marker and a target protein massively in the cell producing the exosomes at a high concentration. The exosomes loaded with HMGB1 protein can be used for the treatment of inflammatory diseases.

NeuroD1

Neurogenic differentiation1, also called (32, is a transcription factor of the NeuroD-type. It mediates transcriptional activation by binding to E box-containing promoter consensus core sequences 5'-CANNTG-3'. It is contributed to the regulation of several cell differentiation pathways. It promotes the formation of early retinal ganglion cells, inner ear sensory neurons and granule cells forming either the cerebellum or the dentate gyrus cell layer of the hippocampus, endocrine islet cells of the pancreas and enteroendocrine cells of the small intestine.

The exosomes comprising NeuroD1 protein are prepared by expressing a fusion protein composed of an exosome specific marker and a target protein massively in the cell producing the exosomes at a high concentration. The exosomes loaded with NeuroD1 protein can be used for the regulation of neuron development.

Tumor-associated macrophages (TAMs) are a type of cell belonging to the macrophage lineage. They are found in close proximity or within tumor masses. TAMs are derived from circulating monocytes or resident tissue macrophages, which form the major leukocytic infiltrate found within the stroma of many tumor types. TAMs have been linked to poor prognosis in breast cancer, ovarian cancer, types of glioma and lymphoma; better prognosis in colon and stomach cancers and both poor and better prognoses in lung and prostate cancers.

TAMs are classified into two major phenotypes, M1 and M2. M1 TAMs suppress cancer progression, while M2 TAMs promote it. Several transcription factors are associated with the transition of M2 macrophage to M1 macrophage. The target proteins loaded in the exosomes in the present invention include transcription factors associated with the M2 to M1 conversion of macrophage. Examples of the target proteins are listed, but not limited to, in the following description.

IRF5

IRF5 is a member of the interferon regulatory factor, a group of transcription factor. It has role in virus-mediated activation of interferon and modulation of cell growth, differentiation, apoptosis and immune system activity. IRF5 work by directly interacting with DNA or with other proteins.

IRF5 acts as a molecular switch that controls whether macrophages will promote or inhibit inflammation. Blocking the production of IRF in macrophage can help treat a wide range of autoimmune disease and upregulating IRF5 levels can help treat people whose immune system are weak or damaged.

The exosomes comprising IRF5 protein are prepared by expressing a fusion protein composed of an exosome specific marker and a target protein massively in the cell producing the exosomes at a high concentration. The exosomes loaded with IRF5 protein can be used for macrophage transition from M2 to M1 for the treatment of varying types of cancers.

IRF3

IRF3 is a member of the interferon regulatory factors, a group of transcription factor. IRF3 includes functional domains, nuclear export signal, a DNA-binding domain, a C-terminal IRF association domain and several regulatory sites. It is found in an inactive form in the cytoplasm of uninfected cells. Upon viral infection, double stranded RNA or toll-like receptor signaling, it is phosphorylated by IKBKE and TBK1 kinases. This leads to dimerization and nuclear localization. IRF3 can activate distinct gene expression programs in macrophages.

The exosomes comprising IRF3 protein are prepared by expressing a fusion protein composed of an exosome specific marker and a target protein massively in the cell producing the exosomes at a high concentration. The exosomes loaded with IRF3 protein can be used for macrophage transition from M2 to M1 for the treatment of varying types of cancers.

STAT1

Signal transducer and activator of transcription 1 is a transcription factor, member of the STAT protein family. STAT1 can be activated by several ligands such as interferon alpha, interferon gamma, epidermal growth factor, platelet derived growth factor or interleukin 6.

Following type I IFN binding to cell surface receptors, JAK gets activated and phosphorylates STAT1 and STAT2. STATs dimerize and associate with ISGF3G/IRF-9 to form a complex termed ISGF3 transcription factor. ISGF3 binds to the IFN stimulated response element to activate the transcription of IFN-stimulated genes.

In response to type II IFN, STAT1 is tyrosine and serine phosphorylates. It forms a homodimer and binds to IFN gamma activated sequence to drive the expression of target genes, inducing a cellular antiviral state.

The exosomes comprising STAT1 protein are prepared by expressing a fusion protein composed of an exosome specific marker and a target protein massively in the cell producing the exosomes at a high concentration. The exosomes loaded with STAT1 protein can be used for the treatment of varying types of cancers.

SOCS3

Suppression of cytokine signaling is a member of STAT-induced STAT inhibitor. STAT-induced STAT inhibitors are cytokine-inducible negative regulators of cytokine signaling. SOCS3 is induced by various cytokines like IL6, IL10, and IFN-gamma.

Overexpression of SOCS3 inhibits insulin signaling in adipose tissue and liver but not in muscle. But deletion of SOCS3 in the skeletal muscle of mice protects against the obesity.

SOCS3 also contributes to both leptin resistance and insulin resistance as a result of increased ceramide synthesis. Study shows that removal of the SOCS gene prevents against insulin resistance in obesity. SOCS3 protein can bind to JAK2 and inhibits the activity of JAK2.

The exosomes comprising SOCS3 protein are prepared by expressing a fusion protein composed of an exosome specific marker and a target protein massively in the cell producing the exosomes at a high concentration. The exosomes loaded with SOCS3 protein can be used for the treatment of varying types of cancers.

<Antibodies>

Antibodies are the proteins that recognize and bind to their specific antigen via the Fab's variable region on the tip of the "Y"-shaped antibody. Antibodies can suppress the activity of the target antigen proteins by binding to them.

The target proteins loaded in the exosomes in the present invention include antibodies and antibody-associated peptides. Examples of the target proteins are listed, but not limited to, in the following description.

—Antibodies and Associated Peptides pYSTAT3 Intrabody

STATs (Signal Transducer and Transcriptions) are transcription factors that have been identified: STAT1, STAT2, STAT3, STAT4, STAT5 (STAT5A and STAT5B), and STATE. STAT3 proteins have C-terminal transactivation domain (Tyrosine 705 and Serine 727 residues for the major phosphorylation sites of STAT3). Tyrosine phosphorylation and subsequent dimerization of STAT3 promote the transportation to the nucleus and transcriptional activation.

The JAK/STAT3 signaling pathway is identified in growth factor-induced activation of interferon signaling and involved in proliferation, differentiation, apoptosis, angiogenesis, oncogenesis and immunity. Therefore, STAT3 proteins can be a good target as a single agent or combination therapeutics for development of anticancer drugs.

The exosomes of the present invention loaded with pYSTAT3 intrabody was prepared and confirmed that pYSTAT3 intrabody was delivered to the cytosol of the target cells. The results indicates that the exosome of the present invention loaded with pYSTAT3 intrabody can be used for treatment of cancer.

<Others>

—Apoptosis-Associated Proteins

Apoptosis (programmed cell death) is the process for eliminating damaged cells by various factors and abnormal apoptosis induces tumorigenicity. Based on this reason, researches about inducing apoptosis of tumor have actively progressed as tumor-eliminating strategy. Condensation of chromatin by cell atrophy, apoptotic body formation, and DNA fragmentation are the features of apoptosis. The apoptosis is induced by two different routes; one is the intrinsic pathway through mitochondria, and the other is the extrinsic pathway through death receptors. The apoptosis is regulated variously, for example activation of pro-apoptotic Bcl-2 family, segmentation of pro-caspase, and fragmentation of poly ADP-ribose polymerase (PARP), and so on. Especially caspases belonged to cysteine proteases are being pro-enzyme in normally proliferated cells and activated by apoptotic inducing signals, then has the significant role in apoptosis through involving cargo proteins such as PARP.

Most apoptotic stimuli induce the apoptosis of mammalian cells through the pathway controlled by members of Bcl-2 gene family which are coding homologous protein group including agonist and antagonist of apoptosis such as Bcl-2, and Bcl-xL. These members share the sequence homologous domain even though they are regulated discriminately. During apoptosis, the anti-apoptotic or pro-apoptotic effect of Bcl-2 and Bax (21% identity with Bcl-2 at the protein level) is regulated by homo- and heterodimers, which are differently formed by the ratio of Bcl-2 to Bax.

Pro-Apoptotic Proteins: Bax

Bax (Bcl-2-associated X protein) is the one of Bcl-2 protein family, so-called Bcl-2 like protein 4. Aforementioned Bax, which binds to the external membrane of mitochondria and its 4 residues of C-terminal protrude on intermembrane space of mitochondria, has the role to activate apoptosis. Specific information about aforementioned protein and base sequence of its gene is noticed on NCBI (GenBank: NM_001291428, NP_001278357, etc.).

Bax is the one of Bcl-2 gene family synthesizing pro-apoptotic protein. Bax is inhibited its transcription by mutant p53. It has well known that insertion or deletion of Bax base sequence is the cause of markedly decreased expression of Bax in cell lines of blood, colon, and rectal cancer.

It is known that Bax involves in apoptosis of neuron in development, homeostatic equilibrium of lymphatic and genital system, cell death by DNA damage, damage of ischemia reperfusion and so on.

The present invention provides exosomes loaded with Bax protein and confirmed that Bax protein was delivered to the cytosol of the target cells. The results indicates that the exosome of the present invention loaded with Bax protein can be used for treatment of cancer.

Anti-Apoptotic Proteins: Bcl-xL

B-cell lymphoma-extra-large (Bcl-xL), encoded by the BCL2-like 1 gene, is a transmembrane molecule in the mitochondria. It is a member of the Bcl-2 family of proteins, and acts as an anti-apoptotic protein by preventing the release of mitochondrial contents such as cytochrome c, which leads to caspase activation and ultimately, programmed cell death.

It is a well-established concept in the field of apoptosis that relative amounts of pro- and anti-survival Bcl-2 family of proteins determine whether the cell will undergo cell death; if more Bcl-xL is present, then pores are non-permeable to pro-apoptotic molecules and the cell survives. Similar to Bcl-2, Bcl-xL has been implicated in the survival of cancer cells by inhibiting the function of p53, a tumor suppressor.

The exosomes comprising Bcl-xL protein are prepared by expressing a fusion protein composed of an exosome specific marker and a target protein massively in the cell producing the exosomes at a high concentration. The exosomes loaded with Bcl-xL protein can be used for the regulation of apoptosis.

—Etc.

Multifunctional Signal Molecules: AIMP (Aminoacyl-tRNA Synthase-Interacting Multifunctional Proteins)

Aminoacyl tRNA synthase complex-interacting multifunctional protein 1 (AIMP1) is a non-catalytic component of the multi-synthase complex. Stimulates the catalytic activity of cytoplasmic arginyl-tRNA synthase. Possesses inflammatory cytokine activity. Negatively regulates TGF-beta signaling through stabilization of SMURF2 by binding to SMURF2 and inhibiting its SMAD7-mediated degradation. Involved in glucose homeostasis through induction of glucagon secretion at low glucose levels. Promotes dermal fibroblast proliferation and wound repair.

Plays a role in angiogenesis by inducing endothelial cell migration at low concentrations and endothelial cell apoptosis at high concentrations. Induces maturation of dendritic cells and monocyte cell adhesion. Modulates endothelial cell responses by degrading HIF-1A through interaction with PSMA7.

Aminoacyl tRNA synthase complex-interacting multifunctional protein 2 (AIMP2) is required for assembly and stability of the aminoacyl-tRNA synthase complex. Mediates ubiquitination and degradation of FUBP1, a transcriptional activator of MYC, leading to MYC down-regulation which is required for alveolar type II cell differentiation. Accumulates in brains affected by autosomal-recessive juvenile Parkinsonism, idiopathic Parkinson disease and diffuse Lewy body disease.

The exosomes comprising AIMP1 and AIMP2 proteins are prepared by expressing a fusion protein composed of an exosome specific marker and a target protein massively in the cell producing the exosomes at a high concentration. The exosomes loaded with AIMP1 or AIMP2 protein can be used for multifunctional regulation.

Fluorescent Proteins (mCherry, GFP)

Fluorescent proteins are members of a structurally homologous class of proteins that share the unique property of being self-sufficient to form a visible wavelength chromophore from a sequence of 3 amino acids within their own polypeptide sequence. It is common research practice for biologists to introduce a gene (or a gene chimera) encoding an engineered fluorescent protein into living cells and subsequently visualize the location and dynamics of the gene product using fluorescence microscopy.

The most popular applications of fluorescent proteins involve exploiting them for imaging of the localization and dynamics of specific organelles or recombinant proteins in live cells. For imaging of a specific organelle, standard molecular biology techniques are used to fuse the gene encoding the fluorescent protein to a cDNA encoding a protein or peptide known to localize to that specific organelle. This fusion is done such that the chimeric gene will be expressed as a single polypeptide, creating a covalent link between the targeting motif and the fluorescent protein. A plasmid containing the chimeric gene under control of a suitable promoter is used to transfect mammalian cells that then express the gene to produce the corresponding chimeric protein. The chimera localizes to the target organelle and thus renders it fluorescent. Through the use of fluorescence microscopy, the morphology, dynamics, and distribution of the organelle can be imaged as a function of time.

mCherry is a monomeric fluorescent construct with peak excitation/emission at 587 nm/610 nm, respectively. It is resistant to photobleaching and is stable. It matures quickly, with a t0.5 of 15 minutes, allowing it to be visualized soon after translation.

The green fluorescent protein (GFP) is a protein composed of 238 amino acid residues (26.9 kDa) that exhibits bright green fluorescence when exposed to light in the blue to ultraviolet range. Although many other marine organisms have similar green fluorescent proteins, GFP traditionally refers to the protein first isolated from the jellyfish Aequorea Victoria. The GFP from A. Victoria has a major excitation peak at a wavelength of 395 nm and a minor one at 475 nm. Its emission peak is at 509 nm, which is in the lower green portion of the visible spectrum.

The present invention prepared exosomes loaded with mCherry or GFP protein and confirmed that mCherry or GFP protein was delivered to the cytosol of the target cells. The results indicate that the exosome of the present invention loaded with mCherry or GFP protein can be used for imaging of the localization and dynamics of exosomes and linked proteins in live cells or animal.

Nucleic Acid-Binding Proteins (Ex. RNPs)

Nucleoproteins are any proteins that are structurally associated with nucleic acids, either DNA or RNA. A deoxyribonucleoprotein (DNP) is a complex of DNA and protein. The prototypical examples are nucleosomes, complexes in which genomic DNA is wrapped around clusters of eight histone proteins in eukaryotic cell nuclei to form chromatin. Protamines replace histones during spermatogenesis. DNPs in this kind of complex interact to generate a multiprotein regulatory complex in which the intervening DNA is looped or wound. The DNPs participate in regulating DNA replication and transcription.

A ribonucleoprotein (RNP) is a complex of RNA and protein. The enzyme telomerase, vault ribonucleoproteins, RNase P, hnRNP and small nuclear RNPs (snRNPs), and ribosomes are ribonucleoproteins. The RNPs play a role of protection. mRNAs never occur as free RNA molecules in the cell. They always associate with ribonucleoproteins and function as ribonucleoprotein complexes.

The exosomes comprising DNPs or RNPs are prepared by expressing a fusion protein composed of an exosome specific marker and a target protein massively in the cell producing the exosomes at a high concentration. The exosomes loaded with DNPs or RNPs can be used for genetic regulations or nucleic acid transportable exosomes.

The present invention confirmed that the cargo protein was successfully delivered to cytosol of a target cell by using the exosome containing the cargo protein therein, and thereby the present invention provides a method to treat disease using exosome by regulating intracellular signaling efficiently in cytosol.

Another object of the present invention is to provide a pharmaceutical composition for preventing or treating inflammatory diseases containing the exosome as an active ingredient.

Another object of the present invention is to provide a pharmaceutical composition for preventing or treating cancer containing the exosome as an active ingredient.

Another object of the present invention is to provide a pharmaceutical composition for preventing or treating oxygen-related diseases containing the exosome as an active ingredient.

Another object of the present invention is to provide a composition for producing a conditional knockout allele of a target gene containing the exosome as an active ingredient.

Another object of the present invention is to provide a DNA sequence manipulating composition containing the exosome as an active ingredient.

Another object of the present invention is to provide a pharmaceutical composition for preventing or treating Gaucher's disease containing the exosome as an active ingredient.

To develop an efficient method for preparing exosome containing a cargo protein, the present inventors studied with various attempts. In the course of our study, the inventors paid attention on exosome specific markers (CD9, CD63, CD81, and CD82). These markers belong to the tetraspanin family and are commonly 4-times penetration type membrane proteins. The present inventors predicted that when a cargo protein was conjugated on the membrane protein of exosome, the cargo protein would be relatively easily included in the inside of exosome.

By expressing the fusion protein composed of an exosome specific marker which is rich especially on exosome membrane and can penetrate cell membrane and a cargo protein in the cell producing exosome endogenously at a high concentration, exosome containing a cargo protein can be massively produced.

Particularly, the method for preparing exosome comprising a cargo protein of the present invention is characterized by introduction of polynucleotide encoding the fusion protein composed of an exosome specific marker and a cargo protein in the cell producing exosome.

At this time, in the prepared exosome, a cargo protein is fused with an exosome specific marker embedded in exosome membrane.

The said cargo protein is bound to the membrane protein of exosome and is not separated even after it arrives at the target cell. To solve this problem, various attempts have been made. As a result, a technique has been developed for the preparation of exosome comprising a cargo protein by conjugating a cargo protein temporarily to a marker protein. For example, a photo-specific binding protein such as CIBN and CRY2 can be used herein. Particularly, CIBN is expressed in a form fused with CD9, which is one of the marker proteins. In the meantime, a gene encoding the fusion protein of CRY2 and a cargo protein is introduced in the cell producing exosome. The CIBN-CD9 fusion protein expressed in the exosome production cell can be included due to CD9. At this time, when the cell is irradiated with blue LED light, CRY2 domain of the cargo protein-CRY2 fusion protein expressed in the exosome production cell is bound to the CD9 fused CIBN domain. As a result, the reversible 'cargo protein-CRY2-CIBN-CD9 fusion protein' is produced. This fusion protein can be included in the inside of exosome due to CD9. Once exosome containing a cargo protein therein is produced and the irradiation with the blue LED light is terminated, CIBN-CRY2 link is broken and thereby the cargo protein remains in exosome as being apart from the cell membrane of exosome, resulting in the preparation of exosome comprising the cargo protein (FIGS. 5-10).

Figure 11:
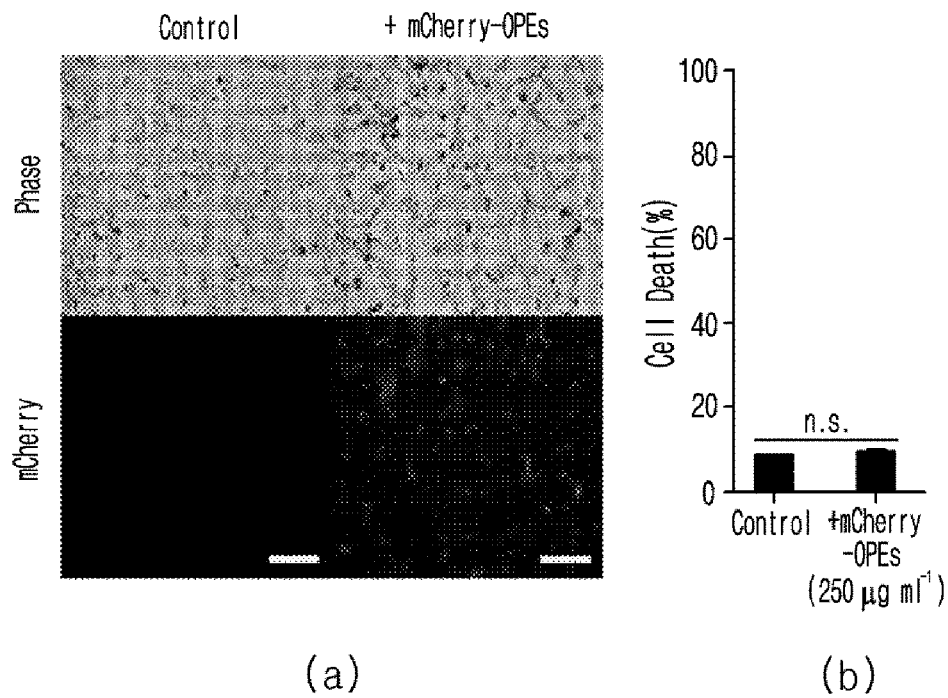
FIG. 11 is a set of a fluorescence image (a) illustrating the results of investigation of the introduction of a cargo protein in target cells after treating the target cells (HT1080) with exosome containing the cargo protein (mCherry); and a graph (b) illustrating the results of comparison of the ratio of apoptotic cells induced by the treatment of exosome.

This kind of exosome prepared by the method of the present invention is completely different in its effect from the conventional exosome containing a target material. The conventional exosome is expressed as being fused onto an exosome specific marker in order to present a cargo protein inside of the exosome, so that the cargo protein, even though it is included in the inside of the exosome, it is not free and instead presented as being attached on the membrane of exosome, suggesting that the cargo protein cannot be separated from the membrane of exosome and therefore it can be delivered into a target cell only when the exosome is fused on the cell wall of the target cell. Moreover, even after the fusion onto the target cell, the cargo protein remains as being conjugated to the membrane of exosome. Therefore, the probability that the cargo protein exhibits its effect in the target cell is very low. However, the exosome of the present invention presents a cargo protein which resides as free and not being conjugated on the membrane of exosome. So, when such exosome enters cytosol by endocytosis of the target cell, it does not adhere to the membrane of exosome, and when the exosome is decomposed therein, the included cargo protein can be delivered in cytosol and is free to move in cytosol of the target cell, suggesting that the cargo protein is fully active with its physiological activity in the target cell cytosol (FIG. 11).

The binding level of the cargo protein to the marker protein can be changed according to the intensity of the light to be irradiated. Therefore, by regulating the intensity of the light, the concentration of the cargo protein collected in exosome can be controlled.

The method for preparing exosome containing a cargo protein by using a photo-specific binding protein has not been reported yet and was proposed first by the present inventors.

Particularly, the method for preparing exosome containing a cargo protein of the present invention is composed of the following steps: (a) introducing the polynucleopeptide encoding the fusion protein (fusion protein I) composed of an exosome specific marker and the first photo-specific binding protein and the polynucleotide encoding the fusion protein (fusion protein II) composed of a cargo protein and the second photo-specific binding protein that can be linked to the first photo-specific binding protein in the exosome production cell; (b) irradiating the exosome production cell with light that can cause the conjugation between the first photo-specific binding protein and the second photo-specific binding protein; and (c) terminating the irradiation after the production of exosome finished in the exosome production cell.

The term "exosome" in the present invention indicates a small vesicle with the plasma membrane structure, which is originated from an intracellular specific compartment called multi-vesicular bodies (MVBs) and is released or secreted from the cell.

In this invention, exosome plays a role as a carrier to deliver a cargo protein into a target cell or tissue by carrying the cargo protein in itself. At this time, the cargo protein carried by the exosome works for the target cell or tissue to help the treatment or diagnosis of a specific disease.

The term "exosome production cell" in this invention indicates the cell that is able to produce exosome.

In this invention, the exosome production cell is not limited but is preferably exemplified by B-lymphocyte, T-lymphocyte, dendritic cell, megakaryocyte, macrophage, stem cell, and tumor cell, etc. For example, in this invention, HEK293T cell that is a kind of immortalized cell line was used as the exosome production cell.

The term "exosome specific marker" in this invention indicates a protein which is rich on the membrane of exosome.

In this invention, the exosome specific marker is not limited but is preferably exemplified by CD9, CD63, CD81, and CD82, etc. For example, in a preferred embodiment of the present invention, CD9 was used as the exosome specific marker. CD9, CD63, CD81, and CD82 are 4-times penetration type membrane proteins that allow the cargo protein to be easily present in exosome when the cargo protein is bound to the membrane protein of the exosome.

The term "photo-specific binding protein" in this invention is also called photo-induced heterodimer formation protein or photo-induced homodimer formation protein, which indicates a protein that is able to form a heterodimer by combining with different proteins or to form a homodimer by combining with another protein in the same kind when the light of a specific wavelength is irradiated.

In this invention, the photo-specific binding protein is not limited but is preferably exemplified by the photo-induced heterodimer formation protein or CIB (cryptochrome-interacting basic-helix-loop-helix protein), CIBN (N-terminal domain of CIB), PhyB (phytochrome B), PIF (phytochrome interacting factor), FKF1 (Flavinbinding, Kelch repeat, F-box 1), GIGANTEA, CRY (cryptochrome), and PHR (phytolyase homologous region), etc.

In particular, when the photo-specific binding protein is the photo-induced heterodimer formation protein, two types of photo-specific binding protein (the first and the second photo-specific binding proteins) can be used. When the first photo-specific binding protein is CIB or CIBN, the second photo-specific binding protein can be CRY or PHR. When the first photo-specific binding protein is PhyB, the second photo-specific binding protein can be PIF. When the first photo-specific binding protein is GIGANTEA, the second photo-specific binding protein can be FKF1.

For example, in a preferred embodiment of the present invention, CIBN was used as the first photo-specific binding protein, and CRY2 was used as the second photo-specific binding protein. The wavelength of the light used herein was the blue light with 460~490 nm. The intensity of the light was 20~50 µW.

In the meantime, in order to confirm the expression and to find out the location of the first fusion protein composed of the exosome specific marker and the first photo-specific binding protein expressed therein, a marker protein can be fused thereto. For example, in a preferred embodiment of the invention, the fluorescent protein EGFP was inserted in the first fusion protein wherein CIBN and CD9 or GIGANTEA and CD are linked together. So, the expression pattern (expression and expression level) and the intracellular location of the first fusion protein can be investigated by the expression of the first fusion protein as harboring the fluorescent protein EGFP.

The term "cargo protein" in this invention indicates a protein which is expressed as a fusion protein conjugated with the second photo-specific binding protein to locate the cargo protein inside the exosome.

In this invention, the cargo protein can be carried by exosome after being expressed in cells. The cargo protein is not limited but is preferably a disease treating protein or disease diagnosing protein. For example, in a preferred embodiment of the present invention, mCherry with fluorescence was used as the cargo protein.

An example of the cargo proteins in the present invention is selected from, but not limited to, Matrix metalloproteinases (MMPs) proteins, Tissue inhibitor of metalloproteinases (TIMPs) proteins, caspases proteins, caspases inhibitory proteins, cathepsins proteins or cathepsin inhibitory proteins,
wherein,
MMPs proteins are such as, but not limited to, MMP1 protein (SEQ ID NO: 13);
TIMPs proteins are such as, but not limited to, TIMP1 protein (SEQ ID NO: 14), TIMP2 protein (SEQ ID NO: 15), TIMP3 protein (SEQ ID NO: 16), or TIMP4 protein (SEQ ID NO: 17);
caspases proteins are such as, but not limited to, casepase 1 protein (SEQ ID NO: 18), casepase 2 protein (SEQ ID NO: 19), casepase 3 protein (SEQ ID NO: 20), casepase 4 protein (SEQ ID NO: 21), casepase 5 protein (SEQ ID NO: 22), casepase 6 protein (SEQ ID NO: 23), casepase 7 protein (SEQ ID NO: 24), casepase 8 protein (SEQ ID NO: 25), casepase 9 protein (SEQ ID NO: 26), casepase 10 protein (SEQ ID NO: 27), casepase 11 protein (SEQ ID NO: 28), casepase 12 protein (SEQ ID NO: 29), casepase 13 protein (SEQ ID NO: 30), or casepase 14 protein (SEQ ID NO: 31);
caspases inhibitory proteins are such as, but not limited to, proteins inhibiting caspase proteins represented by SEQ ID NO: 18-31 or any proteins inhibiting caspase;
cathepsins proteins are such as, but not limited to, cathepsins A protein (SEQ ID NO: 32), cathepsins B protein (SEQ ID NO: 33), cathepsins C protein (SEQ ID NO: 34), cathepsins D protein (SEQ ID NO: 35), cathepsins E protein (SEQ ID NO: 36), cathepsins F protein (SEQ ID NO: 37), cathepsins G protein (SEQ ID NO: 38), cathepsins H protein (SEQ ID NO: 39), cathepsins K protein (SEQ ID NO: 40), cathepsins L1 protein (SEQ ID NO: 41), cathepsins L2 protein (SEQ ID NO: 42), cathepsins 0 protein (SEQ ID NO: 43), cathepsins S protein (SEQ ID NO: 44), cathepsins W protein (SEQ ID NO: 45), or cathepsins Z protein (SEQ ID NO: 46); and
cathepsin inhibitory proteins are such as, but not limited to, proteins inhibiting cathepsin proteins represented by SEQ ID NO: 32-46 or any protein inhibiting cathepsins.

Another example of the cargo proteins in the present invention is selected from, but not limited to, Cre recombinase, Cas protein, Caspase-activated DNase (CAD) proteins, β-glucocerebrosidase (GBA), p38 mitogen-activated protein kinases, Phosphatase and tensin homolog (PTEN), Janus kinase (JAK), ubiquitin ligase, luciferase, peroxiredoxin (Prx) I or II, protein inhibiting NF-κB, MyoD proteins, Tbx18 proteins, p53 proteins, High mobility group box 1 (HMGB1) proteins, neurogenic differentiation1 (Neuro-D1) proteins, Interferon regulatory factor 5 (IRF5) proteins, Interferon regulatory factor 3 (IRF3) proteins, Signal transducer and activator of transcription 1 (STAT1) proteins, Suppressor of cytokine signaling 3 (SOCS3) proteins, Signal transducer and activator of transcription 2 (STAT2) proteins, proteins inhibiting phosphorylated STAT3 (pYSTAT3), Bax (Bcl2-associated X protein), B-cell lymphoma-extra-large (Bcl-xX) proteins, Aminoacyl-tRNA synthase-interacting multifunctional proteins (AIMPs), mCherry proteins, green fluorescent proteins (GFP), or nucleoproteins binding to nucleic acid, wherein, Cre recombinase recombines the DNA between loxP sites by recognizing them in DNA and includes, but not limited, Cre recombinase represented by SEQ ID NO: 9;

Cas protein has endonuclease or nickase activity when it combines the complex with guide RNA. In some embodiment, Cas protein is Cas9 protein such as Cas protein represented by SEQ ID NO: 10, its mutant, or Cpf1 protein such as amino acids represented by SEQ ID NO: 11;

CAD protein is such as the amino acids represented by SEQ ID NO: 47;

β-glucocerebrosidase (GBA) is such as the amino acids represented by SEQ ID NO:12;

p38 mitogen-activated protein kinases (p38 MAPKs) proteins are such as p38-α or its mutants and include amino acids represented by SEQ ID NOs: 48-51;

Inhibitor kappa B kinase (IKK) proteins are such as the amino acids represented by SEQ ID NO: 83;

Nuclear factor-kappa B (NF-κB) proteins are such as the amino acids represented by SEQ ID NO: 84;

Phosphatase and tensin homolog (PTEN) proteins are such as the amino acids represented by SEQ ID NO: 52;

Janus kinase (JAK) proteins include JAK1, JAK2, JAK3 and TYK2, wherein JAK1 proteins are such as the amino acids represented by SEQ ID NO: 53, JAK2 proteins are such as the amino acids represented by SEQ ID NO: 54, JAK3 proteins are such as the amino acids represented by SEQ ID NO: 55, and TYK2 proteins are such as the amino acids represented by SEQ ID NO: 56; ubiquitin ligase proteins include c-CBL, PRKN, RBX1, TRAF2 and Mdm2, wherein ubiquitin ligase proteins are such as the amino acids represented by SEQ ID NO: 57 to 61;

luciferase proteins are such as the amino acids represented by SEQ ID NO: 62;

peroxiredoxin (Prx) I or II has the effect of inhibiting cytotoxicity from oxidative stress, wherein peroxiredoxin I is such as the amino acids represented by SEQ ID NO: 7, and peroxiredoxin II is the amino acids represented by SEQ ID NO: 8;

protein inhibiting NF-κB is super-repressor-IκB which inactivates NF-κB by binding with it in cytoplasm, wherein the super-repressor-IκB protein, which is S32A and S36A mutant form of IκB, is not phosphorylated by IκB Kinase (IKK) and consequently it can continuously inhibit NF-κB, and NF-κB inhibiting proteins are such as the amino acids represented by one of SEQ ID NO: 1 to 5, exemplified by IκB-α, IκB-β, IκB-ε, BCL-3 or their mutant;

MyoD proteins are such as the amino acids represented by SEQ ID NO: 63;

Tbx18 proteins are such as the amino acids represented by SEQ ID NO: 64;

p53 proteins are such as the amino acids represented by SEQ ID NO: 65;

High mobility group box 1 protein (HMGB1) proteins are such as the amino acids represented by SEQ ID NO: 66;

Neurogenic differentiation1 (Neuro-D1) proteins are such as the amino acids represented by SEQ ID NO: 67;

Interferon regulatory factor 5 (IRF5) proteins are such as the amino acids represented by SEQ ID NO: 68;

Interferon regulatory factor 3 (IRF3) proteins are such as the amino acids represented by SEQ ID NO: 69;

Signal transducer and activator of transcription 1 (STAT1) proteins are such as the amino acids represented by SEQ ID NO: 70;

Suppressor of cytokine signaling 3 (SOCS3) proteins are such as the amino acids represented by SEQ ID NO: 71;

Signal transducer and activator of transcription 2 (STAT2) proteins are such as the amino acids represented by SEQ ID NO: 72;

proteins inhibiting phosphorylated STAT3 (pySTAT3) including pySTAT3 intrabody antibody proteins, which binds to pySTAT3 to deactivate pySTAT3, and are such as the amino acids represented by SEQ ID NO: 73 or any proteins inhibiting pySTAT3;

Bax (Bcl2-associated X protein) is such as the amino acids represented by SEQ ID NO: 6;

B-cell lymphoma-extra-large (Bcl-xL) proteins are such as the amino acids represented by SEQ ID NO: 74;

Aminoacyl-tRNA synthase-interacting multifunctional proteins (AIMPs) include AIMP1 and AIMP2, wherein AIMP1 proteins are such as the amino acids represented by SEQ ID NO: 75 and AIMP2 proteins are such as the amino acid represented by SEQ ID NO: 76;

mCherry proteins are such as the amino acids represented by SEQ ID NO: 77;

green fluorescent protein (GFP) are such as the amino acids represented by SEQ ID NO: 78;

nucleoproteins binding to nucleic acids include deoxyribonucleoprotein (DNP) binding to DNA or ribonucleoprotein (RNP) binding to RNA, wherein DNP includes RBBP4 or NAP1L4 and RNP include Telomerase, Heterogenous nuclear ribonucleoprotein K (HNRNPK) and wherein nucleoproteines are such as the amino acids represented by SEQ ID NOs: 79-82, nucleosome, protamine, small nuclear RNPs (snRNPs) or mutants thereof, or any proteins binding to nucleic acid.

The term "culture" in this invention indicates a method to grow cells or microorganisms in a properly controlled environment.

In this invention, a transformant was cultured for 1~3 days and then the medium was replaced with a serum-free medium, followed by further culture for 2~5 days.

In this invention, the method for culturing the transformant is any of those well known to those in the art.

The said medium herein indicates a notified medium widely used for animal cell culture, which can be selected from the group consisting of commercially available serum-free media, protein-free media, and chemically defined media.

The serum-free media above are used for animal cell culture, which are free from bovine serum and are exemplified by SFM4CHO (HyClone) and EX-Cell (JHR Bioscience). Insulin like growth factor I (IGF-I), ethanolamine, ferric chloride, and phosphatidyl choline can be added to the media, but not always limited thereto.

The protein-free media above are animal cell culture media, from which animal originated proteins especially high molecular proteins in particular having the molecular weight of at least 10 kDa are eliminated. The protein-free media can be ProCHO (Lonza) and PF-CHO (HyClone), but not always limited thereto.

The chemically defined media above are animal cell culture media which do not include any animal originated components and instead have components all having defined chemical structures. The chemical defined media can be CDM4CHO (HyClone), PowerCHO2CD (Lonza), and CD-optiCHO (Life Technologies), but not always limited thereto.

The term "the first fusion protein" in this invention indicates the fusion protein made by binding between the exosome specific marker and the first photo-specific binding protein.

In this invention, the order of arrangement of the exosome specific marker and the first photo-specific binding protein contained in the first fusion protein is not limited as long as the first photo-specific binding protein is located in the direction toward the inside of exosome when the first fusion protein is expressed in the exosome production cell. For example, N-terminal of the first photo-specific binding protein can be conjugated to C-terminal of the exosome specific marker.

The exosome specific marker and the first photo-specific binding protein which compose the first fusion protein are linked directly each other or can be connected by a linker. The linker above is not limited as long as the first fusion protein is expressed in the exosome production cell with presenting the first photo-specific binding protein located in the direction toward the inside of exosome, but is preferably a peptide linker composed of amino acids and more preferably a flexible peptide linker. The peptide linker can be expressed by using an expression vector wherein the nucleic acids encoding the linker are connected with other nucleic acids encoding each domain in frame.

The term "the second fusion protein" indicates a fusion protein in which the second photo-specific binding protein and the cargo protein are combined.

In this invention, the order of arrangement of the second photo-specific binding protein and the cargo protein contained in the second fusion protein is not limited as long as the second fusion protein is located inside of exosome as being conjugated with the first photo-specific binding protein region of the first fusion protein in the exosome production cell. For example, N-terminal of the cargo protein can be conjugated to C-terminal of the second photo-specific binding protein.

The second photo-specific binding protein and the cargo protein which compose the second fusion protein are linked directly each other or can be connected by a linker. The linker above is not limited as long as the second fusion protein is located inside of exosome as being conjugated with the first photo-specific binding protein of the first fusion protein in the exosome production cell, but is preferably a peptide linker composed of amino acids and more preferably a flexible peptide linker. The peptide linker can be expressed by using an expression vector wherein the nucleic acids encoding the linker are connected with other nucleic acids encoding each domain in frame.

In addition, each fusion protein above can include a polypeptide having the sequence wherein at least one amino acid residues are different from those in the wild type amino acid sequence of each domain included therein. Amino acid exchange in proteins and polypeptides without changing the overall activity of a molecule is well known to those in the art. The most common exchange occurs between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In addition, a protein having increased structural stability against heat or pH or increased protein activity due to mutation or modification of amino acid sequence can be included.

Lastly, the fusion protein above or the polypeptide of each domain comprising the fusion protein can be prepared by the chemical peptide synthesis method well informed to those in the art, or prepared by the following method. A gene encoding each domain is amplified by PCR (polymerase chain reaction) or synthesized by the conventional method well known to those in the art. The gene is cloned in an expression vector and expressed.

In the meantime, each fusion protein can be expressed in the exosome production cell by introducing a polynucleotide encoding each fusion protein in the exosome production cell. At this time, the polynucleotide is introduced in the exosome production cell by the conventional method well informed to those in the art. For example, an expression vector can be used for the introduction.

The term "expression vector" in this invention is a recombinant vector capable of expressing a target peptide in host cells. This vector indicates a gene construct containing essential regulators operably linked so as to express the gene insert. The expression vector includes expression control elements such as a start codon, a termination codon, a promoter, and an operator. The start codon and termination codon are generally understood as a part of the nucleotide sequence encoding a polypeptide. They are supposed to be working when a gene construct is introduced and to reside in a coding sequence in frame. The promoter of the vector can be constitutive or inductive.

The term "operably linked" in this invention indicates the status when the nucleic acid expression regulation sequence functioning as usual and the nucleic acid sequence encoding a cargo protein or RNA are linked by functional linkage. For example, a promoter is operably linked to a nucleic acid sequence encoding a protein or RNA in order to affect the expression of the coding sequence. The functional linkage with an expression vector can be achieved by the recombinant DNA technology well known to those in the art, and particularly the site-specific DNA cleavage and linkage can be achieved by using the conventional enzyme well known to those in the art.

The said expression vector can include a signal sequence for the discharge of a fusion polypeptide in order to promote the separation of a protein from the cell culture medium. A specific initiation signal might be necessary for the efficient translation of the inserted nucleic acid sequence. These signals contain ATG start codon and its neighboring sequences. In some cases, an exogenous translational control signal, which may include the ATG start codon, should be provided. These exogenous translational control signals and start codon can be various natural and synthetic sources. The expression efficiency can be increased by the introduction of appropriate transcription or translation enhancers.

In a preferred embodiment of the present invention, the expression vector is able to express a cargo protein conjugated with a tag in order to confirm the insertion of a cargo protein inside the exosome. The tag herein is to confirm the presence of a cargo protein, which can be conjugated to the region opposite to the region of the second photo-specific binding protein conjugation. For example, a fluorescent protein such as a red fluorescent protein and a green fluorescent protein is used as a tag to be conjugated to C-terminal of a cargo protein.

The cargo protein prepared as described above is expressed in the exosome production cell. Once exosome is produced, it is investigated whether or not the fluorescent protein tag is detected, by which the presence of the cargo protein in exosome can be confirmed.

The term "light" in this invention indicates the light to be irradiated in order to combine temporarily the first photo-specific binding protein and the second photo-specific binding protein expressed in the exosome production cell.

As described hereinbefore, the first photo-specific binding protein is expressed as the first fusion protein conjugated with the exosome specific marker, while the second photo-specific binding protein is expressed as the second fusion protein conjugated with the cargo protein. When the light is irradiated to the exosome production cell, the first photo-specific binding protein is combined with the second photo-specific binding protein, and as a result the fusion protein complex comprising the exosome specific marker-the first photo-specific binding protein-the second photo-specific binding protein-the cargo protein is formed temporarily. When exosome is produced in the exosome production cell, the cargo protein can be linked to the exosome due to the exosome specific marker. At this time, the cargo protein presents inside the exosome and when the irradiation with the light is stopped after the production of the exosome, the first photo-specific binding protein is separated from the second photo-specific binding protein and thereby the cargo protein included in the exosome is to be discharged together with the exosome as being a part of the exosome. It is preferred for the light to be irradiated to the cell intermittently rather than continually in order to deliver the cargo protein inside the exosome more efficiently. That is, when the light is irradiated intermittently, the conjugation and separation of the first photo-specific binding protein and the second photo-specific binding protein repeat so that the probability that the cargo protein is introduced into the exosome can be increased.

In the meantime, the wavelength of the light enough to induce the binding of the first photo-specific binding protein with the second photo-specific binding protein varies from the kinds of the first and the second photo-specific binding proteins. The wavelength of the light that induces the binding of the first photo-specific binding protein and the second photo-specific binding protein depends on the type of the proteins. So, the proper wavelength of the light can be selected as known to those in the art. For example, in order to link CRY2 to CIBN, the light with the wavelength of 460~490 nm is preferred. If the light is irradiated less than 10 minutes, CRY2 and CIBN are separated from each other. When PhyB is combined with PIF, the light with the wavelength of 650 nm is irradiated for 10 minutes. When light with the wavelength of 750 nm is irradiated for 5 minutes, PhyB and PIF are separated from each other. When FKF1 is combined with GIGANTEA, the light with the wavelength of 460 nm is irradiated for 30 minutes. In a preferred embodiment of the present invention, in order to induce the binding of CIBN and CRY2, the light with the wavelength of 460~490 nm was irradiated.

Figure 7:
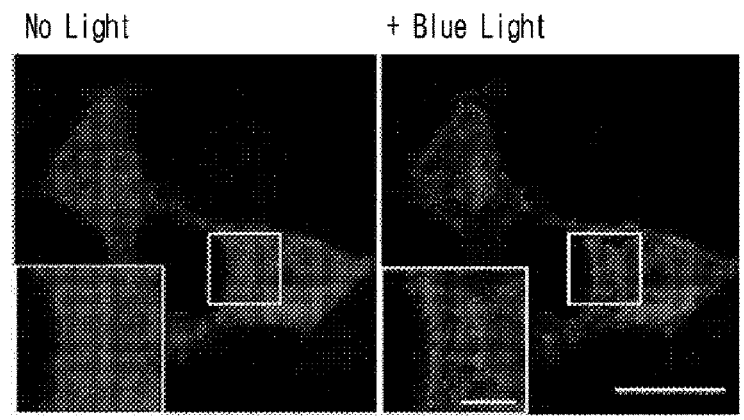
FIG. 7 illustrates the changes in the intracellular location of mCherry protein according to the blue light irradiation in the transformed HEK293T cells introduced with CIBN-EGFP-CD9 gene and mCherry-CRY2 gene.
Figure 9:
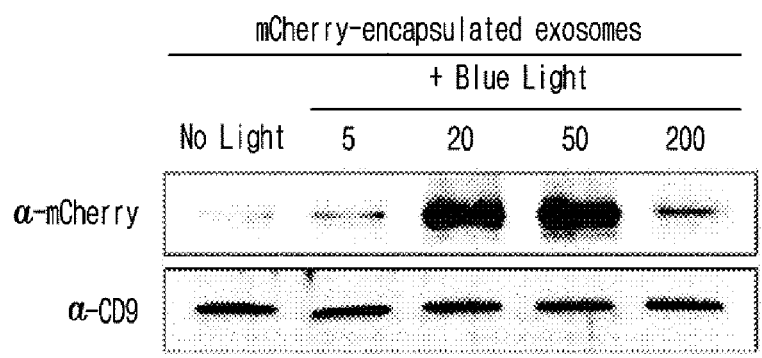
FIG. 9 illustrates the results of measuring the changes of the content of a cargo protein (mCherry protein) captured in exosome according to the intensity of blue light.
Figure 10:
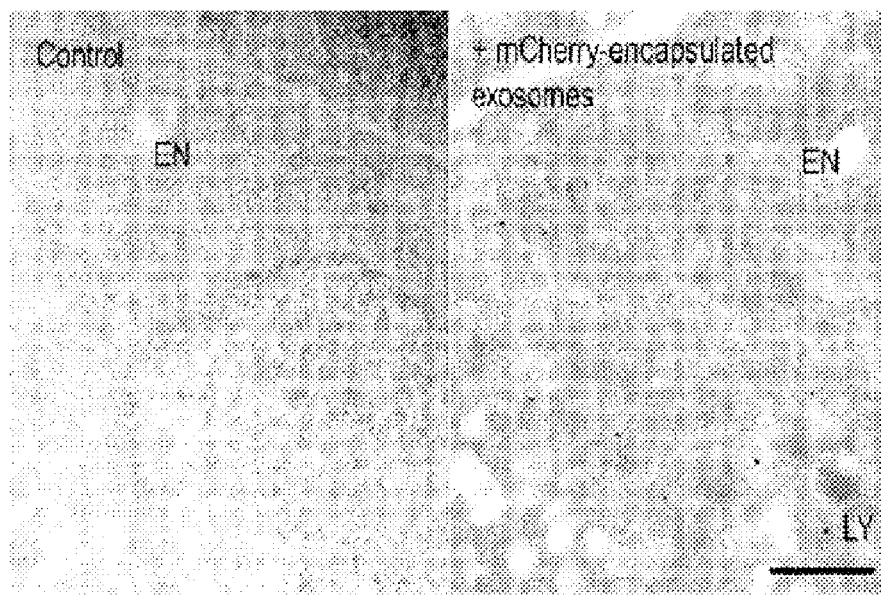
FIG. 10 illustrates the results of investigation of the introduction of a cargo protein in target cells after treating the target cells (HT1080) with exosome containing the cargo protein (mCherry), wherein the left indicates the target cells not-treated with exosome and the right indicates the target cells treated with exosome.
Figure 12:
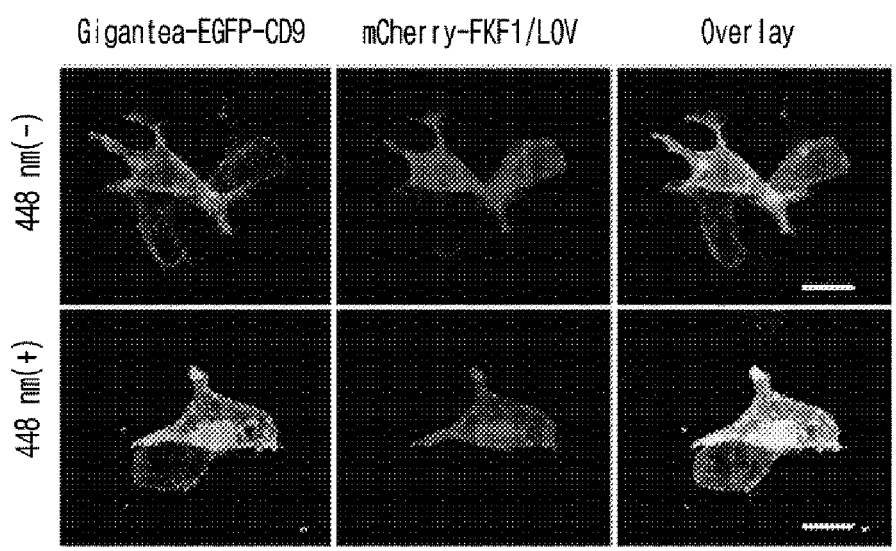
FIG. 12 illustrates the changes in the intracellular location of mCherry protein according to the blue light irradiation in the transformed HEK293T cells introduced with *GIGANTEA*-EGFP-CD9 gene and mCherry-FKF1LOV.
Figure 13:
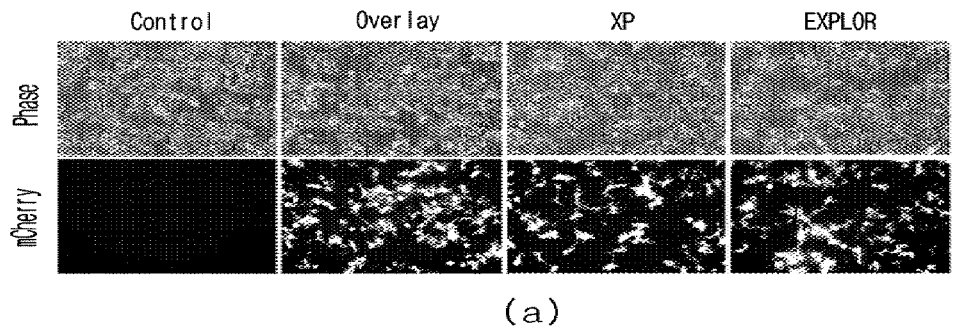
FIG. 13 illustrates the expression of the Luciferase-mCherry fusion protein measured by fluorescence imaging (a) and the luciferase activity (b) and the number of molecules in the production cells (c)
Figure 13:
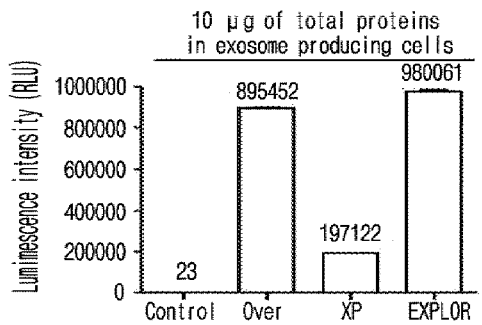
Figure 13:
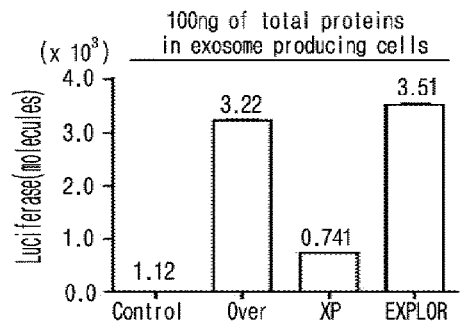

In a preferred embodiment of the present invention, the CRY2/mCherry fusion protein and the CIB/CD9 fusion protein were expressed in HEK293T, the immortalized cell line producing a large amount of exosome. As a result, the distribution of mCherry protein uniformly distributed in cytosol was found to be in cell membrane and endosome-like structure membrane when the blue light was irradiated (FIG. 7). Similar results were observed when the FKF1/mCherry fusion protein and the GIGANTEA/CD9 fusion protein were expressed in HEK293T cells (FIG. 12). The CRY2/mCherry fusion protein and the CIBN/CD9 fusion protein were expressed in HEK293T cells, followed by irradiation with the blue light with regulating the intensity of the light. As a result, when the light was irradiated with the intensity of 20~50 μW, the level of mCherry protein collected in exosome was the highest (FIG. 9). The exosomes isolated from the cells were treated to HT1080 cells at the concentration of approximately 250 μg/ml. As a result, the exosomes did not show any specific cytotoxicity against the HT1080 cells and it was confirmed that the mCherry protein was delivered in the cytosol thereof (FIG. 10).

To compare the efficiency of introducing the cargo protein in exosome and the efficiency of exosome transfer to the target cell with those of the conventional methods, XPACK vector was used for the conventional method and the expression vectors of the CRY2/mCherry fusion protein and the CIBN/CD9 fusion protein were introduced in HEK293T cells. Then, the production of the cargo protein in exosome was compared. As a result, it was confirmed that the introduction efficiency was remarkably high when the method of the present invention was used (FIG. 15). The exosome separated from the exosome production cell was treated to the target cell (HeLa) to compare the expression of the cargo protein. When the exosome separated by the method of the present invention was used, the expression of the cargo protein was the highest in the target cell (FIG. 16).

In another preferred embodiment of the present invention, the present invention provides a vector for the production of exosome comprising (a) the first expression vector containing the polynucleotide encoding the fusion protein of the exosome specific marker and the first photo-specific binding protein (the first fusion protein); and (b) the second expression vector containing the multicloning site to which the polynucleotide encoding the cargo protein can be introduced and the polynucleotide encoding the second photo-specific binding protein to be linked to the first photo-specific binding protein above.

In the vector for the production of exosome provided by the present invention, the exosome specific marker, the first photo-specific binding protein, the exosome production cell, and the second photo-specific binding protein are same as described above.

The term "transformed cells for exosome production" in this invention indicates the cells capable of producing exosome by expressing the first fusion protein wherein the polynucleotide encoding the fusion protein (the first fusion protein) of the exosome specific marker and the first photo-specific binding protein is introduced.

In this invention, the second expression vector includes a polynucleotide encoding the second photo-specific binding protein and a neighboring multicloning site. When a polynucleotide encoding a cargo protein is inserted in the multicloning site, it is expressed as the fusion protein comprising the second photo-specific binding protein and the cargo protein (the second fusion protein).

The vector for preparing exosome provided by the present invention can contain one or more kinds of constituents, solutions, or devices usable not only for the transformed cells for exosome production and the expression vector; but also for the introduction of the expression vector; for the culture of the transformed cells for exosome production; and for the separation and purification of the exosome produced from the transformed cells for exosome production. For example, a buffer proper for the introduction of the expression vector and a medium and a vessel necessary for the culture of the transformed cells for exosome production can be additionally included.

The term "Cas protein" in this invention indicates the essential protein in CRISPR/Cas system which form active endonuclease or nickase when Cas protein form the complex with two RNA called CRSPR RNA (crRNA) and trans-activating crRNA (tracrRNA).

The term "guide RNA" in this invention indicates target DNA-specific RNA which is able to form complex with Cas protein and guides Cas protein to target DNA.

In this invention, aforementioned guide RNA is able to be made by two RNA, CRISPR RNA (crRNA) and transactivating crRNA (tracrRNA) or single-chain RNA (sgRNA) by fusing the essential parts of crRNA and tracrRNA.

Aforementioned guide RNA is able to be dual RNA including crRNA and tracrRNA. If aforementioned RNA includes the essential parts and target complementary parts of crRNA and tracrRNA, any guide RNA is being able to be applied in this invention. Aforementioned crRNA is able to hybridize target DNA.

Aforementioned guide RNA is able to include one or more additional nucleotide on 5' terminal of single-chain guide RNA or crRNA in dual RNA.

Desirably, aforementioned guide RNA is able to include two additional guanine nucleotides on 5' terminal of single-chain guide RNA or crRNA in dual RNA. Guide RNA is able to be delivered to cell or organism as RNA or guide RNA coding DNA. Guide RNA is able to be separated RNA, RNA included in virus vector, or coded in vector. Desirably, aforementioned vector is not limited but is able to be virus vector, plasmid vector, or agrobacterium vector.

Guide RNA coding DNA is able to be vector including guide RNA coding DNA sequence. For example, guide RNA is able to be delivered to cell or organism by transfecting plasmid DNA that includes isolated guide RNA or guide RNA coding sequence and promoter. By other method, guide RNA can be delivered to cell or organism by using virus-mediated gene delivery.

When guide RNA is transfected into cell or organism as isolated RNA, it can be manufactured by in vitro transcription by using any in vitro transcription systems known in industry. Desirably, guide RNA is delivered to cell as isolated RNA rather than plasmid including guide-RNA coding sequence. The term "isolated RNA" can be replaced by "naked RNA" in this invention. It is able to save cost and time in that isolated RNA does not need cloning process. However, the usage of plasmid DNA or virus-mediated gene delivery for guide RNA transfection is not excluded.

The present invention provides the exosome prepared by the method of the invention in which a cargo protein is included.

In another aspect, the present invention provides an exosome produced by the above method, wherein the Cre recombinase is contained in the exosome.

In another aspect, the present invention provides an exosome prepared by the above method, wherein the Cas9 protein is contained therein.

In another aspect, the present invention provides an exosome produced by the above method, wherein GBA (β-glucocerebrosidase) protein is contained therein.

In another aspect, the present invention provides an exosome produced by the above method, wherein the peroxiredoxin (Prx) I or II protein is contained therein.

In another aspect, the present invention provides an exosome produced by the above method and comprising a protein that inhibits NF-kB.

In another aspect, the present invention provides an exosome prepared by the above method, wherein Bax (Bcl-2-associated X protein) protein is contained therein.

The exosome prepared by the method above contains a fusion protein (the first fusion protein) composed of an exosome specific marker and the first photo-specific binding protein on the plasma membrane thereof and another fusion protein (the second fusion protein) composed of the second photo-specific binding protein that can be conjugated to the first photo-specific binding protein and a cargo protein. So, when such exosome is treated to the target tissue cells, the second fusion protein included in the exosome can be delivered to cytosol of the target tissue cells through the fusion of the plasma membrane.

The said exosome containing a cargo protein can be used for the treatment of various diseases in vivo. For example, exosome containing a protein polymer (for example, antibody, etc.) showing the anticancer activity as a cargo protein is prepared, which is then treated to cancer cells. That is, the exosome can be used as a biocompatible anticancer agent better acting than the conventional liposome.

This invention also provides the pharmaceutical components for inflammatory disease prevention and therapy including exosomes with NF-κB inhibiting protein.

Aforementioned inflammatory diseases are not limited but is preferably exemplified by allergy, dermatitis, atopy, conjunctivitis, periodontitis, rhinitis, otitis media, laryngopharyngitis, tonsillitis, pneumonia, gastric ulcer, gastritis, Crohn's disease, colitis, gout, ankylosing spondylitis, rheumatic fever, lupus, fibromyalgia, psoriatic arthritis, osteoarthritis, rheumatoid arthritis, periarthritis of shoulder, tendonitis, tenosynovitis, peritendinitis, myositis, hepatitis, cystitis, nephritis, sjogren's syndrome, multiple sclerosis, acute and chronic inflammatory diseases, sepsis, and ulcerative colitis, etc.

In the experimental examples in this invention, the present inventors confirmed that transfer of NF-κB activated by TNF-α to nucleus is inhibited by pretreating super-repressor-IκB: EXPLOR to HeLa cell to verify inflammation inhibitory effect mediated by TNF-α (FIG. 43. Left). In addition, inhibition of DNA binding of NF-κB activated by TNF-α was confirmed (FIG. 43. Right). Also, the present inventors confirmed that symptom of arthritis is decreased in mouse model which is induced arthritis by collagen through injecting retro-orbital three times to verify inflammation inhibitory effects, and thereby super-repressor-IκB:EXPLOR in this invention can be used as the pharmaceutical components for inflammatory disease prevention and therapy.

This invention also provides the pharmaceutical components for cancer prevention and therapy including exosomes with Bax (Bcl-2 associated X protein).

Aforementioned cancer is not limited but is preferably exemplified by breast cancer, colon cancer, lung cancer, small-cell lung cancer, gastric cancer, liver cancer, blood cancer, bone cancer, pancreatic cancer, skin cancer, head or neck cancer, skin or choroidal melanoma, eye cancer, peritoneal cancer, uterine cancer, ovarian cancer, rectal cancer, anal cancer, and cervical cancer, etc.

In the experimental examples in this invention, the present inventors confirmed that cytochrome c release is increased by pretreating Bax::EXPLOR to HeLa cell, and thereby Bax: EXPLOR can be used as the pharmaceutical components for cancer prevention and therapy.

This invention also provides the pharmaceutical components for anti-oxidation including exosomes with peroxiredoxin (Prx) I or II.

Also, this invention provides the pharmaceutical components for prevention and therapy of reactive oxygen species disease exemplified by cancer, arteriosclerosis, respiratory disease, osteoporosis, obesity, and degenerative dementia including exosomes with peroxiredoxin (Prx) I or II.

Also, this invention provides the cosmetic ingredients for anti-oxidation including exosomes with peroxiredoxin (Prx) I or II.

Also, this invention provides the cosmetic ingredients for anti-aging of skin including exosomes with peroxiredoxin (Prx) I or II.

In the experimental examples in this invention, the present inventors confirmed that cytotoxicity by oxidative stress is inhibited statistically significant by pretreating Prx I/II:: EXPLOR to HeLa cell to verify the inhibitory effect on cytotoxicity by oxidative stress induced by $H_2O_2$, and thereby Prx I/II::EXPLOR can be used as the pharmaceutical components for anti-oxidation or prevention and therapy of reactive oxygen species, or the cosmetic ingredients for anti-oxidation or anti-aging of skin.

This invention also provides the components for creating conditional knockout allele of target gene including exosomes with Cre recombinase.

In the experimental examples of this invention, the present inventors confirmed the expression of ZsGreen reporter protein in Cre::EXPLOR treated HT1080 cell and HeLa cell, with identical results of pCMV-Cre vector transfection as positive control, through detecting ZsGreen reporter expression after transfecting pCAG-loxP-STOP-loxP-ZsGreen encoded DNA into HT1080 and HeLa cell to verify the effect of Cre recombinase (FIGS. 19A and 19B). In addition, the present inventors was able to confirm the ZsGreen expression on Cre::EXPOR treated primary mouse embryo neuron performed by experiment identical to aforementioned (FIG. 20). Also, the present inventors confirmed that EYFP is expressed on Cre::EXPLOR treated group after ventrolateral injection of Cre::EXPLOR on pCAG-lowP-STOP-loxP-eNpHR3.0-EYFP transgenic mouse to verify Cre-EXPLOR function in vivo (FIG. 21). Furthermore, it was confirmed that Cre::EXPLOR mainly targets neuron in mouse brain through merged neuronal region in the results of immunohistochemistry to verify Cre::EXPLOR targeting cell (FIG. 22), and thereby Cre::EXPLOR can be used as the components for creating conditional knockout allele of target gene.

This invention also provides the components for engineering DNA sequence including exosomes with Cas9 protein and target DNA specific guide RNA (gRNA).

Aforementioned components are not limited but preferably induces mutation on normal sequence or proofreads mutation. Mutation can be naturally occurred mutation or induced by pathogenic microbes. In other word, mutation is occurred by infection of pathogenic microbes when pathogenic microbes are detected and it becomes clear that biological sample is infected. Pathogenic microbe is not limited but it can be virus or bacteria.

In the experimental examples in this invention, the present inventors confirmed exosome comprising a CRISPR/Cas9 protein can be prepared with a high yield.

This invention also provides the pharmaceutical components for curing Gaucher disease including exosomes with β-glucocerebrosidase (GBA).

In the experimental examples in this invention, the present inventors confirmed that activity of β-glucocerebrosidase (GBA) is recovered by treating GBA::EXPLOR to cells from Gaucher disease patients (FIG. 30), and thereby GBA::EXPLOR can be used as the pharmaceutical components for curing Gaucher disease.

According to the method for preparing exosome containing a cargo protein of the invention, exosome comprising a cargo protein can be prepared with a high yield. Also, a cargo protein presents as being separated from the membrane of exosome, so that it can be widely applied to treat disease.

EXAMPLES

Practical and presently preferred embodiments of the present invention are illustrative as shown in the following Examples. However, it will be appreciated that those skilled in the art, on consideration of this disclosure, may make modifications and improvements within the spirit and scope of the present invention.

Example 1: Preparation of Exosome

<1-1> Confirmation of the Binding of CIBN and CRY2 for the Production of Exosome PcDNA3.1 (+) vector containing CIBN-EGFP-CD9 gene and pcDNA3.1 (+) vector containing mCherry-CRY2 gene were introduced into HEK293T cells, the exosome production cells, under the light-free condition, followed by culture for 24 hours. The medium was replaced with a serum-free medium, followed by additional culture for 48 hours. Upon completion of the culture, the cells were irradiated with the blue light with the wavelength of 460~490 nm. The location of red fluorescence shown in mCherry before and after the blue light irradiation was confirmed by using a confocal microscope (FIG. 7).

FIG. 7 is a fluorescence image illustrating the changes in the intracellular location of mCherry protein according to the blue light irradiation in the transformed HEK293T cells introduced with CIBN-EGFP-CD9 gene and mCherry-CRY2 gene. As shown in FIG. 7, before the blue light irradiation that could cause the binding of the photo-specific binding proteins CIBN and CRY2, mCherry protein was evenly distributed in the cytosol. However, after the blue light irradiation, mCherry protein was concentrated in the membrane. This clustering of mCherry protein was analyzed to be caused by the binding of CIBN and CRY2, the photo-specific binding proteins.

<1-2> Confirmation of the Binding of GIGANTEA and FKF1 for the Production of Exosome PcDNA3.1 (+) vector containing GIGANTEA-EGFP-CD9 gene and pcDNA3.1 (+) vector containing mCherry-FKF1LOV gene were used in this example. The intracellular Exosome was confirmed by the same manner as described in Example <1-1>. (LOV in the FKF1LOV above is an abbreviation of light-oxygen-voltage domain, which indicates the domain that binds to other proteins by light in FKF1 protein, so FKF1 and FKF1LOV are in fact the same herein).

Like Example <1-1>, as shown in FIG. 12, mCherry protein was evenly distributed in the cytosol before the blue light irradiation that could cause the binding of the photo-specific binding proteins GIGANTEA and FKF1. However, after the blue light irradiation, mCherry protein was concentrated in the membrane. This clustering of mCherry protein was analyzed to be caused by the binding of GIGANTEA and FKF1, the photo-specific binding proteins.

Figure 8:
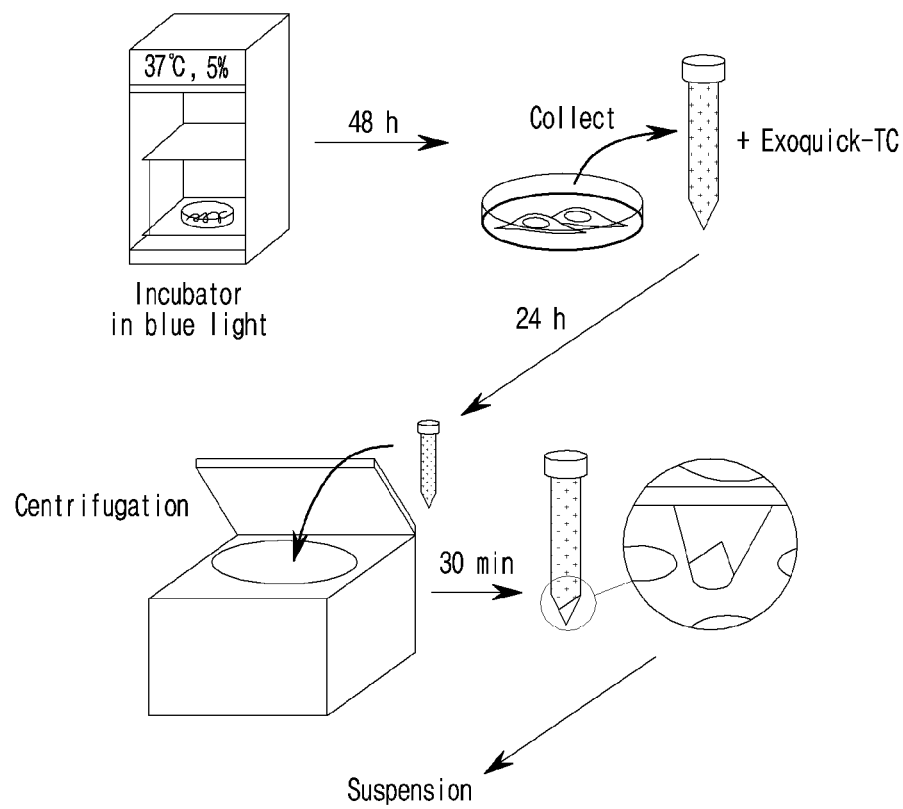
FIG. 8 illustrates the experimental procedure of obtaining EXPLORs according to the present invention.

Example 2: Exosome Production and the Effect of Light Intensity on Exosome Production Each expression vector respectively containing CIBN-EGFP-CD9 gene and mCherry-CRY2 gene was introduced into HEK293T cells under the LED light with the wavelength of 460 nm at the intensity of 0, 5, 20, 50, and 200 μW, followed by culture for 24 hours. Then, the medium was replaced with a serum-free medium, followed by additional culture for 48 hours. Upon completion of the culture, the culture medium was separated, which was centrifuged (3000×g, 15 minutes) to obtain the supernatant excluding cell debris. ExoQuick-TC Exosome Precipitation Solution (System Biosciences, Mountain View, California, USA) was added to the obtained supernatant at the volume of 5 times the supernatant. After the mixing, centrifugation was performed (1500×g, 30 minutes) to obtain the precipitated exosome. The obtained exosome was suspended in PBS, resulting in the exosome suspension. The exosome suspension was filtered with a 0.2 μm filter using a syringe equipped with a 27-G needle. As a result, exosome in the single size was obtained (FIG. 8). Then, exosome lysate was prepared by using lysis buffer, followed by immune-blotting to compare the amount of mCherry protein in the exosome (FIG. 9).

FIG. 9 is an immunoblot analysis image showing the results of measuring the changes of the content of a cargo protein (mCherry protein) captured in exosome according to the intensity of blue light. As shown in FIG. 9, when the cells were irradiated with blue light at the intensity of 20~50 μW, the amount of mCherry, the cargo protein, in exosome was the highest. From the above results, it was confirmed that the content of the cargo protein captured in exosome could be regulated by controlling the intensity of the light irradiated to the cells in the course of the binding of the photo-specific binding proteins.

Example 3: Effect of Exosome Treatment

Each expression vector respectively containing CIBN-EGFP-CD9 gene and mCherry-CRY2 gene was introduced into HEK293T cells under the LED light with the wavelength of 460 nm at the intensity of 50 μW, followed by extracting exosome by the same manner as described in Example 2. The extracted exosome was treated to HT1080 cells at the concentration of 250 μg/ml, for 24 hours. The HT1080 cells were fixed on 10% gelatin gel by adding with 0.1 M phosphate buffer (pH 7.4) containing 4% PFA and 0.01% GA. The cells attached on the gelatin gel were cooled for a day by using liquid nitrogen. Thin sections cut in 45 nm by using cryoultramicrotome were obtained at −120° C. The thin sections were immuno-stained by using anti-mCherry antibody and Protein A-gold. MCherry protein was observed with Tecnai G2 Spirit Twin TEM (FIG. 10).

FIG. 10 is an electron micrograph illustrating the results of investigation of the introduction of a cargo protein in target cells after treating the target cells (HT1080) with exosome containing the cargo protein (mCherry), wherein the left indicates the target cells not-treated with exosome and the right indicates the target cells treated with exosome. As shown in FIG. 10, it was confirmed that the cargo protein was transferred into the target cells when the target cells were treated with the exosome of the present invention.

Example 4: Analysis of Exosome with Cargo Protein

Each expression vector respectively containing CIBN-EGFP-CD9 gene and mCherry-CRY2 gene was introduced into HEK293T cells under the LED light with the wavelength of 460 nm at the intensity of 50 μW, followed by extracting exosome by the same manner as described in Example 2. The extracted exosome was treated to HT1080 cells at the concentration of 250 μg/ml, for 24 hours. Then, red fluorescence was confirmed in mCherry protein under a fluorescent microscope and the ratio of dead cells was compared between the cells treated with exosome and the cells not-treated with exosome by LDH cell death assay (FIG. 11).

FIG. 11 is a set of a fluorescence image (a) illustrating the results of investigation of the introduction of a cargo protein in target cells after treating the target cells (HT1080) with exosome containing the cargo protein (mCherry); and a graph (b) illustrating the results of comparison of the ratio of apoptotic cells induced by the treatment of exosome. As shown in FIG. 11, it was confirmed that apoptosis did not induced by the treatment of exosome.

Example 5: Exosome Production and the Comparison of Introduction Efficiency of a Cargo Protein into the Produced Exosome <5-1> Confirmation of Exosome Production Efficiency To compare the exosome production and the introduction efficiency of a cargo protein into the exosome produced thereby according to the present invention with those of the conventional method, the expression of the cargo protein in the exosome production cells was investigated by measuring the luciferase activity therein.

According to the conventional method, XPACK-Luciferase-mCherry was introduced in HEK293T cells by using XPACK (Systems Biosciences), the commercial vector designed for exosome loading technique (XP). On the other hand, according to the method of the invention, Luciferase-mCherry-CRY2 and CIBN-EGFP-CD9 were introduced in HEK293T cells (EXPLOR). Then, the luciferase activity in both cells was measured to compare the efficiency of the two methods. The luciferase activity was measured according to the manufacturer's instructions (Luciferase Assay Reagent, Promega). The standard curve of the results was plotted, and then the number of exosomes in the cells was quantitatively calculated.

As shown in FIG. 14, it was confirmed that the method using the photo-specific binding proteins CIBN and CRY2 of the present invention was significantly higher in the introduction efficiency into exosome than the conventional method (XP) (FIG. 14).

<5-2> Expression of a Cargo Protein in the Produced Exosome

The cells of Example <5-1> were cultured for 72 hours, followed by extracting exosome (Exoquick-TC, Systems biosciences). The concentration of the cargo protein included in the exosomes separated by the conventional method (XP) or the method of the present invention was compared indirectly by measuring the luciferase activity therein. As shown in FIG. 15, it was confirmed that the method of the present invention could produce exosome containing a remarkably large amount of the cargo protein than the conventional method (FIG. 15).

<5-3> Comparison of the Introduction Efficiency of the Cargo Protein

The introduction efficiency (E) of the cargo protein was calculated by the mathematical formula below based on the luciferase activity measured in Examples <5-1> and <5-2>.

E=measured value of luciferase activity in produced exosome/measured value of luciferase activity in exosome production cell       [Mathematical Formula 1]

As shown in FIG. 15, it was confirmed that the exosome produced using the binding of CRY2 and CIBN of the present invention exhibited 4 to 120 times higher efficiency than those of the other comparative groups (FIG. 15).

Example 6: Comparison of Exosome Transfer Efficiency to Target Cells

To compare the exosome transfer efficiency, the target cells were treated with exosome containing the cargo protein. Particularly, HeLa cells were treated with $5 \times 10^9$ exosomes for 24 hours, and then the fluorescence intensity expressed in the cells was measured. As shown in FIG. 16, it was confirmed that the fluorescence intensity in the exosome of the present invention (EXPLOR) was remarkably high (FIG. 16).

Therefore, it was confirmed that the method using the exosome of the present invention could deliver the cargo protein to the target cells more efficiently.

Experimental Examples

Experimental Example 1: MMPs (Matrix Metalloproteinases)

The binding of CIBN and CRY2 in cells expressing CIBN-EGFP-CD9 and MMP-mCherry-Cry2 at 488 nm wavelength blue light, and the loading of MMPs within the exosome is evaluated.

For the massive production of MMPs-loaded exosomes, cells stably expressing CIBN-EGFP-CD9 gene and MMP-mCherry-CRY2 gene are established, and exosomes are isolated and purified by Tangential Flow Filtration (TFF) method from culture supernatant.

Functional analysis of MMPs-loaded exosomes is performed in target cells:

Target cells are treated with the MMPs-loaded exosomes to evaluate the functional enzymatic activity.

Animal models are administered with the MMPs-loaded exosomes by i.p. or i.v. to show therapeutic effect.

Experimental Example 2: TIMPs (Tissue Inhibitor of Metalloproteinase)

The binding of CIBN and CRY2 in cells expressing CIBN-EGFP-CD9 and TIMP-mCherry-Cry2 at 488 nm wavelength blue light, and the loading of TIMPs within the exosome is evaluated.

For the massive production of TIMPs-loaded exosomes, cells stably expressing CIBN-EGFP-CD9 gene and TIMP-mCherry-CRY2 gene are established, and exosomes are isolated and purified by Tangential Flow Filtration (TFF) method from culture supernatant.

Functional analysis of TIMPs-loaded exosomes is performed in target cells:

Target cells are treated with the TIMPs-loaded exosomes to evaluate the functional enzymatic activity.

Animal models are administered with the TIMPs-loaded exosomes by i.p. or i.v. to show therapeutic effect.

Experimental Example 3: Caspases

The binding of CIBN and CRY2 in cells expressing CIBN-EGFP-CD9 and caspase-mCherry-Cry2 at 488 nm wavelength blue light, and the loading of caspases within the exosome is evaluated.

For the massive production of caspases-loaded exosomes, cells stably expressing CIBN-EGFP-CD9 gene and caspase-mCherry-CRY2 gene are established, and exosomes are isolated and purified by Tangential Flow Filtration (TFF) method from culture supernatant.

Functional analysis of caspases-loaded exosomes is performed in target cells:

Target cells are treated with the caspases-loaded exosomes to evaluate the functional enzymatic activity.

Animal models are administered with the caspases-loaded exosomes by i.p. or i.v. to show therapeutic effect.

Experimental Example 4: Cathepsins

The binding of CIBN and CRY2 in cells expressing CIBN-EGFP-CD9 and cathepsin-mCherry-Cry2 at 488 nm wavelength blue light, and the loading of cathepsins within the exosome is evaluated.

For the massive production of cathepsins-loaded exosomes, cells stably expressing CIBN-EGFP-CD9 gene and cathepsin-mCherry-CRY2 gene are established, and exosomes are isolated and purified by Tangential Flow Filtration (TFF) method from culture supernatant.

Functional analysis of cathepsins-loaded exosomes is performed in target cells:

Target cells are treated with the cathepsins-loaded exosomes to show the functional enzymatic activity.

Animal models are administered with the cathepsins-loaded exosomes by i.p. or i.v. to show therapeutic effect.

Experimental Example 5: Cre Recombinase

<5-1> Production of Cre Recombinase-Loaded Exosome (Cre::EXPLOR)

A. Confirmation of Cre Recombinase in Exosome

The present inventor confirmed the binding of CIBN and CRY2 in cells expressing CIBN-EGFP-CD9 and Cre-mCherry-Cry2 to verify exosome loading of Cre-recombinase with amino acids recorded as SEQ ID NO: 9. In particular, HEK293T exosome producing cells were additionally cultured 48 hrs in Dulbecco's modified Eagle's medium (DMEM) without fetal bovine serum (FBS), after 24 hrs culture with transfected pcDNA3.1 (+) vector including CIBN-EGFP-CD9 gene and Cre-mCherry-CRY2 gene in non-light condition. After finish culture, position of red fluorescence from mCherry was investigated by confocal microscopy before and after the irradiation of 488 nm wavelength blue light. This experiment was performed more than five times.

According to the results, binding between Cre-mCherry-CRY2 (red) and CIBN-EGFP-CD9 was confirmed (FIG. 18) and thereby exosome loading of Cre recombinase was verified.

B. Production of Cre Recombinase-Loaded Exosome (Cre::EXPLOR)

The present inventors performed following experiment to yield the Cre recombinase-loaded exosomes.

In particular, CIBN-EGRP-CD9 gene and Cre-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added Exo-Quick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture (FIG. 8).

In addition, HEK293T exosome producing cells which stably express CIBN-EGFP-CD9 gene and Cre-mCherry-CRY2 gene were cultured in medium without fetal bovine serum during 48~72 hrs on 50 μW power of 488 nm wavelength blue light. After finishing culture, supernatant removed cell debris was yielded by centrifuge (2000×g, 15 min) from isolated culture medium. To remove particles bigger than 200 nm from supernatant, it filtered by 0.2 μl PES membrane (Corning). Tangential Flow Filtration (TFF) method was applied in identical supernatant to remove particles smaller than 20 nm, condense and refine exosomes from filtrate. Vivaflow 50-100 kDa PES membrane (Sartorius) was used in TFF. Exosomes were condensed and refined by rotation of filtrate under 1.5~2 air pressure of TFF. Then, exosome concentrate was eliminated liquid by centrifugation (10000~14000 g, 5 min) on Amicon Ultra-0.5 (100 kDa) (Millipore) filter. Finally, exosomes were obtained by reverse-directional centrifugation (10000~14000 g, 5 min) with preferable buffer on experimental purpose.

<5-2> Confirmation of Cre Recombinase Function by Cre Recombinase-Loaded Exosome (Cre::EXPLOR)

A. Functional Confirmation of Cre::EXPLOR on HT1080 and HeLa Cell

Cre recombinase has the function to recombine DNA on loxP regions. The present inventors performed following experiment to investigate the function of Cre::EXPLOR.

In particular, pCAG-loxP-STOP-loxP-ZsGreen encoded DNA was transfected to HT1080 and HeLa cell and washed after 6 hrs. Then 0.25 mg/ml Cre::EXPLOR or Negative::EXPLOR was treated or pCMV-Cre vector was transfected. After 48 hrs culture, expression of ZsGreen with green fluorescence was investigated. Expression of ZsGreen was confirmed on Cre::EXPLOR treated HT1080 and HeLa cell, unlike Negative::EXPLOR treated HT1080 and HeLa cell, and was similar to the results of pCMV-Cre vector transfection in positive control (FIGS. 19A and 19B).

B. Confirmation of Cre::EXPLOR's Function on Primary Rat Embryonic Neuron

Following experiment was performed to investigate function of Cre::EXPLOR on primary rat embryonic neuron.

In particular, pCAG-loxP-STOP-loxP-ZsGreen encoded DNA was transfected to primary rat embryonic neurons and washed after 6 hrs. Then they were cultured on 0.15 mg/ml Cre::EXPLOR. After 48 hrs culture, expression of ZsGreen with green fluorescence was investigated. This experiment was performed at least three repeats, and thereby expression of ZsGreen was confirmed on Cre::EXPLOR treated primary rat embryonic neuron (FIG. 20).

C. Confirmation of Cre::EXPLOR Function on In Vivo Transgenic Mouse

The present inventors were performed following experiment to verify Cre::EXPLOR's function on in vivo.

In particular, 50 μl Cre:EXPLORs (10 mg/mL) was injected by ventrolateral injection to pCAG-loxP-STOP-loxP-eNpHR3.0-EYFP transgenic mouse. After injection, fixed brain slices by 4% formaldehyde were imaged by fluorescence microscopy. Green fluorescence indicates expression of eNpHR3.0-EYFP, and blue fluorescence indicates cell nuclei. eNpHR3.0-EYFP expression on neuron in zona incerta (ZI) of Cre::EXPLOR treated mouse was investigated by confocal microscopy, and thereby EYFP expression was confirmed on Cre::EXPLOR treated groups of pCAG-loxP-STOP-loxP-eNpHR3.0-EYFP transgenic mouse (FIG. 21).

D. Confirmation of Cre::EXPLOR Target Cell on Transgenic Mouse

To confirm specific cell targeting of Cre::EXPLOR on aforementioned in vivo experiment, immunohistochemistry was performed. NeuN antibody specifically stained neuron, and GFAP antibody specifically stained astrocytes, and thereby it was confirmed that Cre::EXPLOR targets specifically neuron in mouse brain through investigating that merged region mainly was neuron (FIG. 22).

Experimental Example 6: CRISPR-Cas9

<6-1> Production of Cas9-Loaded Exosome (Cas9::EXPLOR)

A. Confirmation of Cas9 within Exosome

The present inventors investigated the binding of CIBN and CRY2 expressing the CIBN-EGFP-CD9 and Cas9-mCherry-CRY2 to confirm the loading of Cas9, which is recorded in amino acid SEQ ID NO: 10.

As described in FIG. 23, Cas9-mCherry-CRY2 inserted pcDNA3.1(+) vector has 11,890 base pair in length, and the three protein parts consist of Cas9 with NLS sequence at 5-terminal, mCherry, and Cryptochrome 2 has 45 and 27 base pairs of linker sequences, respectively. Each protein part has 4194, 699, and 1497 base pairs in lengths, respectively.

In particular, HEK293T exosome producing cells were additionally cultured 48 hrs in Dulbecco's modified Eagle's medium (DMEM) without fetal bovine serum (FBS), after 24 hrs culture with transfected pcDNA3.1(+) vector including CIBN-EGFP-CD9 gene and Cas9-mCherry-CRY2 gene in non-light condition. After finish culture, position of red fluorescence from mCherry was investigated by confocal microscopy before and after the irradiation of 488 nm wavelength blue light. This experiment was performed more than five times, and thereby Cas9 protein is loaded within exosome by confirming that CIBN-EGFP-CD9 binds to Cas9-mCherry-CRY2 by the blue light stimulus (FIG. 23).

B. Production of Cas9-Loaded Exosome (Cas9::EXPLOR)

The present inventors performed following experiment to yield the Cas9-loaded exosomes.

In particular, CIBN-EGRP-CD9 gene and Cas9-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added ExoQuick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture (FIG. 8).

In addition, HEK293T exosome producing cells which stably express CIBN-EGFP-CD9 gene and Cas9-mCherry-CRY2 gene were cultured in medium without fetal bovine serum during 48~72 hrs on 50 μW power of 488 nm wavelength blue light. After finishing culture, supernatant removed cell debris was yielded by centrifuge (2000×g, 15 min) from isolated culture medium. To remove particles bigger than 200 nm from supernatant, it filtered by 0.2 μl PES membrane (Corning). Tangential Flow Filtration (TFF) method was applied in identical supernatant to remove particles smaller than 20 nm, condense and refine exosomes from filtrate. Vivaflow 50-100 kDa PES membrane (Sartorius) was used in TFF. Exosomes were condensed and refined by rotation of filtrate under 1.5~2 air pressure of TFF. Then, exosome concentrate was eliminated liquid by centrifugation (10000~14000 g, 5 min) on Amicon Ultra-0.5 (100 kDa) (Millipore) filter. Finally, exosomes were obtained by reverse-directional centrifugation (10000~14000 g, 5 min) with preferable buffer on experimental purpose. The loading of Cas9 within the exosome was evaluated (FIG. 25).

Functional analysis of Cas9-loaded exosomes is performed in target cells:

Target cells are treated with the Cas9-loaded exosomes to show the functional activity.

Animal models are administered with the Cas9-loaded exosomes by i.p. or i.v. to show therapeutic effect.

Experimental Example 7: Caspase-Activated DNase (CAD)

The binding of CIBN and CRY2 in cells expressing CIBN-EGFP-CD9 and CAD-mCherry-Cry2 at 488 nm wavelength blue light, and the loading of CAD within the exosome is evaluated.

For the massive production of CAD-loaded exosomes, cells stably expressing CIBN-EGFP-CD9 gene and CAD-mCherry-CRY2 gene are established, and exosomes are isolated and purified by Tangential Flow Filtration (TFF) method from culture supernatant.

Functional analysis of CAD-loaded exosomes is performed in target cells:

Target cells are treated with the CAD-loaded exosomes to show the functional activity.

Animal models are administered with the CAD-loaded exosomes by i.p. or i.v. to show therapeutic effect.

Experimental Example 8: β-Glucocerebrosidase

<8-1> Production of GBA-Loaded Exosome (GBA::EXPLOR)

A. Confirmation of GBA within Exosome

The present inventors investigated the binding of CIBN and CRY2 expressing the CIBN-EGFP-CD9 and GBA-mCherry-CRY2 to confirm the loading of GBA, which is recorded in amino acid SEQ ID NO: 12.

TABLE 2

| SEQ. ID | GENE | Nucleotide sequence |
|---|---|---|
| 12 | β-glucocere-brosidase | MEFSSPSREECPKPLSRVSIMAGSLTGLLLLQAVS WASGARPCIPKSFGYSSVVCVCNATYCDSFDPPT FPALGTFSRYESTRSGRRMELSMGPIQANHTGTG LLLTLQPEQKFQKVKGFGGAMTDAAALNILALS PPAQNLLLKSYFSEEGIGYNIIRVPMASCDFSIRT YTYADTPDDFQLHNFSLPEEDTKLKIPLIHRALQL AQRPVSLLASPWTSPTWLKTNGAVNGKGSLKGQP GDIYHQTWARYFVKFLDAYAEHKLQFWAVTAEN EPSAGLLSGYPFQCLGFTPEHQRDFIARDLGPTL ANSTHHNVRLLMLDDQRLLLPHWAKVVLTDPE AAKYVHGIAVHWYLDFLAPAKATLGETHRLFPN TMLFASEACVGSKFWEQSVRLGSWDRGMQYSH SIITNLLYHVVGWTDWNLALNPEGGPNWVRNFV DSPIIVDITKDTFYKQPMFYHLGHFSKFIPEGSQR VGLVASQKNDLDAVALMHPDGSAVVVVLNRSSK DVPLTIKDPAVGFLETISPGYSIHTYLWRRQ |

In particular, HEK293T exosome producing cells were additionally cultured 48 hrs in Dulbecco's modified Eagle's medium (DMEM) without fetal bovine serum (FBS), after 24 hrs culture with transfected pcDNA3.1(+) vector including CIBN-EGFP-CD9 gene and GBA-mCherry-CRY2 gene in non-light condition. After finish culture, position of red fluorescence from mCherry was investigated by confocal microscopy before and after the irradiation of 488 nm wavelength blue light. This experiment was performed more than five times, and thereby GBA protein is loaded within exosome by confirming that CIBN-EGFP-CD9 binds to GBA-mCherry-CRY2 by the blue light stimulus (FIG. 26).

B. Production of GBA-Loaded Exosome (GBA::EXPLOR)

The present inventors performed following experiment to yield the GBA-loaded exosomes.

In particular, CIBN-EGRP-CD9 gene and GBA-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added ExoQuick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture (FIG. 8).

In addition, HEK293T exosome producing cells which stably express CIBN-EGFP-CD9 gene and GBA-mCherry-CRY2 gene were cultured in medium without fetal bovine serum during 48~72 hrs on 50 μW power of 488 nm wavelength blue light. After finishing culture, supernatant removed cell debris was yielded by centrifuge (2000×g, 15 min) from isolated culture medium. To remove particles bigger than 200 nm from supernatant, it filtered by 0.2 μl PES membrane (Corning). Tangential Flow Filtration (TFF) method was applied in identical supernatant to remove particles smaller than 20 nm, condense and refine exosomes from filtrate. Vivaflow 50-100 kDa PES membrane (Sartorius) was used in TFF. Exosomes were condensed and refined by rotation of filtrate under 1.5~2 air pressure of TFF. Then, exosome concentrate was eliminated liquid by centrifugation (10000~14000 g, 5 min) on Amicon Ultra-0.5 (100 kDa) (Millipore) filter. Finally, exosomes were obtained by reverse-directional centrifugation (10000~14000 g, 5 min) with preferable buffer on experimental purpose.

<8-2> Measurement of GBA Expression in GBA-Loaded Exosome Producing Cells

The present inventors performed western blot to measure GBA expression in GBA-loaded exosome.

In particular, CIBN-EGRP-CD9 gene and GBA-mCherry-CRY2 gene included vectors were transfected on HEK293T exosome producing cells and these cells were cultured 24 hrs. The HEK293T cells were lysed using MPER (Mammalian Protein Extraction Reagent) and the proteins were analyzed by western blot. Rat primary astrocyte, human primary astrocyte, and Gaucher disease patient-derived fibroblast where β-glucocerebrosidase is deficient due to GBA gene abnormality were lysed to perform western blot and the proteins were analyzed by western blot.

As a result, endogenous GBA was observed in HEK293T cells including CIBN-EGRP-CD9 gene and GBA-mCherry-CRY2 gene, rat primary astrocyte, human primary astrocyte, except Gaucher disease patient-derived fibroblast (FIG. 27).

In addition, GBA-mCherry-CRY2 fusion protein (151 kDa) was observed in HEK293T cells including CIBN-EGRP-CD9 gene and GBA-mCherry-CRY2 gene, and this presents that GBA-mCherry-CRY2 fusion protein is well expressed in GBA-loaded exosome producing cells (FIG. 28).

<8-3> Confirmation of GBA Activity on Gaucher Disease Patient-Derived Cells by GBA-Loaded Exosome (GBA::EXPLOR)

A. Enzyme Activity of GBA within Exosome

The present inventor performed experiment for β-glucocerebrosidase enzyme activity to investigate glucocerebroside degrading activity of GBA within exosome.

In particular, CIBN-EGRP-CD9 gene and GBA-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added ExoQuick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture.

In addition, HEK293T exosome producing cells which stably express CIBN-EGFP-CD9 gene and GBA-mCherry-CRY2 gene were cultured in medium without fetal bovine serum during 48~72 hrs on 50 μW power of 488 nm wavelength blue light. After finishing culture, supernatant removed cell debris was yielded by centrifuge (2000×g, 15 min) from isolated culture medium. To remove particles bigger than 200 nm from supernatant, it filtered by 0.2 μl PES membrane (Corning). Tangential Flow Filtration (TFF) method was applied in identical supernatant to remove particles smaller than 20 nm, condense and refine exosomes from filtrate. Vivaflow 50-100 kDa PES membrane (Sartorius) was used in TFF. Exosomes were condensed and refined by rotation of filtrate under 1.5~2 air pressure of TFF. Then, exosome concentrate was eliminated liquid by centrifugation (10000~14000 g, 5 min) on Amicon Ultra-0.5 (100 kDa) (Millipore) filter. Finally, exosomes were obtained by reverse-directional centrifugation (10000~14000 g, 5 min). The exosomes were lysed using MPER (Mammalian Protein Extraction Reagent) and the proteins were analyzed.

Increased β-glucocerebrosidase enzyme activity of GBA-loaded GBA::EXPLOR was observed comparing to mCherry-loaded exosomes, and thereby active GBA loading on exosome was confirmed (FIG. 29).

B. Enzyme Activity of β-Glucocerebrosidase (GBA) on Gaucher Disease Patients-Derived Cells The present inventors performed following experiment to confirm the recovery of β-glucocerebrosidase enzyme activity on Gaucher disease patients-derived cells when treated with GBA::EXPLOR.

Gaucher disease patients-derived fibroblast was cultivated at the density of $2\times10^5$ cells in 60 mm dish. Then, mCherry::EXPLORs ($2\times10^9$ exosomes) or GBA::EXPLORs ($1.2\times10^{10}$ exosomes) were treated to Gaucher disease patients-derived fibroblast cultured in serum-free DMEM medium. Hydrolysis activity of GBA-mCh-CRY2 was measured by detecting the fluorescence using substrate 4-methylumbelliferyl-β-D-glucopyranoside (4-MUG; Sigma). Enzyme reaction was performed on 0.2 ml of 0.2 M citrate phosphate buffer (pH 0.5) containing 50 μl cell lysate of 0.15% (v/v) Triton X-100 (Sigma), 0.8% (w/v) sodium taurocholate (Sigma), 10 mM 4-MUG. After 1 hr incubation at 37° C., the enzyme activity was stopped using 100 μl of 0.1 M glycine, 0.1 M NaOH (pH 10.3). Enzyme reaction product, 4-methylumbelliferone (4-MU) was measured at excitation 365 nm, emission 460 nm condition.

As a result, β-glucocerebrosidase enzyme activity of GBA-loaded GBA::EXPLOR treated Gaucher disease patients-derived cells was recovered (FIG. 30).

Experimental Example 9: Mitogen Activated Kinases: p38 MAP Kinase

The present inventors confirm the binding of CIBN and CRY2 in cells expressing CIBN-EGFP-CD9 and p38 MAP kinase-mCherry-Cry2 at 488 nm wavelength blue light, and verify the loading of p38 MAP kinase within exosome.

For the massive production of p38 MAP kinase-loaded exosomes, cells stably expressing CIBN-EGFP-CD9 gene and p38 MAP kinase-mCherry-CRY2 gene are established, and exosomes are isolated and purified by Tangential Flow Filtration (TFF) method from culture supernatant.

Functional analysis of p38 MAP kinase-loaded exosomes is performed in target cells Treatment of p38 MAP kinase-loaded exosomes to target cells shows the functional activity.

Administration of p38 MAP kinase-loaded exosomes by i.p. or i.v. to animal model shows therapeutic effect.

Experimental Example 10: Inhibitor Kappa B Kinase (IKK)

The binding of CIBN and CRY2 in cells expressing CIBN-EGFP-CD9 and IKK-mCherry-Cry2 at 488 nm wavelength blue light, and the loading of IKK within the exosome is evaluated.

For the massive production of IKK-loaded exosomes, cells stably expressing CIBN-EGFP-CD9 gene and IKK-mCherry-CRY2 gene are established, and exosomes are isolated and purified by Tangential Flow Filtration (TFF) method from culture supernatant.

Functional analysis of IKK kinase-loaded exosomes is performed in target cells:

Target cells are treated with the IKK-loaded exosomes to show the functional activity.

Animal models are administered with the IKK-loaded exosomes by i.p. or i.v. to show therapeutic effect.

Experimental Example 11: PTEN Phosphatase

The present inventors confirmed the binding of CIBN and CRY2 in cells expressing CIBN-EGFP-CD9 and PTEN-Cry2 at 488 nm wavelength blue light, and the loading of PTEN within exosome.

For the massive production of PTEN-loaded exosomes, cells stably expressing CIBN-EGFP-CD9 gene and PTEN-CRY2 gene were established (FIG. 31), and exosomes were isolated and purified by Tangential Flow Filtration (TFF) method from culture supernatant.

Functional analysis of PTEN kinase-loaded exosomes is performed in target cells

Treatment of PTEN-loaded exosomes to target cells shows the functional activity.

Administration of PTEN-loaded exosomes by i.p. or i.v. to animal model shows therapeutic effect.

Experimental Example 12: Janus Kinase (JNK)

The binding of CIBN and CRY2 in cells expressing CIBN-EGFP-CD9 and JNK-mCherry-Cry2 at 488 nm wavelength blue light, and the loading of JNK within the exosome is evaluated.

For the massive production of JNK-loaded exosomes, cells stably expressing CIBN-EGFP-CD9 gene and JNK-mCherry-CRY2 gene are established, and exosomes are isolated and purified by Tangential Flow Filtration (TFF) method from culture supernatant.

Functional analysis of JNK-loaded exosomes is performed in target cells:

Target cells are treated with the JNK-loaded exosomes to show the functional activity.

Animal models are administered with the JNK-loaded exosomes by i.p. or i.v. to show therapeutic effect.

Experimental Example 13: Ubiquitin Ligases

The binding of CIBN and CRY2 in cells expressing CIBN-EGFP-CD9 and Ubiquitin ligase-mCherry-Cry2 at 488 nm wavelength blue light, and the loading of Ubiquitin ligases within the exosome is evaluated.

For the massive production of Ubiquitin ligase-loaded exosomes, cells stably expressing CIBN-EGFP-CD9 gene and Ubiquitin ligase-mCherry-CRY2 gene are established, and exosomes are isolated and purified by Tangential Flow Filtration (TFF) method from culture supernatant.

Functional analysis of Ubiquitin ligase-loaded exosomes is performed in target cells:

Target cells are treated with the Ubiquitin ligase-loaded exosomes to show the functional activity.

Animal models are administered with the Ubiquitin ligase-loaded exosomes by i.p. or i.v. to show therapeutic effect.

Experimental Example 14: Luciferase

The present inventors confirmed the binding of CIBN and CRY2 in cells expressing CIBN-EGFP-CD9 and luciferase-mcherry-Cry2 at 488 nm wavelength blue light, and the loading of luciferase within exosome (FIG. 32).

For the massive production of luciferase-loaded exosomes, cells stably expressing CIBN-EGFP-CD9 gene and luciferase-mcherry-CRY2 gene were established, and exosomes were isolated and purified by Tangential Flow Filtration (TFF) method from culture supernatant.

Quantitative luciferase activity based on the number of luciferase molecules was analyzed (FIG. 33).

Experimental Example 15: Peroxiredoxin

<15-1> Production of Prx I or Prx II-Loaded Exosome (Prx I/II:EXPLOR)
A. Confirmation of Prx I/H within Exosome The present inventors investigated the binding of CIBN and CRY2 expressing the CIBN-EGFP-CD9 and Prx I/II-mCherry-CRY2 to confirm the loading of Prx I or Prx II, which is recorded in amino acid SEQ ID NO: 7 or 8.

In particular, HEK293T exosome producing cells were additionally cultured 48 hrs in Dulbecco's modified Eagle's medium (DMEM) without fetal bovine serum (FBS), after 24 hrs culture with transfected pcDNA3.1(+) vector including CIBN-EGFP-CD9 gene and Prx I/II-mCherry-CRY2 gene in non-light condition. After finish culture, position of red fluorescence from mCherry was investigated by confocal microscopy before and after the irradiation of 488 nm wavelength blue light. This experiment was performed more than five times, and thereby aggregation of Prx I/II protein by blue light stimulation was confirmed (FIG. 34). Therefore, Prx I/II protein was loaded in exosome by confirming the co-localization (yellow) of Prx mCherry-CRY2 (red) and CIBN-EGFP-CD9 (green).

B. Production of Prx I/II::EXPLOR

The present inventors performed following experiment to yield the Prx I/II-loaded exosomes.

In particular, CIBN-EGRP-CD9 gene and Prx I/II-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added ExoQuick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture (FIG. 8).

<15-2> Confirmation of Inhibition Effect on Oxidative Stress-Induced Cytotoxicity by Prx I/II::EXPLOR The present inventors performed following experiment to confirm the inhibition effect on oxidative stress-induced cytotoxicity by Prx I/II::EXPLOR.

In particular, after changing the serum-free media of HeLa cells, 100 μg/mL of Prx I/II::EXPLORs was treated and cultivated for 18 hrs. $H_2O_2$ (0, 0.5, 1 mM) was treated and cultivated for additional 8 hrs. WST assays were used to analyze the cell viability.

Due to pretreat of Prx I/II::EXPLORs, the oxidative stress-induced cytotoxicity was significantly inhibited (FIG. 35).

Experimental Example 16: NF-κB

The binding of CIBN and CRY2 in cells expressing CIBN-EGFP-CD9 and NF-κB-mCherry-Cry2 at 488 nm wavelength blue light, and the loading of NF-κB within the exosome is evaluated.

For the massive production of NF-κB-loaded exosomes, cells stably expressing CIBN-EGFP-CD9 gene and NF-κB-mCherry-CRY2 gene are established, and exosomes are isolated and purified by Tangential Flow Filtration (TFF) method from culture supernatant.

Functional analysis of NF-κB-loaded exosomes is performed in target cells:

Target cells are treated with the NF-κB-loaded exosomes to show the functional activity.

Animal models are administered with the NF-κB-loaded exosomes by i.p. or i.v. to show therapeutic effect.

Experimental Example 17: MyoD

The present inventors confirmed the binding of CIBN and CRY2 in cells expressing CIBN-EGFP-CD9 and MyoD-mcherry-Cry2 at 488 nm wavelength blue light (FIG. 36), and verify the loading of MyoD within exosome.

For the massive production of MyoD-loaded exosomes, cells stably expressing CIBN-EGFP-CD9 gene and MyoD-mcherry-CRY2 gene were established, and exosomes were isolated and purified by Tangential Flow Filtration (TFF) method from culture supernatant.

Treatment of MyoD-loaded exosomes to target cells showed the functional activity (FIG. 37).

Experimental Example 18: Tbx18 (T-Box Transcription Factor 18)

The binding of CIBN and CRY2 in cells expressing CIBN-EGFP-CD9 and Tbx18-mCherry-Cry2 at 488 nm wavelength blue light, and the loading of Tbx18 within the exosome is evaluated.

For the massive production of Tbx18-loaded exosomes, cells stably expressing CIBN-EGFP-CD9 gene and Tbx18-mCherry-CRY2 gene are established, and exosomes are isolated and purified by Tangential Flow Filtration (TFF) method from culture supernatant.

Functional analysis of Tbx18-loaded exosomes is performed in target cells:

Target cells are treated with the Tbx18-loaded exosomes to show the functional activity.

Animal models are administered with the Tbx18-loaded exosomes by i.p. or i.v. to show therapeutic effect.

Experimental Example 19: p53

The present inventors confirmed the binding of CIBN and CRY2 in cells expressing CIBN-EGFP-CD9 and p53-mcherry-Cry2 at 488 nm wavelength blue light (FIG. 38), and the loading of PTEN within exosome (FIG. 39)

For the massive production of p53-loaded exosomes, cells stably expressing CIBN-EGFP-CD9 gene and p53-mcherry-CRY2 gene were established, and exosomes were isolated and purified by Tangential Flow Filtration (TFF) method from culture supernatant.

Treatment of p53-loaded exosomes to target cells showed the transcriptional activity (FIG. 40).

Administration of p53-loaded exosomes by i.p. or i.v. to animal model shows therapeutic effect.

Experimental Example 20: HMGB1

The present inventors confirmed the binding of CIBN and CRY2 in cells expressing CIBN-EGFP-CD9 and HMGB1-Cry2 at 488 nm wavelength blue light, and the loading of HMGB1 within exosome (FIG. 41).

For the massive production of HMGB1-loaded exosomes, cells stably expressing CIBN-EGFP-CD9 gene and HMGB1-CRY2 gene were established, and exosomes were isolated and purified by Tangential Flow Filtration (TFF) method from culture supernatant.

Functional analysis of HMGB1-loaded exosomes is performed in target cells

Treatment of HMGB1-loaded exosomes to target cells shows the transcriptional activity.

Administration of HMGB1-loaded exosomes by i.p. or i.v. to animal model shows therapeutic effect.

Experimental Example 21: Super-Repressor KB

<21-1> Production of Super-Repressor-KB-Loaded Exosome (Super-Repressor-IκB:EXPLOR)

A. Confirmation of Super-Repressor-KB in Exosome

The present inventors investigated the binding of CIBN and CRY2 expressing the CIBN-EGFP-CD9 and super-repressor-IκB-mCherry-CRY2 to confirm the loading of super-repressor-IκB, which is recorded in amino acid SEQ ID NO: 5.

In particular, HEK293T exosome producing cells were additionally cultured 48 hrs in Dulbecco's modified Eagle's medium (DMEM) without fetal bovine serum (FBS), after 24 hrs culture with transfected pcDNA3.1(+) vector including CIBN-EGFP-CD9 gene and super-repressor-IκB-mCherry-CRY2 gene in non-light condition. After finish culture, position of red fluorescence from mCherry was investigated by confocal microscopy before and after the irradiation of 488 nm wavelength blue light. This experiment was performed more than five times, and thereby aggregation of super-repressor-IκB protein by blue light stimulation was confirmed (FIG. 42). Therefore, super-repressor-IκB protein was loaded in exosome by confirming the co-localization (yellow) of super-repressor-IκB-mCherry-CRY2 (red) and CIBN-EGFP-CD9 (green).

B. Production of Super-Repressor-IκB::EXPLOR

The present inventors performed following experiment to yield the super-repressor-IκB-loaded exosomes.

In particular, CIBN-EGRP-CD9 gene and super-repressor-IκB-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added ExoQuick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture (FIG. 8).

In addition, HEK293T exosome producing cells which stably express CIBN-EGFP-CD9 gene and super-repressor-IκB-mCherry-CRY2 gene were cultured in medium without fetal bovine serum during 48~72 hrs on 50 μW power of 488 nm wavelength blue light. After finishing culture, supernatant removed cell debris was yielded by centrifuge (2000×g, 15 min) from isolated culture medium. To remove particles bigger than 200 nm from supernatant, it filtered by 0.2 μl PES membrane (Corning). Tangential Flow Filtration (TFF) method was applied in identical supernatant to remove particles smaller than 20 nm, condense and refine exosomes from filtrate. Vivaflow 50-100 kDa PES membrane (Sartorius) was used in TFF. Exosomes were condensed and refined by rotation of filtrate under 1.5~2 air pressure of TFF. Then, exosome concentrate was eliminated liquid by centrifugation (10000~14000 g, 5 min) on Amicon Ultra-0.5 (100 kDa) (Millipore) filter. Finally, exosomes were obtained by reverse-directional centrifugation (10000~14000 g, 5 min) with preferable buffer on experimental purpose.

<21-2> Confirmation of Super-Repressor-IκB:EXPLOR Inhibition Effect of TNF-α Mediated NF-κB Activity The present inventors performed following experiments to confirm the TNF-α mediated anti-inflammatory effect using super-repressor-IκB:EXPLOR.

In particular, HeLa was cultured in 100 mg/mL of mCherry:EXPLORs or super-repressor-IκB-mCherry:EXPLORs treated culture medium for 3 hrs. Then, TNF-α (10 ng/mL) was treated and incubated for additional 30 minutes. After fixing with 4% paraformaldehyde, NF-κB p65 was stained with Alexa Fluor 488-conjugated antibody and inspected using confocal microscopy. To measure the binding activity of p65/c-Rel (NF-kB), nuclei lysate was used in TransAM NF-kB and AP-1 assay kit (ActiveMotif, Carlsbad, California, USA) according to manufacturer's protocol. Data was presented average±SEM (n=3), and applied using Tukey's post hoc test and decided significant group (**, p<0.01) through ANOVA test.

By pretreat of super-repressor-IκB:EXPLOR on HeLa cells, TNF-α-activated NF-κB transport to nucleus and NF-κB DNA binding were inhibited (FIG. 43).

<21-3> Confirmation of Anti-Inflammatory Effect of Super-Repressor-IκB:EXPLOR on Collagen-Induced Arthritis Animal Model The present inventors performed the following experiment to confirm the anti-inflammatory effect of super-repressor-IκB:EXPLOR on Collagen-induced arthritis mouse model.

In particular, mostly used rheumatoid arthritis model, collagen-induced arthritis mouse model was developed by immunization through injecting bovine collagen type II and adjuvant to tail subcutaneous tissue of DBA/1. Super repressor IκB:EXPLOR was retro-orbitally injected 4 times to two collagen-induced arthritis mouse models every 2 days. Progression of rheumatoid arthritis symptom was determined by clinical score as listed in Table 3. Mean Clinical Score is average value of clinical scores from mouse feet according to the aforementioned table.

When super repressor IκB:EXPLOR was retro-orbitally injected to collagen-induced arthritis mouse models, the rheumatoid arthritis mouse showed decreased symptom (FIG. 44).

TABLE 3

| Severity Score | Phenotypic signs |
| --- | --- |
| 0 | No evidence of erythema and swelling |
| 1 | Erythema and mild swelling confined to the tarsals or ankle joint |
| 2 | Erythema and mild swelling extending from the ankle to the tarsals |
| 3 | Erythema and moderate swelling extending from the ankle to metatarsal joint |
| 4 | Erythema and severe swelling encompass the ankle, foot and digits, or ankylosis of the limb |

<21-4> Effect of srIkB-Loaded Exosomes on LPS-Induced Sepsis Model

In addition, when super repressor IκB:EXPLOR was Intraperitoneally injected to LPS-induced sepsis mouse models, the sepsis mouse showed significantly increased survival (FIG. 45).

Experimental Example 22: pySTAT3 Intrabody

The present inventors confirmed the binding of CIBN and CRY2 in cells expressing CIBN-EGFP-CD9 and pySTAT3-mcherry-Cry2 at 488 nm wavelength blue light, and the loading of pySTAT3 within exosome (FIG. 46).

For the massive production of pySTAT3-loaded exosomes, cells stably expressing CIBN-EGFP-CD9 gene and pySTAT3-mcherry-CRY2 gene were established, and exosomes were isolated and purified by Tangential Flow Filtration (TFF) method from culture supernatant.

Treatment of pySTAT3-loaded exosomes to target cells shows the functional activity.

Administration of pySTAT3-loaded exosomes by i.p. or i.v. to animal model shows therapeutic effect.

Experimental Example 23: Bcl-2-Associated X Protein

<23-1> Production of Bax-Loaded Exosome (Bax::EXPLOR)

A. Confirmation of Bax in Exosome

The present inventors investigated the binding of CIBN and CRY2 expressing the CIBN-EGFP-CD9 and Bax-mCherry-CRY2 to confirm the loading of Bax, which is recorded in amino acid SEQ ID NO: 6.

In particular, HEK293T exosome producing cells were additionally cultured 48 hrs in Dulbecco's modified Eagle's medium (DMEM) without fetal bovine serum (FBS), after 24 hrs culture with transfected pcDNA3.1(+) vector including CIBN-EGFP-CD9 gene and Bax-mCherry-CRY2 gene in non-light condition. After finish culture, position of red fluorescence from mCherry was investigated by confocal microscopy before and after the irradiation of 488 nm wavelength blue light. This experiment was performed more than five times, and thereby aggregation of Bax protein by blue light stimulation was confirmed (FIG. 48). Therefore, Bax protein was loaded in exosome by confirming the binding of Bax-mCherry-CRY2 (red) and CIBN-EGFP-CD9 (green).

B. Production of Bax::EXPLOR

The present inventors performed following experiment to yield the Bax-loaded exosomes.

In particular, CIBN-EGRP-CD9 gene and Bax-mCherry-CRY2 gene included vectors were transfected on HEK293T exosome producing cells and these cells were cultured 24 hrs. After 24 hrs culture, cells were changed their medium as it without fetal bovine serum (FBS) and additionally cultured during 48 hrs on 50 μW power of 488 nm wavelength blue light. After finishing culture, supernatant removed cell debris was yielded by centrifuge (2000×g, 15 min) from isolated culture medium. The supernatant was added Exo-Quick-TC Exosome Precipitation Solution (System Biosciences, Mountain View, California, USA) with five times more volume and mixed during 18 hrs on 4° C. Suspended exosomes were obtained by suspending exosome pellet through centrifugation (1500×g, 30 min) of aforementioned supernatant and ExoQuick-TC mixture (FIG. 8).

In addition, HEK293T exosome producing cells which stably express CIBN-EGFP-CD9 gene and Bax-mCherry-CRY2 gene were cultured in medium without fetal bovine serum during 48~72 hrs on 50 μW power of 488 nm wavelength blue light. After finishing culture, supernatant removed cell debris was yielded by centrifuge (2000×g, 15 min) from isolated culture medium. To remove particles bigger than 200 nm from supernatant, it filtered by 0.2 μl PES membrane (Corning). Tangential Flow Filtration (TFF) method was applied in identical supernatant to remove particles smaller than 20 nm, condense and refine exosomes from filtrate. Vivaflow 50-100 kDa PES membrane (Sartorius) was used in TFF. Exosomes were condensed and refined by rotation of filtrate under 1.5~2 air pressure of TFF. Then, exosome concentrate was eliminated liquid by centrifugation (10000~14000 g, 5 min) on Amicon Ultra-0.5 (100 kDa) (Millipore) filter. Finally, exosomes were obtained by reverse-directional centrifugation (10000~14000 g, 5 min) with preferable buffer on experimental purpose.

<23-2> Confirmation of Apoptosis by Bax:EXPLOR

Bax is apoptotic regulator, thus the BAX overexpression release cytochrome c by binding to mitochondrial membrane, and inducing the apoptosis. The present inventors confirmed the excretion of cytochrome c using Bax:EXPLOR.

In particular, HeLa in 0.1 mg/mL of mCherry:EXPLORs or Bax:EXPLORs containing medium was cultured for 12 hrs. After fixing using 4% paraformaldehyde, to measure the excretion of cytochrome c, the HeLa was stained with Alexa Fluor 647-conjugated antibody and imaged using confocal microscope and the ratio of cytochrome c was analyzed by counting the number of cells (Scale bars, 20 μm). Data was presented average±SEM (n=3), and applied using Tukey's post hoc test and decided significant group (**, p<0.01) through ANOVA test.

As a result, larger amount of cytochrome c release was observed in Bax:EXPLOR treated HeLa than mCherry:EXPLOR treated HeLa (FIG. 49).

Experimental Example 24: Bcl-xL

The binding of CIBN and CRY2 in cells expressing CIBN-EGFP-CD9 and Bcl-xL-mCherry-Cry2 at 488 nm wavelength blue light, and the loading of Bcl-xL within the exosome is evaluated.

For the massive production of Bcl-xL-loaded exosomes, cells stably expressing CIBN-EGFP-CD9 gene and Bcl-xL-mCherry-CRY2 gene are established, and exosomes are isolated and purified by Tangential Flow Filtration (TFF) method from culture supernatant.

Functional analysis of Bcl-xL-loaded exosomes is performed in target cells:

Target cells are treated with Bcl-xL-loaded exosomes to show the functional activity.

Animal models are administered with Bcl-xL-loaded exosomes by i.p. or i.v. to show therapeutic effect.

Experimental Example 25: AIMP

The present inventors confirmed the binding of CIBN and CRY2 in cells expressing CIBN-EGFP-CD9 and AIMP-mcherry-Cry2 at 488 nm wavelength blue light (FIG. 50), and the loading of AIMP within exosome (FIG. 51).

For the massive production of AIMP-loaded exosomes, cells stably expressing CIBN-EGFP-CD9 gene and AIMP-mcherry-CRY2 gene were established, and exosomes were isolated and purified by Tangential Flow Filtration (TFF) method from culture supernatant.

Treatment of AIMP-loaded exosomes to target cells shows the functional activity.

Administration of AIMP-loaded exosomes by i.p. or i.v. to animal model shows therapeutic effect.

Experimental Example 26: mCherry (Fluorescent Protein)

The present inventors confirmed the binding of CIBN and CRY2 in cells expressing CIBN-EGFP-CD9 and mCherry-Cry2 at 488 nm wavelength blue light (FIG. 52), and the loading of AIMP within exosome.

For the massive production of mCherry-loaded exosomes, cells stably expressing CIBN-EGFP-CD9 gene and mCherry-CRY2 gene were established, and exosomes were isolated and purified by Tangential Flow Filtration (TFF) method from culture supernatant.

Experimental Example 27: Nucleic Acid-Binding Proteins

The binding of CIBN and CRY2 in cells expressing CIBN-EGFP-CD9 and Nucleic acid-binding protein-mCherry-Cry2 at 488 nm wavelength blue light, and the loading of Nucleic acid-binding protein within the exosome is evaluated.

For the massive production of Nucleic acid-binding protein-loaded exosomes, cells stably expressing CIBN-EGFP-CD9 gene and Nucleic acid-binding protein-mCherry-CRY2 gene are established, and exosomes are isolated and purified by Tangential Flow Filtration (TFF) method from culture supernatant.

Functional analysis of Nucleic acid-binding protein-loaded exosomes is performed in target cells:

Target cells are treated with Nucleic acid-binding protein-loaded exosomes to show the functional activity.

Animal models are administered with Nucleic acid-binding protein-loaded exosomes by i.p. or i.v. to show therapeutic effect.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

The invention claimed is:

1. An exosome comprising:
   a cargo protein; and
   a photo-specific binding protein.

2. The exosome of claim 1, wherein the photo-specific binding protein comprises a first photo-specific binding protein or a second photo-specific binding protein.

3. The exosome of claim 2, wherein
   the first photo-specific binding protein is conjugated to an exosome specific marker to form a first fusion protein; and
   the second photo-specific binding protein is conjugated to the cargo protein to form a second fusion protein.

4. The exosome of claim 3, wherein, the first fusion protein and the second fusion protein are linked reversibly through the first photo-specific binding protein and the second photo-specific binding protein.

5. The exosome of claim 3, wherein the first photo-specific binding protein is conjugated to the exosome specific marker to be located in the direction toward inside of the exosome.

6. The exosome of claim 3, wherein the first photo-specific binding protein and the second photo-specific binding protein comprise at least one selected from the group consisting of CIB, CIBN, PhyB, PIF, FKF1, GIGANTEA, CRY and PHR.

7. The exosome of claim 3, wherein
   the first photo-specific binding protein comprises CIB or CIBN, and the second photo-specific binding protein comprises CRY or PHR; or
   the first photo-specific binding protein comprises CRY or PHR, and the second photo-specific binding protein comprises CIB or CIBN.

8. The exosome of claim 3, wherein
   the first photo-specific binding protein comprises PhyB, and the second photo-specific bind protein comprises PIF; or
   the first photo-specific binding protein comprises PIF, and the second photo-specific binding protein comprises PhyB.

9. The exosome of claim 3, wherein
the first photo-specific binding protein comprises GIGANTEA, and the second photo-specific binding protein comprises FKF1; or
the first photo-specific binding protein comprises FKF1, and the second photo-specific binding protein comprises GIGANTEA.

10. The exosome of claim 3, wherein the exosome specific marker comprises at least one selected from the group consisting of CD9, CD63, CD81 and CD82.

11. The exosome of claim 1, wherein the cargo protein comprises at least one selected from the group consisting of MMPs, TIMPs, caspases, Cathepsins, Cre recombinase, Cas9, caspase-activated DNase, β-glucocerebrosidase, Mitogen activated kinase, Inhibitor kappa B kinase, PTEN phosphatase, Janus kinase, Ubiquitin ligases, Luciferase, Peroxiredoxin, NF-κB, MyoD, Tbx18, p53, HMGB1, Super-repressor IκB, pYSTAT3 Intrabody, Bcl-2-associated X protein, BcL-xL, AIMP, mCherry and Nucleic acid binding proteins.

12. The exosome of claim 1, wherein the cargo protein comprises at least one selected from the group consisting of Cre recombinase, Cas9, β-glucocerebrosidase, PTEN phosphatase, Ubiquitin ligase, Luciferase, Peroxiredoxin, NF-κB, MyoD, p53, HMGB1, Super-repressor IκB, pYSTAT3 Intrabody, Bcl-2-associated X protein, BcL-xL, AIMP, and mCherry.

13. The exosome of claim 1, wherein the cargo protein comprises at least cone selected form the group consisting of Cre recombinase, Cas9, β-glucocerebrosidase, Peroxiredoxin, Super-repressor IκB, pYSTAT3 Intrabody, Bcl-2-associated X protein.

14. The exosome of claim 1, wherein the cargo protein comprises Cre recombinase.

15. The exosome of claim 1, wherein the cargo protein comprises Cas9 or Cpf1 protein.

16. The exosome of claim 1, wherein the cargo protein comprises β-glucocerebrosidase.

17. The exosome of claim 1, wherein the cargo protein comprises Peroxiredoxin I or Peroxiredoxin II protein.

18. The exosome of claim 1, wherein the cargo protein comprises Super-repressor IκB protein.

19. The exosome of claim 1, wherein the cargo protein comprises Bcl-2-associated X protein (Bax protein).

20. The exosome of claim 1, wherein the cargo protein comprises pYSTAT3 Intrabody.

* * * * *